US007485468B2

(12) United States Patent
Brys et al.

(10) Patent No.: US 7,485,468 B2
(45) Date of Patent: Feb. 3, 2009

(54) MOLECULAR TARGETS AND COMPOUNDS, AND METHODS TO IDENTIFY THE SAME, USEFUL IN THE TREATMENT OF JOINT DEGENERATIVE AND INFLAMMATORY DISEASES

(75) Inventors: Reginald Brys, Korbeek-Dijle (BE); Nick Vandeghinste, Duffel (BE); Peter Herwig Maria Tomme, Gent (BE); Hubertus Johanus Matheus Klaassen, Herent (BE)

(73) Assignee: Galapagos BV (BE)

( * ) Notice: Subject to any disclaimer, the term of this patent is extended or adjusted under 35 U.S.C. 154(b) by 330 days.

(21) Appl. No.: 11/251,465

(22) Filed: Oct. 14, 2005

(65) Prior Publication Data

US 2006/0094061 A1 May 4, 2006

Related U.S. Application Data

(60) Provisional application No. 60/619,384, filed on Oct. 15, 2004.

(51) Int. Cl.
*A61K 38/00* (2006.01)
*A61K 1/00* (2006.01)
*C07K 1/00* (2006.01)
*G01N 33/566* (2006.01)

(52) U.S. Cl. .......................... 436/501; 435/6; 435/91.1; 435/91.31; 530/300; 530/324; 530/350

(58) Field of Classification Search ..................... 435/6, 435/91.1, 91.31, 455; 424/9.1, 9.2; 536/23.1, 536/24; 514/1, 2, 44; 436/501; 530/300, 530/324, 350
See application file for complete search history.

(56) References Cited

FOREIGN PATENT DOCUMENTS

| | | | |
|---|---|---|---|
| WO | WO 03/025148 | * | 3/2003 |
| WO | WO 2004/094636 | | 11/2004 |

OTHER PUBLICATIONS

A. Peracchi et al, Rev. Med. Virol., 14:47-64 (2004).*
A. Branch, Trends in Biochem. Sci. 23: 45-50 (1998).*
S. Crooke, Antisense Res. and Application, Chapter 1, pp. 1-50, (Ed. by S. Crooke) (Publ. Springer-Verlag).*
Chirila et al., Biomaterials, 23: 321-342 (2002).*
Opalinska et al, Nature Rev., 1: 503-514 (2002).*
Agrawal et al, Molecular Med. Today, vol. 6, pp. 82-81 (2000).*
Andreakos et al., "Heterogeneous Requirement of IkappaB Kinase 2 for Inflammatory Cytokine and Matrix Metalloproteinase Production in Rheumatoid Arthritis: Implication for Therapy"; Arthritis & Rheumatism, vol. 48, No. 7, pp. 1901-1912 (2003).
Choy and Panayi, "Cytokine Pathways and Joint Inflammation in Rheumatoid Arthritis"; N Engl J. Med., 344, No. 12, pp. 907-916 (2001).
Coussens, et al., "Matrix Metalloproteinase Inhibitors and Cancer: Trials and Tribulations"; Science, vol. 295, pp. 2387-2392 (2002).
Creemers, et al., "Matrix Metalloproteinase Inhibition after Myocardial Infarction: A New Approach to Prevent Heart Failure"; Circulation Research, vol. 89(3) pp. 201-210 (2001).
Cunnane, et al., "Early Joint Erosions and Serum Levels of Matrix Metalloproteinase 1, Matrix Metalloprloteinase 3, and Tissue Inhibitor of Metalloproteinases 1 in Rheumatoid Arthritis"; Arthritis & Rheumtism, vol. 44, No. 10, pp. 2263-2274 (2001).
Edwards, et al., "Efficacy of B-Cell-Targeted Therapy with Rituximab in Patients With Rheumatoid Arthritis"; N. Engl. J. Med. 350(25), pp. 2572-2581 (2004).
Firestein, G., "Evolving concepts of rheumatoid arthritis"; Nature 423 , pp. 356-361 (2003).
Gapski, et al., "Effect of Systemic Matrix Metalloproteinase Inhibition on Periodontal Wound Repair: A Proof of Concept Trial"; J. Periodontol. 75(3), pp. 441-452 (2004).
Gomez-Rhino, et al., "Treatment of Rheumatoid ArthritisWith Tumor Necrosis Factor Inhibitors may Predispose to Significant Increase in Tuberculosis Risk: A Multicenter Active-Surveillance Report"; Arthritis Rheumatism, vol. 48, No. 8, pp. 2122-2127 (2003).
Kramer, et al., "Etanercept Added to Background Methotrexate Therapy in Patients with Rheumatoid Arthritis"; Arthritis & Rheumatism, vol. 48, No. 6, pp. 1493-1499 (2003).
Lee and Weinblatt, "Rheumatoid Arthritis"; The Lancet, vol. 358, pp. 903-911 (2001).
O'Dell, "Efficacy of Triple DMARD Therapy in Patients with RA With Suboptimal Response to Methotrexate"; J. of Rheumatology, vol. 23: Suppl. 44, pp. 72-74 (1996).
O'Dell, "Therapeutic Strategies for Rheumatoid Arthritis"; N. Engl. J. Med., 350 (25), pp. 2591-2602 (2004).
Reif, et al., "Matrix Metalloproteinases 2 and 9 are Markers of Inflammation but not of the Degree of Fibrosis in Chromin Hepatitis C"; Digestion, vol. 71, No. 2, pp. 124-130 (2005).
Rosenberg, "Matrix Metalloproteinases in Neuroinflammation"; Glia. 39(3), pp. 279-291 (2002).
Schanstra, et al., "In vivo bradykinin B2 receptor activation reduces renal fibrosis"; J. Clin. Invest., vol. 110, No. 3, pp. 371-391 (2002).
Schett, et al., "Adenovirus-Based Overexpression of Tissue Inhibitor of Metalloproteinases 1 Reduces Tissue Damage in the Joints of Tumor Necrosis Factor α Transgenic Mice"; Arthritis Rheumatism, vol. 44, No. 12, pp. 2888-2898 (2001).
Smolen & Steiner, "Therapeutic Strategies for Rheumatoid Arthritis"; Nature Reviews Drug Discovery, vol. 2 (6) pp. 473-488 (2003).

(Continued)

*Primary Examiner*—Jane Zara
(74) *Attorney, Agent, or Firm*—Martin Savitzky

(57) ABSTRACT

The application discloses methods for identifying and using compounds that inhibit extra-cellular matrix (ECM) degradation and inflammation, using a polypeptide sequence including SEQ ID NO: 17-127 (hereinafter "TARGETS") and fragments thereof, expression inhibitory agents such as antisense polynucleotide, a ribozyme, and a small interfering RNA (siRNA), comprising a nucleic acid sequence complementary to, or engineered from, a naturally occurring polynucleotide sequence encoding a polypeptide of SEQ ID NO: 17-127, useful in pharmaceutical compositions comprising said agent, for the treatment, or prevention, of chronic joint degenerative and/or inflammatory diseases such as rheumatoid arthritis.

17 Claims, 15 Drawing Sheets

OTHER PUBLICATIONS

St. Clair, et al., "Combination of Infliximab and Methotrexate Therapy for Early Rheumatoid Arthritis: A Randomized, Controlled Trial"; Arthritis Rheumatism, vol. 50, No. 11, pp. 3432-3443 (2004).

Suzuki, et al., "Matrix metalloproteinases in the parthogenesis of asthma and COPD: implications for therapy"; Treat Respir Med., 3(1), pp. 17-27 (2004).

Vincenti, et al, "Transcriptional regulation of collagenase (MMP-1, MMP-13) genes in arthritis: integration of complex signaling pathways for the recruitment of gene-specific transcription factors"; Arthritis Research., vol. 4, No. 3, pp. 157-164 (2002).

Yang, et al, "Modulation of Inflammation and Response to Dexamethasone by Annexin 1 in Antigen-Induced Arthritis"; vol. 50, No. 3, pp. 976-984 (2004).

* cited by examiner

Schematic view of a normal joint and its changes in rheumatoid arthritis (From Smolen and Steiner, 2003).

Characterization of the expression of MMP1 by synovial fibroblasts.

Increased expression of MMP1 by SFs
triggered with various model adenoviruses

Increased expression of MMP1 by SFs triggered
with various cytokines relevant in rheumatoid arthritis pathology Dose-dependent inhibition of the "TNFα-based trigger"-induced expression of MMP1 by SFs by a known anti-inflammatory compound.

Schematic representation of the screening of the SilenceSelect collection using the reverse MMP1 assay

Figure 7

Layout and performance of the control plate produced for the reverse MMP1 ELISA assay

A

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|
| A | P1 | P1 | N1 | N1 | P2 | P2 | N2 | N2 | P3 | P3 | N3 | N3 | P1 | P1 | N1 | N1 | P2 | P2 | N2 | N2 | P3 | P3 | N3 | N3 |
| B | P1 | Bl | N1 | Bl | P2 | Bl | N2 | Bl | P3 | Bl | N3 | Bl | P1 | Bl | N1 | Bl | P2 | Bl | N2 | Bl | P3 | Bl | N3 | Bl |
| C | N1 | N1 | P2 | P2 | N2 | N2 | P3 | P3 | N3 | N3 | P1 | P1 | N1 | N1 | P2 | P2 | N2 | N2 | P3 | P3 | N3 | N3 | P1 | P1 |
| D | N1 | Bl | P2 | Bl | N2 | Bl | P3 | Bl | N3 | Bl | P1 | Bl | N1 | Bl | P2 | Bl | N2 | Bl | P3 | Bl | N3 | Bl | P1 | Bl |
| E | P2 | P2 | N2 | N2 | P3 | P3 | N3 | N3 | P1 | P1 | N1 | N1 | P2 | P2 | N2 | N2 | P3 | P3 | N3 | N3 | P1 | P1 | N1 | N1 |
| F | P2 | Bl | N2 | Bl | P3 | Bl | N3 | Bl | P1 | Bl | N1 | Bl | P2 | Bl | N2 | Bl | P3 | Bl | N3 | Bl | P1 | Bl | N1 | Bl |
| G | N2 | N2 | P3 | P3 | N3 | N3 | P1 | P1 | N1 | N1 | P2 | P2 | N2 | N2 | P3 | P3 | N3 | N3 | P1 | P1 | N1 | N1 | P2 | P2 |
| H | N2 | Bl | P3 | Bl | N3 | Bl | P1 | Bl | N1 | Bl | P2 | Bl | N2 | Bl | P3 | Bl | N3 | Bl | P1 | Bl | N1 | Bl | P2 | Bl |
| I | P3 | P3 | N3 | N3 | P1 | P1 | N1 | N1 | P2 | P2 | N2 | N2 | P3 | P3 | N3 | N3 | P1 | P1 | N1 | N1 | P2 | P2 | N2 | N2 |
| J | P3 | Bl | N3 | Bl | P1 | Bl | N1 | Bl | P2 | Bl | N2 | Bl | P3 | Bl | N3 | Bl | P1 | Bl | N1 | Bl | P2 | Bl | N2 | Bl |
| K | N3 | N3 | P1 | P1 | N1 | N1 | P2 | P2 | N2 | N2 | P3 | P3 | N3 | N3 | P1 | P1 | N1 | N1 | P2 | P2 | N2 | N2 | P3 | P3 |
| L | N3 | Bl | P1 | Bl | N1 | Bl | P2 | Bl | N2 | Bl | P3 | Bl | N3 | Bl | P1 | Bl | N1 | Bl | P2 | Bl | N2 | Bl | P3 | Bl |
| M | P1 | P1 | N1 | N1 | P2 | P2 | N2 | N2 | P3 | P3 | N3 | N3 | P1 | P1 | N1 | N1 | P2 | P2 | N2 | N2 | P3 | P3 | N3 | N3 |
| N | P1 | Bl | N1 | Bl | P2 | Bl | N2 | Bl | P3 | Bl | N3 | Bl | P1 | Bl | N1 | Bl | P2 | Bl | N2 | Bl | P3 | Bl | N3 | Bl |
| O | N1 | N1 | P2 | P2 | N2 | N2 | P3 | P3 | N3 | N3 | P1 | P1 | N1 | N1 | P2 | P2 | N2 | N2 | P3 | P3 | N3 | N3 | P1 | P1 |
| P | N1 | Bl | P2 | Bl | N2 | Bl | P3 | Bl | N3 | Bl | P1 | Bl | N1 | Bl | P2 | Bl | N2 | Bl | P3 | Bl | N3 | Bl | P1 | Bl |

B

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|
| A | 1052 | 872 | 1124 | 1205 | 1000 | 948 | 1306 | 1282 | 771 | 835 | 1165 | 1097 | 690 | 701 | 1029 | 1074 | 918 | 962 | 1332 | 1331 | 812 | 955 | 1189 | 1233 |
| B | 1072 | 796 | 1025 | 632 | 655 | 571 | 1209 | 831 | 654 | 538 | 975 | 538 | 494 | 483 | 981 | 502 | 694 | 684 | 1104 | 552 | 630 | 675 | 1165 | 927 |
| C | 1265 | 1118 | 718 | 738 | 1068 | 1016 | 444 | 554 | 1007 | 996 | 367 | 409 | 891 | 892 | 622 | 652 | 1188 | 1152 | 513 | 578 | 983 | 1093 | 696 | 834 |
| D | 1293 | 723 | 677 | 611 | 1155 | 517 | 538 | 644 | 1105 | 560 | 476 | 476 | 962 | 643 | 598 | 641 | 1186 | 652 | 511 | 586 | 1110 | 744 | 718 | 882 |
| E | 1064 | 828 | 1207 | 1163 | 601 | 489 | 991 | 1025 | 436 | 461 | 983 | 912 | 584 | 706 | 1149 | 1166 | 564 | 596 | 995 | 986 | 457 | 570 | 945 | 1061 |
| F | 1194 | 697 | 1185 | 666 | 578 | 557 | 1098 | 670 | 574 | 522 | 1030 | 619 | 674 | 615 | 1220 | 703 | 605 | 609 | 1048 | 648 | 535 | 679 | 1021 | 854 |
| G | 1407 | 1248 | 640 | 645 | 1075 | 1040 | 549 | 542 | 1162 | 1105 | 724 | 693 | 1155 | 1216 | 725 | 585 | 1003 | 1067 | 470 | 539 | 1007 | 1082 | 814 | 898 |
| H | 1379 | 796 | 604 | 663 | 1088 | 575 | 515 | 599 | 1110 | 634 | 767 | 666 | 1183 | 673 | 600 | 704 | 1014 | 642 | 482 | 539 | 1084 | 613 | 828 | 858 |
| I | 977 | 687 | 1059 | 1064 | 547 | 576 | 1105 | 1108 | 727 | 823 | 1154 | 1250 | 624 | 666 | 1068 | 1130 | 456 | 578 | 1071 | 1008 | 644 | 720 | 1230 | 1259 |
| J | 899 | 687 | 1027 | 603 | 535 | 662 | 1118 | 734 | 720 | 688 | 1191 | 568 | 548 | 642 | 1053 | 571 | 464 | 560 | 1010 | 614 | 666 | 551 | 1224 | 849 |
| K | 1268 | 1142 | 515 | 492 | 962 | 954 | 556 | 703 | 1197 | 1229 | 571 | 575 | 1005 | 1040 | 512 | 582 | 945 | 982 | 621 | 675 | 1206 | 1136 | 644 | 819 |
| L | 1273 | 791 | 516 | 640 | 1026 | 530 | 629 | 654 | 1137 | 639 | 608 | 554 | 948 | 600 | 419 | 655 | 929 | 544 | 626 | 621 | 1137 | 667 | 746 | 868 |
| M | 974 | 698 | 966 | 1005 | 645 | 719 | 1029 | 1075 | 626 | 580 | 1014 | 973 | 478 | 483 | 956 | 928 | 565 | 690 | 1025 | 1157 | 513 | 597 | 1013 | 1207 |
| N | 965 | 789 | 909 | 605 | 654 | 485 | 1070 | 683 | 542 | 525 | 939 | 518 | 354 | 555 | 922 | 545 | 579 | 500 | 1026 | 512 | 482 | 565 | 1047 | 983 |
| O | 1241 | 1086 | 742 | 687 | 1204 | 1143 | 630 | 570 | 1028 | 1040 | 618 | 618 | 888 | 946 | 638 | 717 | 1018 | 1104 | 635 | 747 | 980 | 1010 | 782 | 950 |
| P | 1255 | 1017 | 986 | 945 | 1219 | 857 | 827 | 935 | 1174 | 921 | 839 | 962 | 1093 | 909 | 991 | 1048 | 1315 | 923 | 854 | 938 | 1201 | 988 | 912 | 1026 |

| | Average | Standard deviation | Cutoff | % positive | |
|---|---|---|---|---|---|
| P1 | 611.9 | 185.9 | | 87.5 | of 48 |
| P2 | 743.2 | 142.3 | | 81.3 | of 48 |
| P3 | 645.6 | 124.2 | | 93.8 | of 48 |
| N1 | 1036.9 | 103.7 | | 0.0 | of 48 |
| N2 | 1182.1 | 91.6 | | 0.0 | of 48 |
| N3 | 1067.7 | 83.3 | | 0.0 | of 48 |
| Blanco | 681.6 | 146.3 | | 85.4 | of 96 |
| All positives | 666.9 | 161.9 | | | |
| All negatives | 1095.6 | 111.8 | 872.0 | | |

Figure 8
Representative example of the performance of the reverse MMP1 ELISA assay run on a subset of 384 Ad-siRNAs of the SilenceSelect collection that are tested in duplicate in a primary screen (A) and a repeat screen (B).
A.
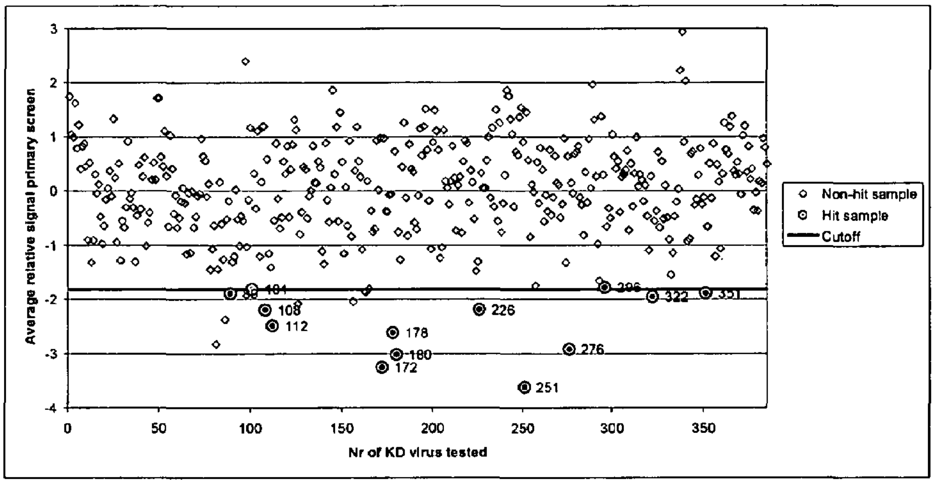
B.
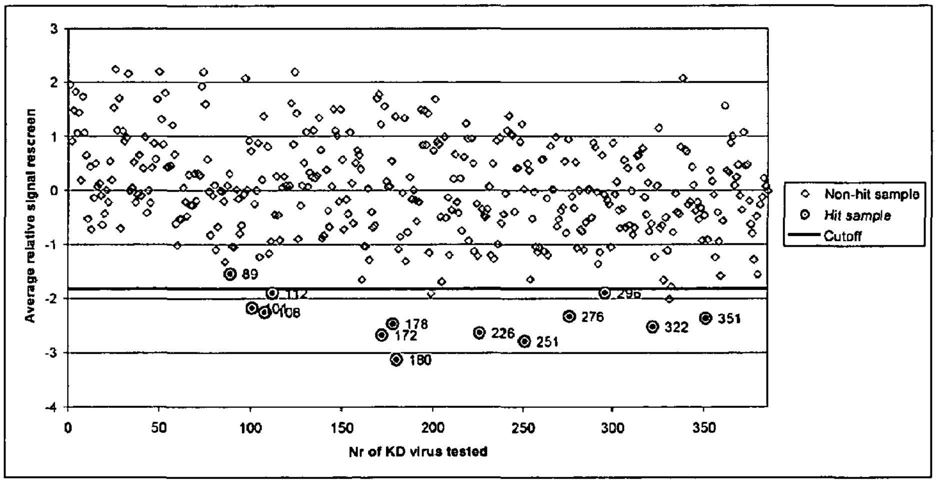

Scatter plot

Figure 10A

Layout of the plates used for the 3 MOI rescreen of the reverse MMP1 assay

| | 1 | 2 | 3 | 4 | 5 | 6 | 7 | 8 | 9 | 10 |
|---|---|---|---|---|---|---|---|---|---|---|
| A | | | | | | | | | | |
| B | | Hit 1 | Hit 2 | Hit 3 | Hit 4 | Hit 5 | Hit 6 | Hit 7 | Hit 8 | Hit 9 |
| C | | Hit 11 | Hit 12 | Hit 13 | Hit 14 | Hit 15 | Hit 16 | Hit 17 | Hit 18 | Hit 19 |
| D | | Hit 21 | Hit 22 | Hit 23 | Hit 24 | Hit 25 | Hit 26 | Hit 27 | Hit 28 | Hit 29 |
| E | | Hit 31 | Hit 32 | Hit 33 | Hit 34 | Hit 35 | Hit 36 | Hit 37 | Hit 38 | Hit 39 |
| F | | Hit 41 | Hit 42 | Hit 43 | Hit 44 | Hit 45 | Hit 46 | Hit 47 | Hit 48 | Hit 49 |
| G | | Ad5-eGFP_KD_v5 | Ad5-luc_KD_v13 | Ad5-eGFP | Ad5-M6PR_KD_v1 | Ad5-MMP1 | Ad5-eGFP_KD_v5 | Ad5-luc_KD_v13 | Ad5-eGFP | Ad5-M6PR_KD_v1 |
| H | | | | | | | | | | |

Figure 10B

Layout of the plates used for the cytotoxicity and secretion rescreen of the reverse MMP1 assay

| | 1 | 2 | 3 | 4 | 5 | 6 | 7 | 8 | 9 | 10 |
|---|---|---|---|---|---|---|---|---|---|---|
| A | | | | | | | | | | |
| B | | Hit 1 | Hit 2 | Hit 3 | Hit 4 | Hit 5 | Hit 6 | Hit 7 | Hit 8 | Hit 9 |
| C | | Ad5-eGFP_KD_v5 | Ad5-luc_KD_v13 | Ad5-eGFP | Ad5-M6PR_KD_v1 | Ad5-MMP1 | Ad5-eGFP_KD_v5 | Ad5-luc_KD_v13 | Ad5-eGFP | Ad5-M6PR_KD_v1 |
| D | | Hit 21 | Hit 22 | Hit 23 | Hit 24 | Hit 25 | Hit 26 | Hit 27 | Hit 28 | Hit 29 |
| E | | Ad5-eGFP_KD_v5 | Ad5-luc_KD_v13 | Ad5-eGFP | Ad5-M6PR_KD_v1 | Ad5-MMP1 | Ad5-eGFP_KD_v5 | Ad5-luc_KD_v13 | Ad5-eGFP | Ad5-M6PR_KD_v1 |
| F | | | | | | | | | | |
| G | | | | | | | | | | |
| H | | | | | | | | | | |

Reduction of the expression of the TARGETS in primary SFs by Ad-siRNAs inhibits cytokine-induced MMP1 expression in a dose dependent manner Reduction of the expression of the TARGETS in primary SFs by Ad-siRNAs inhibits cytokine-induced MMP1 expression in a dose dependent manner Reduction of the expression of the TARGETS in primary SFs by Ad-siRNAs inhibits cytokine-induced native collagen degradation Reduction of the expression of the TARGETS in primary SFs by Ad-siRNAs inhibits cytokine-induced native collagen degradation Reduction of the expression of the TARGETS in primary SFs by Ad-siRNAs modulates TNFα-induced IL-8 expression

SEQUENCE LISTING

```
<160> NUMBER OF SEQ ID NOS: 880

<210> SEQ ID NO 1
<211> LENGTH: 2304
<212> TYPE: DNA
<213> ORGANISM: Homo sapiens

<400> SEQUENCE: 1

ttgtgtttag aaaaggctcg ggcaaagcca gcccaagttc gctctctgca cacctcgagc      60

acctcgcgga cggcgtgggt ccgccagctc cgggacctgc cgccgctgcc tgcgcgcccc     120

ggggcggagg acggtgccag ccgcccacga ggagaccccg ctcccgcagg aggccgagct     180

gaagcggcgg agcgcgccgc cagccagccg gggtgagtgc cccgggcgag gccggcggcc     240
```

-continued

```
gccaaagccc ccgcgggctc gcccgggcgc ccggatgcca gccccgagcc ccgccgccgg    300
gtgcatgcct cccccgcggc gcgcccccgc aggctgctgc ccgctgtgac cgcccttccc    360
cgcaggcggg cgccggccag gctctccccg agatcagcgc acgggtggca cccgccggac    420
ccccagcggc agcggcggcg gcggctgcag ggggcgcggg gcggaggctg cgagggcgcg    480
cgcggggagg atggacgggt ccggggagcg cagcctcccg gagccgggca gccagagctc    540
cgctgccagc gacgacatag agatagtcgt caacgtgggg ggcgtgcggc aggtgctgta    600
cggggacctc ctcagtcagt accctgagac ccggctggcg gagctcatca actgcttggc    660
tgggggctac gacaccatct tctccctgtg cgacgactac gaccccggca agcgcgagtt    720
ctactttgac agggacccgg acgccttcaa gtgtgtcatc gaggtgtact atttcgggga    780
ggtccacatg aagaagggca tctgccccat ctgcttcaag aacgagatgg acttctggaa    840
ggtggacctc aagttcctgg acgactgttg caagagccac ctgagcgaga agcgcgagga    900
gctggaggag atcgcgcgcc gcgtgcagct catcctggac gacctgggcg tggacgcagc    960
cgagggccgc tggcgccgct gccagaagtg cgtctggaag ttcctggaga agcccgagtc   1020
gtcgtgcccg gcgcgggtgg tggccgtgct ctccttcctg ctcatcctcg tctcgtccgt   1080
ggtcatgtgc atgggcacca tccccgagct gcaggtgctg gacgccgagg gcaaccgcgt   1140
ggagcacccg acgctggaga acgtggagac ggcgtgcatt ggctggttca ccctggagta   1200
cctgctgcgc ctcttctcgt cacccaacaa gctgcacttc gcgctgtcct tcatgaacat   1260
tgtggacgtg ctggccatcc tccccttcta cgtgagcctc acgctcacgc acctgggtgc   1320
ccgcatgatg gagctgacca acgtgcagca ggccgtgcag gcgctgcgga tcatgcgcat   1380
cgcgcgcatc ttcaagctgg cccgccactc ctcgggcctg cagaccctca cctatgccct   1440
caagcgcagc ttcaaggaac tggggctgct gctcatgtac ctggcagtgg gtatcttcgt   1500
cttctctgcc ctgggctaca ccatggagca gagccatcca gagaccctgt ttaagagcat   1560
cccccagtcc ttctggtggg ccatcatcac catgaccacc gtcggctacg gcgacatcta   1620
ccccaagacc acgctgggca agctcaacgc ggccatcagc ttcttgtgtg gtgtcatcgc   1680
catcgccctg cccatccacc ccatcatcaa caactttgtc aggtactaca acaagcagcg   1740
cgtcctggag accgcggcca agcacgagct ggagctgatg gaactcaact ccagcagcgg   1800
gggcgagggc aagaccgggg gctcccgcag tgacctggac aacctccctc cagagcctgc   1860
ggggaaggag gcgccgagct gcagcagccg gctgaagctc tcccacagcg acaccttcat   1920
ccccctcctg accgaggaga agcaccacag gacccggctc cagagttgca agtgacagga   1980
gggcccctca ggcagagatg gaccaggcgg tggacagatg ggtagatgtg gcaggcatgt   2040
catcgacagc acagaagggc tgtcctgtgt ccccccaacc ctcccctgga cagactctga   2100
aggccctccc ggcacctctg ccaaggctgg gtaagactcc tctatgttgc ctgctgtcca   2160
ggagcccggg agggaggggt gtgcaggagc cgcagggccg tgtgggacga gtggaggccg   2220
cggcctggct ggcacgagag cccacgcccg cttctgtatc tccctcaata aagcctcctg   2280
ctctgtgcaa aaaaaaaaaa aaaa                                          2304
```

<210> SEQ ID NO 2
<211> LENGTH: 6255
<212> TYPE: DNA
<213> ORGANISM: Homo sapiens

<400> SEQUENCE: 2

-continued

```
ccgaaagccc cgagagagac taagaagcaa tcctcccacg cgctttctcc caccctcggg     60
ccactgagac ggagggacag agggccgccc tcgcgcggcc gaggccccgc ctcccgctcg    120
cccgcccgcg cctccagcgg aagccggaag caaaagcggg ttctgctagc cccgcggctc    180
cgaactcggt ggtcctggaa gctccgcagg atgggggaga agatggcgga agaggagagg    240
ttccccaata caactcatga gggtttcaat gtcaccctcc acaccaccct ggttgtcacg    300
acgaaactgg tgctcccgac ccctggcaag cccatcctcc ccgtgcagac aggggagcag    360
gcccagcaag aggagcagtc cagcggcatg accattttct tcagcctcct tgtcctagct    420
atctgcatca tattggtgca tttactgatc cgatacagat tacatttctt gccagagagt    480
gttgctgttg tttctttagg tattctcatg ggagcagtta taaaaattat agagtttaaa    540
aaactggcga attggaagga agaagaaatg tttcgtccaa acatgttttt cctcctcctg    600
cttcccccta ttatctttga gtctggatat tcattacaca agggtaactt ctttcaaaat    660
attggttcca tcaccctgtt tgctgttttt gggacggcaa tctccgcttt tgtagtaggt    720
ggaggaattt attttctggg tcaggctgat gtaatctcta aactcaacat gacagacagt    780
tttgcgtttg gctccctaat atctgctgtc gatccagtgg ccactattgc catttttcaat    840
gcacttcatg tggaccccgt gctcaacatg ctggtctttg gagaaagtat tctcaacgat    900
gcagtctcca ttgttctgac caacacagct gaaggtttaa caagaaaaaa tatgtcagat    960
gtcagtgggt ggcaaacatt tttacaagcc cttgactact tcctcaaaat gttctttggc   1020
tctgcagcgc tcggcactct cactggctta atttctgcat tagtgctgaa gcatattgac   1080
ttgaggaaaa cgccttcctt ggagtttggc atgatgatca tttttgctta tctgccttat   1140
gggcttgcag aaggaatctc actctcaggc atcatggcca tcctttttctc aggcatcgtg   1200
atgtcccact acacgcacca taacctctcc ccagtcaccc agatcctcat gcagcagacc   1260
ctccgcaccg tggccttctt atgtgaaaca tgtgtgtttg catttcttgg cctgtccatt   1320
tttagttttc ctcacaagtt tgaaatttcc tttgtcatct ggtgcatagt gcttgtacta   1380
tttggcagag cggtaaacat tttccctctt tcctacctcc tgaatttctt ccgggatcat   1440
aaaatcacac cgaagatgat gttcatcatg tggtttagtg gcctgcgggg agccatcccc   1500
tatgccctga gcctacacct ggacctggag cccatggaga agcggcagct catcggcacc   1560
accaccatcg tcatcgtgct cttcaccatc ctgctgctgg gcggcagcac catgcccctc   1620
attcgcctca tggacatcga ggacgccaag gcacaccgca ggaacaagaa ggacgtcaac   1680
ctcagcaaga ctgagaagat gggcaacact gtggagtcgg agcacctgtc ggagctcacg   1740
gaggaggagt acgaggccca ctacatcagg cggcaggacc ttaagggctt cgtgtggctg   1800
gacgccaagt acctgaaccc cttcttcact cggaggctga cgcaggagga cctgcaccac   1860
gggcgcatcc agatgaaaac tctcaccaac aagtggtacg aggaggtacg ccagggcccc   1920
tccggctccg aggacgacga gcaggagctg ctctgacgcc aggtgccaag gcttcaggca   1980
ggcaggccca ggatgggcgt ttgctgcgca cagacactca gcaggggcct cgcagagatg   2040
cgtgcatcca gcagcccctt caagacataa gagggcgggg cgaggtactg gctgcagagt   2100
cgccttagtc cagaacctga caggcctctg gagccaggcg acttcttggg aaactgtcat   2160
ctcccgactc ctccctgagc cagcctccgc tcagtgtggc tcctcagccc acagagggga   2220
gggagcatgg ggccaggtgc cagtcatctg tgaagctagg gcgcctaccc ccccacccgg   2280
aggacccctg cggcccccctg cctagaggag caccatctac agttgtgcca ttccccagcc   2340
actgccttca tgctgccccc gccggactgg cagagccagg ggtcagccac ctgcctttga   2400
```

-continued

```
gtcatcaaga tgcctctgca gccacaattc tgacctaagt ggcagggccc agaaatcctg   2460
aaaacctccc gctgcctttt gtgatacttc ctgtgctccc tcagagagaa acggagtgac   2520
cttttgtcct ttacctgatt ggcacttcgc agtctatctc cctgggtagc agacggctgc   2580
tgcccttctc tgggcatgtt ctgaatgttt acactggtac cttctggtat cttctttaga   2640
gccccctgca agctgcaact ctaggctttt atcttgcggg gtcagagcgc cctctagagg   2700
gaaaagctag aggcacaggg tttctgccgg cccacaactg ctgtcttgat ttgcatttta   2760
cagcaaagtg ctgagagcct ctagtcgcct cctgccatct gatctccctc cccaccattc   2820
ccgtactcag ttgttctttt gtctaatcgg aggccactgt gctgaggccc tgcagtgtct   2880
gctcactgct gccatcttcg ctgctagtca gggttccatc ctctttcccc tctcccagtt   2940
ccctaccacg ttggatccca ttcgtcaccc atgctagggt ccccaaagca ctggggcagg   3000
ggccagagca gcagcaccca gtgctccctc ctctactctg acctggggcc ccagcatcct   3060
ggagcacacg ctccacgcac acacacccca gccctgtccc aggggcctgg ccccctcagc   3120
catctcaggg tgaggagctg ccagtcatgt ccagatggaa tgactcccat cctctcctca   3180
tctccccttt gacgagcctc aaactgctca gctcatcaaa gagccattgc caacttccgt   3240
atgtggttct gggtcccagg gagccttgga acctggcacc ctggggtggt ttaattcatc   3300
attaagaagc attcctgctt ctcaagggac acagtggcct gcatgggcca gcatggaccc   3360
tgggctgatc atgtgcattc ctgcttctct ggggacacag tgggcccaca tgggccagca   3420
tggaccctgg gctagagcaa gcacatctcc atctcttcca cctcaggcag tgtggctcca   3480
gatgtcagga gggactgacc tcaggacctt ccaggttcct ctgtgccagg aatgagaggc   3540
caggcccgat cctaccacct cgccttgacc ctgaagtcag agcaggccag ccaagcagga   3600
agcacactgt ttactttttg catgaaaagt aaatgtgtac ttgatagagc taaaatatga   3660
tctttttttaa tttctcaacc ccataatttg agccattgcc ttgcttaatt ttggtttcca   3720
ccatttcctt ttagtggaga agagaggaag tcagagggta gggacctttg cctgcccctg   3780
ggcgagtgcg ggcagggatc tgagaccaga ttgttctcgc acccctgcca gaactcactc   3840
tcccctgaag tttagggtcc catctcccag atgtaagttg ttttgcaaac tcagtttgcc   3900
aggatttctt tctttcctaa tcttaaattc acagataaag caatgaaaag agtcagatcc   3960
catttccgtc tgccccctcg tcaccaggtg tgatagcccc agccaggtca cacctggcct   4020
cacactttga gctgagactt gaaaacgatg ctgtggcgga agagcatgtg gggcttggtg   4080
gaggggcccc aggatttgtt gggggcaaag ggggtggcgg gaccgttccc aggaggtacc   4140
agcacctgcc tcgatctcct ctgagcctct tctgcccccct gtcggccagg tgaggtcagc   4200
agcctgggag agtgccccca agagatgagg gcacccccgtg ttccttggca atcttggctc   4260
accttggtaa caaaaggcca tagaagtctg tttttctggg tcagtttttt ttgcctgaga   4320
ataacaaatt gctgctgtct acctttagca cacccaataa ttctatttgg ggcagtgaat   4380
gcatagaaga tataaaaata cgcagcttaa ctatatcttc ctgcgtgtgt atttattttc   4440
ttctgggtct aggccatggt acaggagaac tgtggcgtgt aggaggaata cttcaggatg   4500
agtgaaggct ggagccaggg agcgctggag gaaaccagcc ctttagccag cagcccctcc   4560
accacaggca ctgctgtgtg gaacgagttc ttggaatgaa tcccatgctt tctgcagcct   4620
gtagttgtta tgacccctcg gaacaaccac cccgtggctt gtgtggggtc tcgcagggaa   4680
aagggctggc ttctaggtcc ccgagataag tgtgcagggg gatgggccag ggccaggcta   4740
```

-continued

```
agggtggctc agttccatca tctggaggtc agacacactg tccagaggca gaactgaagc   4800

cctctcggcc cctaccctaa gccagccacc cctcttcaca gtgggtgagc tgggctgggc   4860

tggctggcat gaggccaagg ggtaggcctg agcgccagag tcgcccaggt tagcccacag   4920

gattcctttg tgtgccatgg aatgctgaaa gatgggtgac tggggaccct tcttaaaacc   4980

tttggcaaag gtgccatcgg cagggcttgg cctcatgaag tctcaggtcc gtgttcccgc   5040

agggcgcaca tgcttggaga gtcctcagca gggtagccga ggccaggcca cttctgctga   5100

ggatggggca ggctggggtg tgggtgtggc ctggggtggc tcagggctgg aactgctgcc   5160

tgattcctgt gtggggagaa gctcagtggc cgtttgctgc cactgacaag gatttcacat   5220

gcagaagaga aaaggccccc ctccaccccc cgcattccct gccgagtgag agccagtgtt   5280

tgctgccctt gctgggggcg ggtaggaaac cctgagcttc ctgatgcgga gtcatgaagc   5340

agagtcctcg ggaaggcatc tccacagccc cgggtcctct gtctaacgcc ctccatttca   5400

cgccctccat ctcacagtca agataaaggc ctcgagaata aagagccagc cccccttccat   5460

ttagtctcct gccgtttccc aaacagttgt ccaacagtta gacattgagg ggcttcactg   5520

ttaccaggca tgtaacagaa ggaggaagac taacacacac cccctgcccc atcccatccc   5580

cctctcccga gctattttct tgctgtggcc tctggtgccc ttgagttggt ctccccggct   5640

gctctgcggg ggcttcactg gcttcggagt gagcgcgaag tgctggtgag cagtgggcct   5700

gtgattggat gggaagatgt gcatccgtgg tcaaaagtca gctgccagcc ctgcggaacc   5760

agagcctcag gctgggatgg ggaggcctcc ctgcttccac ctgcatggtg ggcatggcct   5820

ggcttacacc aaaggctttg acggtttctc caagtaagga tctgcaaatc ttgaatcgtc   5880

ctcaaaatga cgaagcttga attgtcctca agatggatgt gaatcttaca ttccttttca   5940

tcatttcctt tgtaaaaatg acgagtgctg ggtttttgtt ttaagaagca ttatgaaggc   6000

cagacttact catttttctc ccccaagtga gctgcaagag gcccctgtta ggcccctgtt   6060

tcctgagcag tgatgtgctg ctcttcttgg tggggctttg ggctgggagg ggaaggcggg   6120

tcagagatgg gggacctgtg gctgccatgc aggagcccct gcgtcatctc gttggactct   6180

ttaagggagt caggaataga tgtatgaaca gtcgtgtcac tggatgccta tttagaaata   6240

aagtgtatgc tgctg                                                    6255
```

<210> SEQ ID NO 3
<211> LENGTH: 2466
<212> TYPE: DNA
<213> ORGANISM: Homo sapiens

<400> SEQUENCE: 3

```
acgtgaccct gacccaataa gggtggaagg ctgagtccgc agagccaata acgagagtcc     60

gagaggcgac ggaggcggac tctgtgagga aacaagaaga gaggcccaag atggagacgg    120

cggcggctgt agcggcgtga caggagcccc atggcacctg cccagcccca cctcagccca    180

tcttgacaaa atctaaggct ccatggagcc accacggggc ccccctgcca atggggccga    240

gccatcccgg gcagtgggca ccgtcaaagt atacctgccc aacaagcaac gcacggtggt    300

gactgtccgg gatggcatga gtgtctacga ctctctagac aaggccctga aggtgcgggg    360

tctaaatcag gactgctgtg tggtctaccg actcatcaag ggacgaaaga cggtcactgc    420

ctgggacaca gccattgctc ccctggatgg cgaggagctc attgtcgagg tccttgaaga    480

tgtcccgctg accatgcaca attttgtacg gaagaccttc ttcagcctgg cgttctgtga    540

cttctgcctt aagtttctgt tccatggctt ccgttgccaa acctgtggct acaagttcca    600
```

-continued

```
ccagcattgt tcctccaagg tccccacagt ctgtgttgac atgagtacca accgccaaca    660
gttctaccac agtgtccagg atttgtccgg aggctccaga cagcatgagg ctccctcgaa    720
ccgccccctg aatgagttgc taaccccca gggtcccagc ccccgcaccc agcactgtga    780
cccggagcac ttccccttcc ctgccccagc caatgccccc ctacagcgca tccgctccac    840
gtccactccc aacgtccata tggtcagcac cacggccccc atggactcca acctcatcca    900
gctcactggc cagagtttca gcactgatgc tgccggtagt agaggaggta gtgatggaac    960
cccccggggg agccccagcc cagccagcgt gtcctcgggg aggaagtccc cacattccaa   1020
gtcaccagca gagcagcgcg agcggaagtc cttggccgat gacaagaaga aagtgaagaa   1080
cctggggtac cgggactcag gctattactg ggaggtacca cccagtgagg tgcagctgct   1140
gaagaggatc gggacgggct cgtttggcac cgtgtttcga gggcggtggc atggcgatgt   1200
ggccgtgaag gtgctcaagg tgtcccagcc cacagctgag caggcccagg ctttcaagaa   1260
tgagatgcag gtgctcagga agacgcgaca tgtcaacatc ttgctgttta tgggcttcat   1320
gacccggccg ggatttgcca tcatcacaca gtggtgtgag ggctccagcc tctaccatca   1380
cctgcatgtg gccgacacac gcttcgacat ggtccagctc atcgacgtgg cccggcagac   1440
tgcccagggc atggactacc tccatgccaa gaacatcatc caccgagatc tcaagtctaa   1500
caacatcttc ctacatgagg ggctcacggt gaagatcggt gactttggct tggccacagt   1560
gaagactcga tggagcgggg cccagccctt ggagcagccc tcaggatctg tgctgtggat   1620
ggcagctgag gtgatccgta tgcaggaccc gaacccctac agcttccagt cagacgtcta   1680
tgcctacggg gttgtgctct acgagcttat gactggctca ctgccttaca gccacattgg   1740
ctgccgtgac cagattatct ttatggtggg ccgtggctat ctgtccccgg acctcagcaa   1800
aatctccagc aactgcccca aggccatgcg gcgcctgctg tctgactgcc tcaagttcca   1860
gcgggaggag cggcccctct tcccccagat cctggccaca attgagctgc tgcaacggtc   1920
actccccaag attgagcgga gtgcctcgga accctccttg caccgcaccc aggccgatga   1980
gttgcctgcc tgcctactca gcgcagcccg ccttgtgcct taggccccgc ccaagccacc   2040
agggagccaa tctcagccct ccacgccaag gagccttgcc caccagccaa tcaatgttcg   2100
tctctgccct gatgctgcct caggatcccc cattccccac cctgggagat gagggggtcc   2160
ccatgtgctt ttccagttct tctggaattg ggggaccccc gccaaagact gagccccctg   2220
tctcctccat catttggttt cctctttggc tttggggata cttctaaatt ttgggagctc   2280
ctccatctcc aatggctggg atttgtggca gggattccac tcagaacctc tctggaattt   2340
gtgcctgatg tgccttccac tggattttgg ggttcccagc accccatgtg gatttttgggg   2400
gtcccttttg tgtctccccc gccattcaag gactcctctc tttcttcacc aagaagcaca   2460
gaattc                                                              2466
```

<210> SEQ ID NO 4
<211> LENGTH: 4987
<212> TYPE: DNA
<213> ORGANISM: Homo sapiens

<400> SEQUENCE: 4

```
gagtggagtt ctggaggaat gtttaccaga cacagagccc agagggacag cgcccagagc     60
ccagatagag agacacggcc tcactggctc agcaccaggg tccccttccc cctcctcagc    120
tccctccctg gcccctttaa gaaagagctg atcctctcct ctcttgagtt aacccctgat    180
```

-continued

```
tgtccaggtg gcccctggct ctggcctggt gggcggaggc aaagggggag ccaggggcgg    240
agaaagggtt gcccaagtct gggagtgagg gaaggaggca ggggtgctga gaaggcggct    300
gctgggcaga gccggtggca agggcctccc ctgccgctgt gccaggcagg cagtgccaaa    360
tccggggagc ctggagctgg ggggagggcc ggggacagcc cggccctgcc ccctcccccg    420
ctgggagccc agcaacttct gaggaaagtt tggcacccat ggcgtggcgg tgccccagga    480
tgggcagggt cccgctggcc tggtgcttgg cgctgtgcgg ctgggcgtgc atggccccca    540
ggggcacgca ggctgaagaa agtcccttcg tgggcaaccc agggaatatc acaggtgccc    600
ggggactcac gggcaccctt cggtgtcagc tccaggttca gggagagccc cccgaggtac    660
attggcttcg ggatggacag atcctggagc tcgcggacag cacccagacc caggtgcccc    720
tgggtgagga tgaacaggat gactggatag tggtcagcca gctcagaatc acctccctgc    780
agctttccga cacgggacag taccagtgtt tggtgtttct gggacatcag accttcgtgt    840
cccagcctgg ctatgttggg ctggagggct tgccttactt cctggaggag cccgaagaca    900
ggactgtggc cgccaacacc cccttcaacc tgagctgcca agctcaggga cccccagagc    960
ccgtggacct actctggctc caggatgctg tcccccctggc cacggctcca ggtcacggcc   1020
cccagcgcag cctgcatgtt ccagggctga acaagacatc ctctttctcc tgcgaagccc   1080
ataacgccaa gggggtcacc acatcccgca cagccaccat cacagtgctc ccccagcagc   1140
cccgtaacct ccacctggtc tcccgccaac ccacggagct ggaggtggct tggactccag   1200
gcctgagcgg catctacccc ctgacccact gcaccctgca ggctgtgctg tcagacgatg   1260
ggatgggcat ccaggcggga gaaccagacc ccccagagga gcccctcacc tcgcaagcat   1320
ccgtgccccc ccatcagctt cggctaggca gcctccatcc tcacacccct tatcacatcc   1380
gcgtggcatg caccagcagc cagggcccct catcctggac ccactggctt cctgtggaga   1440
cgccggaggg agtgcccctg ggccccccctg agaacattag tgctacgcgg aatgggagcc   1500
aggccttcgt gcattggcaa gagccccggg cgcccctgca gggtaccctg ttagggtacc   1560
ggctggcgta tcaaggccag gacaccccag aggtgctaat ggacataggg ctaaggcaag   1620
aggtgaccct ggagctgcag ggggacgggt ctgtgtccaa tctgacagtg tgtgtggcag   1680
cctacactgc tgctggggat ggaccctgga gcctcccagt acccctggag gcctggcgcc   1740
cagtgaagga accttcaact cctgccttct cgtggccctg gtggtatgta ctgctaggag   1800
cagtcgtggc cgctgcctgt gtcctcatct tggctctctt ccttgtccac cggcgaaaga   1860
aggagacccg ttatggagaa gtgtttgaac caacagtgga aagaggtgaa ctggtagtca   1920
ggtaccgcgt gcgcaagtcc tacagtcgtc ggaccactga agctaccttg aacagcctgg   1980
gcatcagtga agagctgaag gagaagctgc gggatgtgat ggtggaccgg cacaaggtgg   2040
ccctggggaa gactctggga gagggagagt ttggagctgt gatggaaggc cagctcaacc   2100
aggacgactc catcctcaag gtggctgtga agacgatgaa gattgccatc tgcacgaggt   2160
cagagctgga ggatttcctg agtgaagcgg tctgcatgaa ggaatttgac catcccaacg   2220
tcatgaggct catcggtgtc tgtttccagg gttctgaacg agagagcttc ccagcacctg   2280
tggtcatctt acctttcatg aaacatggag acctacacag cttcctcctc tattcccggc   2340
tcggggacca gccagtgtac ctgcccactc agatgctagt gaagttcatg gcagacatcg   2400
ccagtggcat ggagtatctg agtaccaaga gattcataca ccgggacctg gcggccagga   2460
actgcatgct gaatgagaac atgtccgtgt gtgtggcgga cttcgggctc tccaagaaga   2520
tctacaatgg ggactactac cgccagggac gtatcgccaa gatgccagtc aagtggattg   2580
```

-continued

```
ccattgagag tctagctgac cgtgtctaca ccagcaagag cgatgtgtgg tccttcgggg   2640
tgacaatgtg ggagattgcc acaagaggcc aaaccccata tccgggcgtg gagaacagcg   2700
agatttatga ctatctgcgc cagggaaatc gcctgaagca gcctgcggac tgtctggatg   2760
gactgtatgc cttgatgtcg cggtgctggg agctaaatcc ccaggaccgg ccaagtttta   2820
cagagctgcg ggaagatttg gagaacacac tgaaggcctt gcctcctgcc caggagcctg   2880
acgaaatcct ctatgtcaac atggatgagg gtggaggtta tcctgaaccc cctggagctg   2940
caggaggagc tgacccccca acccagccag accctaagga ttcctgtagc tgcctcactg   3000
cggctgaggt ccatcctgct ggacgctatg tcctctgccc ttccacaacc cctagccccg   3060
ctcagcctgc tgatagggc tccccagcag ccccagggca ggaggatggt gcctgagaca   3120
accctccacc tggtactccc tctcaggatc caagctaagc actgccactg gggaaaactc   3180
caccttccca ctttcccacc ccacgcctta tccccacttg cagccctgtc ttcctaccta   3240
tcccacctcc atcccagaca ggtccctccc cttctctgtg cagtagcatc accttgaaag   3300
cagtagcatc accatctgta aaaggaaggg gttggattgc aatatctgaa gccctcccag   3360
gtgttaacat tccaagactc tagagtccaa ggtttaaaga gtctagattc aaaggttcta   3420
ggtttcaaag atgctgtgag tctttggttc taaggacctg aaattccaaa gtctctaatt   3480
ctattaaagt gctaaggttc taaggcctac tttttttttt tttttttttt tttttttttt   3540
ttttgcgata gagtctcact gtgtcaccca ggctggagtg cagtggtgca atctcgcctc   3600
actgcaacct tcacctaccg agttcaagtg attttcctgc cttggcctcc caagtagctg   3660
ggattacagg tgtgtgccac cacacccggc taatttttat atttttagta gagacagggt   3720
ttcaccatgt tggccaggct ggtctaaaac tcctgacctc aagtgatctg cccacctcag   3780
cctcccaaag tgctgagatt acaggcatga gccactgcac tcaaccttaa gacctactgt   3840
tctaaagctc tgacattatg tggttttaga ttttctggtt ctaacatttt tgataaagcc   3900
tcaaggtttt aggttctaaa gttctaagat tctgatttta ggagctaagg ctctatgagt   3960
ctagatgttt attcttctag agttcagagt ccttaaaatg taagattata gattctaaag   4020
attctatagt tctagacatg gaggttctaa ggcctaggat tctaaaatgt gatgttctaa   4080
ggctctgaga gtctagattc tctggctgta aggctctaga tcataaggct tcaaaatgtt   4140
atcttctcaa gttctaagat tctaatgatg atcaattata gtttctgagg ctttatgata   4200
atagattctc ttgtataaga tcctagatcc taagggtcga aagctctaga atctgcaatt   4260
caaaagttcc aagagtctaa agatggagtt tctaaggtcc ggtgttctaa gatgtgatat   4320
tctaagactt actctaagat cttagattct ctgtgtctaa gattctagat cagatgctcc   4380
aagattctag atgattaaat aagattctaa cggtctgttc tgtttcaagg cactctagat   4440
tccattggtc caagattccg gatcctaagc atctaagtta taagactctc acactcagtt   4500
gtgactaact agacaccaaa gttctaataa tttctaatgt tggacacctt taggttcttt   4560
gctgcattct gcctctctag gaccatggtt aagagtccaa gaatccacat ttctaaaatc   4620
ttatagttct aggcactgta gttctaagac tcaaatgttc taagtttcta agattctaaa   4680
ggtccacagg tctagactat taggtgcaat ttcaaggttc taaccctata ctgtagtatt   4740
ctttggggtg cccctctcct tcttagctat cattgcttcc tcctccccaa ctgtgggggt   4800
gtgcccccctt caagcctgtg caatgcatta gggatgcctc ctttcccgca ggggatggac   4860
gatctcccac ctttcgggcc atgttgcccc cgtgagccaa tccctcacct tctgagtaca   4920
```

-continued

```
gagtgtggac tctggtgcct ccagaggggc tcaggtcaca taaaactttg tatatcaacg   4980

aaaaaaa                                                              4987


<210> SEQ ID NO 5
<211> LENGTH: 5014
<212> TYPE: DNA
<213> ORGANISM: Homo sapiens

<400> SEQUENCE: 5

gagtggagtt ctggaggaat gtttaccaga cacagagccc agagggacag cgcccagagc     60

ccagatagag agacacggcc tcactggctc agcaccaggg tccccttccc cctcctcagc    120

tccctccctg gcccctttaa gaaagagctg atcctctcct ctcttgagtt aacccctgat    180

tgtccaggtg gcccctggct ctggcctggt gggcggaggc aaagggggag ccaggggcgg    240

agaaagggtt gcccaagtct gggagtgagg gaaggaggca ggggtgctga gaaggcggct    300

gctgggcaga gccggtggca agggcctccc ctgccgctgt gccaggcagg cagtgccaaa    360

tccggggagc ctggagctgg ggggagggcc ggggacagcc cggccctgcc ccctccccg     420

ctgggagccc agcaacttct gaggaaagtt tggcacccat ggcgtggcgg tgccccagga    480

tgggcagggt cccgctggcc tggtgcttgg cgctgtgcgg ctgggcgtgc atggcccccca   540

ggggcacgca ggctgaagaa agtcccttcg tgggcaaccc agggaatatc acaggtgccc    600

ggggactcac gggcaccctt cggtgtcagc tccaggttca gggagagccc cccgaggtac    660

attggcttcg ggatggacag atcctggagc tcgcggacag cacccagacc caggtgcccc    720

tgggtgagga tgaacaggat gactggatag tggtcagcca gctcagaatc acctccctgc    780

agctttccga cacgggacag taccagtgtt tggtgtttct gggacatcag accttcgtgt    840

cccagcctgg ctatgttggg ctggagggct tgccttactt cctggaggag cccgaagaca    900

ggactgtggc cgccaacacc cccttcaacc tgagctgcca agctcaggga cccccagagc    960

ccgtggacct actctggctc caggatgctg tcccccctggc cacggctcca ggtcacggcc  1020

cccagcgcag cctgcatgtt ccagggctga acaagacatc ctctttctcc tgcgaagccc   1080

ataacgccaa gggggtcacc acatcccgca cagccaccat cacagtgctc ccccagcagc   1140

cccgtaacct ccacctggtc tcccgccaac ccacggagct ggaggtggct tggactccag   1200

gcctgagcgg catctacccc ctgacccact gcaccctgca ggctgtgctg tcagacgatg   1260

ggatgggcat ccaggcggga gaaccagacc ccccagagga gcccctcacc tcgcaagcat   1320

ccgtgccccc ccatcagctt cggctaggca gcctccatcc tcacacccct tatcacatcc   1380

gcgtggcatg caccagcagc cagggcccct catcctggac ccactggctt cctgtggaga   1440

cgccggaggg agtgcccctg ggcccccctg agaacattag tgctacgcgg aatgggagcc   1500

aggccttcgt gcattggcaa gagccccggg cgcccctgca gggtaccctg ttagggtacc   1560

ggctggcgta tcaaggccag gacaccccag aggtgctaat ggacataggg ctaaggcaag   1620

aggtgaccct ggagctgcag ggggacgggt ctgtgtccaa tctgacagtg tgtgtggcag   1680

cctacactgc tgctggggat ggaccctgga gcctcccagt acccctggag gcctggcgcc   1740

cagggcaagc acagccagtc caccagctgg tgaaggaacc ttcaactcct gccttctcgt   1800

ggccctggtg gtatgtactg ctaggagcag tcgtggccgc tgcctgtgtc ctcatcttgg   1860

ctctcttcct tgtccaccgg cgaaagaagg agacccgtta tggagaagtg tttgaaccaa   1920

cagtggaaag aggtgaactg gtagtcaggt accgcgtgcg caagtcctac agtcgtcgga   1980

ccactgaagc taccttgaac agcctgggca tcagtgaaga gctgaaggag aagctgcggg   2040
```

-continued

```
atgtgatggt ggaccggcac aaggtggccc tggggaagac tctgggagag ggagagtttg   2100
gagctgtgat ggaaggccag ctcaaccagg acgactccat cctcaaggtg gctgtgaaga   2160
cgatgaagat tgccatctgc acgaggtcag agctggagga tttcctgagt gaagcggtct   2220
gcatgaagga atttgaccat cccaacgtca tgaggctcat cggtgtctgt ttccagggtt   2280
ctgaacgaga gagcttccca gcacctgtgg tcatcttacc tttcatgaaa catggagacc   2340
tacacagctt cctcctctat tcccggctcg gggaccagcc agtgtacctg cccactcaga   2400
tgctagtgaa gttcatggca gacatcgcca gtggcatgga gtatctgagt accaagagat   2460
tcatacaccg ggacctggcg gccaggaact gcatgctgaa tgagaacatg tccgtgtgtg   2520
tggcggactt cgggctctcc aagaagatct acaatgggga ctactaccgc cagggacgta   2580
tcgccaagat gccagtcaag tggattgcca ttgagagtct agctgaccgt gtctacacca   2640
gcaagagcga tgtgtggtcc ttcggggtga caatgtggga gattgccaca agaggccaaa   2700
ccccatatcc gggcgtggag aacagcgaga tttatgacta tctgcgccag ggaaatcgcc   2760
tgaagcagcc tgcggactgt ctggatggac tgtatgcctt gatgtcgcgg tgctgggagc   2820
taaatcccca ggaccggcca agttttacag agctgcggga agatttggag aacacactga   2880
aggccttgcc tcctgcccag gagcctgacg aaatcctcta tgtcaacatg gatgagggtg   2940
gaggttatcc tgaaccccct ggagctgcag gaggagctga ccccccaacc cagccagacc   3000
ctaaggattc ctgtagctgc ctcactgcgg ctgaggtcca tcctgctgga cgctatgtcc   3060
tctgcccttc cacaacccct agccccgctc agcctgctga taggggctcc ccagcagccc   3120
cagggcagga ggatggtgcc tgagacaacc ctccacctgg tactccctct caggatccaa   3180
gctaagcact gccactgggg aaaactccac cttcccactt tcccacccca cgccttatcc   3240
ccacttgcag ccctgtcttc ctacctatcc cacctccatc ccagacaggt ccctcccctt   3300
ctctgtgcag tagcatcacc ttgaaagcag tagcatcacc atctgtaaaa ggaaggggtt   3360
ggattgcaat atctgaagcc ctcccaggtg ttaacattcc aagactctag agtccaaggt   3420
ttaaagagtc tagattcaaa ggttctaggt ttcaaagatg ctgtgagtct ttggttctaa   3480
ggacctgaaa ttccaaagtc tctaattcta ttaaagtgct aaggttctaa ggcctacttt   3540
tttttttttt tttttttttt tttttttttt tgcgatagag tctcactgtg tcacccaggc   3600
tggagtgcag tggtgcaatc tcgcctcact gcaaccttca cctaccgagt tcaagtgatt   3660
ttcctgcctt ggcctcccaa gtagctggga ttacaggtgt gtgccaccac acccggctaa   3720
tttttatatt tttagtagag acagggtttc accatgttgg ccaggctggt ctaaaactcc   3780
tgacctcaag tgatctgccc acctcagcct cccaaagtgc tgagattaca ggcatgagcc   3840
actgcactca accttaagac ctactgttct aaagctctga cattatgtgg ttttagattt   3900
tctggttcta acatttttga taaagcctca aggttttagg ttctaaagtt ctaagattct   3960
gattttagga gctaaggctc tatgagtcta gatgtttatt cttctagagt tcagagtcct   4020
taaaatgtaa gattatagat tctaaagatt ctatagttct agacatggag gttctaaggc   4080
ctaggattct aaaatgtgat gttctaaggc tctgagagtc tagattctct ggctgtaagg   4140
ctctagatca taaggcttca aaatgttatc ttctcaagtt ctaagattct aatgatgatc   4200
aattatagtt tctgaggctt tatgataata gattctcttg tataagatcc tagatcctaa   4260
gggtcgaaag ctctagaatc tgcaattcaa aagttccaag agtctaaaga tggagtttct   4320
aaggtccggt gttctaagat gtgatattct aagacttact ctaagatctt agattctctg   4380
```

-continued

```
tgtctaagat tctagatcag atgctccaag attctagatg attaaataag attctaacgg   4440

tctgttctgt ttcaaggcac tctagattcc attggtccaa gattccggat cctaagcatc   4500

taagttataa gactctcaca ctcagttgtg actaactaga caccaaagtt ctaataattt   4560

ctaatgttgg acacctttag gttctttgct gcattctgcc tctctaggac catggttaag   4620

agtccaagaa tccacatttc taaaatctta tagttctagg cactgtagtt ctaagactca   4680

aatgttctaa gtttctaaga ttctaaaggt ccacaggtct agactattag gtgcaatttc   4740

aaggttctaa ccctatactg tagtattctt tggggtgccc ctctccttct tagctatcat   4800

tgcttcctcc tccccaactg tgggggtgtg cccccttcaa gcctgtgcaa tgcattaggg   4860

atgcctcctt tcccgcaggg gatggacgat ctcccacctt tcgggccatg ttgcccccgt   4920

gagccaatcc ctcaccttct gagtacagag tgtggactct ggtgcctcca gaggggctca   4980

ggtcacataa aactttgtat atcaacgaaa aaaa                                5014
```

<210> SEQ ID NO 6
<211> LENGTH: 4093
<212> TYPE: DNA
<213> ORGANISM: Homo sapiens

<400> SEQUENCE: 6

```
cgcgcgctgc ctgaggacgc cgcggccccc gcccccgcca tgggcgcccc tgcctgcgcc     60

ctcgcgctct gcgtggccgt ggccatcgtg gccggcgcct cctcggagtc cttggggacg    120

gagcagcgcg tcgtggggcg agcggcagaa gtcccgggcc cagagcccgg ccagcaggag    180

cagttggtct tcggcagcgg ggatgctgtg gagctgagct gtcccccgcc cgggggtggt    240

cccatggggc ccactgtctg ggtcaaggat ggcacagggc tggtgccctc ggagcgtgtc    300

ctggtggggc cccagcggct gcaggtgctg aatgcctccc acgaggactc cggggcctac    360

agctgccggc agcggctcac gcagcgcgta ctgtgccact tcagtgtgcg ggtgacagac    420

gctccatcct cgggagatga cgaagacggg gaggacgagg ctgaggacac aggtgtggac    480

acaggggccc cttactggac acggcccgag cggatggaca agaagctgct ggccgtgccg    540

gccgccaaca ccgtccgctt ccgctgccca gccgctggca accccactcc ctccatctcc    600

tggctgaaga acggcaggga gttccgcggc gagcaccgca ttggaggcat caagctgcgg    660

catcagcagt ggagcctggt catggaaagc gtggtgccct cggaccgcgg caactacacc    720

tgcgtcgtgg agaacaagtt tggcagcatc cggcagacgt acacgctgga cgtgctggag    780

cgctccccgc accggcccat cctgcaggcg gggctgccgg ccaaccagac ggcggtgctg    840

ggcagcgacg tggagttcca ctgcaaggtg tacagtgacg cacagcccca catccagtgg    900

ctcaagcacg tggaggtgaa cggcagcaag gtgggcccgg acggcacacc ctacgttacc    960

gtgctcaaga cggcgggcgc taacaccacc gacaaggagc tagaggttct ctccttgcac   1020

aacgtcacct ttgaggacgc cggggagtac acctgcctgg cgggcaattc tattgggttt   1080

tctcatcact ctgcgtggct ggtggtgctg ccagccgagg aggagctggt ggaggctgac   1140

gaggcgggca gtgtgtatgc aggcatcctc agctacgggg tgggcttctt cctgttcatc   1200

ctggtggtgg cggctgtgac gctctgccgc ctgcgcagcc cccccaagaa aggcctgggc   1260

tcccccaccg tgcacaagat ctcccgcttc ccgctcaagc gacaggtgtc cctggagtcc   1320

aacgcgtcca tgagctccaa cacaccactg gtgcgcatcg caaggctgtc ctcaggggag   1380

ggccccacgc tggccaatgt ctccgagctc gagctgcctg ccgaccccaa atgggagctg   1440

tctcgggccc ggctgaccct gggcaagccc cttggggagg gctgcttcgg ccaggtggtc   1500
```

-continued

```
atggcggagg ccatcggcat tgacaaggac cgggccgcca agcctgtcac cgtagccgtg   1560
aagatgctga aagacgatgc cactgacaag gacctgtcgg acctggtgtc tgagatggag   1620
atgatgaaga tgatcgggaa acacaaaaac atcatcaacc tgctgggcgc ctgcacgcag   1680
ggcgggcccc tgtacgtgct ggtggagtac gcggccaagg gtaacctgcg ggagtttctg   1740
cgggcgcggc ggcccccggg cctggactac tccttcgaca cctgcaagcc gcccgaggag   1800
cagctcacct tcaaggacct ggtgtcctgt gcctaccagg tggcccgggg catggagtac   1860
ttggcctccc agaagtgcat ccacagggac ctggctgccc gcaatgtgct ggtgaccgag   1920
gacaacgtga tgaagatcgc agacttcggg ctggcccggg acgtgcacaa cctcgactac   1980
tacaagaaga caaccaacgg ccggctgccc gtgaagtgga tggcgcctga ggccttgttt   2040
gaccgagtct acactcacca gagtgacgtc tggtcctttg gggtcctgct ctgggagatc   2100
ttcacgctgg ggggctcccc gtaccccggc atccctgtgg aggagctctt caagctgctg   2160
aaggagggcc accgcatgga caagcccgcc aactgcacac acgacctgta catgatcatg   2220
cgggagtgct ggcatgccgc gccctcccag aggcccacct tcaagcagct ggtggaggac   2280
ctggaccgtg tccttaccgt gacgtccacc gacgagtacc tggacctgtc ggcgcctttc   2340
gagcagtact ccccgggtgg ccaggacacc cccagctcca gctcctcagg ggacgactcc   2400
gtgtttgccc acgacctgct gcccccggcc ccacccagca gtgggggctc gcggacgtga   2460
agggccactg gtccccaaca atgtgagggg tccctagcag ccctccctgc tgctggtgca   2520
cagccactcc ccggcatgag actcagtgca gatggagaga cagctacaca gagctttggt   2580
ctgtgtgtgt gtgtgtgcgt gtgtgtgtgt gtgtgcacat ccgcgtgtgc ctgtgtgcgt   2640
gcgcatcttg cctccaggtg cagaggtacc ctgggtgtcc ccgctgctgt gcaacggtct   2700
cctgactggt gctgcagcac cgaggggcct ttgttctggg gggacccagt gcagaatgta   2760
agtgggccca cccggtggga ccccgtgggg cagggagctg ggcccgacat ggctcggcct   2820
ctgcctttgc accacgggac atcacagggt gcgctcggcc cctcccacac ccaaagctga   2880
gcctgcaggg aagccccaca tgtccagcac cttgtgcctg gggtgttagt ggcaccgcct   2940
ccccacctcc aggctttccc acttcccacc ctgcccctca gagactgaaa ttacgggtac   3000
ctgaagatgg gagcctttac cttttatgca aaaggtttat tccggaaact agtgtacatt   3060
tctataaata gatgctgtgt atatggtata tatacatata tatatataac atatatggaa   3120
gaggaaaagg ctggtacaac ggaggcctgc gaccctgggg gcacaggagg caggcatggc   3180
cctgggcggg gcgtgggggg gcgtggaggg aggccccagg ggtctcaccc atgcaagcag   3240
aggaccaggg ctttttctgg caccgcagtt ttgttttaaa actggacctg tatatttgta   3300
aagctattta tgggcccctg gcactcttgt tcccacaccc caacacttcc agcatttagc   3360
tggccacatg gcggagagtt ttaattttta acttattgac aaccgagaag gtttatcccg   3420
ccgatagagg gacggccaag aatgtacgtc cagcctgccc cggagctgga ggatcccctc   3480
caagcctaaa aggttgttaa tagttggagg tgattccagt gaagatattt tatttgcttt   3540
gtcctttttc aggagaatta gatttctata ggatttttct ttaggagatt tattttttgg   3600
acttcaaagc aagctggtat tttcatacaa attcttctaa ttgctgtgtg tcccaggcag   3660
ggagacggtt tccagggagg ggccggccct gtgtgcaggt tccgatgtta ttagatgtta   3720
caagtttata tatatctata tatataattt attgagtttt tacaagatgt atttgttgta   3780
gacttaacac ttcttacgca atgcttctag agttttatag cctggactgc tacctttcaa   3840
```

-continued

```
agcttggagg gaagccgtga attcagttgg ttcgttctgt actgttactg ggccctgagt   3900

ctgggcagct gtcccttgct tgcctgcagg gccatggctc agggtggtct cttcttgggg   3960

cccagtgcat ggtggccaga ggtgtcaccc aaaccggcag gtgcgatttt gttaacccag   4020

cgacgaactt tccgaaaaat aaagacacct ggttgctaac ctgaaaaaaa aaaaaaaaaa   4080

aaaaaaaaaa aaa                                                      4093


<210> SEQ ID NO 7
<211> LENGTH: 1804
<212> TYPE: DNA
<213> ORGANISM: Homo sapiens

<400> SEQUENCE: 7

gtgcagcccg tgccccccgc gcgccggggc cgaatgcgcg ccgcgtaggg tcccccgggc     60

cgagaggggt gcccggaggg aagagcgcgg tgggggcgcc ccggccccgc tgccctgggg    120

ctatggccat ggtgaccggc ggctggggcg gccccggcgg cgacacgaac ggcgtggaca    180

aggcgggcgg ctacccgcgc gcggccgagg acgactcggc ctcgcccccc ggtgccgcca    240

gcgacgccga gccgggcgac gaggagcggc cggggctgca ggtggactgc gtggtgtgcg    300

gggacaagtc gagcggcaag cattacggtg tcttcacctg cgagggctgc aagagctttt    360

tcaagcgaag catccgccgc aacctcagct acacctgccg gtccaaccgt gactgccaga    420

tcgaccagca ccaccggaac cagtgccagt actgccgtct caagaagtgc ttccgggtgg    480

gcatgaggaa ggaggcggtg cagcgcggcc gcatcccgca ctcgctgcct ggtgccgtgg    540

ccgcctcctc gggcagcccc ccgggctcgg cgctggcggc agtggcgagc ggcggagacc    600

tcttcccggg gcagccggtg tccgaactga tcgcgcagct gctgcgcgct gagccctacc    660

ctgcggcggc cggacgcttc ggcgcagggg gcggcgcggc gggcgcggtg ctgggcatcg    720

acaacgtgtg cgagctggcg gcgcggctgc tcttcagcac cgtggagtgg gcgcgccacg    780

cgcccttctt ccccgagctg ccggtggccg accaggtggc gctgctgcgc ctgagctgga    840

gcgagctctt cgtgctgaac gcggcgcagg cggcgctgcc cctgcacacg gcgccgctac    900

tggccgccgc cggcctccac gccgcgccta tggccgccga gcgcgccgtg gctttcatgg    960

accaggtgcg cgccttccag gagcaggtgg acaagctggg ccgcctgcag gtcgactcgg   1020

ccgagtatgg ctgcctcaag gccatcgcgc tcttcacgcc cgacgcctgt ggcctctcag   1080

acccggccca cgttgagagc ctgcaggaga aggcgcaggt ggccctcacc gagtatgtgc   1140

gggcgcagta cccgtcccag ccccagcgct tcgggcgcct gctgctgcgg ctccccgccc   1200

tgcgcgcggt ccctgcctcc ctcatctccc agctgttctt catgcgcctg gtggggaaga   1260

cgcccattga gacactgatc agagacatgc tgctgtcggg gagtaccttc aactggccct   1320

acggctcggg ccagtgacca tgacggggcc acgtgtgctg tggccaggcc tgcagacaga   1380

cctcaaggga cagggaatgc tgaggcctcg aggggcctcc cggggcccag gactctggct   1440

tctctcctca gacttctatt ttttaaagac tgtgaaatgt ttgtcttttc tgttttttaa   1500

atgatcatga aaccaaaaag agactgatca tccaggcctc agcctcatcc tccccaggac   1560

ccctgtccag gatggagggt ccaatcctag gacagccttg ttcctcagca cccctagcat   1620

gaacttgtgg gatggtgggg ttggcttccc tggcatgatg gacaaaggcc tggcgtcggc   1680

cagaggggct gctccagtgg gcaggggtag ctagcgtgtg ccaggcagat cctctggaca   1740

cgtaacctat gtcagacact acatgatgac tcaaggccaa taataaagac atttcctacc   1800

tgca                                                                1804
```

-continued

<210> SEQ ID NO 8
<211> LENGTH: 6371
<212> TYPE: DNA
<213> ORGANISM: Homo sapiens

<400> SEQUENCE: 8
ctcttatgtg aggagctgaa gaggaattaa aatatacagg atgaaaagat ggcaatgttg 60
cctcccccag gacctcagag ctttgtccat ttcacaaaac agtctcttgc cctcattgaa 120
caacgcattg ctgaaagaaa atcaaaggaa cccaaagaag aaaagaaaga tgatgatgaa 180
gaagccccaa agccaagcag tgacttggaa gctggcaaac aactgccctt catctatggg 240
gacattcctc ccggcatggt gtcagagccc ctggaggact tggaccccta ctatgcagac 300
aaaaagactt tcatagtatt gaacaaaggg aaaacaatct tccgtttcaa tgccacacct 360
gctttatata tgctttctcc tttcagtcct ctaagaagaa tatctattaa gattttagta 420
cactccttat tcagcatgct catcatgtgc actattctga caaactgcat atttatgacc 480
atgaataacc cgccggactg gaccaaaaat gtcgagtaca cttttactgg aatatatact 540
tttgaatcac ttgtaaaaat ccttgcaaga ggcttctgtg taggagaatt cacttttctt 600
cgtgacccgt ggaactggct ggattttgtc gtcattgttt ttgcgtattt aacagaattt 660
gtaaacctag gcaatgtttc agctcttcga actttcagag tattgagagc tttgaaaact 720
atttctgtaa tcccaggcct gaagacaatt gtaggggctt tgatccagtc agtgaagaag 780
ctttctgatg tcatgatcct gactgtgttc tgtctgagtg tgtttgcact aattggacta 840
cagctgttca tgggaaacct gaagcataaa tgttttcgaa attcacttga aaataatgaa 900
acattagaaa gcataatgaa taccctagag agtgaagaag actttagaaa atatttttat 960
tacttggaag gatccaaaga tgctctcctt tgtggtttca gcacagattc aggtcagtgt 1020
ccagaggggt acacctgtgt gaaaattggc agaaaccctg attatggcta cacgagcttt 1080
gacactttca gctgggcctt cttagccttg tttaggctaa tgacccaaga ttactgggaa 1140
aacctttacc aacagacgct gcgtgctgct ggcaaaacct acatgatctt ctttgtcgta 1200
gtgattttcc tgggctcctt ttatctaata aacttgatcc tggctgtggt tgccatggca 1260
tatgaagaac agaaccaggc aaacattgaa gaagctaaac agaaagaatt agaatttcaa 1320
cagatgttag accgtcttaa aaaagagcaa gaagaagctg aggcaattgc agcggcagcg 1380
gctgaatata caagtattag gagaagcaga attatgggcc tctcagagag ttcttctgaa 1440
acatccaaac tgagctctaa aagtgctaaa gaaagaagaa acagaagaaa gaaaaagaat 1500
caaaagaagc tctccagtgg agaggaaaag ggagatgctg agaaattgtc gaaatcagaa 1560
tcagaggaca gcatcagaag aaaaagtttc caccttggtg tcgaagggca taggcgagca 1620
catgaaaaga ggttgtctac ccccaatcag tcaccactca gcattcgtgg ctccttgttt 1680
tctgcaaggc gaagcagcag aacaagtctt tttagtttca aaggcagagg aagagatata 1740
ggatctgaga ctgaatttgc cgatgatgag cacagcattt ttggagacaa tgagagcaga 1800
aggggctcac tgtttgtgcc ccacagaccc caggagcgac gcagcagtaa catcagccaa 1860
gccagtaggt ccccaccaat gctgccggtg aacgggaaaa tgcacagtgc tgtggactgc 1920
aacggtgtgg tctccctggt tgatggacgc tcagccctca tgctccccaa tggacagctt 1980
ctgccagagg gcacgaccaa tcaaatacac aagaaaaggc gttgtagttc ctatctcctt 2040
tcagaggata tgctgaatga tcccaacctc agacagagag caatgagtag agcaagcata 2100

-continued

```
ttaacaaaca ctgtggaaga acttgaagag tccagacaaa aatgtccacc ttggtggtac   2160
agatttgcac acaaattctt gatctggaat tgctctccat attggataaa attcaaaaag   2220
tgtatctatt ttattgtaat ggatcctttt gtagatcttg caattaccat ttgcatagtt   2280
ttaaacacat tatttatggc tatggaacac cacccaatga ctgaggaatt caaaaatgta   2340
cttgctatag gaaatttggt ctttactgga atctttgcag ctgaaatggt attaaaactg   2400
attgccatgg atccatatga gtatttccaa gtaggctgga atatttttga cagccttatt   2460
gtgactttaa gtttagtgga gctctttcta gcagatgtgg aaggattgtc agttctgcga   2520
tcattcagac tgctccgagt cttcaagttg gcaaaatcct ggccaacatt gaacatgctg   2580
attaagatca ttggtaactc agtaggggct ctaggtaacc tcaccttagt gttggccatc   2640
atcgtcttca tttttgctgt ggtcggcatg cagctctttg gtaagagcta caaagaatgt   2700
gtctgcaaga tcaatgatga ctgtacgctc ccacggtggc acatgaacga cttcttccac   2760
tccttcctga ttgtgttccg cgtgctgtgt ggagagtgga tagagaccat gtgggactgt   2820
atggaggtcg ctggtcaagc tatgtgcctt attgtttaca tgatggtcat ggtcattgga   2880
aacctggtgg tcctaaacct atttctggcc ttattattga gctcatttag ttcagacaat   2940
cttacagcaa ttgaagaaga ccctgatgca aacaacctcc agattgcagt gactagaatt   3000
aaaaagggaa taaattatgt gaaacaaacc ttacgtgaat ttattctaaa agcattttcc   3060
aaaaagccaa agatttccag ggagataaga caagcagaag atctgaatac taagaaggaa   3120
aactatattt ctaaccatac acttgctgaa atgagcaaag gtcacaattt cctcaaggaa   3180
aaagataaaa tcagtggttt tggaagcagc gtggacaaac acttgatgga agacagtgat   3240
ggtcaatcat ttattcacaa tcccagcctc acagtgacag tgccaattgc acctggggaa   3300
tccgatttgg aaaatatgaa tgctgaggaa cttagcagtg attcggatag tgaatacagc   3360
aaagtgagat taaaccggtc aagctcctca gagtgcagca cagttgataa ccctttgcct   3420
ggagaaggag aagaagcaga ggctgaacct atgaattccg atgagccaga ggcctgtttc   3480
acagatggtt gtgtacggag gttctcatgc tgccaagtta acatagagtc agggaaagga   3540
aaaatctggt ggaacatcag gaaaacctgc tacaagattg ttgaacacag ttggtttgaa   3600
agcttcattg tcctcatgat cctgctcagc agtggtgccc tggcttttga agatatttat   3660
attgaaagga aaaagaccat taagattatc ctggagtatg cagacaagat cttcacttac   3720
atcttcattc tggaaatgct tctaaaatgg atagcatatg gttataaaac atatttcacc   3780
aatgcctggt gttggctgga tttcctaatt gttgatgttt ctttggttac tttagtggca   3840
aacactcttg gctactcaga tcttggcccc attaaatccc ttcggacact gagagcttta   3900
agacctctaa gagccttatc tagatttgaa ggaatgaggg tcgttgtgaa tgcactcata   3960
ggagcaattc cttccatcat gaatgtgcta cttgtgtgtc ttatattctg gctgatattc   4020
agcatcatgg gagtaaattt gtttgctggc aagttctatg agtgtattaa caccacagat   4080
gggtcacggt ttcctgcaag tcaagttcca aatcgttccg aatgttttgc ccttatgaat   4140
gttagtcaaa atgtgcgatg gaaaaacctg aaagtgaact ttgataatgt cggacttggt   4200
tacctatctc tgcttcaagt tgcaactttt aagggatgga cgattattat gtatgcagca   4260
gtggattctg ttaatgtaga caagcagccc aaatatgaat atagcctcta catgtatatt   4320
tattttgtcg tctttatcat ctttgggtca ttcttcactt tgaacttgtt cattggtgtc   4380
atcatagata atttcaacca acagaaaaag aagcttggag gtcaagacat ctttatgaca   4440
gaagaacaga agaaatacta taatgcaatg aaaaagctgg ggtccaagaa gccacaaaag   4500
```

-continued ccaattcctc gaccagggaa caaaatccaa ggatgtatat ttgacctagt gacaaatcaa 4560
gcctttgata ttagtatcat ggttcttatc tgtctcaaca tggtaaccat gatggtagaa 4620
aaggagggtc aaagtcaaca tatgactgaa gttttatatt ggataaatgt ggtttttata 4680
atccttttca ctggagaatg tgtgctaaaa ctgatctccc tcagacacta ctacttcact 4740
gtaggatgga atatttttga ttttgtggtt gtgattatct ccattgtagg tatgtttcta 4800
gctgatttga ttgaaacgta ttttgtgtcc cctaccctgt tccgagtgat ccgtcttgcc 4860
aggattggcc gaatcctacg tctagtcaaa ggagcaaagg ggatccgcac gctgctcttt 4920
gctttgatga tgtcccttcc tgcgttgttt aacatcggcc tcctgctctt cctggtcatg 4980
ttcatctacg ccatctttgg aatgtccaac tttgcctatg ttaaaaagga agatggaatt 5040
aatgacatgt tcaattttga gacctttggc aacagtatga tttgcctgtt ccaaattaca 5100
acctctgctg gctgggatgg attgctagca cctattctta acagtaagcc acccgactgt 5160
gacccaaaaa aagttcatcc tggaagttca gttgaaggag actgtggtaa cccatctgtt 5220
ggaatattct actttgttag ttatatcatc atatccttcc tggttgtggt gaacatgtac 5280
attgcagtca tactggagaa ttttagtgtt gccactgaag aaagtactga acctctgagt 5340
gaggatgact ttgagatgtt ctatgaggtt tgggagaagt ttgatcccga tgcgacccag 5400
tttatagagt tctctaaact ctctgatttt gcagctgccc tggatcctcc tcttctcata 5460
gcaaaaccca acaaagtcca gctcattgcc atggatctgc ccatggttag tggtgaccgg 5520
atccattgtc ttgacatctt atttgctttt acaaagcgtg ttttgggtga gagtggggag 5580
atggattctc ttcgttcaca gatggaagaa aggttcatgt ctgcaaatcc ttccaaagtg 5640
tcctatgaac ccatcacaac cacactaaaa cggaaacaag aggatgtgtc tgctactgtc 5700
attcagcgtg cttatagacg ttaccgctta aggcaaaatg tcaaaaatat atcaagtata 5760
tacataaaag atggagacag agatgatgat ttactcaata aaaaagatat ggcttttgat 5820
aatgttaatg agaactcaag tccagaaaaa acagatgcca cttcatccac cacctctcca 5880
ccttcatatg atagtgtaac aaagccagac aaagagaaat atgaacaaga cagaacagaa 5940
aaggaagaca aagggaaaga cagcaaggaa agcaaaaaat agagcttcat ttttgatata 6000
ttgtttacag cctgtgaaag tgatttattt gtgttaataa aactcttttg aggaagtcta 6060
tgccaaaatc ctttttatca aaatattctc gaaggcagtg cagtcactaa ctctgatttc 6120
ctaagaaagg tgggcagcat tagcagatgg ttatttttgc actgatgatt ctttaagaat 6180
cgtaagagaa ctctgtagga attattgatt atagcataca aaagtgattg attcagtttt 6240
ttggttttta ataaatcaga agaccatgta gaaaactttt acatctgcct tgtcatcttt 6300
tcacaggatt gtaattagtc ttgtttccca tgtaaataaa caacacacgc atacagaaaa 6360
aaaaaaaaaa a 6371

<210> SEQ ID NO 9
<211> LENGTH: 1888
<212> TYPE: DNA
<213> ORGANISM: Homo sapiens

<400> SEQUENCE: 9
gcggcgcggg gcgggcgcag cgggggtcgg ggcgctggga gcccgttggg ccgcgaacgc 60
agccgccacg ccggggccgc cgagatcggg tgcccgggat gagcctcatc cggaaaaagg 120
gcttctacaa gcaggacgtc aacaagaccg cctgggagct gcccaagacc tacgtgtccc 180

-continued cgacgcacgt cggcagcggg gcctatggct ccgtgtgctc ggccatcgac aagcggtcag 240
gggagaaggt ggccatcaag aagctgagcc gaccctttca gtccgagatc ttcgccaagc 300
gcgcctaccg ggagctgctg ctgctgaagc acatgcagca tgagaacgtc attgggctcc 360
tggatgtctt caccccagcc tcctccctgc gcaacttcta tgacttctac ctggtgatgc 420
ccttcatgca gacggatctg cagaagatca tggggatgga gttcagtgag gagaagatcc 480
agtacctggt gtatcagatg ctcaaaggcc ttaagtacat ccactctgct ggggtcgtgc 540
acagggacct gaagccaggc aacctggctg tgaatgagga ctgtgaactg aagattctgg 600
attttgggct ggcgcgacat gcagacgccg agatgactgg ctacgtggtg acccgctggt 660
accgagcccc cgaggtgatc ctcagctgga tgcactacaa ccagacagtg gacatctggt 720
ctgtgggctg tatcatggca gagatgctga cagggaaaac tctgttcaag ggaaaagatt 780
acctggacca gctgacccag atcctgaaag tgaccggggt gcctggcacg gagtttgtgc 840
agaagctgaa cgacaaagcg gccaaatcct acatccagtc cctgccacag acccccagga 900
aggatttcac tcagctgttc ccacgggcca gcccccaggc tgcggacctg ctggagaaga 960
tgctggagct agacgtggac aagcgcctga cggccgcgca ggccctcacc catcccttct 1020
ttgaaccctt ccgggaccct gaggaagaga cggaggccca gcagccgttt gatgattcct 1080
tagaacacga gaaactcaca gtggatgaat ggaagcagca catctacaag gagattgtga 1140
acttcagccc cattgcccgg aaggactcac ggcgccggag tggcatgaag ctgtagggac 1200
tcatcttgca tggcaccacc ggccagacac tgcccaagga ccagtatttg tcactaccaa 1260
actcagccct tcttggaata cagcctttca agcagaggac agaagggtcc ttctccttat 1320
gtgggaaatg ggcctagtag atgcagaatt caaagatgtc ggttgggaga aactagctct 1380
gatcctaaca ggccacgtta aactgcccat ctggagaatc gcctgcaggt ggggcccttt 1440
ccttcccgcc agagtggggc tgagtgggcg ctgagccagg ccgggggcct atggcagtga 1500
tgctgtgttg gtttcctagg gatgctctaa cgaattacca caaacctggt ggattgaaac 1560
agcagaactt gattccctta cagttctgga ggctggaaat ctgggatgga ggtgttggca 1620
gggctgtggt ccctttgaag gctctgggga agaatccttc cttggctctt tttagcttgt 1680
ggcggcagtg ggcagtccgt ggcattcccc agcttattgc tgcatcactc cagtctctgt 1740
ctcttctgtt ctctcctctt ttaacaacag tcattggatt tagggcccac cctaatcctg 1800
tgtgatctta tcttgatcct tattaattaa acctgcaaat actctagttc caaataaagt 1860
cacattctca ggttccaggt ggacatga 1888

<210> SEQ ID NO 10
<211> LENGTH: 1817
<212> TYPE: DNA
<213> ORGANISM: Homo sapiens

<400> SEQUENCE: 10
agcgccacgg gcggggcggg gccggcggcg ggctgcgggc gcggccggac gggagttccc 60
cggagaagga tcctgcagcc cgagtcccga ggataaagct tggggttcat cctccttccc 120
tggatcactc cacagtcctc aggcttcccc aatccagggg actcggcgcc gggacgctgc 180
tatggacgac attttcactc agtgccggga gggcaacgca gtcgccgttc gcctgtggct 240
ggacaacacg gagaacgacc tcaaccaggg ggacgatcat ggcttctccc ccttgcactg 300
ggcctgccga gagggccgct ctgctgtggt tgagatgttg atcatgcggg gggcacggat 360
caatgtaatg aaccgtgggg atgacacccc cctgcatctg gcagccagtc atggacaccg 420

-continued

```
tgatattgta cagaagctat tgcagtacaa ggcagacatc aatgcagtga atgaacacgg    480

gaatgtgccc ctgcactatg cctgtttttg gggccaagat caagtggcag aggacctggt    540

ggcaaatggg gcccttgtca gcatctgtaa caagtatgga gagatgcctg tggacaaagc    600

caaggcaccc ctgagagagc ttctccgaga gcgggcagag aagatgggcc agaatctcaa    660

ccgtattcca tacaaggaca cattctggaa ggggaccacc cgcactcggc cccgaaatgg    720

aaccctgaac aaacactctg gcattgactt caaacagctt aacttcctga cgaagctcaa    780

cgagaatcac tctggagagc tatggaaggg ccgctggcag ggcaatgaca ttgtcgtgaa    840

ggtgctgaag gttcgagact ggagtacaag gaagagcagg gacttcaatg aagagtgtcc    900

ccggctcagg attttctcgc atccaaatgt gctcccagtg ctaggtgcct gccagtctcc    960

acctgctcct catcctactc tcatcacaca ctggatgccg tatggatccc tctacaatgt   1020

actacatgaa ggcaccaatt tcgtcgtgga ccagagccag gctgtgaagt ttgctttgga   1080

catggcaagg ggcatggcct tcctacacac actagagccc ctcatcccac gacatgcact   1140

caatagccgt agtgtaatga ttgatgagga catgactgcc cgaattagca tggctgatgt   1200

caagttctct ttccaatgtc ctggtcgcat gtatgcacct gcctgggtag cccccgaagc   1260

tctgcagaag aagcctgaag acacaaacag acgctcagca gacatgtgga gttttgcagt   1320

gcttctgtgg gaactggtga cacgggaggt accctttgct gacctctcca atatggagat   1380

tggaatgaag gtggcattgg aaggccttcg gcctaccatc ccaccaggta tttcccctca   1440

tgtgtgtaag ctcatgaaga tctgcatgaa tgaagaccct gcaaagcgac ccaaatttga   1500

catgattgtg cctatccttg agaagatgca ggacaagtag gactggaagg tccttgcctg   1560

aactccagag gtgtcgggac atggttgggg gaatgcacct ccccaaagca gcaggcctct   1620

ggttgcctcc cccgcctcca gtcatggtac taccccagcc atggggtcca tccccttccc   1680

ccatccctac cactgtggcc ccaagagggg cgggctcaga gctttgtcac ttgccacatg   1740

gtgtctccca acatgggagg gatcagcccc gcctgtcaca ataaagttta ttatgaaaaa   1800

aaaaaaaaaa aaaaaaa                                                  1817
```

<210> SEQ ID NO 11
<211> LENGTH: 1679
<212> TYPE: DNA
<213> ORGANISM: Homo sapiens

<400> SEQUENCE: 11

```
gggagctgtg gcgcggagcg gcccctctgc tgcgtctgcc ctcgttttgt ctcacgactc     60

acactcagtg ctccattccc caagagttcg cgttccccgc gcggcggtcg agaggcggct    120

gcccgcggtc ccgcgcgggc gcggggcgat ggcggcgcgg gggtcagggc cccgcgcgct    180

ccgcctgctg ctcttggtcc agctggtcgc gggggcgctg cggtctagcc gggcgcggcg    240

ggcggcgcgc agaggattat ctgaaccttc ttctattgca aaacatgaag atagtttgct    300

taaggattta tttcaagact acgaaagatg ggttcgtcct gtggaacacc tgaatgacaa    360

aataaaaata aaatttggac ttgcaatatc tcaattggtg gatgtggatg agaaaaatca    420

gttaatgaca acaaacgtct ggttgaaaca ggaatggata gatgtaaaat taagatggaa    480

ccctgatgac tatggtggaa taaaagttat acgtgttcct tcagactctt cgtggacacc    540

agacatcgtt ttgtttgata atgcagatgg acgttttgaa gggaccagta cgaaaacagt    600

catcaggtac aatggcactg tcacctggac tccaccggca aactacaaaa gttcctgtac    660
```

-continued

```
catagatgtc acgtttttcc catttgacct tcagaactgt tccatgaaat ttggttcttg    720

gacttatgat ggatcacagg ttgatataat tctagaggac caagatgtag acaagagaga    780

tttttttgat aatggagaat gggagattgt gagtgcaaca gggagcaaag gaaacagaac    840

cgacagctgt tgctggtatc cgtatgtcac ttactcattt gtaatcaagc gcctgcctct    900

cttttatacc ttgttcctta taataccctg tattgggctc tcatttttaa ctgtacttgt    960

cttctatctt ccttcaaatg aaggtgaaaa gatttgtctc tgcacttcag tacttgtgtc   1020

tttgactgtc ttccttctgg ttattgaaga gatcatacca tcatcttcaa aagtcatacc   1080

tctaattgga gagtatctgg tatttaccat gatttttgtg acactgtcaa ttatggtaac   1140

cgtcttcgct atcaacattc atcatcgttc ttcctcaaca cataatgcca tggcgccttt   1200

ggtccgcaag atatttcttc acacgcttcc caaactgctt tcgatgagaa gtcatgtaga   1260

caggtacttc actcagaaag aggaaactga gagtggtagt ggaccaaaat cttctagaaa   1320

cacattggaa gctgcgctcg attctattcg ctacattaca acacacatca tgaaggaaaa   1380

tgatgtccgt gaggttgttg aagattggaa attcatagcc caggttcttg atcggatgtt   1440

tctgtggact tttcttttcg tttcaattgt tggatctctt gggcttttttg ttcctgttat   1500

ttataaatgg gcaaatatat taataccagt tcatattgga aatgcaaata agtgaagcct   1560

cccaagggac tgaagtatac atttagttaa cacacatata tctgatggca cctataaaat   1620

tatgaaaatg taagttatgt gttaaattta gtgcaagctt taacagacta agttgctaa    1679
```

<210> SEQ ID NO 12
<211> LENGTH: 976
<212> TYPE: DNA
<213> ORGANISM: Homo sapiens

<400> SEQUENCE: 12

```
cccggaacct ggcgcaactc ctagagcggt ccttggggag acgcgggtcc cagtcctgcg     60

gctcctactg gggagtgcgc tggtcggaag attgctggac tcgctgaaga gagactacgc    120

aggaaagccc cagccaccca tcaaatcaga gagaaggaat ccaccttctt acgctatggc    180

aggtaagaaa gtactcattg tctatgcaca ccaggaaccc aagtctttca acggatcctt    240

gaagaatgtg gctgtagatg aactgagcag gcagggctgc accgtcacag tgtctgattt    300

gtatgccatg aactttgagc cgagggccac agacaaagat atcactggta ctctttctaa    360

tcctgaggtt ttcaattatg gagtggaaac ccacgaagcc tacaagcaaa ggtctctggc    420

tagcgacatc actgatgagc agaaaaaggt tcgggaggct gacctagtga tatttcagtt    480

cccgctgtac tggttcagcg tgccggccat cctgaagggc tggatggata gggtgctgtg    540

ccagggcttt gcctttgaca tcccaggatt ctacgattcc ggtttgctcc agggtaaact    600

agcgctcctt tccgtaacca cgggaggcac ggccgagatg tacacgaaga caggagtcaa    660

tggagattct cgatacttcc tgtggccact ccagcatggc acattacact tctgtggatt    720

taaagtcctt gcccctcaga tcagctttgc tcctgaaatt gcatccgaag aagaaagaaa    780

ggggatggtg gctgcgtggt cccagaggct gcagaccatc tggaaggaag agcccatccc    840

ctgcacagcc cactggcact tcgggcaata actctgtggc acgtgggcat cacgtaagca    900

gcacactagg aggcccaggc gcaggcaaag agaagatggt gctgtcatga aataaaatta    960

caacatagct acctgg                                                    976
```

<210> SEQ ID NO 13
<211> LENGTH: 3172

-continued

<212> TYPE: DNA
<213> ORGANISM: Homo sapiens

<400> SEQUENCE: 13

```
atgacaaacc aggaaaaatg ggcccacctc agcccttcgg aattttccca acttcagaaa     60
tatgctgagt attctacaaa gaaattaaag gatgttcttg aagaattcca tggtaatggt    120
gtgcttgcaa agtataatcc tgaagggaaa caagacattc ttaaccaaac aatagatttt    180
gaaggtttca aactattcat gaagacattc ctggaagccg agcttcctga tgatttcact    240
gcacaccttt tcatgtcatt tagcaacaag tttcctcatt ctagtccaat ggtaaaaagt    300
aagcctgctc tcctatcagg cggtctgaga atgaataaag gtgccatcac ccctccccga    360
actacttctc ctgcaaatac gtgttcccca gaagtaatcc atctgaagga cattgtctgt    420
tacctgtctc tgcttgaaag aggaagacct gaggataagc ttgagtttat gtttcgcctt    480
tatgacacgg atgggaatgg cttcctggac agctcggagc tagaaaatat catcagtcag    540
atgatgcatg ttgcagaata ccttgagtgg gatgtcactg aacttaatcc aatcctccat    600
gaaatgatgg aagaaattga ctatgatcat gatggaaccg tgtctctgga ggaatggatt    660
caaggaggaa tgacaacgat tccacttctt gtgctcctgg gcttagaaaa taacgtgaag    720
gatgatggac agcacgtgtg gcgactgaag cactttaaca aacctgccta ttgcaacctt    780
tgcctgaaca tgctgattgg cgtggggaag cagggcctct gctgttcctt ctgcaagtac    840
acagtccatg agcgctgtgt ggctcgagca cctccctctt gcatcaagac ctatgtgaag    900
tccaaaagga acactgatgt catgcaccat tactgggttg aaggtaactg cccaaccaag    960
tgtgataagt gccacaaaac tgttaaatgt taccagggcc tgacaggact gcattgtgtt   1020
tggtgtcaga tcacactgca taataaatgt gcttctcatc taaaacctga atgtgactgt   1080
ggacctttga aggaccatat tttaccaccc acaacaatct gtccagtggt actgcagact   1140
ctgcccactt caggagtttc agttcctgag gaaagacaat caacagtgaa aaaggaaaag   1200
agtggttccc agcagccaaa caaagtgatt gacaagaata aaatgcaaag agccaactct   1260
gttactgtag atggacaagg cctgcaggtc actcctgtgc ctggtactca cccactttta   1320
gtttttgtga accccaaaag tggtggaaaa caaggagaac gaatttacag aaaattccag   1380
tatctattaa atcctcgtca ggtttacagt ctttctggaa atggaccaat gccagggtta   1440
aactttttcc gtgatgttcc tgacttcaga gtgttagcct gtggtggaga tggaaccgtg   1500
ggctgggttt tggattgcat agaaaaggcc aatgtaggca agcatcctcc agttgcgatt   1560
ctgcctcttg ggactggcaa tgatctagca agatgcctgc gatggggagg aggttacgaa   1620
ggtgagaatc tgatgaaaat tctaaaagac attgaaaaca gcacagaaat catgttggac   1680
aggtggaagt ttgaagtcat acctaatgac aaagatgaga aaggagaccc agtgccttac   1740
agtatcatca ataattactt ttccattggc gtggatgcct ccattgcaca cagattccac   1800
atcatgagag aaaaacaccc agagaaattc aacagtagaa tgaagaacaa attttggtat   1860
tttgagtttg gcacatctga aactttctca gccacctgca agaagctaca tgaatctgta   1920
gaaatagaat gtgatggagt acagatagat ttaataaaca tctctctgga aggaattgct   1980
attttgaata taccaagcat gcatggagga tccaatcttt ggggagagtc taagaaaaga   2040
cgaagccatc gacgaataga gaaaaaaggg tctgacaaaa ggaccaccgt cacagatgcc   2100
aaagagttga agtttgcaag tcaagatctc agtgaccagc tgctggaggt ggtcggcttg   2160
gaaggagcca tggagatggg gcaaatatac acaggcctga aaagtgctgg ccggcggctg   2220
```

-continued

```
gctcagtgct cctgcgtggt catcaggacg agcaagtctc tgccaatgca aattgatggg   2280

gagccatgga tgcagacccc atgcacagtg agtacagagt agttgatatg ctatgtcaat   2340

ctcagttttg ctttcctctt tgactaaata accacaataa ctgatttttt tctttatttc   2400

ttttcaacct atcagcaaat agtctttttg ttgttgttgt tatgtgtgtg tcagagccac   2460

tacatttagg ctgtagacat tatataccct tggcaatgat ttagctcttg aatgtttgtg   2520

ctagcctaag tataaataga tcttttaaat agatcaatta taaaccatag atcaattata   2580

aactatggag ctaaacaaaa tattaataaa agtttatctg aaactttttt gtttatttca   2640

gagcacatta ttagaatatt atttgcgaga aatgcagacc taagcttata tgtgaactta   2700

tttctcagct tttctatgcc tccatttggg gatttgaggg ctttcttctc cataagaaaa   2760

aaatttctct ccagtttcta ccataattaa ttgtgttttc cagaatgagg tattatttaa   2820

ggcagacact gcccctctca aaaaaaatca gttttcattt gcatagtgaa tattttattg   2880

catttcaaaa acatgctagg aactgctttt ggcactggga gtagacacat gaacaagacc   2940

aacagtgtaa tttccttcaa gttacttaca ttcctataat agaggaccga ataaataaac   3000

aactacatga taaatataac ttcagactgt gagagttatt aaaaaataag gtgaaatgat   3060

gataagaagc tggattaggt gtggagaata aatactactt gagataaggg agacctcttt   3120

gaaaggacat agccaaaagc ttagtataaa attaaaaaaa ataaaaaaaa aa           3172
```

```
<210> SEQ ID NO 14
<211> LENGTH: 3926
<212> TYPE: DNA
<213> ORGANISM: Homo sapiens

<400> SEQUENCE: 14
```

```
atgacaaacc aggaaaaatg ggcccacctc agcccttcgg aattttccca acttcagaaa     60

tatgctgagt attctacaaa gaaattaaag gatgttcttg aagaattcca tggtaatggt    120

gtgcttgcaa agtataatcc tgaagggaaa caagacattc ttaaccaaac aatagatttt    180

gaaggtttca aactattcat gaagacattc ctggaagccg agcttcctga tgatttcact    240

gcacaccttt tcatgtcatt tagcaacaag tttcctcatt ctagtccaat ggtaaaaagt    300

aagcctgctc tcctatcagg cggtctgaga atgaataaag gtgccatcac ccctccccga    360

actacttctc ctgcaaatac gtgttcccca gaagtaatcc atctgaagga cattgtctgt    420

tacctgtctc tgcttgaaag aggaagacct gaggataagc ttgagtttat gtttcgcctt    480

tatgacacgg atgggaatgg cttcctggac agctcggagc tagaaaatat catcagtcag    540

atgatgcatg ttgcagaata ccttgagtgg gatgtcactg aacttaatcc aatcctccat    600

gaaatgatgg aagaaattga ctatgatcat gatggaaccg tgtctctgga ggaatggatt    660

caaggaggaa tgacaacgat tccacttctt gtgctcctgg gcttagaaaa taacgtgaag    720

gatgatggac agcacgtgtg gcgactgaag cactttaaca aacctgccta ttgcaacctt    780

tgcctgaaca tgctgattgg cgtggggaag cagggcctct gctgttcctt ctgcaagtac    840

acagtccatg agcgctgtgt ggctcgagca cctccctctt gcatcaagac ctatgtgaag    900

tccaaaagga acactgatgt catgcaccat tactgggttg aaggtaactg cccaaccaag    960

tgtgataagt gccacaaaac tgttaaatgt taccagggcc tgacaggact gcattgtgtt   1020

tggtgtcaga tcacactgca taataaatgt gcttctcatc taaaacctga atgtgactgt   1080

ggacctttga aggaccatat tttaccaccc acaacaatct gtccagtggt actgcagact   1140

ctgcccactt caggagtttc agttcctgag gaaagacaat caacagtgaa aaaggaaaag   1200
```

-continued

```
agtggttccc agcagccaaa caaagtgatt gacaagaata aaatgcaaag agccaactct   1260
gttactgtag atggacaagg cctgcaggtc actcctgtgc ctggtactca cccactttta   1320
gtttttgtga accccaaaag tggtggaaaa caaggagaac gaatttacag aaaattccag   1380
tatctattaa atcctcgtca ggtttacagt ctttctggaa atggaccaat gccagggtta   1440
aactttttcc gtgatgttcc tgacttcaga gtgttagcct gtggtggaga tggaaccgtg   1500
ggctgggttt tggattgcat agaaaaggcc aatgtaggca agcatcctcc agttgcgatt   1560
ctgcctcttg ggactggcaa tgatctagca agatgcctgc gatggggagg aggttacgaa   1620
ggtgagaatc tgatgaaaat tctaaaagac attgaaaaca gcacagaaat catgttggac   1680
aggtggaagt ttgaagtcat acctaatgac aaagatgaga aaggagaccc agtgccttac   1740
agtatcatca ataattactt ttccattggc gtggatgcct ccattgcaca cagattccac   1800
atcatgagag aaaaacaccc agagaaattc aacagtagaa tgaagaacaa attttggtat   1860
tttgagtttg gcacatctga aactttctca gccacctgca agaagctaca tgaatctgta   1920
gaaatagaat gtgatggagt acagatagat ttaataaaca tctctctgga aggaattgct   1980
attttgaata taccaagcat gcatggagga tccaatcttt ggggagagtc taagaaaaga   2040
cgaagccatc gacgaataga gaaaaaaggg tctgacaaaa ggaccaccgt cacagatgcc   2100
aaagagttga agtttgcaag tcaagatctc agtgaccagc tgctggaggt ggtcggcttg   2160
gaaggagcca tggagatggg gcaaatatac acaggcctga aaagtgctgg ccggcggctg   2220
gctcagtgct cctgcgtggt catcaggacg agcaagtctc tgccaatgca aattgatggg   2280
gagccatgga tgcagacccc atgcacaata aaaattacac acaagaacca agccccaatg   2340
ctgatgggcc cgcctccaaa aaccggttta ttctgctccc tcgtcaaaag gacaagaaac   2400
cgaagcaagg aataatcctg tgttgtttca ctcttagaaa ttgaattagc ataattgggc   2460
catggaacac atatgctgga aatctttgaa ccatttcaag tctcctgctc atgcaaaatc   2520
atggaagtgg tttaacagtt tttgttacta agctaatgta aaattcagct attagaaaat   2580
ttattgtctc agtttttata ggcatctttg catgaagaaa gcagaagttt acctgaagtg   2640
atactgcata tttttggtgc atgcattccc atagattttt acatctccca cccaactctt   2700
ccccaatttc cttttactaa cctgtgagaa aaacccgtga aacatgaaaa aggaaatacc   2760
atgggaaacg tgattctcag tgtgattcca attattacga agcactaatc agtaacgcta   2820
caatgatcat aattgcagat tgctatacgt ttcccttta gaatcagtgt atcagtgacc   2880
tatgacttga ggagaaactt ttaattcgaa gattttatta aatagttgac tacaatacct   2940
tgctatatat acatagtttt tcttcaacat cttaactctt ctgagtggaa ataaaaatat   3000
caggcataag gttttctcat gctgaaaaat agaacgcggt ttttattttg cttagttttc   3060
tttttaattc cagaaataag tgaaaacatg ttacttgaca gtcaagtgtg gtaatatggc   3120
aagccttgtt cctttctgca tgagaatcta ggagagaatt cataaccaca ccaataacga   3180
aatagaagtt ttaaactatg tgcctaatca atgtgtttcc caccaaagat tcagaaaaca   3240
atgcttgaga gaaatgggtt aatgcataat taattaagca ttgtggagca aatttagggt   3300
tcctgtgatt aattttgtga tgactaaaat gctggaaagc aagtgagttg cccattaatt   3360
atgattaaaa ttctcacctt tcacagacag acaataagcc agacaacaca atcaaagctc   3420
aatagatgat ttcttgcttt tttcagtcat ttataaatat aggtgtaatt tttcatggat   3480
cagttaagta cacttgaagg aagtaaatga ttgtatcagt ttatttctag tataaatggg   3540
```

-continued

```
tacctgtaat aatactgagc tcttggaagc gaatcatgca tgcaattagc tccctcctcc   3600

tcacctactc cactcccatc tttatgacat ttcaaatgtt tatttggaaa caacagccta   3660

gatcactgtt gaaggtgttc atggcatagt tggagtctct gactgtttaa agaaatcaca   3720

gaacagtact tttcttttag tgtttcatta agcctatgat gtaaaatgaa atgcttctga   3780

gcagtcttgt aatattgttc attcatattg acctgcatct catcattgca tgttttatgt   3840

tttcaaacat gccataagga aaacgagtgc ctgaactgca tgatttatta gtttctctcc   3900

actctgcatt aaagtgctaa tgattt                                        3926
```

```
<210> SEQ ID NO 15
<211> LENGTH: 3536
<212> TYPE: DNA
<213> ORGANISM: Homo sapiens

<400> SEQUENCE: 15

atggggacga cggccccagg gcccattcac ctgctggagc tatgtgacca gaagctcatg     60

gagtttctct gcaacatgga taataaggac ttggtgtggc ttgaggagat ccaagaggag    120

gccgagcgca tgttcaccag agaattcagc aaagagccag agctgatgcc caaaacacct    180

tctcagaaga accgacggaa gaagagacgg atttcttatg ttcaggatga aaacagagat    240

cccatcagga gaaggttatc ccgcagaaag tctcggagca gccagctgag ctcccgacgc    300

ctccgcagca aggacagtgt agagaagctg gctacagtgg tcggggagaa cggctccgtt    360

ctgcggcgtg tgacccgtgc tgcggctgca gctgccgcgg ctaccatggc attggctgca    420

ccttcttcac ccaccccctga gtctcccacg atgctgacta agaagcccga ggataaccac    480

acccagtgcc agctggtgcc tgtggtggag atcggcatca gtgagcgcca gaatgctgag    540

cagcatgtca cccagctcat gtccaccgag cctctgcccc gcactctgtc cccgactcca    600

gcttcagcca cagctccaac ctcccagggc atcccgacat cagatgagga atcaacacct    660

aagaagtcga aggccaggat actggagtcc atcacagtga gctccctgat ggctacaccc    720

caggacccca agggtcaagg ggtcgggacg gggcggtctg cgtctaagct caggattgcg    780

caggtctccc ctggcccacg ggactcgcca gcctttccag attctccatg gcgggagcgg    840

gtgctggctc ccatcctgcc ggataacttc tccacgccca cgggctctcg cacggactct    900

caatcggtgc ggcacagccc gatcgccccg tcttccccga gtccccaagt cttagcccag    960

aagtactctc tggtggccaa acaggaaagt gttgtccgca gggcgagcag aaggcttgcc   1020

aagaagactg ccgaagagcc agctgcctct ggccgcatca tctgtcacag ttacctggag   1080

aggctcctga atgttgaggt gccccagaaa gttggttctg agcagaagga acccccgag   1140

gaggctgagc ctgtggcggc agctgagcca gaggtccctg agaacaacgg aaataactcg   1200

tggccccaca atgacacgga gattgccaac agcacaccca acccgaagcc tgcagccagc   1260

agcccggaaa caccctctgc agggcagcaa gaggccaaga cggaccaagc agatggaccc   1320

agagagccac cgcagagtgc caggaggaag cgcagctaca agcaggccgt gagtgagctg   1380

gacgaggagc agcacctgga ggatgaggag ctgcagcccc ccaggagcaa gacccccttcc   1440

tcaccctgcc cagccagcaa ggtggtacgg cccctccgga cctttctgca cacagtgcag   1500

aggaaccaga tgctcatgac ccctacctca gccccacgca gcgtcatgaa gtcctttatt   1560

aagcgcaaca ctcccctgcg catggacccc aaggagaagg agcggcagcg cctggagaat   1620

ctgcggcgga aggaggaggc cgagcagctg cgcaggcaga aggtggagga ggacaagcgg   1680

cggcggctgg aggaggtgaa gctgaagcgt gaggaacgcc tccgcaaggt gctgcaggcc   1740
```

-continued

```
cgcgagcggg tggagcagat gaaggaggag aagaagaagc agattgagca gaagtttgct   1800
cagatcgacg agaagactga gaaggccaag gaggagcggc tggcagagga gaaggccaag   1860
aaaaaggcgg cggccaagaa gatggaggag gtggaagcac gcaggaagca ggaagaggat   1920
gcacgtaggc tcaggtggct gcagcaggag gaggaagagc ggcggcacca agagctgctg   1980
cagaagaaga aggaagagga gcaggagcgg ctgcggaagg cggccgaggc taagcggctg   2040
gcagagcagc gggagcagga gcggcgggag caggagcggc gggagcagga gcggcgcgag   2100
caggagcggc gcgagcagga gcggcgggag caggagcggc gcgagcagga gcgacagctg   2160
gcagagcagg agcgtcggcg ggagcaggag cggctccaag ccgagaggga gctgcaggag   2220
cgggagaagg ccctgcggct gcagaaggag cagctgcaga gggaactgga ggagaagaag   2280
aagaaggaag agcagcagcg tctggctgag cggcagctgc aggaggagca agagaagaaa   2340
gccaaggagg cagcaggggc cagcaaggcc ctgaatgtga ctgtggacgt gcagtctcca   2400
gcttgtacct catctcccat cactccgcaa gggcacaagg cccctcccca gatcaacccc   2460
cacaactacg ggatggatct gaatagcgac gactccaccg atgatgaggc ccatccccgg   2520
aagcccatcc ccacctgggc ccgaggcacc ccgctcagcc aggctatcat tcaccagtac   2580
taccagccac cgaaccttct ggagctcttt ggaaccattc tcccactgga cttggaggat   2640
atcttcaaga agagcaagcc ccgctatcac aagcgcacca gctctgctgt ctggaactca   2700
ccgcccctgc agggcgccag ggtccccagc agcctggcct acagcctgaa gaagcactga   2760
ggctggcctg cggccttctt ggcagcctcg cctcctgtcc atgtctatct gtctgtctgt   2820
cggtctgtgt cttggtctgt tgccctcctt cttggcatgc cattgtggag ggcttggcca   2880
ggtgtatata aacgtcctct gtgctgggtg tttctgctgc aggtggcagg tggccccagg   2940
cctgtttgga ggatgggctg ggtgggtggg tggggaagaa atgggcccag ccccacatgg   3000
cctgcagaca gtgctctgta aatagttgtt ttaatttagc tgaatgttag cattttagtc   3060
tttggcattt tagcgtttgg gaggtagatt aataaagtat attccttcaa gcctgctgtt   3120
gataccatga agactgggcg cctcagtccc agccctgtag ctgtgtgtct tgggccacca   3180
gtggcctgca ggacgaaggt actgttccat cacctgcggt gtgcctcagg atcaccaggt   3240
gcaggccccc accctcggag atgctgctgc agtgagtggt tccactgcct ggataaccct   3300
tgaggaacac gtcagttact gtcacgatgg ggcaggtgga gctccttcct atttttttggg  3360
gtgctccctg tttgtaaagg ggagtttgtt cattgggaaa gacctgggtc ttgacacggc   3420
cctgccactt agtcccctac cctctccatt ccccaggctc cacccgtgct gctcaagtgc   3480
aaatggactt gagagtattt atgtgctggt gaagtatgag gtctgagtag aaaagg       3536
```

<210> SEQ ID NO 16
<211> LENGTH: 1778
<212> TYPE: DNA
<213> ORGANISM: Homo sapiens

<400> SEQUENCE: 16

```
gggagcggga gcgccccagc ggccggcggg cgggcgggcg agcggacgag cggcgcggag     60
ccggcccgag gcgcgcgccg agggagcccc gtccccggtc gtgggggcac cgcccgcagg    120
ctctgcgggg tgggcagctc ccgggcctgc catgagctct ccgccgcccg cccgcagtgg    180
cttttaccgc caggaggtga ccaagacggc ctgggaggtg cgcgccgtgt accgggacct    240
gcagcccgtg ggctcgggcg cctacggcgc ggtgtgctcg gccgtggacg gccgcaccgg    300
```

-continued

```
cgctaaggtg gccatcaaga agctgtatcg gcccttccag tccgagctgt tcgccaagcg    360

cgcctaccgc gagctgcgcc tgctcaagca catgcgccac gagaacgtga tcgggctgct    420

ggacgtattc actcctgatg agaccctgga tgacttcacg gacttttacc tggtgatgcc    480

gttcatgggc accgacctgg gcaagctcat gaaacatgag aagctaggcg aggaccggat    540

ccagttcctc gtgtaccaga tgctgaaggg gctgaggtat atccacgctg ccggcatcat    600

ccacagagac ctgaagcccg gcaacctggc tgtgaacgaa gactgtgagc tgaagatcct    660

ggacttcggc ctggccaggc aggcagacag tgagatgact gggtacgtgg tgacccggtg    720

gtaccgggct cccgaggtca tcttgaattg gatgcgctac acgcagacgg tggacatctg    780

gtctgtgggc tgcatcatgg cggagatgat cacaggcaag acgctgttca agggcagcga    840

ccacctggac cagctgaagg agatcatgaa ggtgacgggg acgcctccgg ctgagtttgt    900

gcagcggctg cagagcgatg aggccaagaa ctacatgaag ggcctccccg aattggagaa    960

gaaggatttt gcctctatcc tgaccaatgc aagccctctg gctgtgaacc tcctggagaa   1020

gatgctggtg ctggacgcgg agcagcgggt gacggcaggc gaggcgctgg cccatcccta   1080

cttcgagtcc ctgcacgaca cggaagatga gccccaggtc cagaagtatg atgactcctt   1140

tgacgacgtt gaccgcacac tggatgaatg gaagcgtgtt acttacaaag aggtgctcag   1200

cttcaagcct ccccggcagc tgggggccag ggtctccaag gagacgcctc tgtgaagatc   1260

tctgggctcc ggggtggcag tgaggaccac cttcaccttc cacctgagag ggactctcg    1320

ttgccacctt gaccttggct ggggcttgca tcccaaggca tccatcagag cagacgcccg   1380

ggttccatgg accctcctcc ccacggccat gcctctgctc ttgggcgccc atcatggagg   1440

agcacctgaa ctttctggac aagacctctg gccgacctgg ggatggcctc tgatccctgg   1500

agcagtggcc cacttgcccg gtgctctcag aaacctcaga gctggtgggg ctccagatca   1560

ggccttggcc tctgagccct gcctgctctg ggccatgcag aggaaggaca gagggtgggc   1620

gcagggcacc aactcaggga catcccctct cctgggcgac gtcagtggac cttcctgcac   1680

ccccagcctg gaatgtaaat cagctgtgtg gtgcccgcgt ggctggaagg aaatagaccc   1740

ttttgtagct ccctaaaaaa aaaaaaaaaa aaaaaaaa                           1778


<210> SEQ ID NO 17
<211> LENGTH: 494
<212> TYPE: PRT
<213> ORGANISM: Homo sapiens

<400> SEQUENCE: 17

Met Asp Gly Ser Gly Glu Arg Ser Leu Pro Glu Pro Gly Ser Gln Ser
1               5                   10                  15

Ser Ala Ala Ser Asp Asp Ile Glu Ile Val Val Asn Val Gly Gly Val
            20                  25                  30

Arg Gln Val Leu Tyr Gly Asp Leu Leu Ser Gln Tyr Pro Glu Thr Arg
        35                  40                  45

Leu Ala Glu Leu Ile Asn Cys Leu Ala Gly Gly Tyr Asp Thr Ile Phe
    50                  55                  60

Ser Leu Cys Asp Asp Tyr Asp Pro Gly Lys Arg Glu Phe Tyr Phe Asp
65                  70                  75                  80

Arg Asp Pro Asp Ala Phe Lys Cys Val Ile Glu Val Tyr Tyr Phe Gly
                85                  90                  95

Glu Val His Met Lys Lys Gly Ile Cys Pro Ile Cys Phe Lys Asn Glu
            100                 105                 110
```

-continued

```
Met Asp Phe Trp Lys Val Asp Leu Lys Phe Leu Asp Asp Cys Cys Lys
        115                 120                 125

Ser His Leu Ser Glu Lys Arg Glu Glu Leu Glu Glu Ile Ala Arg Arg
    130                 135                 140

Val Gln Leu Ile Leu Asp Asp Leu Gly Val Asp Ala Ala Glu Gly Arg
145                 150                 155                 160

Trp Arg Arg Cys Gln Lys Cys Val Trp Lys Phe Leu Glu Lys Pro Glu
                165                 170                 175

Ser Ser Cys Pro Ala Arg Val Val Ala Val Leu Ser Phe Leu Leu Ile
            180                 185                 190

Leu Val Ser Ser Val Val Met Cys Met Gly Thr Ile Pro Glu Leu Gln
        195                 200                 205

Val Leu Asp Ala Glu Gly Asn Arg Val Glu His Pro Thr Leu Glu Asn
    210                 215                 220

Val Glu Thr Ala Cys Ile Gly Trp Phe Thr Leu Glu Tyr Leu Leu Arg
225                 230                 235                 240

Leu Phe Ser Ser Pro Asn Lys Leu His Phe Ala Leu Ser Phe Met Asn
                245                 250                 255

Ile Val Asp Val Leu Ala Ile Leu Pro Phe Tyr Val Ser Leu Thr Leu
            260                 265                 270

Thr His Leu Gly Ala Arg Met Met Glu Leu Thr Asn Val Gln Gln Ala
        275                 280                 285

Val Gln Ala Leu Arg Ile Met Arg Ile Ala Arg Ile Phe Lys Leu Ala
    290                 295                 300

Arg His Ser Ser Gly Leu Gln Thr Leu Thr Tyr Ala Leu Lys Arg Ser
305                 310                 315                 320

Phe Lys Glu Leu Gly Leu Leu Leu Met Tyr Leu Ala Val Gly Ile Phe
                325                 330                 335

Val Phe Ser Ala Leu Gly Tyr Thr Met Glu Gln Ser His Pro Glu Thr
            340                 345                 350

Leu Phe Lys Ser Ile Pro Gln Ser Phe Trp Trp Ala Ile Ile Thr Met
        355                 360                 365

Thr Thr Val Gly Tyr Gly Asp Ile Tyr Pro Lys Thr Thr Leu Gly Lys
    370                 375                 380

Leu Asn Ala Ala Ile Ser Phe Leu Cys Gly Val Ile Ala Ile Ala Leu
385                 390                 395                 400

Pro Ile His Pro Ile Ile Asn Asn Phe Val Arg Tyr Tyr Asn Lys Gln
                405                 410                 415

Arg Val Leu Glu Thr Ala Ala Lys His Glu Leu Glu Leu Met Glu Leu
            420                 425                 430

Asn Ser Ser Ser Gly Gly Glu Gly Lys Thr Gly Gly Ser Arg Ser Asp
        435                 440                 445

Leu Asp Asn Leu Pro Pro Glu Pro Ala Gly Lys Glu Ala Pro Ser Cys
    450                 455                 460

Ser Ser Arg Leu Lys Leu Ser His Ser Asp Thr Phe Ile Pro Leu Leu
465                 470                 475                 480

Thr Glu Glu Lys His His Arg Thr Arg Leu Gln Ser Cys Lys
                485                 490
```

<210> SEQ ID NO 18
<211> LENGTH: 581
<212> TYPE: PRT
<213> ORGANISM: Homo sapiens

<400> SEQUENCE: 18

-continued

```
Met Gly Glu Lys Met Ala Glu Glu Glu Arg Phe Pro Asn Thr Thr His
1               5                   10                  15

Glu Gly Phe Asn Val Thr Leu His Thr Thr Leu Val Val Thr Thr Lys
            20                  25                  30

Leu Val Leu Pro Thr Pro Gly Lys Pro Ile Leu Pro Val Gln Thr Gly
        35                  40                  45

Glu Gln Ala Gln Gln Glu Glu Gln Ser Ser Gly Met Thr Ile Phe Phe
    50                  55                  60

Ser Leu Leu Val Leu Ala Ile Cys Ile Ile Leu Val His Leu Leu Ile
65                  70                  75                  80

Arg Tyr Arg Leu His Phe Leu Pro Glu Ser Val Ala Val Val Ser Leu
                85                  90                  95

Gly Ile Leu Met Gly Ala Val Ile Lys Ile Ile Glu Phe Lys Lys Leu
            100                 105                 110

Ala Asn Trp Lys Glu Glu Glu Met Phe Arg Pro Asn Met Phe Phe Leu
        115                 120                 125

Leu Leu Leu Pro Pro Ile Ile Phe Glu Ser Gly Tyr Ser Leu His Lys
    130                 135                 140

Gly Asn Phe Phe Gln Asn Ile Gly Ser Ile Thr Leu Phe Ala Val Phe
145                 150                 155                 160

Gly Thr Ala Ile Ser Ala Phe Val Val Gly Gly Gly Ile Tyr Phe Leu
                165                 170                 175

Gly Gln Ala Asp Val Ile Ser Lys Leu Asn Met Thr Asp Ser Phe Ala
            180                 185                 190

Phe Gly Ser Leu Ile Ser Ala Val Asp Pro Val Ala Thr Ile Ala Ile
        195                 200                 205

Phe Asn Ala Leu His Val Asp Pro Val Leu Asn Met Leu Val Phe Gly
    210                 215                 220

Glu Ser Ile Leu Asn Asp Ala Val Ser Ile Val Leu Thr Asn Thr Ala
225                 230                 235                 240

Glu Gly Leu Thr Arg Lys Asn Met Ser Asp Val Ser Gly Trp Gln Thr
                245                 250                 255

Phe Leu Gln Ala Leu Asp Tyr Phe Leu Lys Met Phe Phe Gly Ser Ala
            260                 265                 270

Ala Leu Gly Thr Leu Thr Gly Leu Ile Ser Ala Leu Val Leu Lys His
        275                 280                 285

Ile Asp Leu Arg Lys Thr Pro Ser Leu Glu Phe Gly Met Met Ile Ile
    290                 295                 300

Phe Ala Tyr Leu Pro Tyr Gly Leu Ala Glu Gly Ile Ser Leu Ser Gly
305                 310                 315                 320

Ile Met Ala Ile Leu Phe Ser Gly Ile Val Met Ser His Tyr Thr His
                325                 330                 335

His Asn Leu Ser Pro Val Thr Gln Ile Leu Met Gln Gln Thr Leu Arg
            340                 345                 350

Thr Val Ala Phe Leu Cys Glu Thr Cys Val Phe Ala Phe Leu Gly Leu
        355                 360                 365

Ser Ile Phe Ser Phe Pro His Lys Phe Glu Ile Ser Phe Val Ile Trp
    370                 375                 380

Cys Ile Val Leu Val Leu Phe Gly Arg Ala Val Asn Ile Phe Pro Leu
385                 390                 395                 400

Ser Tyr Leu Leu Asn Phe Phe Arg Asp His Lys Ile Thr Pro Lys Met
                405                 410                 415
```

-continued

```
Met Phe Ile Met Trp Phe Ser Gly Leu Arg Gly Ala Ile Pro Tyr Ala
            420                 425                 430

Leu Ser Leu His Leu Asp Leu Glu Pro Met Glu Lys Arg Gln Leu Ile
        435                 440                 445

Gly Thr Thr Thr Ile Val Ile Val Leu Phe Thr Ile Leu Leu Leu Gly
    450                 455                 460

Gly Ser Thr Met Pro Leu Ile Arg Leu Met Asp Ile Glu Asp Ala Lys
465                 470                 475                 480

Ala His Arg Arg Asn Lys Lys Asp Val Asn Leu Ser Lys Thr Glu Lys
                485                 490                 495

Met Gly Asn Thr Val Glu Ser Glu His Leu Ser Glu Leu Thr Glu Glu
            500                 505                 510

Glu Tyr Glu Ala His Tyr Ile Arg Arg Gln Asp Leu Lys Gly Phe Val
        515                 520                 525

Trp Leu Asp Ala Lys Tyr Leu Asn Pro Phe Phe Thr Arg Arg Leu Thr
    530                 535                 540

Gln Glu Asp Leu His His Gly Arg Ile Gln Met Lys Thr Leu Thr Asn
545                 550                 555                 560

Lys Trp Tyr Glu Glu Val Arg Gln Gly Pro Ser Gly Ser Glu Asp Asp
                565                 570                 575

Glu Gln Glu Leu Leu
            580


<210> SEQ ID NO 19
<211> LENGTH: 606
<212> TYPE: PRT
<213> ORGANISM: Homo sapiens

<400> SEQUENCE: 19

Met Glu Pro Pro Arg Gly Pro Pro Ala Asn Gly Ala Glu Pro Ser Arg
1               5                   10                  15

Ala Val Gly Thr Val Lys Val Tyr Leu Pro Asn Lys Gln Arg Thr Val
            20                  25                  30

Val Thr Val Arg Asp Gly Met Ser Val Tyr Asp Ser Leu Asp Lys Ala
        35                  40                  45

Leu Lys Val Arg Gly Leu Asn Gln Asp Cys Cys Val Val Tyr Arg Leu
    50                  55                  60

Ile Lys Gly Arg Lys Thr Val Thr Ala Trp Asp Thr Ala Ile Ala Pro
65                  70                  75                  80

Leu Asp Gly Glu Glu Leu Ile Val Glu Val Leu Glu Asp Val Pro Leu
                85                  90                  95

Thr Met His Asn Phe Val Arg Lys Thr Phe Phe Ser Leu Ala Phe Cys
            100                 105                 110

Asp Phe Cys Leu Lys Phe Leu Phe His Gly Phe Arg Cys Gln Thr Cys
        115                 120                 125

Gly Tyr Lys Phe His Gln His Cys Ser Ser Lys Val Pro Thr Val Cys
    130                 135                 140

Val Asp Met Ser Thr Asn Arg Gln Gln Phe Tyr His Ser Val Gln Asp
145                 150                 155                 160

Leu Ser Gly Gly Ser Arg Gln His Glu Ala Pro Ser Asn Arg Pro Leu
                165                 170                 175

Asn Glu Leu Leu Thr Pro Gln Gly Pro Ser Pro Arg Thr Gln His Cys
            180                 185                 190

Asp Pro Glu His Phe Pro Phe Pro Ala Pro Ala Asn Ala Pro Leu Gln
        195                 200                 205
```

-continued

```
Arg Ile Arg Ser Thr Ser Thr Pro Asn Val His Met Val Ser Thr Thr
    210                 215                 220

Ala Pro Met Asp Ser Asn Leu Ile Gln Leu Thr Gly Gln Ser Phe Ser
225                 230                 235                 240

Thr Asp Ala Ala Gly Ser Arg Gly Gly Ser Asp Gly Thr Pro Arg Gly
                245                 250                 255

Ser Pro Ser Pro Ala Ser Val Ser Ser Gly Arg Lys Ser Pro His Ser
            260                 265                 270

Lys Ser Pro Ala Glu Gln Arg Glu Arg Lys Ser Leu Ala Asp Asp Lys
        275                 280                 285

Lys Lys Val Lys Asn Leu Gly Tyr Arg Asp Ser Gly Tyr Tyr Trp Glu
    290                 295                 300

Val Pro Pro Ser Glu Val Gln Leu Leu Lys Arg Ile Gly Thr Gly Ser
305                 310                 315                 320

Phe Gly Thr Val Phe Arg Gly Arg Trp His Gly Asp Val Ala Val Lys
                325                 330                 335

Val Leu Lys Val Ser Gln Pro Thr Ala Glu Gln Ala Gln Ala Phe Lys
            340                 345                 350

Asn Glu Met Gln Val Leu Arg Lys Thr Arg His Val Asn Ile Leu Leu
        355                 360                 365

Phe Met Gly Phe Met Thr Arg Pro Gly Phe Ala Ile Ile Thr Gln Trp
    370                 375                 380

Cys Glu Gly Ser Ser Leu Tyr His His Leu His Val Ala Asp Thr Arg
385                 390                 395                 400

Phe Asp Met Val Gln Leu Ile Asp Val Ala Arg Gln Thr Ala Gln Gly
                405                 410                 415

Met Asp Tyr Leu His Ala Lys Asn Ile Ile His Arg Asp Leu Lys Ser
            420                 425                 430

Asn Asn Ile Phe Leu His Glu Gly Leu Thr Val Lys Ile Gly Asp Phe
        435                 440                 445

Gly Leu Ala Thr Val Lys Thr Arg Trp Ser Gly Ala Gln Pro Leu Glu
    450                 455                 460

Gln Pro Ser Gly Ser Val Leu Trp Met Ala Ala Glu Val Ile Arg Met
465                 470                 475                 480

Gln Asp Pro Asn Pro Tyr Ser Phe Gln Ser Asp Val Tyr Ala Tyr Gly
                485                 490                 495

Val Val Leu Tyr Glu Leu Met Thr Gly Ser Leu Pro Tyr Ser His Ile
            500                 505                 510

Gly Cys Arg Asp Gln Ile Ile Phe Met Val Gly Arg Gly Tyr Leu Ser
        515                 520                 525

Pro Asp Leu Ser Lys Ile Ser Ser Asn Cys Pro Lys Ala Met Arg Arg
    530                 535                 540

Leu Leu Ser Asp Cys Leu Lys Phe Gln Arg Glu Glu Arg Pro Leu Phe
545                 550                 555                 560

Pro Gln Ile Leu Ala Thr Ile Glu Leu Leu Gln Arg Ser Leu Pro Lys
                565                 570                 575

Ile Glu Arg Ser Ala Ser Glu Pro Ser Leu His Arg Thr Gln Ala Asp
            580                 585                 590

Glu Leu Pro Ala Cys Leu Leu Ser Ala Ala Arg Leu Val Pro
        595                 600                 605
```

<210> SEQ ID NO 20
<211> LENGTH: 885

-continued

```
<212> TYPE: PRT
<213> ORGANISM: Homo sapiens

<400> SEQUENCE: 20

Met Ala Trp Arg Cys Pro Arg Met Gly Arg Val Pro Leu Ala Trp Cys
1               5                   10                  15

Leu Ala Leu Cys Gly Trp Ala Cys Met Ala Pro Arg Gly Thr Gln Ala
            20                  25                  30

Glu Glu Ser Pro Phe Val Gly Asn Pro Gly Asn Ile Thr Gly Ala Arg
        35                  40                  45

Gly Leu Thr Gly Thr Leu Arg Cys Gln Leu Gln Val Gln Gly Glu Pro
    50                  55                  60

Pro Glu Val His Trp Leu Arg Asp Gly Gln Ile Leu Glu Leu Ala Asp
65                  70                  75                  80

Ser Thr Gln Thr Gln Val Pro Leu Gly Glu Asp Glu Gln Asp Asp Trp
                85                  90                  95

Ile Val Val Ser Gln Leu Arg Ile Thr Ser Leu Gln Leu Ser Asp Thr
            100                 105                 110

Gly Gln Tyr Gln Cys Leu Val Phe Leu Gly His Gln Thr Phe Val Ser
        115                 120                 125

Gln Pro Gly Tyr Val Gly Leu Glu Gly Leu Pro Tyr Phe Leu Glu Glu
    130                 135                 140

Pro Glu Asp Arg Thr Val Ala Ala Asn Thr Pro Phe Asn Leu Ser Cys
145                 150                 155                 160

Gln Ala Gln Gly Pro Pro Glu Pro Val Asp Leu Leu Trp Leu Gln Asp
                165                 170                 175

Ala Val Pro Leu Ala Thr Ala Pro Gly His Gly Pro Gln Arg Ser Leu
            180                 185                 190

His Val Pro Gly Leu Asn Lys Thr Ser Ser Phe Ser Cys Glu Ala His
        195                 200                 205

Asn Ala Lys Gly Val Thr Thr Ser Arg Thr Ala Thr Ile Thr Val Leu
    210                 215                 220

Pro Gln Gln Pro Arg Asn Leu His Leu Val Ser Arg Gln Pro Thr Glu
225                 230                 235                 240

Leu Glu Val Ala Trp Thr Pro Gly Leu Ser Gly Ile Tyr Pro Leu Thr
                245                 250                 255

His Cys Thr Leu Gln Ala Val Leu Ser Asp Asp Gly Met Gly Ile Gln
            260                 265                 270

Ala Gly Glu Pro Asp Pro Pro Glu Glu Pro Leu Thr Ser Gln Ala Ser
        275                 280                 285

Val Pro Pro His Gln Leu Arg Leu Gly Ser Leu His Pro His Thr Pro
    290                 295                 300

Tyr His Ile Arg Val Ala Cys Thr Ser Ser Gln Gly Pro Ser Ser Trp
305                 310                 315                 320

Thr His Trp Leu Pro Val Glu Thr Pro Glu Gly Val Pro Leu Gly Pro
                325                 330                 335

Pro Glu Asn Ile Ser Ala Thr Arg Asn Gly Ser Gln Ala Phe Val His
            340                 345                 350

Trp Gln Glu Pro Arg Ala Pro Leu Gln Gly Thr Leu Leu Gly Tyr Arg
        355                 360                 365

Leu Ala Tyr Gln Gly Gln Asp Thr Pro Glu Val Leu Met Asp Ile Gly
    370                 375                 380

Leu Arg Gln Glu Val Thr Leu Glu Leu Gln Gly Asp Gly Ser Val Ser
385                 390                 395                 400
```

-continued

```
Asn Leu Thr Val Cys Val Ala Ala Tyr Thr Ala Ala Gly Asp Gly Pro
                405                 410                 415

Trp Ser Leu Pro Val Pro Leu Glu Ala Trp Arg Pro Val Lys Glu Pro
            420                 425                 430

Ser Thr Pro Ala Phe Ser Trp Pro Trp Trp Tyr Val Leu Leu Gly Ala
        435                 440                 445

Val Val Ala Ala Ala Cys Val Leu Ile Leu Ala Leu Phe Leu Val His
    450                 455                 460

Arg Arg Lys Lys Glu Thr Arg Tyr Gly Glu Val Phe Glu Pro Thr Val
465                 470                 475                 480

Glu Arg Gly Glu Leu Val Val Arg Tyr Arg Val Arg Lys Ser Tyr Ser
                485                 490                 495

Arg Arg Thr Thr Glu Ala Thr Leu Asn Ser Leu Gly Ile Ser Glu Glu
            500                 505                 510

Leu Lys Glu Lys Leu Arg Asp Val Met Val Asp Arg His Lys Val Ala
        515                 520                 525

Leu Gly Lys Thr Leu Gly Glu Gly Glu Phe Gly Ala Val Met Glu Gly
    530                 535                 540

Gln Leu Asn Gln Asp Asp Ser Ile Leu Lys Val Ala Val Lys Thr Met
545                 550                 555                 560

Lys Ile Ala Ile Cys Thr Arg Ser Glu Leu Glu Asp Phe Leu Ser Glu
                565                 570                 575

Ala Val Cys Met Lys Glu Phe Asp His Pro Asn Val Met Arg Leu Ile
            580                 585                 590

Gly Val Cys Phe Gln Gly Ser Glu Arg Glu Ser Phe Pro Ala Pro Val
        595                 600                 605

Val Ile Leu Pro Phe Met Lys His Gly Asp Leu His Ser Phe Leu Leu
    610                 615                 620

Tyr Ser Arg Leu Gly Asp Gln Pro Val Tyr Leu Pro Thr Gln Met Leu
625                 630                 635                 640

Val Lys Phe Met Ala Asp Ile Ala Ser Gly Met Glu Tyr Leu Ser Thr
                645                 650                 655

Lys Arg Phe Ile His Arg Asp Leu Ala Ala Arg Asn Cys Met Leu Asn
            660                 665                 670

Glu Asn Met Ser Val Cys Val Ala Asp Phe Gly Leu Ser Lys Lys Ile
        675                 680                 685

Tyr Asn Gly Asp Tyr Tyr Arg Gln Gly Arg Ile Ala Lys Met Pro Val
    690                 695                 700

Lys Trp Ile Ala Ile Glu Ser Leu Ala Asp Arg Val Tyr Thr Ser Lys
705                 710                 715                 720

Ser Asp Val Trp Ser Phe Gly Val Thr Met Trp Glu Ile Ala Thr Arg
                725                 730                 735

Gly Gln Thr Pro Tyr Pro Gly Val Glu Asn Ser Glu Ile Tyr Asp Tyr
            740                 745                 750

Leu Arg Gln Gly Asn Arg Leu Lys Gln Pro Ala Asp Cys Leu Asp Gly
        755                 760                 765

Leu Tyr Ala Leu Met Ser Arg Cys Trp Glu Leu Asn Pro Gln Asp Arg
    770                 775                 780

Pro Ser Phe Thr Glu Leu Arg Glu Asp Leu Glu Asn Thr Leu Lys Ala
785                 790                 795                 800

Leu Pro Pro Ala Gln Glu Pro Asp Glu Ile Leu Tyr Val Asn Met Asp
                805                 810                 815
```

-continued

```
Glu Gly Gly Gly Tyr Pro Glu Pro Pro Gly Ala Ala Gly Gly Ala Asp
            820                 825                 830

Pro Pro Thr Gln Pro Asp Pro Lys Asp Ser Cys Ser Cys Leu Thr Ala
        835                 840                 845

Ala Glu Val His Pro Ala Gly Arg Tyr Val Leu Cys Pro Ser Thr Thr
    850                 855                 860

Pro Ser Pro Ala Gln Pro Ala Asp Arg Gly Ser Pro Ala Ala Pro Gly
865                 870                 875                 880

Gln Glu Asp Gly Ala
                885


<210> SEQ ID NO 21
<211> LENGTH: 894
<212> TYPE: PRT
<213> ORGANISM: Homo sapiens

<400> SEQUENCE: 21

Met Ala Trp Arg Cys Pro Arg Met Gly Arg Val Pro Leu Ala Trp Cys
1               5                   10                  15

Leu Ala Leu Cys Gly Trp Ala Cys Met Ala Pro Arg Gly Thr Gln Ala
            20                  25                  30

Glu Glu Ser Pro Phe Val Gly Asn Pro Gly Asn Ile Thr Gly Ala Arg
        35                  40                  45

Gly Leu Thr Gly Thr Leu Arg Cys Gln Leu Gln Val Gln Gly Glu Pro
    50                  55                  60

Pro Glu Val His Trp Leu Arg Asp Gly Gln Ile Leu Glu Leu Ala Asp
65                  70                  75                  80

Ser Thr Gln Thr Gln Val Pro Leu Gly Glu Asp Glu Gln Asp Asp Trp
                85                  90                  95

Ile Val Val Ser Gln Leu Arg Ile Thr Ser Leu Gln Leu Ser Asp Thr
            100                 105                 110

Gly Gln Tyr Gln Cys Leu Val Phe Leu Gly His Gln Thr Phe Val Ser
        115                 120                 125

Gln Pro Gly Tyr Val Gly Leu Glu Gly Leu Pro Tyr Phe Leu Glu Glu
    130                 135                 140

Pro Glu Asp Arg Thr Val Ala Ala Asn Thr Pro Phe Asn Leu Ser Cys
145                 150                 155                 160

Gln Ala Gln Gly Pro Pro Glu Pro Val Asp Leu Leu Trp Leu Gln Asp
                165                 170                 175

Ala Val Pro Leu Ala Thr Ala Pro Gly His Gly Pro Gln Arg Ser Leu
            180                 185                 190

His Val Pro Gly Leu Asn Lys Thr Ser Ser Phe Ser Cys Glu Ala His
        195                 200                 205

Asn Ala Lys Gly Val Thr Thr Ser Arg Thr Ala Thr Ile Thr Val Leu
    210                 215                 220

Pro Gln Gln Pro Arg Asn Leu His Leu Val Ser Arg Gln Pro Thr Glu
225                 230                 235                 240

Leu Glu Val Ala Trp Thr Pro Gly Leu Ser Gly Ile Tyr Pro Leu Thr
                245                 250                 255

His Cys Thr Leu Gln Ala Val Leu Ser Asp Asp Gly Met Gly Ile Gln
            260                 265                 270

Ala Gly Glu Pro Asp Pro Pro Glu Glu Pro Leu Thr Ser Gln Ala Ser
        275                 280                 285

Val Pro Pro His Gln Leu Arg Leu Gly Ser Leu His Pro His Thr Pro
    290                 295                 300
```

-continued

```
Tyr His Ile Arg Val Ala Cys Thr Ser Ser Gln Gly Pro Ser Ser Trp
305                 310                 315                 320

Thr His Trp Leu Pro Val Glu Thr Pro Glu Gly Val Pro Leu Gly Pro
                325                 330                 335

Pro Glu Asn Ile Ser Ala Thr Arg Asn Gly Ser Gln Ala Phe Val His
            340                 345                 350

Trp Gln Glu Pro Arg Ala Pro Leu Gln Gly Thr Leu Leu Gly Tyr Arg
        355                 360                 365

Leu Ala Tyr Gln Gly Gln Asp Thr Pro Glu Val Leu Met Asp Ile Gly
    370                 375                 380

Leu Arg Gln Glu Val Thr Leu Glu Leu Gln Gly Asp Gly Ser Val Ser
385                 390                 395                 400

Asn Leu Thr Val Cys Val Ala Ala Tyr Thr Ala Ala Gly Asp Gly Pro
                405                 410                 415

Trp Ser Leu Pro Val Pro Leu Glu Ala Trp Arg Pro Gly Gln Ala Gln
            420                 425                 430

Pro Val His Gln Leu Val Lys Glu Pro Ser Thr Pro Ala Phe Ser Trp
        435                 440                 445

Pro Trp Trp Tyr Val Leu Leu Gly Ala Val Val Ala Ala Ala Cys Val
    450                 455                 460

Leu Ile Leu Ala Leu Phe Leu Val His Arg Arg Lys Lys Glu Thr Arg
465                 470                 475                 480

Tyr Gly Glu Val Phe Glu Pro Thr Val Glu Arg Gly Glu Leu Val Val
                485                 490                 495

Arg Tyr Arg Val Arg Lys Ser Tyr Ser Arg Arg Thr Thr Glu Ala Thr
            500                 505                 510

Leu Asn Ser Leu Gly Ile Ser Glu Glu Leu Lys Glu Lys Leu Arg Asp
        515                 520                 525

Val Met Val Asp Arg His Lys Val Ala Leu Gly Lys Thr Leu Gly Glu
    530                 535                 540

Gly Glu Phe Gly Ala Val Met Glu Gly Gln Leu Asn Gln Asp Asp Ser
545                 550                 555                 560

Ile Leu Lys Val Ala Val Lys Thr Met Lys Ile Ala Ile Cys Thr Arg
                565                 570                 575

Ser Glu Leu Glu Asp Phe Leu Ser Glu Ala Val Cys Met Lys Glu Phe
            580                 585                 590

Asp His Pro Asn Val Met Arg Leu Ile Gly Val Cys Phe Gln Gly Ser
        595                 600                 605

Glu Arg Glu Ser Phe Pro Ala Pro Val Val Ile Leu Pro Phe Met Lys
    610                 615                 620

His Gly Asp Leu His Ser Phe Leu Leu Tyr Ser Arg Leu Gly Asp Gln
625                 630                 635                 640

Pro Val Tyr Leu Pro Thr Gln Met Leu Val Lys Phe Met Ala Asp Ile
                645                 650                 655

Ala Ser Gly Met Glu Tyr Leu Ser Thr Lys Arg Phe Ile His Arg Asp
            660                 665                 670

Leu Ala Ala Arg Asn Cys Met Leu Asn Glu Asn Met Ser Val Cys Val
        675                 680                 685

Ala Asp Phe Gly Leu Ser Lys Lys Ile Tyr Asn Gly Asp Tyr Tyr Arg
    690                 695                 700

Gln Gly Arg Ile Ala Lys Met Pro Val Lys Trp Ile Ala Ile Glu Ser
705                 710                 715                 720
```

-continued

```
Leu Ala Asp Arg Val Tyr Thr Ser Lys Ser Asp Val Trp Ser Phe Gly
                725                 730                 735

Val Thr Met Trp Glu Ile Ala Thr Arg Gly Gln Thr Pro Tyr Pro Gly
            740                 745                 750

Val Glu Asn Ser Glu Ile Tyr Asp Tyr Leu Arg Gln Gly Asn Arg Leu
        755                 760                 765

Lys Gln Pro Ala Asp Cys Leu Asp Gly Leu Tyr Ala Leu Met Ser Arg
    770                 775                 780

Cys Trp Glu Leu Asn Pro Gln Asp Arg Pro Ser Phe Thr Glu Leu Arg
785                 790                 795                 800

Glu Asp Leu Glu Asn Thr Leu Lys Ala Leu Pro Pro Ala Gln Glu Pro
                805                 810                 815

Asp Glu Ile Leu Tyr Val Asn Met Asp Glu Gly Gly Gly Tyr Pro Glu
            820                 825                 830

Pro Pro Gly Ala Ala Gly Gly Ala Asp Pro Pro Thr Gln Pro Asp Pro
        835                 840                 845

Lys Asp Ser Cys Ser Cys Leu Thr Ala Ala Glu Val His Pro Ala Gly
    850                 855                 860

Arg Tyr Val Leu Cys Pro Ser Thr Thr Pro Ser Pro Ala Gln Pro Ala
865                 870                 875                 880

Asp Arg Gly Ser Pro Ala Ala Pro Gly Gln Glu Asp Gly Ala
                885                 890


<210> SEQ ID NO 22
<211> LENGTH: 806
<212> TYPE: PRT
<213> ORGANISM: Homo sapiens

<400> SEQUENCE: 22

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205
```

-continued

```
Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
        275                 280                 285

Lys His Val Glu Val Asn Gly Ser Lys Val Gly Pro Asp Gly Thr Pro
    290                 295                 300

Tyr Val Thr Val Leu Lys Thr Ala Gly Ala Asn Thr Thr Asp Lys Glu
305                 310                 315                 320

Leu Glu Val Leu Ser Leu His Asn Val Thr Phe Glu Asp Ala Gly Glu
                325                 330                 335

Tyr Thr Cys Leu Ala Gly Asn Ser Ile Gly Phe Ser His His Ser Ala
            340                 345                 350

Trp Leu Val Val Leu Pro Ala Glu Glu Glu Leu Val Glu Ala Asp Glu
        355                 360                 365

Ala Gly Ser Val Tyr Ala Gly Ile Leu Ser Tyr Gly Val Gly Phe Phe
    370                 375                 380

Leu Phe Ile Leu Val Val Ala Ala Val Thr Leu Cys Arg Leu Arg Ser
385                 390                 395                 400

Pro Pro Lys Lys Gly Leu Gly Ser Pro Thr Val His Lys Ile Ser Arg
                405                 410                 415

Phe Pro Leu Lys Arg Gln Val Ser Leu Glu Ser Asn Ala Ser Met Ser
            420                 425                 430

Ser Asn Thr Pro Leu Val Arg Ile Ala Arg Leu Ser Ser Gly Glu Gly
        435                 440                 445

Pro Thr Leu Ala Asn Val Ser Glu Leu Glu Leu Pro Ala Asp Pro Lys
    450                 455                 460

Trp Glu Leu Ser Arg Ala Arg Leu Thr Leu Gly Lys Pro Leu Gly Glu
465                 470                 475                 480

Gly Cys Phe Gly Gln Val Val Met Ala Glu Ala Ile Gly Ile Asp Lys
                485                 490                 495

Asp Arg Ala Ala Lys Pro Val Thr Val Ala Val Lys Met Leu Lys Asp
            500                 505                 510

Asp Ala Thr Asp Lys Asp Leu Ser Asp Leu Val Ser Glu Met Glu Met
        515                 520                 525

Met Lys Met Ile Gly Lys His Lys Asn Ile Ile Asn Leu Leu Gly Ala
    530                 535                 540

Cys Thr Gln Gly Gly Pro Leu Tyr Val Leu Val Glu Tyr Ala Ala Lys
545                 550                 555                 560

Gly Asn Leu Arg Glu Phe Leu Arg Ala Arg Arg Pro Pro Gly Leu Asp
                565                 570                 575

Tyr Ser Phe Asp Thr Cys Lys Pro Pro Glu Glu Gln Leu Thr Phe Lys
            580                 585                 590

Asp Leu Val Ser Cys Ala Tyr Gln Val Ala Arg Gly Met Glu Tyr Leu
        595                 600                 605

Ala Ser Gln Lys Cys Ile His Arg Asp Leu Ala Ala Arg Asn Val Leu
    610                 615                 620
```

-continued

Val Thr Glu Asp Asn Val Met Lys Ile Ala Asp Phe Gly Leu Ala Arg
625 630 635 640

Asp Val His Asn Leu Asp Tyr Tyr Lys Lys Thr Thr Asn Gly Arg Leu
645 650 655

Pro Val Lys Trp Met Ala Pro Glu Ala Leu Phe Asp Arg Val Tyr Thr
660 665 670

His Gln Ser Asp Val Trp Ser Phe Gly Val Leu Leu Trp Glu Ile Phe
675 680 685

Thr Leu Gly Gly Ser Pro Tyr Pro Gly Ile Pro Val Glu Glu Leu Phe
690 695 700

Lys Leu Leu Lys Glu Gly His Arg Met Asp Lys Pro Ala Asn Cys Thr
705 710 715 720

His Asp Leu Tyr Met Ile Met Arg Glu Cys Trp His Ala Ala Pro Ser
725 730 735

Gln Arg Pro Thr Phe Lys Gln Leu Val Glu Asp Leu Asp Arg Val Leu
740 745 750

Thr Val Thr Ser Thr Asp Glu Tyr Leu Asp Leu Ser Ala Pro Phe Glu
755 760 765

Gln Tyr Ser Pro Gly Gly Gln Asp Thr Pro Ser Ser Ser Ser Ser Gly
770 775 780

Asp Asp Ser Val Phe Ala His Asp Leu Leu Pro Pro Ala Pro Pro Ser
785 790 795 800

Ser Gly Gly Ser Arg Thr
805

<210> SEQ ID NO 23
<211> LENGTH: 404
<212> TYPE: PRT
<213> ORGANISM: Homo sapiens

<400> SEQUENCE: 23

Met Ala Met Val Thr Gly Gly Trp Gly Gly Pro Gly Gly Asp Thr Asn
1 5 10 15

Gly Val Asp Lys Ala Gly Gly Tyr Pro Arg Ala Ala Glu Asp Asp Ser
20 25 30

Ala Ser Pro Pro Gly Ala Ala Ser Asp Ala Glu Pro Gly Asp Glu Glu
35 40 45

Arg Pro Gly Leu Gln Val Asp Cys Val Val Cys Gly Asp Lys Ser Ser
50 55 60

Gly Lys His Tyr Gly Val Phe Thr Cys Glu Gly Cys Lys Ser Phe Phe
65 70 75 80

Lys Arg Ser Ile Arg Arg Asn Leu Ser Tyr Thr Cys Arg Ser Asn Arg
85 90 95

Asp Cys Gln Ile Asp Gln His His Arg Asn Gln Cys Gln Tyr Cys Arg
100 105 110

Leu Lys Lys Cys Phe Arg Val Gly Met Arg Lys Glu Ala Val Gln Arg
115 120 125

Gly Arg Ile Pro His Ser Leu Pro Gly Ala Val Ala Ala Ser Ser Gly
130 135 140

Ser Pro Pro Gly Ser Ala Leu Ala Ala Val Ala Ser Gly Gly Asp Leu
145 150 155 160

Phe Pro Gly Gln Pro Val Ser Glu Leu Ile Ala Gln Leu Leu Arg Ala
165 170 175

Glu Pro Tyr Pro Ala Ala Ala Gly Arg Phe Gly Ala Gly Gly Gly Ala
180 185 190

-continued

```
Ala Gly Ala Val Leu Gly Ile Asp Asn Val Cys Glu Leu Ala Ala Arg
        195                 200                 205

Leu Leu Phe Ser Thr Val Glu Trp Ala Arg His Ala Pro Phe Phe Pro
    210                 215                 220

Glu Leu Pro Val Ala Asp Gln Val Ala Leu Leu Arg Leu Ser Trp Ser
225                 230                 235                 240

Glu Leu Phe Val Leu Asn Ala Ala Gln Ala Ala Leu Pro Leu His Thr
                245                 250                 255

Ala Pro Leu Leu Ala Ala Ala Gly Leu His Ala Ala Pro Met Ala Ala
            260                 265                 270

Glu Arg Ala Val Ala Phe Met Asp Gln Val Arg Ala Phe Gln Glu Gln
        275                 280                 285

Val Asp Lys Leu Gly Arg Leu Gln Val Asp Ser Ala Glu Tyr Gly Cys
    290                 295                 300

Leu Lys Ala Ile Ala Leu Phe Thr Pro Asp Ala Cys Gly Leu Ser Asp
305                 310                 315                 320

Pro Ala His Val Glu Ser Leu Gln Glu Lys Ala Gln Val Ala Leu Thr
                325                 330                 335

Glu Tyr Val Arg Ala Gln Tyr Pro Ser Gln Pro Gln Arg Phe Gly Arg
            340                 345                 350

Leu Leu Leu Arg Leu Pro Ala Leu Arg Ala Val Pro Ala Ser Leu Ile
        355                 360                 365

Ser Gln Leu Phe Phe Met Arg Leu Val Gly Lys Thr Pro Ile Glu Thr
    370                 375                 380

Leu Ile Arg Asp Met Leu Leu Ser Gly Ser Thr Phe Asn Trp Pro Tyr
385                 390                 395                 400

Gly Ser Gly Gln


<210> SEQ ID NO 24
<211> LENGTH: 1977
<212> TYPE: PRT
<213> ORGANISM: Homo sapiens

<400> SEQUENCE: 24

Met Ala Met Leu Pro Pro Pro Gly Pro Gln Ser Phe Val His Phe Thr
1               5                   10                  15

Lys Gln Ser Leu Ala Leu Ile Glu Gln Arg Ile Ala Glu Arg Lys Ser
            20                  25                  30

Lys Glu Pro Lys Glu Glu Lys Lys Asp Asp Asp Glu Glu Ala Pro Lys
        35                  40                  45

Pro Ser Ser Asp Leu Glu Ala Gly Lys Gln Leu Pro Phe Ile Tyr Gly
    50                  55                  60

Asp Ile Pro Pro Gly Met Val Ser Glu Pro Leu Glu Asp Leu Asp Pro
65                  70                  75                  80

Tyr Tyr Ala Asp Lys Lys Thr Phe Ile Val Leu Asn Lys Gly Lys Thr
                85                  90                  95

Ile Phe Arg Phe Asn Ala Thr Pro Ala Leu Tyr Met Leu Ser Pro Phe
            100                 105                 110

Ser Pro Leu Arg Arg Ile Ser Ile Lys Ile Leu Val His Ser Leu Phe
        115                 120                 125

Ser Met Leu Ile Met Cys Thr Ile Leu Thr Asn Cys Ile Phe Met Thr
    130                 135                 140

Met Asn Asn Pro Pro Asp Trp Thr Lys Asn Val Glu Tyr Thr Phe Thr
145                 150                 155                 160
```

-continued

```
Gly Ile Tyr Thr Phe Glu Ser Leu Val Lys Ile Leu Ala Arg Gly Phe
                165                 170                 175

Cys Val Gly Glu Phe Thr Phe Leu Arg Asp Pro Trp Asn Trp Leu Asp
            180                 185                 190

Phe Val Val Ile Val Phe Ala Tyr Leu Thr Glu Phe Val Asn Leu Gly
        195                 200                 205

Asn Val Ser Ala Leu Arg Thr Phe Arg Val Leu Arg Ala Leu Lys Thr
    210                 215                 220

Ile Ser Val Ile Pro Gly Leu Lys Thr Ile Val Gly Ala Leu Ile Gln
225                 230                 235                 240

Ser Val Lys Lys Leu Ser Asp Val Met Ile Leu Thr Val Phe Cys Leu
                245                 250                 255

Ser Val Phe Ala Leu Ile Gly Leu Gln Leu Phe Met Gly Asn Leu Lys
            260                 265                 270

His Lys Cys Phe Arg Asn Ser Leu Glu Asn Asn Glu Thr Leu Glu Ser
        275                 280                 285

Ile Met Asn Thr Leu Glu Ser Glu Glu Asp Phe Arg Lys Tyr Phe Tyr
    290                 295                 300

Tyr Leu Glu Gly Ser Lys Asp Ala Leu Leu Cys Gly Phe Ser Thr Asp
305                 310                 315                 320

Ser Gly Gln Cys Pro Glu Gly Tyr Thr Cys Val Lys Ile Gly Arg Asn
                325                 330                 335

Pro Asp Tyr Gly Tyr Thr Ser Phe Asp Thr Phe Ser Trp Ala Phe Leu
            340                 345                 350

Ala Leu Phe Arg Leu Met Thr Gln Asp Tyr Trp Glu Asn Leu Tyr Gln
        355                 360                 365

Gln Thr Leu Arg Ala Ala Gly Lys Thr Tyr Met Ile Phe Phe Val Val
    370                 375                 380

Val Ile Phe Leu Gly Ser Phe Tyr Leu Ile Asn Leu Ile Leu Ala Val
385                 390                 395                 400

Val Ala Met Ala Tyr Glu Glu Gln Asn Gln Ala Asn Ile Glu Glu Ala
                405                 410                 415

Lys Gln Lys Glu Leu Glu Phe Gln Gln Met Leu Asp Arg Leu Lys Lys
            420                 425                 430

Glu Gln Glu Glu Ala Glu Ala Ile Ala Ala Ala Ala Ala Glu Tyr Thr
        435                 440                 445

Ser Ile Arg Arg Ser Arg Ile Met Gly Leu Ser Glu Ser Ser Ser Glu
    450                 455                 460

Thr Ser Lys Leu Ser Ser Lys Ser Ala Lys Glu Arg Arg Asn Arg Arg
465                 470                 475                 480

Lys Lys Lys Asn Gln Lys Lys Leu Ser Ser Gly Glu Glu Lys Gly Asp
                485                 490                 495

Ala Glu Lys Leu Ser Lys Ser Glu Ser Glu Asp Ser Ile Arg Arg Lys
            500                 505                 510

Ser Phe His Leu Gly Val Glu Gly His Arg Arg Ala His Glu Lys Arg
        515                 520                 525

Leu Ser Thr Pro Asn Gln Ser Pro Leu Ser Ile Arg Gly Ser Leu Phe
    530                 535                 540

Ser Ala Arg Arg Ser Ser Arg Thr Ser Leu Phe Ser Phe Lys Gly Arg
545                 550                 555                 560

Gly Arg Asp Ile Gly Ser Glu Thr Glu Phe Ala Asp Asp Glu His Ser
                565                 570                 575
```

-continued

```
Ile Phe Gly Asp Asn Glu Ser Arg Arg Gly Ser Leu Phe Val Pro His
            580                 585                 590

Arg Pro Gln Glu Arg Arg Ser Ser Asn Ile Ser Gln Ala Ser Arg Ser
        595                 600                 605

Pro Pro Met Leu Pro Val Asn Gly Lys Met His Ser Ala Val Asp Cys
    610                 615                 620

Asn Gly Val Val Ser Leu Val Asp Gly Arg Ser Ala Leu Met Leu Pro
625                 630                 635                 640

Asn Gly Gln Leu Leu Pro Glu Gly Thr Thr Asn Gln Ile His Lys Lys
                645                 650                 655

Arg Arg Cys Ser Ser Tyr Leu Leu Ser Glu Asp Met Leu Asn Asp Pro
            660                 665                 670

Asn Leu Arg Gln Arg Ala Met Ser Arg Ala Ser Ile Leu Thr Asn Thr
        675                 680                 685

Val Glu Glu Leu Glu Glu Ser Arg Gln Lys Cys Pro Pro Trp Trp Tyr
    690                 695                 700

Arg Phe Ala His Lys Phe Leu Ile Trp Asn Cys Ser Pro Tyr Trp Ile
705                 710                 715                 720

Lys Phe Lys Lys Cys Ile Tyr Phe Ile Val Met Asp Pro Phe Val Asp
                725                 730                 735

Leu Ala Ile Thr Ile Cys Ile Val Leu Asn Thr Leu Phe Met Ala Met
            740                 745                 750

Glu His His Pro Met Thr Glu Glu Phe Lys Asn Val Leu Ala Ile Gly
        755                 760                 765

Asn Leu Val Phe Thr Gly Ile Phe Ala Ala Glu Met Val Leu Lys Leu
    770                 775                 780

Ile Ala Met Asp Pro Tyr Glu Tyr Phe Gln Val Gly Trp Asn Ile Phe
785                 790                 795                 800

Asp Ser Leu Ile Val Thr Leu Ser Leu Val Glu Leu Phe Leu Ala Asp
                805                 810                 815

Val Glu Gly Leu Ser Val Leu Arg Ser Phe Arg Leu Leu Arg Val Phe
            820                 825                 830

Lys Leu Ala Lys Ser Trp Pro Thr Leu Asn Met Leu Ile Lys Ile Ile
        835                 840                 845

Gly Asn Ser Val Gly Ala Leu Gly Asn Leu Thr Leu Val Leu Ala Ile
    850                 855                 860

Ile Val Phe Ile Phe Ala Val Val Gly Met Gln Leu Phe Gly Lys Ser
865                 870                 875                 880

Tyr Lys Glu Cys Val Cys Lys Ile Asn Asp Asp Cys Thr Leu Pro Arg
                885                 890                 895

Trp His Met Asn Asp Phe Phe His Ser Phe Leu Ile Val Phe Arg Val
            900                 905                 910

Leu Cys Gly Glu Trp Ile Glu Thr Met Trp Asp Cys Met Glu Val Ala
        915                 920                 925

Gly Gln Ala Met Cys Leu Ile Val Tyr Met Met Val Met Val Ile Gly
    930                 935                 940

Asn Leu Val Val Leu Asn Leu Phe Leu Ala Leu Leu Leu Ser Ser Phe
945                 950                 955                 960

Ser Ser Asp Asn Leu Thr Ala Ile Glu Glu Asp Pro Asp Ala Asn Asn
                965                 970                 975

Leu Gln Ile Ala Val Thr Arg Ile Lys Lys Gly Ile Asn Tyr Val Lys
            980                 985                 990

Gln Thr Leu Arg Glu Phe Ile Leu  Lys Ala Phe Ser Lys  Lys Pro Lys
```

-continued

```
        995                 1000                1005

Ile Ser  Arg Glu Ile Arg Gln  Ala Glu Asp Leu Asn  Thr Lys Lys
    1010                 1015                 1020

Glu Asn  Tyr Ile Ser Asn His  Thr Leu Ala Glu Met  Ser Lys Gly
    1025                 1030                 1035

His Asn  Phe Leu Lys Glu Lys  Asp Lys Ile Ser Gly  Phe Gly Ser
    1040                 1045                 1050

Ser Val  Asp Lys His Leu Met  Glu Asp Ser Asp Gly  Gln Ser Phe
    1055                 1060                 1065

Ile His  Asn Pro Ser Leu Thr  Val Thr Val Pro Ile  Ala Pro Gly
    1070                 1075                 1080

Glu Ser  Asp Leu Glu Asn Met  Asn Ala Glu Glu Leu  Ser Ser Asp
    1085                 1090                 1095

Ser Asp  Ser Glu Tyr Ser Lys  Val Arg Leu Asn Arg  Ser Ser Ser
    1100                 1105                 1110

Ser Glu  Cys Ser Thr Val Asp  Asn Pro Leu Pro Gly  Glu Gly Glu
    1115                 1120                 1125

Glu Ala  Glu Ala Glu Pro Met  Asn Ser Asp Glu Pro  Glu Ala Cys
    1130                 1135                 1140

Phe Thr  Asp Gly Cys Val Arg  Arg Phe Ser Cys Cys  Gln Val Asn
    1145                 1150                 1155

Ile Glu  Ser Gly Lys Gly Lys  Ile Trp Trp Asn Ile  Arg Lys Thr
    1160                 1165                 1170

Cys Tyr  Lys Ile Val Glu His  Ser Trp Phe Glu Ser  Phe Ile Val
    1175                 1180                 1185

Leu Met  Ile Leu Leu Ser Ser  Gly Ala Leu Ala Phe  Glu Asp Ile
    1190                 1195                 1200

Tyr Ile  Glu Arg Lys Lys Thr  Ile Lys Ile Ile Leu  Glu Tyr Ala
    1205                 1210                 1215

Asp Lys  Ile Phe Thr Tyr Ile  Phe Ile Leu Glu Met  Leu Leu Lys
    1220                 1225                 1230

Trp Ile  Ala Tyr Gly Tyr Lys  Thr Tyr Phe Thr Asn  Ala Trp Cys
    1235                 1240                 1245

Trp Leu  Asp Phe Leu Ile Val  Asp Val Ser Leu Val  Thr Leu Val
    1250                 1255                 1260

Ala Asn  Thr Leu Gly Tyr Ser  Asp Leu Gly Pro Ile  Lys Ser Leu
    1265                 1270                 1275

Arg Thr  Leu Arg Ala Leu Arg  Pro Leu Arg Ala Leu  Ser Arg Phe
    1280                 1285                 1290

Glu Gly  Met Arg Val Val Val  Asn Ala Leu Ile Gly  Ala Ile Pro
    1295                 1300                 1305

Ser Ile  Met Asn Val Leu Leu  Val Cys Leu Ile Phe  Trp Leu Ile
    1310                 1315                 1320

Phe Ser  Ile Met Gly Val Asn  Leu Phe Ala Gly Lys  Phe Tyr Glu
    1325                 1330                 1335

Cys Ile  Asn Thr Thr Asp Gly  Ser Arg Phe Pro Ala  Ser Gln Val
    1340                 1345                 1350

Pro Asn  Arg Ser Glu Cys Phe  Ala Leu Met Asn Val  Ser Gln Asn
    1355                 1360                 1365

Val Arg  Trp Lys Asn Leu Lys  Val Asn Phe Asp Asn  Val Gly Leu
    1370                 1375                 1380

Gly Tyr  Leu Ser Leu Leu Gln  Val Ala Thr Phe Lys  Gly Trp Thr
    1385                 1390                 1395
```

-continued

```
Ile Ile  Met Tyr Ala Ala Val  Asp Ser Val Asn Val  Asp Lys Gln
    1400                 1405                 1410

Pro Lys  Tyr Glu Tyr Ser Leu  Tyr Met Tyr Ile Tyr  Phe Val Val
    1415                 1420                 1425

Phe Ile  Ile Phe Gly Ser Phe  Phe Thr Leu Asn Leu  Phe Ile Gly
    1430                 1435                 1440

Val Ile  Ile Asp Asn Phe Asn  Gln Gln Lys Lys Lys  Leu Gly Gly
    1445                 1450                 1455

Gln Asp  Ile Phe Met Thr Glu  Glu Gln Lys Lys Tyr  Tyr Asn Ala
    1460                 1465                 1470

Met Lys  Lys Leu Gly Ser Lys  Lys Pro Gln Lys Pro  Ile Pro Arg
    1475                 1480                 1485

Pro Gly  Asn Lys Ile Gln Gly  Cys Ile Phe Asp Leu  Val Thr Asn
    1490                 1495                 1500

Gln Ala  Phe Asp Ile Ser Ile  Met Val Leu Ile Cys  Leu Asn Met
    1505                 1510                 1515

Val Thr  Met Met Val Glu Lys  Glu Gly Gln Ser Gln  His Met Thr
    1520                 1525                 1530

Glu Val  Leu Tyr Trp Ile Asn  Val Val Phe Ile Ile  Leu Phe Thr
    1535                 1540                 1545

Gly Glu  Cys Val Leu Lys Leu  Ile Ser Leu Arg His  Tyr Tyr Phe
    1550                 1555                 1560

Thr Val  Gly Trp Asn Ile Phe  Asp Phe Val Val Val  Ile Ile Ser
    1565                 1570                 1575

Ile Val  Gly Met Phe Leu Ala  Asp Leu Ile Glu Thr  Tyr Phe Val
    1580                 1585                 1590

Ser Pro  Thr Leu Phe Arg Val  Ile Arg Leu Ala Arg  Ile Gly Arg
    1595                 1600                 1605

Ile Leu  Arg Leu Val Lys Gly  Ala Lys Gly Ile Arg  Thr Leu Leu
    1610                 1615                 1620

Phe Ala  Leu Met Met Ser Leu  Pro Ala Leu Phe Asn  Ile Gly Leu
    1625                 1630                 1635

Leu Leu  Phe Leu Val Met Phe  Ile Tyr Ala Ile Phe  Gly Met Ser
    1640                 1645                 1650

Asn Phe  Ala Tyr Val Lys Lys  Glu Asp Gly Ile Asn  Asp Met Phe
    1655                 1660                 1665

Asn Phe  Glu Thr Phe Gly Asn  Ser Met Ile Cys Leu  Phe Gln Ile
    1670                 1675                 1680

Thr Thr  Ser Ala Gly Trp Asp  Gly Leu Leu Ala Pro  Ile Leu Asn
    1685                 1690                 1695

Ser Lys  Pro Pro Asp Cys Asp  Pro Lys Lys Val His  Pro Gly Ser
    1700                 1705                 1710

Ser Val  Glu Gly Asp Cys Gly  Asn Pro Ser Val Gly  Ile Phe Tyr
    1715                 1720                 1725

Phe Val  Ser Tyr Ile Ile Ile  Ser Phe Leu Val Val  Val Asn Met
    1730                 1735                 1740

Tyr Ile  Ala Val Ile Leu Glu  Asn Phe Ser Val Ala  Thr Glu Glu
    1745                 1750                 1755

Ser Thr  Glu Pro Leu Ser Glu  Asp Asp Phe Glu Met  Phe Tyr Glu
    1760                 1765                 1770

Val Trp  Glu Lys Phe Asp Pro  Asp Ala Thr Gln Phe  Ile Glu Phe
    1775                 1780                 1785
```

-continued

```
Ser Lys  Leu Ser Asp Phe Ala  Ala Ala Leu Asp Pro  Pro Leu Leu
    1790                 1795                 1800

Ile Ala  Lys Pro Asn Lys Val  Gln Leu Ile Ala Met  Asp Leu Pro
    1805                 1810                 1815

Met Val  Ser Gly Asp Arg Ile  His Cys Leu Asp Ile  Leu Phe Ala
    1820                 1825                 1830

Phe Thr  Lys Arg Val Leu Gly  Glu Ser Gly Glu Met  Asp Ser Leu
    1835                 1840                 1845

Arg Ser  Gln Met Glu Glu Arg  Phe Met Ser Ala Asn  Pro Ser Lys
    1850                 1855                 1860

Val Ser  Tyr Glu Pro Ile Thr  Thr Thr Leu Lys Arg  Lys Gln Glu
    1865                 1870                 1875

Asp Val  Ser Ala Thr Val Ile  Gln Arg Ala Tyr Arg  Arg Tyr Arg
    1880                 1885                 1890

Leu Arg  Gln Asn Val Lys Asn  Ile Ser Ser Ile Tyr  Ile Lys Asp
    1895                 1900                 1905

Gly Asp  Arg Asp Asp Asp Leu  Leu Asn Lys Lys Asp  Met Ala Phe
    1910                 1915                 1920

Asp Asn  Val Asn Glu Asn Ser  Ser Pro Glu Lys Thr  Asp Ala Thr
    1925                 1930                 1935

Ser Ser  Thr Thr Ser Pro Pro  Ser Tyr Asp Ser Val  Thr Lys Pro
    1940                 1945                 1950

Asp Lys  Glu Lys Tyr Glu Gln  Asp Arg Thr Glu Lys  Glu Asp Lys
    1955                 1960                 1965

Gly Lys  Asp Ser Lys Glu Ser  Lys Lys
    1970                 1975
```

<210> SEQ ID NO 25
<211> LENGTH: 365
<212> TYPE: PRT
<213> ORGANISM: Homo sapiens

<400> SEQUENCE: 25

```
Met Ser Leu Ile Arg Lys Lys Gly Phe Tyr Lys Gln Asp Val Asn Lys
1               5                   10                  15

Thr Ala Trp Glu Leu Pro Lys Thr Tyr Val Ser Pro Thr His Val Gly
            20                  25                  30

Ser Gly Ala Tyr Gly Ser Val Cys Ser Ala Ile Asp Lys Arg Ser Gly
        35                  40                  45

Glu Lys Val Ala Ile Lys Lys Leu Ser Arg Pro Phe Gln Ser Glu Ile
    50                  55                  60

Phe Ala Lys Arg Ala Tyr Arg Glu Leu Leu Leu Leu Lys His Met Gln
65                  70                  75                  80

His Glu Asn Val Ile Gly Leu Leu Asp Val Phe Thr Pro Ala Ser Ser
                85                  90                  95

Leu Arg Asn Phe Tyr Asp Phe Tyr Leu Val Met Pro Phe Met Gln Thr
            100                 105                 110

Asp Leu Gln Lys Ile Met Gly Met Glu Phe Ser Glu Glu Lys Ile Gln
        115                 120                 125

Tyr Leu Val Tyr Gln Met Leu Lys Gly Leu Lys Tyr Ile His Ser Ala
    130                 135                 140

Gly Val Val His Arg Asp Leu Lys Pro Gly Asn Leu Ala Val Asn Glu
145                 150                 155                 160

Asp Cys Glu Leu Lys Ile Leu Asp Phe Gly Leu Ala Arg His Ala Asp
                165                 170                 175
```

-continued

```
Ala Glu Met Thr Gly Tyr Val Val Thr Arg Trp Tyr Arg Ala Pro Glu
            180                 185                 190

Val Ile Leu Ser Trp Met His Tyr Asn Gln Thr Val Asp Ile Trp Ser
        195                 200                 205

Val Gly Cys Ile Met Ala Glu Met Leu Thr Gly Lys Thr Leu Phe Lys
    210                 215                 220

Gly Lys Asp Tyr Leu Asp Gln Leu Thr Gln Ile Leu Lys Val Thr Gly
225                 230                 235                 240

Val Pro Gly Thr Glu Phe Val Gln Lys Leu Asn Asp Lys Ala Ala Lys
                245                 250                 255

Ser Tyr Ile Gln Ser Leu Pro Gln Thr Pro Arg Lys Asp Phe Thr Gln
            260                 265                 270

Leu Phe Pro Arg Ala Ser Pro Gln Ala Ala Asp Leu Leu Glu Lys Met
        275                 280                 285

Leu Glu Leu Asp Val Asp Lys Arg Leu Thr Ala Ala Gln Ala Leu Thr
    290                 295                 300

His Pro Phe Phe Glu Pro Phe Arg Asp Pro Glu Glu Glu Thr Glu Ala
305                 310                 315                 320

Gln Gln Pro Phe Asp Asp Ser Leu Glu His Glu Lys Leu Thr Val Asp
                325                 330                 335

Glu Trp Lys Gln His Ile Tyr Lys Glu Ile Val Asn Phe Ser Pro Ile
            340                 345                 350

Ala Arg Lys Asp Ser Arg Arg Arg Ser Gly Met Lys Leu
        355                 360                 365


<210> SEQ ID NO 26
<211> LENGTH: 452
<212> TYPE: PRT
<213> ORGANISM: Homo sapiens

<400> SEQUENCE: 26

Met Asp Asp Ile Phe Thr Gln Cys Arg Glu Gly Asn Ala Val Ala Val
1               5                   10                  15

Arg Leu Trp Leu Asp Asn Thr Glu Asn Asp Leu Asn Gln Gly Asp Asp
            20                  25                  30

His Gly Phe Ser Pro Leu His Trp Ala Cys Arg Glu Gly Arg Ser Ala
        35                  40                  45

Val Val Glu Met Leu Ile Met Arg Gly Ala Arg Ile Asn Val Met Asn
    50                  55                  60

Arg Gly Asp Asp Thr Pro Leu His Leu Ala Ala Ser His Gly His Arg
65                  70                  75                  80

Asp Ile Val Gln Lys Leu Leu Gln Tyr Lys Ala Asp Ile Asn Ala Val
                85                  90                  95

Asn Glu His Gly Asn Val Pro Leu His Tyr Ala Cys Phe Trp Gly Gln
            100                 105                 110

Asp Gln Val Ala Glu Asp Leu Val Ala Asn Gly Ala Leu Val Ser Ile
        115                 120                 125

Cys Asn Lys Tyr Gly Glu Met Pro Val Asp Lys Ala Lys Ala Pro Leu
    130                 135                 140

Arg Glu Leu Leu Arg Glu Arg Ala Glu Lys Met Gly Gln Asn Leu Asn
145                 150                 155                 160

Arg Ile Pro Tyr Lys Asp Thr Phe Trp Lys Gly Thr Thr Arg Thr Arg
                165                 170                 175

Pro Arg Asn Gly Thr Leu Asn Lys His Ser Gly Ile Asp Phe Lys Gln
```

-continued

```
        180                 185                 190

Leu Asn Phe Leu Thr Lys Leu Asn Glu Asn His Ser Gly Glu Leu Trp
    195                 200                 205

Lys Gly Arg Trp Gln Gly Asn Asp Ile Val Val Lys Val Leu Lys Val
    210                 215                 220

Arg Asp Trp Ser Thr Arg Lys Ser Arg Asp Phe Asn Glu Glu Cys Pro
225                 230                 235                 240

Arg Leu Arg Ile Phe Ser His Pro Asn Val Leu Pro Val Leu Gly Ala
                245                 250                 255

Cys Gln Ser Pro Pro Ala Pro His Pro Thr Leu Ile Thr His Trp Met
            260                 265                 270

Pro Tyr Gly Ser Leu Tyr Asn Val Leu His Glu Gly Thr Asn Phe Val
        275                 280                 285

Val Asp Gln Ser Gln Ala Val Lys Phe Ala Leu Asp Met Ala Arg Gly
    290                 295                 300

Met Ala Phe Leu His Thr Leu Glu Pro Leu Ile Pro Arg His Ala Leu
305                 310                 315                 320

Asn Ser Arg Ser Val Met Ile Asp Glu Asp Met Thr Ala Arg Ile Ser
                325                 330                 335

Met Ala Asp Val Lys Phe Ser Phe Gln Cys Pro Gly Arg Met Tyr Ala
            340                 345                 350

Pro Ala Trp Val Ala Pro Glu Ala Leu Gln Lys Lys Pro Glu Asp Thr
        355                 360                 365

Asn Arg Arg Ser Ala Asp Met Trp Ser Phe Ala Val Leu Leu Trp Glu
    370                 375                 380

Leu Val Thr Arg Glu Val Pro Phe Ala Asp Leu Ser Asn Met Glu Ile
385                 390                 395                 400

Gly Met Lys Val Ala Leu Glu Gly Leu Arg Pro Thr Ile Pro Pro Gly
                405                 410                 415

Ile Ser Pro His Val Cys Lys Leu Met Lys Ile Cys Met Asn Glu Asp
            420                 425                 430

Pro Ala Lys Arg Pro Lys Phe Asp Met Ile Val Pro Ile Leu Glu Lys
        435                 440                 445

Met Gln Asp Lys
    450


<210> SEQ ID NO 27
<211> LENGTH: 468
<212> TYPE: PRT
<213> ORGANISM: Homo sapiens

<400> SEQUENCE: 27

Met Ala Ala Arg Gly Ser Gly Pro Arg Ala Leu Arg Leu Leu Leu Leu
1               5                   10                  15

Val Gln Leu Val Ala Gly Ala Leu Arg Ser Ser Arg Ala Arg Arg Ala
            20                  25                  30

Ala Arg Arg Gly Leu Ser Glu Pro Ser Ser Ile Ala Lys His Glu Asp
        35                  40                  45

Ser Leu Leu Lys Asp Leu Phe Gln Asp Tyr Glu Arg Trp Val Arg Pro
    50                  55                  60

Val Glu His Leu Asn Asp Lys Ile Lys Ile Lys Phe Gly Leu Ala Ile
65                  70                  75                  80

Ser Gln Leu Val Asp Val Asp Glu Lys Asn Gln Leu Met Thr Thr Asn
                85                  90                  95
```

-continued

```
Val Trp Leu Lys Gln Glu Trp Ile Asp Val Lys Leu Arg Trp Asn Pro
            100                 105                 110

Asp Asp Tyr Gly Gly Ile Lys Val Ile Arg Val Pro Ser Asp Ser Ser
        115                 120                 125

Trp Thr Pro Asp Ile Val Leu Phe Asp Asn Ala Asp Gly Arg Phe Glu
    130                 135                 140

Gly Thr Ser Thr Lys Thr Val Ile Arg Tyr Asn Gly Thr Val Thr Trp
145                 150                 155                 160

Thr Pro Pro Ala Asn Tyr Lys Ser Ser Cys Thr Ile Asp Val Thr Phe
                165                 170                 175

Phe Pro Phe Asp Leu Gln Asn Cys Ser Met Lys Phe Gly Ser Trp Thr
            180                 185                 190

Tyr Asp Gly Ser Gln Val Asp Ile Ile Leu Glu Asp Gln Asp Val Asp
        195                 200                 205

Lys Arg Asp Phe Phe Asp Asn Gly Glu Trp Glu Ile Val Ser Ala Thr
    210                 215                 220

Gly Ser Lys Gly Asn Arg Thr Asp Ser Cys Cys Trp Tyr Pro Tyr Val
225                 230                 235                 240

Thr Tyr Ser Phe Val Ile Lys Arg Leu Pro Leu Phe Tyr Thr Leu Phe
                245                 250                 255

Leu Ile Ile Pro Cys Ile Gly Leu Ser Phe Leu Thr Val Leu Val Phe
            260                 265                 270

Tyr Leu Pro Ser Asn Glu Gly Glu Lys Ile Cys Leu Cys Thr Ser Val
        275                 280                 285

Leu Val Ser Leu Thr Val Phe Leu Leu Val Ile Glu Glu Ile Ile Pro
    290                 295                 300

Ser Ser Ser Lys Val Ile Pro Leu Ile Gly Glu Tyr Leu Val Phe Thr
305                 310                 315                 320

Met Ile Phe Val Thr Leu Ser Ile Met Val Thr Val Phe Ala Ile Asn
                325                 330                 335

Ile His His Arg Ser Ser Ser Thr His Asn Ala Met Ala Pro Leu Val
            340                 345                 350

Arg Lys Ile Phe Leu His Thr Leu Pro Lys Leu Leu Ser Met Arg Ser
        355                 360                 365

His Val Asp Arg Tyr Phe Thr Gln Lys Glu Glu Thr Glu Ser Gly Ser
    370                 375                 380

Gly Pro Lys Ser Ser Arg Asn Thr Leu Glu Ala Ala Leu Asp Ser Ile
385                 390                 395                 400

Arg Tyr Ile Thr Thr His Ile Met Lys Glu Asn Asp Val Arg Glu Val
                405                 410                 415

Val Glu Asp Trp Lys Phe Ile Ala Gln Val Leu Asp Arg Met Phe Leu
            420                 425                 430

Trp Thr Phe Leu Phe Val Ser Ile Val Gly Ser Leu Gly Leu Phe Val
        435                 440                 445

Pro Val Ile Tyr Lys Trp Ala Asn Ile Leu Ile Pro Val His Ile Gly
    450                 455                 460

Asn Ala Asn Lys
465
```

<210> SEQ ID NO 28
<211> LENGTH: 231
<212> TYPE: PRT
<213> ORGANISM: Homo sapiens

<400> SEQUENCE: 28

-continued

Met Ala Gly Lys Lys Val Leu Ile Val Tyr Ala His Gln Glu Pro Lys
1 5 10 15

Ser Phe Asn Gly Ser Leu Lys Asn Val Ala Val Asp Glu Leu Ser Arg
20 25 30

Gln Gly Cys Thr Val Thr Val Ser Asp Leu Tyr Ala Met Asn Phe Glu
35 40 45

Pro Arg Ala Thr Asp Lys Asp Ile Thr Gly Thr Leu Ser Asn Pro Glu
50 55 60

Val Phe Asn Tyr Gly Val Glu Thr His Glu Ala Tyr Lys Gln Arg Ser
65 70 75 80

Leu Ala Ser Asp Ile Thr Asp Glu Gln Lys Lys Val Arg Glu Ala Asp
85 90 95

Leu Val Ile Phe Gln Phe Pro Leu Tyr Trp Phe Ser Val Pro Ala Ile
100 105 110

Leu Lys Gly Trp Met Asp Arg Val Leu Cys Gln Gly Phe Ala Phe Asp
115 120 125

Ile Pro Gly Phe Tyr Asp Ser Gly Leu Leu Gln Gly Lys Leu Ala Leu
130 135 140

Leu Ser Val Thr Thr Gly Gly Thr Ala Glu Met Tyr Thr Lys Thr Gly
145 150 155 160

Val Asn Gly Asp Ser Arg Tyr Phe Leu Trp Pro Leu Gln His Gly Thr
165 170 175

Leu His Phe Cys Gly Phe Lys Val Leu Ala Pro Gln Ile Ser Phe Ala
180 185 190

Pro Glu Ile Ala Ser Glu Glu Glu Arg Lys Gly Met Val Ala Ala Trp
195 200 205

Ser Gln Arg Leu Gln Thr Ile Trp Lys Glu Glu Pro Ile Pro Cys Thr
210 215 220

Ala His Trp His Phe Gly Gln
225 230

<210> SEQ ID NO 29
<211> LENGTH: 773
<212> TYPE: PRT
<213> ORGANISM: Homo sapiens

<400> SEQUENCE: 29

Met Thr Asn Gln Glu Lys Trp Ala His Leu Ser Pro Ser Glu Phe Ser
1 5 10 15

Gln Leu Gln Lys Tyr Ala Glu Tyr Ser Thr Lys Lys Leu Lys Asp Val
20 25 30

Leu Glu Glu Phe His Gly Asn Gly Val Leu Ala Lys Tyr Asn Pro Glu
35 40 45

Gly Lys Gln Asp Ile Leu Asn Gln Thr Ile Asp Phe Glu Gly Phe Lys
50 55 60

Leu Phe Met Lys Thr Phe Leu Glu Ala Glu Leu Pro Asp Asp Phe Thr
65 70 75 80

Ala His Leu Phe Met Ser Phe Ser Asn Lys Phe Pro His Ser Ser Pro
85 90 95

Met Val Lys Ser Lys Pro Ala Leu Leu Ser Gly Gly Leu Arg Met Asn
100 105 110

Lys Gly Ala Ile Thr Pro Pro Arg Thr Thr Ser Pro Ala Asn Thr Cys
115 120 125

Ser Pro Glu Val Ile His Leu Lys Asp Ile Val Cys Tyr Leu Ser Leu

-continued

```
    130                 135                 140

Leu Glu Arg Gly Arg Pro Glu Asp Lys Leu Glu Phe Met Phe Arg Leu
145                 150                 155                 160

Tyr Asp Thr Asp Gly Asn Gly Phe Leu Asp Ser Ser Glu Leu Glu Asn
                165                 170                 175

Ile Ile Ser Gln Met Met His Val Ala Glu Tyr Leu Glu Trp Asp Val
            180                 185                 190

Thr Glu Leu Asn Pro Ile Leu His Glu Met Met Glu Glu Ile Asp Tyr
        195                 200                 205

Asp His Asp Gly Thr Val Ser Leu Glu Glu Trp Ile Gln Gly Gly Met
    210                 215                 220

Thr Thr Ile Pro Leu Leu Val Leu Leu Gly Leu Glu Asn Asn Val Lys
225                 230                 235                 240

Asp Asp Gly Gln His Val Trp Arg Leu Lys His Phe Asn Lys Pro Ala
                245                 250                 255

Tyr Cys Asn Leu Cys Leu Asn Met Leu Ile Gly Val Gly Lys Gln Gly
            260                 265                 270

Leu Cys Cys Ser Phe Cys Lys Tyr Thr Val His Glu Arg Cys Val Ala
        275                 280                 285

Arg Ala Pro Pro Ser Cys Ile Lys Thr Tyr Val Lys Ser Lys Arg Asn
    290                 295                 300

Thr Asp Val Met His His Tyr Trp Val Glu Gly Asn Cys Pro Thr Lys
305                 310                 315                 320

Cys Asp Lys Cys His Lys Thr Val Lys Cys Tyr Gln Gly Leu Thr Gly
                325                 330                 335

Leu His Cys Val Trp Cys Gln Ile Thr Leu His Asn Lys Cys Ala Ser
            340                 345                 350

His Leu Lys Pro Glu Cys Asp Cys Gly Pro Leu Lys Asp His Ile Leu
        355                 360                 365

Pro Pro Thr Thr Ile Cys Pro Val Val Leu Gln Thr Leu Pro Thr Ser
    370                 375                 380

Gly Val Ser Val Pro Glu Glu Arg Gln Ser Thr Val Lys Lys Glu Lys
385                 390                 395                 400

Ser Gly Ser Gln Gln Pro Asn Lys Val Ile Asp Lys Asn Lys Met Gln
                405                 410                 415

Arg Ala Asn Ser Val Thr Val Asp Gly Gln Gly Leu Gln Val Thr Pro
            420                 425                 430

Val Pro Gly Thr His Pro Leu Leu Val Phe Val Asn Pro Lys Ser Gly
        435                 440                 445

Gly Lys Gln Gly Glu Arg Ile Tyr Arg Lys Phe Gln Tyr Leu Leu Asn
    450                 455                 460

Pro Arg Gln Val Tyr Ser Leu Ser Gly Asn Gly Pro Met Pro Gly Leu
465                 470                 475                 480

Asn Phe Phe Arg Asp Val Pro Asp Phe Arg Val Leu Ala Cys Gly Gly
                485                 490                 495

Asp Gly Thr Val Gly Trp Val Leu Asp Cys Ile Glu Lys Ala Asn Val
            500                 505                 510

Gly Lys His Pro Pro Val Ala Ile Leu Pro Leu Gly Thr Gly Asn Asp
        515                 520                 525

Leu Ala Arg Cys Leu Arg Trp Gly Gly Gly Tyr Glu Gly Glu Asn Leu
    530                 535                 540

Met Lys Ile Leu Lys Asp Ile Glu Asn Ser Thr Glu Ile Met Leu Asp
545                 550                 555                 560
```

-continued

```
Arg Trp Lys Phe Glu Val Ile Pro Asn Asp Lys Asp Glu Lys Gly Asp
                565                 570                 575

Pro Val Pro Tyr Ser Ile Ile Asn Asn Tyr Phe Ser Ile Gly Val Asp
            580                 585                 590

Ala Ser Ile Ala His Arg Phe His Ile Met Arg Glu Lys His Pro Glu
        595                 600                 605

Lys Phe Asn Ser Arg Met Lys Asn Lys Phe Trp Tyr Phe Glu Phe Gly
    610                 615                 620

Thr Ser Glu Thr Phe Ser Ala Thr Cys Lys Lys Leu His Glu Ser Val
625                 630                 635                 640

Glu Ile Glu Cys Asp Gly Val Gln Ile Asp Leu Ile Asn Ile Ser Leu
                645                 650                 655

Glu Gly Ile Ala Ile Leu Asn Ile Pro Ser Met His Gly Gly Ser Asn
            660                 665                 670

Leu Trp Gly Glu Ser Lys Lys Arg Arg Ser His Arg Arg Ile Glu Lys
        675                 680                 685

Lys Gly Ser Asp Lys Arg Thr Thr Val Thr Asp Ala Lys Glu Leu Lys
    690                 695                 700

Phe Ala Ser Gln Asp Leu Ser Asp Gln Leu Leu Glu Val Val Gly Leu
705                 710                 715                 720

Glu Gly Ala Met Glu Met Gly Gln Ile Tyr Thr Gly Leu Lys Ser Ala
                725                 730                 735

Gly Arg Arg Leu Ala Gln Cys Ser Cys Val Val Ile Arg Thr Ser Lys
            740                 745                 750

Ser Leu Pro Met Gln Ile Asp Gly Glu Pro Trp Met Gln Thr Pro Cys
        755                 760                 765

Thr Val Ser Thr Glu
    770


<210> SEQ ID NO 30
<211> LENGTH: 804
<212> TYPE: PRT
<213> ORGANISM: Homo sapiens

<400> SEQUENCE: 30

Met Thr Asn Gln Glu Lys Trp Ala His Leu Ser Pro Ser Glu Phe Ser
1               5                   10                  15

Gln Leu Gln Lys Tyr Ala Glu Tyr Ser Thr Lys Lys Leu Lys Asp Val
            20                  25                  30

Leu Glu Glu Phe His Gly Asn Gly Val Leu Ala Lys Tyr Asn Pro Glu
        35                  40                  45

Gly Lys Gln Asp Ile Leu Asn Gln Thr Ile Asp Phe Glu Gly Phe Lys
    50                  55                  60

Leu Phe Met Lys Thr Phe Leu Glu Ala Glu Leu Pro Asp Asp Phe Thr
65                  70                  75                  80

Ala His Leu Phe Met Ser Phe Ser Asn Lys Phe Pro His Ser Ser Pro
                85                  90                  95

Met Val Lys Ser Lys Pro Ala Leu Leu Ser Gly Gly Leu Arg Met Asn
            100                 105                 110

Lys Gly Ala Ile Thr Pro Pro Arg Thr Thr Ser Pro Ala Asn Thr Cys
        115                 120                 125

Ser Pro Glu Val Ile His Leu Lys Asp Ile Val Cys Tyr Leu Ser Leu
    130                 135                 140

Leu Glu Arg Gly Arg Pro Glu Asp Lys Leu Glu Phe Met Phe Arg Leu
```

-continued

```
145                 150                 155                 160

Tyr Asp Thr Asp Gly Asn Gly Phe Leu Asp Ser Ser Glu Leu Glu Asn
                165                 170                 175

Ile Ile Ser Gln Met Met His Val Ala Glu Tyr Leu Glu Trp Asp Val
            180                 185                 190

Thr Glu Leu Asn Pro Ile Leu His Glu Met Met Glu Glu Ile Asp Tyr
        195                 200                 205

Asp His Asp Gly Thr Val Ser Leu Glu Glu Trp Ile Gln Gly Gly Met
    210                 215                 220

Thr Thr Ile Pro Leu Leu Val Leu Leu Gly Leu Glu Asn Asn Val Lys
225                 230                 235                 240

Asp Asp Gly Gln His Val Trp Arg Leu Lys His Phe Asn Lys Pro Ala
                245                 250                 255

Tyr Cys Asn Leu Cys Leu Asn Met Leu Ile Gly Val Gly Lys Gln Gly
            260                 265                 270

Leu Cys Cys Ser Phe Cys Lys Tyr Thr Val His Glu Arg Cys Val Ala
        275                 280                 285

Arg Ala Pro Pro Ser Cys Ile Lys Thr Tyr Val Lys Ser Lys Arg Asn
    290                 295                 300

Thr Asp Val Met His His Tyr Trp Val Glu Gly Asn Cys Pro Thr Lys
305                 310                 315                 320

Cys Asp Lys Cys His Lys Thr Val Lys Cys Tyr Gln Gly Leu Thr Gly
                325                 330                 335

Leu His Cys Val Trp Cys Gln Ile Thr Leu His Asn Lys Cys Ala Ser
            340                 345                 350

His Leu Lys Pro Glu Cys Asp Cys Gly Pro Leu Lys Asp His Ile Leu
        355                 360                 365

Pro Pro Thr Thr Ile Cys Pro Val Val Leu Gln Thr Leu Pro Thr Ser
    370                 375                 380

Gly Val Ser Val Pro Glu Glu Arg Gln Ser Thr Val Lys Lys Glu Lys
385                 390                 395                 400

Ser Gly Ser Gln Gln Pro Asn Lys Val Ile Asp Lys Asn Lys Met Gln
                405                 410                 415

Arg Ala Asn Ser Val Thr Val Asp Gly Gln Gly Leu Gln Val Thr Pro
            420                 425                 430

Val Pro Gly Thr His Pro Leu Leu Val Phe Val Asn Pro Lys Ser Gly
        435                 440                 445

Gly Lys Gln Gly Glu Arg Ile Tyr Arg Lys Phe Gln Tyr Leu Leu Asn
    450                 455                 460

Pro Arg Gln Val Tyr Ser Leu Ser Gly Asn Gly Pro Met Pro Gly Leu
465                 470                 475                 480

Asn Phe Phe Arg Asp Val Pro Asp Phe Arg Val Leu Ala Cys Gly Gly
                485                 490                 495

Asp Gly Thr Val Gly Trp Val Leu Asp Cys Ile Glu Lys Ala Asn Val
            500                 505                 510

Gly Lys His Pro Pro Val Ala Ile Leu Pro Leu Gly Thr Gly Asn Asp
        515                 520                 525

Leu Ala Arg Cys Leu Arg Trp Gly Gly Gly Tyr Glu Gly Glu Asn Leu
    530                 535                 540

Met Lys Ile Leu Lys Asp Ile Glu Asn Ser Thr Glu Ile Met Leu Asp
545                 550                 555                 560

Arg Trp Lys Phe Glu Val Ile Pro Asn Asp Lys Asp Glu Lys Gly Asp
                565                 570                 575
```

-continued

Pro Val Pro Tyr Ser Ile Ile Asn Asn Tyr Phe Ser Ile Gly Val Asp
580 585 590

Ala Ser Ile Ala His Arg Phe His Ile Met Arg Glu Lys His Pro Glu
595 600 605

Lys Phe Asn Ser Arg Met Lys Asn Lys Phe Trp Tyr Phe Glu Phe Gly
610 615 620

Thr Ser Glu Thr Phe Ser Ala Thr Cys Lys Lys Leu His Glu Ser Val
625 630 635 640

Glu Ile Glu Cys Asp Gly Val Gln Ile Asp Leu Ile Asn Ile Ser Leu
645 650 655

Glu Gly Ile Ala Ile Leu Asn Ile Pro Ser Met His Gly Gly Ser Asn
660 665 670

Leu Trp Gly Glu Ser Lys Lys Arg Arg Ser His Arg Arg Ile Glu Lys
675 680 685

Lys Gly Ser Asp Lys Arg Thr Thr Val Thr Asp Ala Lys Glu Leu Lys
690 695 700

Phe Ala Ser Gln Asp Leu Ser Asp Gln Leu Leu Glu Val Val Gly Leu
705 710 715 720

Glu Gly Ala Met Glu Met Gly Gln Ile Tyr Thr Gly Leu Lys Ser Ala
725 730 735

Gly Arg Arg Leu Ala Gln Cys Ser Cys Val Val Ile Arg Thr Ser Lys
740 745 750

Ser Leu Pro Met Gln Ile Asp Gly Glu Pro Trp Met Gln Thr Pro Cys
755 760 765

Thr Ile Lys Ile Thr His Lys Asn Gln Ala Pro Met Leu Met Gly Pro
770 775 780

Pro Pro Lys Thr Gly Leu Phe Cys Ser Leu Val Lys Arg Thr Arg Asn
785 790 795 800

Arg Ser Lys Glu

<210> SEQ ID NO 31
<211> LENGTH: 919
<212> TYPE: PRT
<213> ORGANISM: Homo sapiens

<400> SEQUENCE: 31

Met Gly Thr Thr Ala Pro Gly Pro Ile His Leu Leu Glu Leu Cys Asp
1 5 10 15

Gln Lys Leu Met Glu Phe Leu Cys Asn Met Asp Asn Lys Asp Leu Val
20 25 30

Trp Leu Glu Glu Ile Gln Glu Glu Ala Glu Arg Met Phe Thr Arg Glu
35 40 45

Phe Ser Lys Glu Pro Glu Leu Met Pro Lys Thr Pro Ser Gln Lys Asn
50 55 60

Arg Arg Lys Lys Arg Arg Ile Ser Tyr Val Gln Asp Glu Asn Arg Asp
65 70 75 80

Pro Ile Arg Arg Arg Leu Ser Arg Arg Lys Ser Arg Ser Ser Gln Leu
85 90 95

Ser Ser Arg Arg Leu Arg Ser Lys Asp Ser Val Glu Lys Leu Ala Thr
100 105 110

Val Val Gly Glu Asn Gly Ser Val Leu Arg Arg Val Thr Arg Ala Ala
115 120 125

Ala Ala Ala Ala Ala Ala Thr Met Ala Leu Ala Ala Pro Ser Ser Pro
130 135 140

-continued

```
Thr Pro Glu Ser Pro Thr Met Leu Thr Lys Lys Pro Glu Asp Asn His
145                 150                 155                 160

Thr Gln Cys Gln Leu Val Pro Val Val Glu Ile Gly Ile Ser Glu Arg
                165                 170                 175

Gln Asn Ala Glu Gln His Val Thr Gln Leu Met Ser Thr Glu Pro Leu
            180                 185                 190

Pro Arg Thr Leu Ser Pro Thr Pro Ala Ser Ala Thr Ala Pro Thr Ser
        195                 200                 205

Gln Gly Ile Pro Thr Ser Asp Glu Glu Ser Thr Pro Lys Lys Ser Lys
    210                 215                 220

Ala Arg Ile Leu Glu Ser Ile Thr Val Ser Ser Leu Met Ala Thr Pro
225                 230                 235                 240

Gln Asp Pro Lys Gly Gln Gly Val Gly Thr Gly Arg Ser Ala Ser Lys
                245                 250                 255

Leu Arg Ile Ala Gln Val Ser Pro Gly Pro Arg Asp Ser Pro Ala Phe
            260                 265                 270

Pro Asp Ser Pro Trp Arg Glu Arg Val Leu Ala Pro Ile Leu Pro Asp
        275                 280                 285

Asn Phe Ser Thr Pro Thr Gly Ser Arg Thr Asp Ser Gln Ser Val Arg
    290                 295                 300

His Ser Pro Ile Ala Pro Ser Ser Pro Ser Pro Gln Val Leu Ala Gln
305                 310                 315                 320

Lys Tyr Ser Leu Val Ala Lys Gln Glu Ser Val Val Arg Arg Ala Ser
                325                 330                 335

Arg Arg Leu Ala Lys Lys Thr Ala Glu Glu Pro Ala Ala Ser Gly Arg
            340                 345                 350

Ile Ile Cys His Ser Tyr Leu Glu Arg Leu Leu Asn Val Glu Val Pro
        355                 360                 365

Gln Lys Val Gly Ser Glu Gln Lys Glu Pro Pro Glu Glu Ala Glu Pro
    370                 375                 380

Val Ala Ala Ala Glu Pro Glu Val Pro Glu Asn Asn Gly Asn Asn Ser
385                 390                 395                 400

Trp Pro His Asn Asp Thr Glu Ile Ala Asn Ser Thr Pro Asn Pro Lys
                405                 410                 415

Pro Ala Ala Ser Ser Pro Glu Thr Pro Ser Ala Gly Gln Gln Glu Ala
            420                 425                 430

Lys Thr Asp Gln Ala Asp Gly Pro Arg Glu Pro Pro Gln Ser Ala Arg
        435                 440                 445

Arg Lys Arg Ser Tyr Lys Gln Ala Val Ser Glu Leu Asp Glu Glu Gln
    450                 455                 460

His Leu Glu Asp Glu Glu Leu Gln Pro Pro Arg Ser Lys Thr Pro Ser
465                 470                 475                 480

Ser Pro Cys Pro Ala Ser Lys Val Val Arg Pro Leu Arg Thr Phe Leu
                485                 490                 495

His Thr Val Gln Arg Asn Gln Met Leu Met Thr Pro Thr Ser Ala Pro
            500                 505                 510

Arg Ser Val Met Lys Ser Phe Ile Lys Arg Asn Thr Pro Leu Arg Met
        515                 520                 525

Asp Pro Lys Glu Lys Glu Arg Gln Arg Leu Glu Asn Leu Arg Arg Lys
    530                 535                 540

Glu Glu Ala Glu Gln Leu Arg Arg Gln Lys Val Glu Glu Asp Lys Arg
545                 550                 555                 560
```

-continued

```
Arg Arg Leu Glu Glu Val Lys Leu Lys Arg Glu Glu Arg Leu Arg Lys
                565                 570                 575

Val Leu Gln Ala Arg Glu Arg Val Glu Gln Met Lys Glu Glu Lys Lys
            580                 585                 590

Lys Gln Ile Glu Gln Lys Phe Ala Gln Ile Asp Glu Lys Thr Glu Lys
        595                 600                 605

Ala Lys Glu Glu Arg Leu Ala Glu Glu Lys Ala Lys Lys Lys Ala Ala
    610                 615                 620

Ala Lys Lys Met Glu Glu Val Glu Ala Arg Arg Lys Gln Glu Glu Asp
625                 630                 635                 640

Ala Arg Arg Leu Arg Trp Leu Gln Gln Glu Glu Glu Glu Arg Arg His
                645                 650                 655

Gln Glu Leu Leu Gln Lys Lys Lys Glu Glu Glu Gln Glu Arg Leu Arg
            660                 665                 670

Lys Ala Ala Glu Ala Lys Arg Leu Ala Glu Gln Arg Glu Gln Glu Arg
        675                 680                 685

Arg Glu Gln Glu Arg Arg Glu Gln Glu Arg Arg Glu Gln Glu Arg Arg
    690                 695                 700

Glu Gln Glu Arg Arg Glu Gln Glu Arg Arg Glu Gln Glu Arg Gln Leu
705                 710                 715                 720

Ala Glu Gln Glu Arg Arg Arg Glu Gln Glu Arg Leu Gln Ala Glu Arg
                725                 730                 735

Glu Leu Gln Glu Arg Glu Lys Ala Leu Arg Leu Gln Lys Glu Gln Leu
            740                 745                 750

Gln Arg Glu Leu Glu Glu Lys Lys Lys Lys Glu Glu Gln Gln Arg Leu
        755                 760                 765

Ala Glu Arg Gln Leu Gln Glu Glu Gln Glu Lys Lys Ala Lys Glu Ala
    770                 775                 780

Ala Gly Ala Ser Lys Ala Leu Asn Val Thr Val Asp Val Gln Ser Pro
785                 790                 795                 800

Ala Cys Thr Ser Ser Pro Ile Thr Pro Gln Gly His Lys Ala Pro Pro
                805                 810                 815

Gln Ile Asn Pro His Asn Tyr Gly Met Asp Leu Asn Ser Asp Asp Ser
            820                 825                 830

Thr Asp Asp Glu Ala His Pro Arg Lys Pro Ile Pro Thr Trp Ala Arg
        835                 840                 845

Gly Thr Pro Leu Ser Gln Ala Ile Ile His Gln Tyr Tyr Gln Pro Pro
    850                 855                 860

Asn Leu Leu Glu Leu Phe Gly Thr Ile Leu Pro Leu Asp Leu Glu Asp
865                 870                 875                 880

Ile Phe Lys Lys Ser Lys Pro Arg Tyr His Lys Arg Thr Ser Ser Ala
                885                 890                 895

Val Trp Asn Ser Pro Pro Leu Gln Gly Ala Arg Val Pro Ser Ser Leu
            900                 905                 910

Ala Tyr Ser Leu Lys Lys His
        915
```

<210> SEQ ID NO 32
<211> LENGTH: 367
<212> TYPE: PRT
<213> ORGANISM: Homo sapiens

<400> SEQUENCE: 32

```
Met Ser Ser Pro Pro Pro Ala Arg Ser Gly Phe Tyr Arg Gln Glu Val
1               5                   10                  15
```

-continued

```
Thr Lys Thr Ala Trp Glu Val Arg Ala Val Tyr Arg Asp Leu Gln Pro
            20                  25                  30

Val Gly Ser Gly Ala Tyr Gly Ala Val Cys Ser Ala Val Asp Gly Arg
        35                  40                  45

Thr Gly Ala Lys Val Ala Ile Lys Lys Leu Tyr Arg Pro Phe Gln Ser
    50                  55                  60

Glu Leu Phe Ala Lys Arg Ala Tyr Arg Glu Leu Arg Leu Leu Lys His
65                  70                  75                  80

Met Arg His Glu Asn Val Ile Gly Leu Leu Asp Val Phe Thr Pro Asp
                85                  90                  95

Glu Thr Leu Asp Asp Phe Thr Asp Phe Tyr Leu Val Met Pro Phe Met
            100                 105                 110

Gly Thr Asp Leu Gly Lys Leu Met Lys His Glu Lys Leu Gly Glu Asp
        115                 120                 125

Arg Ile Gln Phe Leu Val Tyr Gln Met Leu Lys Gly Leu Arg Tyr Ile
    130                 135                 140

His Ala Ala Gly Ile Ile His Arg Asp Leu Lys Pro Gly Asn Leu Ala
145                 150                 155                 160

Val Asn Glu Asp Cys Glu Leu Lys Ile Leu Asp Phe Gly Leu Ala Arg
                165                 170                 175

Gln Ala Asp Ser Glu Met Thr Gly Tyr Val Val Thr Arg Trp Tyr Arg
            180                 185                 190

Ala Pro Glu Val Ile Leu Asn Trp Met Arg Tyr Thr Gln Thr Val Asp
        195                 200                 205

Ile Trp Ser Val Gly Cys Ile Met Ala Glu Met Ile Thr Gly Lys Thr
    210                 215                 220

Leu Phe Lys Gly Ser Asp His Leu Asp Gln Leu Lys Glu Ile Met Lys
225                 230                 235                 240

Val Thr Gly Thr Pro Pro Ala Glu Phe Val Gln Arg Leu Gln Ser Asp
                245                 250                 255

Glu Ala Lys Asn Tyr Met Lys Gly Leu Pro Glu Leu Glu Lys Lys Asp
            260                 265                 270

Phe Ala Ser Ile Leu Thr Asn Ala Ser Pro Leu Ala Val Asn Leu Leu
        275                 280                 285

Glu Lys Met Leu Val Leu Asp Ala Glu Gln Arg Val Thr Ala Gly Glu
    290                 295                 300

Ala Leu Ala His Pro Tyr Phe Glu Ser Leu His Asp Thr Glu Asp Glu
305                 310                 315                 320

Pro Gln Val Gln Lys Tyr Asp Asp Ser Phe Asp Asp Val Asp Arg Thr
                325                 330                 335

Leu Asp Glu Trp Lys Arg Val Thr Tyr Lys Glu Val Leu Ser Phe Lys
            340                 345                 350

Pro Pro Arg Gln Leu Gly Ala Arg Val Ser Lys Glu Thr Pro Leu
        355                 360                 365
```

<210> SEQ ID NO 33
<211> LENGTH: 182
<212> TYPE: PRT
<213> ORGANISM: Artificial Sequence
<220> FEATURE:
<223> OTHER INFORMATION: Protein domain

<400> SEQUENCE: 33

```
Met Asp Gly Ser Gly Glu Arg Ser Leu Pro Glu Pro Gly Ser Gln Ser
1               5                   10                  15
```

-continued

```
Ser Ala Ala Ser Asp Asp Ile Glu Ile Val Val Asn Val Gly Gly Val
            20                  25                  30

Arg Gln Val Leu Tyr Gly Asp Leu Leu Ser Gln Tyr Pro Glu Thr Arg
        35                  40                  45

Leu Ala Glu Leu Ile Asn Cys Leu Ala Gly Gly Tyr Asp Thr Ile Phe
    50                  55                  60

Ser Leu Cys Asp Asp Tyr Asp Pro Gly Lys Arg Glu Phe Tyr Phe Asp
65                  70                  75                  80

Arg Asp Pro Asp Ala Phe Lys Cys Val Ile Glu Val Tyr Tyr Phe Gly
                85                  90                  95

Glu Val His Met Lys Lys Gly Ile Cys Pro Ile Cys Phe Lys Asn Glu
            100                 105                 110

Met Asp Phe Trp Lys Val Asp Leu Lys Phe Leu Asp Asp Cys Cys Lys
        115                 120                 125

Ser His Leu Ser Glu Lys Arg Glu Glu Leu Glu Glu Ile Ala Arg Arg
    130                 135                 140

Val Gln Leu Ile Leu Asp Asp Leu Gly Val Asp Ala Ala Glu Gly Arg
145                 150                 155                 160

Trp Arg Arg Cys Gln Lys Cys Val Trp Lys Phe Leu Glu Lys Pro Glu
                165                 170                 175

Ser Ser Cys Pro Ala Arg
            180


<210> SEQ ID NO 34
<211> LENGTH: 23
<212> TYPE: PRT
<213> ORGANISM: Artificial Sequence
<220> FEATURE:
<223> OTHER INFORMATION: Protein domain

<400> SEQUENCE: 34

Val Val Ala Val Leu Ser Phe Leu Leu Ile Leu Val Ser Ser Val Val
1               5                   10                  15

Met Cys Met Gly Thr Ile Pro
            20


<210> SEQ ID NO 35
<211> LENGTH: 42
<212> TYPE: PRT
<213> ORGANISM: Artificial Sequence
<220> FEATURE:
<223> OTHER INFORMATION: Protein domain

<400> SEQUENCE: 35

Glu Leu Gln Val Leu Asp Ala Glu Gly Asn Arg Val Glu His Pro Thr
1               5                   10                  15

Leu Glu Asn Val Glu Thr Ala Cys Ile Gly Trp Phe Thr Leu Glu Tyr
            20                  25                  30

Leu Leu Arg Leu Phe Ser Ser Pro Asn Lys
        35                  40


<210> SEQ ID NO 36
<211> LENGTH: 23
<212> TYPE: PRT
<213> ORGANISM: Artificial Sequence
<220> FEATURE:
<223> OTHER INFORMATION: Protein domain

<400> SEQUENCE: 36
```

-continued

```
Leu His Phe Ala Leu Ser Phe Met Asn Ile Val Asp Val Leu Ala Ile
1               5                   10                  15

Leu Pro Phe Tyr Val Ser Leu
            20


<210> SEQ ID NO 37
<211> LENGTH: 53
<212> TYPE: PRT
<213> ORGANISM: Artificial Sequence
<220> FEATURE:
<223> OTHER INFORMATION: Protein domain

<400> SEQUENCE: 37

Thr Leu Thr His Leu Gly Ala Arg Met Met Glu Leu Thr Asn Val Gln
1               5                   10                  15

Gln Ala Val Gln Ala Leu Arg Ile Met Arg Ile Ala Arg Ile Phe Lys
            20                  25                  30

Leu Ala Arg His Ser Ser Gly Leu Gln Thr Leu Thr Tyr Ala Leu Lys
        35                  40                  45

Arg Ser Phe Lys Glu
    50


<210> SEQ ID NO 38
<211> LENGTH: 23
<212> TYPE: PRT
<213> ORGANISM: Artificial Sequence
<220> FEATURE:
<223> OTHER INFORMATION: Protein domain

<400> SEQUENCE: 38

Leu Gly Leu Leu Leu Met Tyr Leu Ala Val Gly Ile Phe Val Phe Ser
1               5                   10                  15

Ala Leu Gly Tyr Thr Met Glu
            20


<210> SEQ ID NO 39
<211> LENGTH: 40
<212> TYPE: PRT
<213> ORGANISM: Artificial Sequence
<220> FEATURE:
<223> OTHER INFORMATION: Protein domain

<400> SEQUENCE: 39

Gln Ser His Pro Glu Thr Leu Phe Lys Ser Ile Pro Gln Ser Phe Trp
1               5                   10                  15

Trp Ala Ile Ile Thr Met Thr Thr Val Gly Tyr Gly Asp Ile Tyr Pro
            20                  25                  30

Lys Thr Thr Leu Gly Lys Leu Asn
        35                  40


<210> SEQ ID NO 40
<211> LENGTH: 23
<212> TYPE: PRT
<213> ORGANISM: Artificial Sequence
<220> FEATURE:
<223> OTHER INFORMATION: Protein domain

<400> SEQUENCE: 40

Ala Ala Ile Ser Phe Leu Cys Gly Val Ile Ala Ile Ala Leu Pro Ile
1               5                   10                  15

His Pro Ile Ile Asn Asn Phe
            20
```

-continued

<210> SEQ ID NO 41
<211> LENGTH: 85
<212> TYPE: PRT
<213> ORGANISM: Artificial Sequence
<220> FEATURE:
<223> OTHER INFORMATION: Protein domain

<400> SEQUENCE: 41

Val Arg Tyr Tyr Asn Lys Gln Arg Val Leu Glu Thr Ala Ala Lys His
1 5 10 15

Glu Leu Glu Leu Met Glu Leu Asn Ser Ser Ser Gly Gly Glu Gly Lys
20 25 30

Thr Gly Gly Ser Arg Ser Asp Leu Asp Asn Leu Pro Pro Glu Pro Ala
35 40 45

Gly Lys Glu Ala Pro Ser Cys Ser Ser Arg Leu Lys Leu Ser His Ser
50 55 60

Asp Thr Phe Ile Pro Leu Leu Thr Glu Glu Lys His His Arg Thr Arg
65 70 75 80

Leu Gln Ser Cys Lys
85

<210> SEQ ID NO 42
<211> LENGTH: 60
<212> TYPE: PRT
<213> ORGANISM: Artificial Sequence
<220> FEATURE:
<223> OTHER INFORMATION: Protein domain

<400> SEQUENCE: 42

Met Gly Glu Lys Met Ala Glu Glu Glu Arg Phe Pro Asn Thr Thr His
1 5 10 15

Glu Gly Phe Asn Val Thr Leu His Thr Thr Leu Val Val Thr Thr Lys
20 25 30

Leu Val Leu Pro Thr Pro Gly Lys Pro Ile Leu Pro Val Gln Thr Gly
35 40 45

Glu Gln Ala Gln Gln Glu Glu Gln Ser Ser Gly Met
50 55 60

<210> SEQ ID NO 43
<211> LENGTH: 20
<212> TYPE: PRT
<213> ORGANISM: Artificial Sequence
<220> FEATURE:
<223> OTHER INFORMATION: Protein domain

<400> SEQUENCE: 43

Thr Ile Phe Phe Ser Leu Leu Val Leu Ala Ile Cys Ile Ile Leu Val
1 5 10 15

His Leu Leu Ile
20

<210> SEQ ID NO 44
<211> LENGTH: 9
<212> TYPE: PRT
<213> ORGANISM: Artificial Sequence
<220> FEATURE:
<223> OTHER INFORMATION: Protein domain

<400> SEQUENCE: 44

Arg Tyr Arg Leu His Phe Leu Pro Glu
1 5

<210> SEQ ID NO 45
<211> LENGTH: 20
<212> TYPE: PRT
<213> ORGANISM: Artificial Sequence
<220> FEATURE:
<223> OTHER INFORMATION: Protein domain

<400> SEQUENCE: 45

Ser Val Ala Val Val Ser Leu Gly Ile Leu Met Gly Ala Val Ile Lys
1 5 10 15

Ile Ile Glu Phe
20

<210> SEQ ID NO 46
<211> LENGTH: 11
<212> TYPE: PRT
<213> ORGANISM: Artificial Sequence
<220> FEATURE:
<223> OTHER INFORMATION: Protein domain

<400> SEQUENCE: 46

Lys Lys Leu Ala Asn Trp Lys Glu Glu Glu Met
1 5 10

<210> SEQ ID NO 47
<211> LENGTH: 20
<212> TYPE: PRT
<213> ORGANISM: Artificial Sequence
<220> FEATURE:
<223> OTHER INFORMATION: Protein domain

<400> SEQUENCE: 47

Phe Arg Pro Asn Met Phe Phe Leu Leu Leu Leu Pro Pro Ile Ile Phe
1 5 10 15

Glu Ser Gly Tyr
20

<210> SEQ ID NO 48
<211> LENGTH: 14
<212> TYPE: PRT
<213> ORGANISM: Artificial Sequence
<220> FEATURE:
<223> OTHER INFORMATION: Protein domain

<400> SEQUENCE: 48

Ser Leu His Lys Gly Asn Phe Phe Gln Asn Ile Gly Ser Ile
1 5 10

<210> SEQ ID NO 49
<211> LENGTH: 23
<212> TYPE: PRT
<213> ORGANISM: Artificial Sequence
<220> FEATURE:
<223> OTHER INFORMATION: Protein domain

<400> SEQUENCE: 49

Thr Leu Phe Ala Val Phe Gly Thr Ala Ile Ser Ala Phe Val Val Gly
1 5 10 15

Gly Gly Ile Tyr Phe Leu Gly
20

<210> SEQ ID NO 50
<211> LENGTH: 12
<212> TYPE: PRT
<213> ORGANISM: Artificial Sequence -continued
<220> FEATURE:
<223> OTHER INFORMATION: Protein domain

<400> SEQUENCE: 50

Gln Ala Asp Val Ile Ser Lys Leu Asn Met Thr Asp
1 5 10

<210> SEQ ID NO 51
<211> LENGTH: 23
<212> TYPE: PRT
<213> ORGANISM: Artificial Sequence
<220> FEATURE:
<223> OTHER INFORMATION: Protein domain

<400> SEQUENCE: 51

Ser Phe Ala Phe Gly Ser Leu Ile Ser Ala Val Asp Pro Val Ala Thr
1 5 10 15

Ile Ala Ile Phe Asn Ala Leu
20

<210> SEQ ID NO 52
<211> LENGTH: 51
<212> TYPE: PRT
<213> ORGANISM: Artificial Sequence
<220> FEATURE:
<223> OTHER INFORMATION: Protein domain

<400> SEQUENCE: 52

His Val Asp Pro Val Leu Asn Met Leu Val Phe Gly Glu Ser Ile Leu
1 5 10 15

Asn Asp Ala Val Ser Ile Val Leu Thr Asn Thr Ala Glu Gly Leu Thr
20 25 30

Arg Lys Asn Met Ser Asp Val Ser Gly Trp Gln Thr Phe Leu Gln Ala
35 40 45

Leu Asp Tyr
50

<210> SEQ ID NO 53
<211> LENGTH: 23
<212> TYPE: PRT
<213> ORGANISM: Artificial Sequence
<220> FEATURE:
<223> OTHER INFORMATION: Protein domain

<400> SEQUENCE: 53

Phe Leu Lys Met Phe Phe Gly Ser Ala Ala Leu Gly Thr Leu Thr Gly
1 5 10 15

Leu Ile Ser Ala Leu Val Leu
20

<210> SEQ ID NO 54
<211> LENGTH: 20
<212> TYPE: PRT
<213> ORGANISM: Artificial Sequence
<220> FEATURE:
<223> OTHER INFORMATION: Protein domain

<400> SEQUENCE: 54

Lys His Ile Asp Leu Arg Lys Thr Pro Ser Leu Glu Phe Gly Met Met
1 5 10 15

Ile Ile Phe Ala
20

-continued

<210> SEQ ID NO 55
<211> LENGTH: 23
<212> TYPE: PRT
<213> ORGANISM: Artificial Sequence
<220> FEATURE:
<223> OTHER INFORMATION: Protein domain

<400> SEQUENCE: 55

Tyr Leu Pro Tyr Gly Leu Ala Glu Gly Ile Ser Leu Ser Gly Ile Met
1               5                   10                  15

Ala Ile Leu Phe Ser Gly Ile
            20

<210> SEQ ID NO 56
<211> LENGTH: 21
<212> TYPE: PRT
<213> ORGANISM: Artificial Sequence
<220> FEATURE:
<223> OTHER INFORMATION: Protein domain

<400> SEQUENCE: 56

Val Met Ser His Tyr Thr His His Asn Leu Ser Pro Val Thr Gln Ile
1               5                   10                  15

Leu Met Gln Gln Thr
            20

<210> SEQ ID NO 57
<211> LENGTH: 23
<212> TYPE: PRT
<213> ORGANISM: Artificial Sequence
<220> FEATURE:
<223> OTHER INFORMATION: Protein domain

<400> SEQUENCE: 57

Leu Arg Thr Val Ala Phe Leu Cys Glu Thr Cys Val Phe Ala Phe Leu
1               5                   10                  15

Gly Leu Ser Ile Phe Ser Phe
            20

<210> SEQ ID NO 58
<211> LENGTH: 6
<212> TYPE: PRT
<213> ORGANISM: Artificial Sequence
<220> FEATURE:
<223> OTHER INFORMATION: Protein domain

<400> SEQUENCE: 58

Pro His Lys Phe Glu Ile
1               5

<210> SEQ ID NO 59
<211> LENGTH: 23
<212> TYPE: PRT
<213> ORGANISM: Artificial Sequence
<220> FEATURE:
<223> OTHER INFORMATION: Protein domain

<400> SEQUENCE: 59

Ser Phe Val Ile Trp Cys Ile Val Leu Val Leu Phe Gly Arg Ala Val
1               5                   10                  15

Asn Ile Phe Pro Leu Ser Tyr
            20

<210> SEQ ID NO 60
<211> LENGTH: 14

-continued

<212> TYPE: PRT
<213> ORGANISM: Artificial Sequence
<220> FEATURE:
<223> OTHER INFORMATION: Protein domain

<400> SEQUENCE: 60

Leu Leu Asn Phe Phe Arg Asp His Lys Ile Thr Pro Lys Met
1 5 10

<210> SEQ ID NO 61
<211> LENGTH: 19
<212> TYPE: PRT
<213> ORGANISM: Artificial Sequence
<220> FEATURE:
<223> OTHER INFORMATION: Protein domain

<400> SEQUENCE: 61

Met Phe Ile Met Trp Phe Ser Gly Leu Arg Gly Ala Ile Pro Tyr Ala
1 5 10 15

Leu Ser Leu

<210> SEQ ID NO 62
<211> LENGTH: 11
<212> TYPE: PRT
<213> ORGANISM: Artificial Sequence
<220> FEATURE:
<223> OTHER INFORMATION: Protein domain

<400> SEQUENCE: 62

His Leu Asp Leu Glu Pro Met Glu Lys Arg Gln
1 5 10

<210> SEQ ID NO 63
<211> LENGTH: 23
<212> TYPE: PRT
<213> ORGANISM: Artificial Sequence
<220> FEATURE:
<223> OTHER INFORMATION: Protein domain

<400> SEQUENCE: 63

Leu Ile Gly Thr Thr Thr Ile Val Ile Val Leu Phe Thr Ile Leu Leu
1 5 10 15

Leu Gly Gly Ser Thr Met Pro
20

<210> SEQ ID NO 64
<211> LENGTH: 112
<212> TYPE: PRT
<213> ORGANISM: Artificial Sequence
<220> FEATURE:
<223> OTHER INFORMATION: Protein domain

<400> SEQUENCE: 64

Leu Ile Arg Leu Met Asp Ile Glu Asp Ala Lys Ala His Arg Arg Asn
1 5 10 15

Lys Lys Asp Val Asn Leu Ser Lys Thr Glu Lys Met Gly Asn Thr Val
20 25 30

Glu Ser Glu His Leu Ser Glu Leu Thr Glu Glu Glu Tyr Glu Ala His
35 40 45

Tyr Ile Arg Arg Gln Asp Leu Lys Gly Phe Val Trp Leu Asp Ala Lys
50 55 60

Tyr Leu Asn Pro Phe Phe Thr Arg Arg Leu Thr Gln Glu Asp Leu His
65 70 75 80

-continued

His Gly Arg Ile Gln Met Lys Thr Leu Thr Asn Lys Trp Tyr Glu Glu
85 90 95

Val Arg Gln Gly Pro Ser Gly Ser Glu Asp Asp Glu Gln Glu Leu Leu
100 105 110

<210> SEQ ID NO 65
<211> LENGTH: 440
<212> TYPE: PRT
<213> ORGANISM: Artificial Sequence
<220> FEATURE:
<223> OTHER INFORMATION: Protein domain

<400> SEQUENCE: 65

Met Ala Trp Arg Cys Pro Arg Met Gly Arg Val Pro Leu Ala Trp Cys
1 5 10 15

Leu Ala Leu Cys Gly Trp Ala Cys Met Ala Pro Arg Gly Thr Gln Ala
20 25 30

Glu Glu Ser Pro Phe Val Gly Asn Pro Gly Asn Ile Thr Gly Ala Arg
35 40 45

Gly Leu Thr Gly Thr Leu Arg Cys Gln Leu Gln Val Gln Gly Glu Pro
50 55 60

Pro Glu Val His Trp Leu Arg Asp Gly Gln Ile Leu Glu Leu Ala Asp
65 70 75 80

Ser Thr Gln Thr Gln Val Pro Leu Gly Glu Asp Glu Gln Asp Asp Trp
85 90 95

Ile Val Val Ser Gln Leu Arg Ile Thr Ser Leu Gln Leu Ser Asp Thr
100 105 110

Gly Gln Tyr Gln Cys Leu Val Phe Leu Gly His Gln Thr Phe Val Ser
115 120 125

Gln Pro Gly Tyr Val Gly Leu Glu Gly Leu Pro Tyr Phe Leu Glu Glu
130 135 140

Pro Glu Asp Arg Thr Val Ala Ala Asn Thr Pro Phe Asn Leu Ser Cys
145 150 155 160

Gln Ala Gln Gly Pro Pro Glu Pro Val Asp Leu Leu Trp Leu Gln Asp
165 170 175

Ala Val Pro Leu Ala Thr Ala Pro Gly His Gly Pro Gln Arg Ser Leu
180 185 190

His Val Pro Gly Leu Asn Lys Thr Ser Ser Phe Ser Cys Glu Ala His
195 200 205

Asn Ala Lys Gly Val Thr Thr Ser Arg Thr Ala Thr Ile Thr Val Leu
210 215 220

Pro Gln Gln Pro Arg Asn Leu His Leu Val Ser Arg Gln Pro Thr Glu
225 230 235 240

Leu Glu Val Ala Trp Thr Pro Gly Leu Ser Gly Ile Tyr Pro Leu Thr
245 250 255

His Cys Thr Leu Gln Ala Val Leu Ser Asp Asp Gly Met Gly Ile Gln
260 265 270

Ala Gly Glu Pro Asp Pro Pro Glu Glu Pro Leu Thr Ser Gln Ala Ser
275 280 285

Val Pro Pro His Gln Leu Arg Leu Gly Ser Leu His Pro His Thr Pro
290 295 300

Tyr His Ile Arg Val Ala Cys Thr Ser Ser Gln Gly Pro Ser Ser Trp
305 310 315 320

Thr His Trp Leu Pro Val Glu Thr Pro Glu Gly Val Pro Leu Gly Pro
325 330 335

-continued

```
Pro Glu Asn Ile Ser Ala Thr Arg Asn Gly Ser Gln Ala Phe Val His
            340                 345                 350

Trp Gln Glu Pro Arg Ala Pro Leu Gln Gly Thr Leu Leu Gly Tyr Arg
        355                 360                 365

Leu Ala Tyr Gln Gly Gln Asp Thr Pro Glu Val Leu Met Asp Ile Gly
    370                 375                 380

Leu Arg Gln Glu Val Thr Leu Glu Leu Gln Gly Asp Gly Ser Val Ser
385                 390                 395                 400

Asn Leu Thr Val Cys Val Ala Ala Tyr Thr Ala Ala Gly Asp Gly Pro
                405                 410                 415

Trp Ser Leu Pro Val Pro Leu Glu Ala Trp Arg Pro Val Lys Glu Pro
            420                 425                 430

Ser Thr Pro Ala Phe Ser Trp Pro
        435                 440


<210> SEQ ID NO 66
<211> LENGTH: 23
<212> TYPE: PRT
<213> ORGANISM: Artificial Sequence
<220> FEATURE:
<223> OTHER INFORMATION: Protein domain

<400> SEQUENCE: 66

Trp Trp Tyr Val Leu Leu Gly Ala Val Val Ala Ala Ala Cys Val Leu
1               5                   10                  15

Ile Leu Ala Leu Phe Leu Val
            20


<210> SEQ ID NO 67
<211> LENGTH: 422
<212> TYPE: PRT
<213> ORGANISM: Artificial Sequence
<220> FEATURE:
<223> OTHER INFORMATION: Protein domain

<400> SEQUENCE: 67

His Arg Arg Lys Lys Glu Thr Arg Tyr Gly Glu Val Phe Glu Pro Thr
1               5                   10                  15

Val Glu Arg Gly Glu Leu Val Val Arg Tyr Arg Val Arg Lys Ser Tyr
            20                  25                  30

Ser Arg Arg Thr Thr Glu Ala Thr Leu Asn Ser Leu Gly Ile Ser Glu
        35                  40                  45

Glu Leu Lys Glu Lys Leu Arg Asp Val Met Val Asp Arg His Lys Val
    50                  55                  60

Ala Leu Gly Lys Thr Leu Gly Glu Gly Glu Phe Gly Ala Val Met Glu
65                  70                  75                  80

Gly Gln Leu Asn Gln Asp Asp Ser Ile Leu Lys Val Ala Val Lys Thr
                85                  90                  95

Met Lys Ile Ala Ile Cys Thr Arg Ser Glu Leu Glu Asp Phe Leu Ser
            100                 105                 110

Glu Ala Val Cys Met Lys Glu Phe Asp His Pro Asn Val Met Arg Leu
        115                 120                 125

Ile Gly Val Cys Phe Gln Gly Ser Glu Arg Glu Ser Phe Pro Ala Pro
    130                 135                 140

Val Val Ile Leu Pro Phe Met Lys His Gly Asp Leu His Ser Phe Leu
145                 150                 155                 160

Leu Tyr Ser Arg Leu Gly Asp Gln Pro Val Tyr Leu Pro Thr Gln Met
                165                 170                 175
```

-continued

```
Leu Val Lys Phe Met Ala Asp Ile Ala Ser Gly Met Glu Tyr Leu Ser
            180                 185                 190

Thr Lys Arg Phe Ile His Arg Asp Leu Ala Ala Arg Asn Cys Met Leu
        195                 200                 205

Asn Glu Asn Met Ser Val Cys Val Ala Asp Phe Gly Leu Ser Lys Lys
    210                 215                 220

Ile Tyr Asn Gly Asp Tyr Tyr Arg Gln Gly Arg Ile Ala Lys Met Pro
225                 230                 235                 240

Val Lys Trp Ile Ala Ile Glu Ser Leu Ala Asp Arg Val Tyr Thr Ser
                245                 250                 255

Lys Ser Asp Val Trp Ser Phe Gly Val Thr Met Trp Glu Ile Ala Thr
            260                 265                 270

Arg Gly Gln Thr Pro Tyr Pro Gly Val Glu Asn Ser Glu Ile Tyr Asp
        275                 280                 285

Tyr Leu Arg Gln Gly Asn Arg Leu Lys Gln Pro Ala Asp Cys Leu Asp
    290                 295                 300

Gly Leu Tyr Ala Leu Met Ser Arg Cys Trp Glu Leu Asn Pro Gln Asp
305                 310                 315                 320

Arg Pro Ser Phe Thr Glu Leu Arg Glu Asp Leu Glu Asn Thr Leu Lys
                325                 330                 335

Ala Leu Pro Pro Ala Gln Glu Pro Asp Glu Ile Leu Tyr Val Asn Met
            340                 345                 350

Asp Glu Gly Gly Gly Tyr Pro Glu Pro Pro Gly Ala Ala Gly Gly Ala
        355                 360                 365

Asp Pro Pro Thr Gln Pro Asp Pro Lys Asp Ser Cys Ser Cys Leu Thr
    370                 375                 380

Ala Ala Glu Val His Pro Ala Gly Arg Tyr Val Leu Cys Pro Ser Thr
385                 390                 395                 400

Thr Pro Ser Pro Ala Gln Pro Ala Asp Arg Gly Ser Pro Ala Ala Pro
                405                 410                 415

Gly Gln Glu Asp Gly Ala
            420


<210> SEQ ID NO 68
<211> LENGTH: 449
<212> TYPE: PRT
<213> ORGANISM: Artificial Sequence
<220> FEATURE:
<223> OTHER INFORMATION: Protein domain

<400> SEQUENCE: 68

Met Ala Trp Arg Cys Pro Arg Met Gly Arg Val Pro Leu Ala Trp Cys
1               5                   10                  15

Leu Ala Leu Cys Gly Trp Ala Cys Met Ala Pro Arg Gly Thr Gln Ala
            20                  25                  30

Glu Glu Ser Pro Phe Val Gly Asn Pro Gly Asn Ile Thr Gly Ala Arg
        35                  40                  45

Gly Leu Thr Gly Thr Leu Arg Cys Gln Leu Gln Val Gln Gly Glu Pro
    50                  55                  60

Pro Glu Val His Trp Leu Arg Asp Gly Gln Ile Leu Glu Leu Ala Asp
65                  70                  75                  80

Ser Thr Gln Thr Gln Val Pro Leu Gly Glu Asp Glu Gln Asp Asp Trp
                85                  90                  95

Ile Val Val Ser Gln Leu Arg Ile Thr Ser Leu Gln Leu Ser Asp Thr
            100                 105                 110
```

-continued

```
Gly Gln Tyr Gln Cys Leu Val Phe Leu Gly His Gln Thr Phe Val Ser
        115                 120                 125

Gln Pro Gly Tyr Val Gly Leu Glu Gly Leu Pro Tyr Phe Leu Glu Glu
    130                 135                 140

Pro Glu Asp Arg Thr Val Ala Ala Asn Thr Pro Phe Asn Leu Ser Cys
145                 150                 155                 160

Gln Ala Gln Gly Pro Pro Glu Pro Val Asp Leu Leu Trp Leu Gln Asp
                165                 170                 175

Ala Val Pro Leu Ala Thr Ala Pro Gly His Gly Pro Gln Arg Ser Leu
            180                 185                 190

His Val Pro Gly Leu Asn Lys Thr Ser Ser Phe Ser Cys Glu Ala His
        195                 200                 205

Asn Ala Lys Gly Val Thr Thr Ser Arg Thr Ala Thr Ile Thr Val Leu
    210                 215                 220

Pro Gln Gln Pro Arg Asn Leu His Leu Val Ser Arg Gln Pro Thr Glu
225                 230                 235                 240

Leu Glu Val Ala Trp Thr Pro Gly Leu Ser Gly Ile Tyr Pro Leu Thr
                245                 250                 255

His Cys Thr Leu Gln Ala Val Leu Ser Asp Asp Gly Met Gly Ile Gln
            260                 265                 270

Ala Gly Glu Pro Asp Pro Pro Glu Glu Pro Leu Thr Ser Gln Ala Ser
        275                 280                 285

Val Pro Pro His Gln Leu Arg Leu Gly Ser Leu His Pro His Thr Pro
    290                 295                 300

Tyr His Ile Arg Val Ala Cys Thr Ser Ser Gln Gly Pro Ser Ser Trp
305                 310                 315                 320

Thr His Trp Leu Pro Val Glu Thr Pro Glu Gly Val Pro Leu Gly Pro
                325                 330                 335

Pro Glu Asn Ile Ser Ala Thr Arg Asn Gly Ser Gln Ala Phe Val His
            340                 345                 350

Trp Gln Glu Pro Arg Ala Pro Leu Gln Gly Thr Leu Leu Gly Tyr Arg
        355                 360                 365

Leu Ala Tyr Gln Gly Gln Asp Thr Pro Glu Val Leu Met Asp Ile Gly
    370                 375                 380

Leu Arg Gln Glu Val Thr Leu Glu Leu Gln Gly Asp Gly Ser Val Ser
385                 390                 395                 400

Asn Leu Thr Val Cys Val Ala Ala Tyr Thr Ala Ala Gly Asp Gly Pro
                405                 410                 415

Trp Ser Leu Pro Val Pro Leu Glu Ala Trp Arg Pro Gly Gln Ala Gln
            420                 425                 430

Pro Val His Gln Leu Val Lys Glu Pro Ser Thr Pro Ala Phe Ser Trp
        435                 440                 445

Pro


<210> SEQ ID NO 69
<211> LENGTH: 23
<212> TYPE: PRT
<213> ORGANISM: Artificial Sequence
<220> FEATURE:
<223> OTHER INFORMATION: Protein domain

<400> SEQUENCE: 69

Trp Trp Tyr Val Leu Leu Gly Ala Val Val Ala Ala Ala Cys Val Leu
1               5                   10                  15
```

-continued

```
Ile Leu Ala Leu Phe Leu Val
            20


<210> SEQ ID NO 70
<211> LENGTH: 422
<212> TYPE: PRT
<213> ORGANISM: Artificial Sequence
<220> FEATURE:
<223> OTHER INFORMATION: Protein domain

<400> SEQUENCE: 70

His Arg Arg Lys Lys Glu Thr Arg Tyr Gly Glu Val Phe Glu Pro Thr
1               5                   10                  15

Val Glu Arg Gly Glu Leu Val Val Arg Tyr Arg Val Arg Lys Ser Tyr
            20                  25                  30

Ser Arg Arg Thr Thr Glu Ala Thr Leu Asn Ser Leu Gly Ile Ser Glu
        35                  40                  45

Glu Leu Lys Glu Lys Leu Arg Asp Val Met Val Asp Arg His Lys Val
    50                  55                  60

Ala Leu Gly Lys Thr Leu Gly Glu Gly Glu Phe Gly Ala Val Met Glu
65                  70                  75                  80

Gly Gln Leu Asn Gln Asp Asp Ser Ile Leu Lys Val Ala Val Lys Thr
                85                  90                  95

Met Lys Ile Ala Ile Cys Thr Arg Ser Glu Leu Glu Asp Phe Leu Ser
            100                 105                 110

Glu Ala Val Cys Met Lys Glu Phe Asp His Pro Asn Val Met Arg Leu
        115                 120                 125

Ile Gly Val Cys Phe Gln Gly Ser Glu Arg Glu Ser Phe Pro Ala Pro
    130                 135                 140

Val Val Ile Leu Pro Phe Met Lys His Gly Asp Leu His Ser Phe Leu
145                 150                 155                 160

Leu Tyr Ser Arg Leu Gly Asp Gln Pro Val Tyr Leu Pro Thr Gln Met
                165                 170                 175

Leu Val Lys Phe Met Ala Asp Ile Ala Ser Gly Met Glu Tyr Leu Ser
            180                 185                 190

Thr Lys Arg Phe Ile His Arg Asp Leu Ala Ala Arg Asn Cys Met Leu
        195                 200                 205

Asn Glu Asn Met Ser Val Cys Val Ala Asp Phe Gly Leu Ser Lys Lys
    210                 215                 220

Ile Tyr Asn Gly Asp Tyr Tyr Arg Gln Gly Arg Ile Ala Lys Met Pro
225                 230                 235                 240

Val Lys Trp Ile Ala Ile Glu Ser Leu Ala Asp Arg Val Tyr Thr Ser
                245                 250                 255

Lys Ser Asp Val Trp Ser Phe Gly Val Thr Met Trp Glu Ile Ala Thr
            260                 265                 270

Arg Gly Gln Thr Pro Tyr Pro Gly Val Glu Asn Ser Glu Ile Tyr Asp
        275                 280                 285

Tyr Leu Arg Gln Gly Asn Arg Leu Lys Gln Pro Ala Asp Cys Leu Asp
    290                 295                 300

Gly Leu Tyr Ala Leu Met Ser Arg Cys Trp Glu Leu Asn Pro Gln Asp
305                 310                 315                 320

Arg Pro Ser Phe Thr Glu Leu Arg Glu Asp Leu Glu Asn Thr Leu Lys
                325                 330                 335

Ala Leu Pro Pro Ala Gln Glu Pro Asp Glu Ile Leu Tyr Val Asn Met
            340                 345                 350
```

-continued

```
Asp Glu Gly Gly Gly Tyr Pro Glu Pro Pro Gly Ala Ala Gly Gly Ala
        355                 360                 365

Asp Pro Pro Thr Gln Pro Asp Pro Lys Asp Ser Cys Ser Cys Leu Thr
    370                 375                 380

Ala Ala Glu Val His Pro Ala Gly Arg Tyr Val Leu Cys Pro Ser Thr
385                 390                 395                 400

Thr Pro Ser Pro Ala Gln Pro Ala Asp Arg Gly Ser Pro Ala Ala Pro
                405                 410                 415

Gly Gln Glu Asp Gly Ala
            420


<210> SEQ ID NO 71
<211> LENGTH: 372
<212> TYPE: PRT
<213> ORGANISM: Artificial Sequence
<220> FEATURE:
<223> OTHER INFORMATION: Protein domain

<400> SEQUENCE: 71

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205

Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
        275                 280                 285
```

-continued

```
Lys His Val Glu Val Asn Gly Ser Lys Val Gly Pro Asp Gly Thr Pro
    290                 295                 300

Tyr Val Thr Val Leu Lys Thr Ala Gly Ala Asn Thr Thr Asp Lys Glu
305                 310                 315                 320

Leu Glu Val Leu Ser Leu His Asn Val Thr Phe Glu Asp Ala Gly Glu
                325                 330                 335

Tyr Thr Cys Leu Ala Gly Asn Ser Ile Gly Phe Ser His His Ser Ala
            340                 345                 350

Trp Leu Val Val Leu Pro Ala Glu Glu Glu Leu Val Glu Ala Asp Glu
        355                 360                 365

Ala Gly Ser Val
    370


<210> SEQ ID NO 72
<211> LENGTH: 23
<212> TYPE: PRT
<213> ORGANISM: Artificial Sequence
<220> FEATURE:
<223> OTHER INFORMATION: Protein domain

<400> SEQUENCE: 72

Tyr Ala Gly Ile Leu Ser Tyr Gly Val Gly Phe Phe Leu Phe Ile Leu
1               5                   10                  15

Val Val Ala Ala Val Thr Leu
            20


<210> SEQ ID NO 73
<211> LENGTH: 141
<212> TYPE: PRT
<213> ORGANISM: Artificial Sequence
<220> FEATURE:
<223> OTHER INFORMATION: Protein domain

<400> SEQUENCE: 73

Cys Arg Leu Arg Ser Pro Pro Lys Lys Gly Leu Gly Ser Pro Thr Val
1               5                   10                  15

His Lys Ile Ser Arg Phe Pro Leu Lys Arg Gln Val Ser Leu Glu Ser
            20                  25                  30

Asn Ala Ser Met Ser Ser Asn Thr Pro Leu Val Arg Ile Ala Arg Leu
        35                  40                  45

Ser Ser Gly Glu Gly Pro Thr Leu Ala Asn Val Ser Glu Leu Glu Leu
    50                  55                  60

Pro Ala Asp Pro Lys Trp Glu Leu Ser Arg Ala Arg Leu Thr Leu Gly
65                  70                  75                  80

Lys Pro Leu Gly Glu Gly Cys Phe Gly Gln Val Val Met Ala Glu Ala
                85                  90                  95

Ile Gly Ile Asp Lys Asp Arg Ala Ala Lys Pro Val Thr Val Ala Val
            100                 105                 110

Lys Met Leu Lys Asp Asp Ala Thr Asp Lys Asp Leu Ser Asp Leu Val
        115                 120                 125

Ser Glu Met Glu Met Met Lys Met Ile Gly Lys His Lys
    130                 135                 140


<210> SEQ ID NO 74
<211> LENGTH: 23
<212> TYPE: PRT
<213> ORGANISM: Artificial Sequence
<220> FEATURE:
<223> OTHER INFORMATION: Protein domain
```

-continued

<400> SEQUENCE: 74

Asn Ile Ile Asn Leu Leu Gly Ala Cys Thr Gln Gly Gly Pro Leu Tyr
1 5 10 15

Val Leu Val Glu Tyr Ala Ala
20

<210> SEQ ID NO 75
<211> LENGTH: 247
<212> TYPE: PRT
<213> ORGANISM: Artificial Sequence
<220> FEATURE:
<223> OTHER INFORMATION: Protein domain

<400> SEQUENCE: 75

Lys Gly Asn Leu Arg Glu Phe Leu Arg Ala Arg Arg Pro Pro Gly Leu
1 5 10 15

Asp Tyr Ser Phe Asp Thr Cys Lys Pro Pro Glu Glu Gln Leu Thr Phe
20 25 30

Lys Asp Leu Val Ser Cys Ala Tyr Gln Val Ala Arg Gly Met Glu Tyr
35 40 45

Leu Ala Ser Gln Lys Cys Ile His Arg Asp Leu Ala Ala Arg Asn Val
50 55 60

Leu Val Thr Glu Asp Asn Val Met Lys Ile Ala Asp Phe Gly Leu Ala
65 70 75 80

Arg Asp Val His Asn Leu Asp Tyr Tyr Lys Lys Thr Thr Asn Gly Arg
85 90 95

Leu Pro Val Lys Trp Met Ala Pro Glu Ala Leu Phe Asp Arg Val Tyr
100 105 110

Thr His Gln Ser Asp Val Trp Ser Phe Gly Val Leu Leu Trp Glu Ile
115 120 125

Phe Thr Leu Gly Gly Ser Pro Tyr Pro Gly Ile Pro Val Glu Glu Leu
130 135 140

Phe Lys Leu Leu Lys Glu Gly His Arg Met Asp Lys Pro Ala Asn Cys
145 150 155 160

Thr His Asp Leu Tyr Met Ile Met Arg Glu Cys Trp His Ala Ala Pro
165 170 175

Ser Gln Arg Pro Thr Phe Lys Gln Leu Val Glu Asp Leu Asp Arg Val
180 185 190

Leu Thr Val Thr Ser Thr Asp Glu Tyr Leu Asp Leu Ser Ala Pro Phe
195 200 205

Glu Gln Tyr Ser Pro Gly Gly Gln Asp Thr Pro Ser Ser Ser Ser Ser
210 215 220

Gly Asp Asp Ser Val Phe Ala His Asp Leu Leu Pro Pro Ala Pro Pro
225 230 235 240

Ser Ser Gly Gly Ser Arg Thr
245

<210> SEQ ID NO 76
<211> LENGTH: 122
<212> TYPE: PRT
<213> ORGANISM: Artificial Sequence
<220> FEATURE:
<223> OTHER INFORMATION: Protein domain

<400> SEQUENCE: 76

Met Ala Met Leu Pro Pro Pro Gly Pro Gln Ser Phe Val His Phe Thr
1 5 10 15

-continued

```
Lys Gln Ser Leu Ala Leu Ile Glu Gln Arg Ile Ala Glu Arg Lys Ser
            20                  25                  30

Lys Glu Pro Lys Glu Glu Lys Lys Asp Asp Asp Glu Glu Ala Pro Lys
        35                  40                  45

Pro Ser Ser Asp Leu Glu Ala Gly Lys Gln Leu Pro Phe Ile Tyr Gly
    50                  55                  60

Asp Ile Pro Pro Gly Met Val Ser Glu Pro Leu Glu Asp Leu Asp Pro
65                  70                  75                  80

Tyr Tyr Ala Asp Lys Lys Thr Phe Ile Val Leu Asn Lys Gly Lys Thr
                85                  90                  95

Ile Phe Arg Phe Asn Ala Thr Pro Ala Leu Tyr Met Leu Ser Pro Phe
            100                 105                 110

Ser Pro Leu Arg Arg Ile Ser Ile Lys Ile
        115                 120


<210> SEQ ID NO 77
<211> LENGTH: 23
<212> TYPE: PRT
<213> ORGANISM: Artificial Sequence
<220> FEATURE:
<223> OTHER INFORMATION: Protein domain

<400> SEQUENCE: 77

Leu Val His Ser Leu Phe Ser Met Leu Ile Met Cys Thr Ile Leu Thr
1               5                   10                  15

Asn Cys Ile Phe Met Thr Met
            20


<210> SEQ ID NO 78
<211> LENGTH: 42
<212> TYPE: PRT
<213> ORGANISM: Artificial Sequence
<220> FEATURE:
<223> OTHER INFORMATION: Protein domain

<400> SEQUENCE: 78

Asn Asn Pro Pro Asp Trp Thr Lys Asn Val Glu Tyr Thr Phe Thr Gly
1               5                   10                  15

Ile Tyr Thr Phe Glu Ser Leu Val Lys Ile Leu Ala Arg Gly Phe Cys
            20                  25                  30

Val Gly Glu Phe Thr Phe Leu Arg Asp Pro
        35                  40


<210> SEQ ID NO 79
<211> LENGTH: 23
<212> TYPE: PRT
<213> ORGANISM: Artificial Sequence
<220> FEATURE:
<223> OTHER INFORMATION: Protein domain

<400> SEQUENCE: 79

Trp Asn Trp Leu Asp Phe Val Val Ile Val Phe Ala Tyr Leu Thr Glu
1               5                   10                  15

Phe Val Asn Leu Gly Asn Val
            20


<210> SEQ ID NO 80
<211> LENGTH: 6
<212> TYPE: PRT
<213> ORGANISM: Artificial Sequence
<220> FEATURE:
<223> OTHER INFORMATION: Protein domain
```

<400> SEQUENCE: 80

Ser Ala Leu Arg Thr Phe
1 5

<210> SEQ ID NO 81
<211> LENGTH: 23
<212> TYPE: PRT
<213> ORGANISM: Artificial Sequence
<220> FEATURE:
<223> OTHER INFORMATION: Protein domain

<400> SEQUENCE: 81

Arg Val Leu Arg Ala Leu Lys Thr Ile Ser Val Ile Pro Gly Leu Lys
1 5 10 15

Thr Ile Val Gly Ala Leu Ile
20

<210> SEQ ID NO 82
<211> LENGTH: 9
<212> TYPE: PRT
<213> ORGANISM: Artificial Sequence
<220> FEATURE:
<223> OTHER INFORMATION: Protein domain

<400> SEQUENCE: 82

Gln Ser Val Lys Lys Leu Ser Asp Val
1 5

<210> SEQ ID NO 83
<211> LENGTH: 23
<212> TYPE: PRT
<213> ORGANISM: Artificial Sequence
<220> FEATURE:
<223> OTHER INFORMATION: Protein domain

<400> SEQUENCE: 83

Met Ile Leu Thr Val Phe Cys Leu Ser Val Phe Ala Leu Ile Gly Leu
1 5 10 15

Gln Leu Phe Met Gly Asn Leu
20

<210> SEQ ID NO 84
<211> LENGTH: 67
<212> TYPE: PRT
<213> ORGANISM: Artificial Sequence
<220> FEATURE:
<223> OTHER INFORMATION: Protein domain

<400> SEQUENCE: 84

Lys His Lys Cys Phe Arg Asn Ser Leu Glu Asn Asn Glu Thr Leu Glu
1 5 10 15

Ser Ile Met Asn Thr Leu Glu Ser Glu Glu Asp Phe Arg Lys Tyr Phe
20 25 30

Tyr Tyr Leu Glu Gly Ser Lys Asp Ala Leu Leu Cys Gly Phe Ser Thr
35 40 45

Asp Ser Gly Gln Cys Pro Glu Gly Tyr Thr Cys Val Lys Ile Gly Arg
50 55 60

Asn Pro Asp
65

<210> SEQ ID NO 85
<211> LENGTH: 20

-continued

<212> TYPE: PRT
<213> ORGANISM: Artificial Sequence
<220> FEATURE:
<223> OTHER INFORMATION: Protein domain

<400> SEQUENCE: 85

Tyr Gly Tyr Thr Ser Phe Asp Thr Phe Ser Trp Ala Phe Leu Ala Leu
1 5 10 15

Phe Arg Leu Met
20

<210> SEQ ID NO 86
<211> LENGTH: 19
<212> TYPE: PRT
<213> ORGANISM: Artificial Sequence
<220> FEATURE:
<223> OTHER INFORMATION: Protein domain

<400> SEQUENCE: 86

Thr Gln Asp Tyr Trp Glu Asn Leu Tyr Gln Gln Thr Leu Arg Ala Ala
1 5 10 15

Gly Lys Thr

<210> SEQ ID NO 87
<211> LENGTH: 23
<212> TYPE: PRT
<213> ORGANISM: Artificial Sequence
<220> FEATURE:
<223> OTHER INFORMATION: Protein domain

<400> SEQUENCE: 87

Tyr Met Ile Phe Phe Val Val Val Ile Phe Leu Gly Ser Phe Tyr Leu
1 5 10 15

Ile Asn Leu Ile Leu Ala Val
20

<210> SEQ ID NO 88
<211> LENGTH: 326
<212> TYPE: PRT
<213> ORGANISM: Artificial Sequence
<220> FEATURE:
<223> OTHER INFORMATION: Protein domain

<400> SEQUENCE: 88

Val Ala Met Ala Tyr Glu Glu Gln Asn Gln Ala Asn Ile Glu Glu Ala
1 5 10 15

Lys Gln Lys Glu Leu Glu Phe Gln Gln Met Leu Asp Arg Leu Lys Lys
20 25 30

Glu Gln Glu Glu Ala Glu Ala Ile Ala Ala Ala Ala Ala Glu Tyr Thr
35 40 45

Ser Ile Arg Arg Ser Arg Ile Met Gly Leu Ser Glu Ser Ser Ser Glu
50 55 60

Thr Ser Lys Leu Ser Ser Lys Ser Ala Lys Glu Arg Arg Asn Arg Arg
65 70 75 80

Lys Lys Lys Asn Gln Lys Lys Leu Ser Ser Gly Glu Glu Lys Gly Asp
85 90 95

Ala Glu Lys Leu Ser Lys Ser Glu Ser Glu Asp Ser Ile Arg Arg Lys
100 105 110

Ser Phe His Leu Gly Val Glu Gly His Arg Arg Ala His Glu Lys Arg
115 120 125

Leu Ser Thr Pro Asn Gln Ser Pro Leu Ser Ile Arg Gly Ser Leu Phe

-continued

```
    130                 135                 140

Ser Ala Arg Arg Ser Ser Arg Thr Ser Leu Phe Ser Phe Lys Gly Arg
145                 150                 155                 160

Gly Arg Asp Ile Gly Ser Glu Thr Glu Phe Ala Asp Asp Glu His Ser
                165                 170                 175

Ile Phe Gly Asp Asn Glu Ser Arg Arg Gly Ser Leu Phe Val Pro His
            180                 185                 190

Arg Pro Gln Glu Arg Arg Ser Ser Asn Ile Ser Gln Ala Ser Arg Ser
        195                 200                 205

Pro Pro Met Leu Pro Val Asn Gly Lys Met His Ser Ala Val Asp Cys
    210                 215                 220

Asn Gly Val Val Ser Leu Val Asp Gly Arg Ser Ala Leu Met Leu Pro
225                 230                 235                 240

Asn Gly Gln Leu Leu Pro Glu Gly Thr Thr Asn Gln Ile His Lys Lys
                245                 250                 255

Arg Arg Cys Ser Ser Tyr Leu Leu Ser Glu Asp Met Leu Asn Asp Pro
            260                 265                 270

Asn Leu Arg Gln Arg Ala Met Ser Arg Ala Ser Ile Leu Thr Asn Thr
        275                 280                 285

Val Glu Glu Leu Glu Glu Ser Arg Gln Lys Cys Pro Pro Trp Trp Tyr
    290                 295                 300

Arg Phe Ala His Lys Phe Leu Ile Trp Asn Cys Ser Pro Tyr Trp Ile
305                 310                 315                 320

Lys Phe Lys Lys Cys Ile
                325


<210> SEQ ID NO 89
<211> LENGTH: 23
<212> TYPE: PRT
<213> ORGANISM: Artificial Sequence
<220> FEATURE:
<223> OTHER INFORMATION: Protein domain

<400> SEQUENCE: 89

Tyr Phe Ile Val Met Asp Pro Phe Val Asp Leu Ala Ile Thr Ile Cys
1               5                   10                  15

Ile Val Leu Asn Thr Leu Phe
            20


<210> SEQ ID NO 90
<211> LENGTH: 14
<212> TYPE: PRT
<213> ORGANISM: Artificial Sequence
<220> FEATURE:
<223> OTHER INFORMATION: Protein domain

<400> SEQUENCE: 90

Met Ala Met Glu His His Pro Met Thr Glu Glu Phe Lys Asn
1               5                   10


<210> SEQ ID NO 91
<211> LENGTH: 23
<212> TYPE: PRT
<213> ORGANISM: Artificial Sequence
<220> FEATURE:
<223> OTHER INFORMATION: Protein domain

<400> SEQUENCE: 91

Val Leu Ala Ile Gly Asn Leu Val Phe Thr Gly Ile Phe Ala Ala Glu
1               5                   10                  15
```

-continued

```
Met Val Leu Lys Leu Ile Ala
            20


<210> SEQ ID NO 92
<211> LENGTH: 6
<212> TYPE: PRT
<213> ORGANISM: Artificial Sequence
<220> FEATURE:
<223> OTHER INFORMATION: Protein domain

<400> SEQUENCE: 92

Met Asp Pro Tyr Glu Tyr
1               5


<210> SEQ ID NO 93
<211> LENGTH: 23
<212> TYPE: PRT
<213> ORGANISM: Artificial Sequence
<220> FEATURE:
<223> OTHER INFORMATION: Protein domain

<400> SEQUENCE: 93

Phe Gln Val Gly Trp Asn Ile Phe Asp Ser Leu Ile Val Thr Leu Ser
1               5                   10                  15

Leu Val Glu Leu Phe Leu Ala
            20


<210> SEQ ID NO 94
<211> LENGTH: 35
<212> TYPE: PRT
<213> ORGANISM: Artificial Sequence
<220> FEATURE:
<223> OTHER INFORMATION: Protein domain

<400> SEQUENCE: 94

Asp Val Glu Gly Leu Ser Val Leu Arg Ser Phe Arg Leu Leu Arg Val
1               5                   10                  15

Phe Lys Leu Ala Lys Ser Trp Pro Thr Leu Asn Met Leu Ile Lys Ile
            20                  25                  30

Ile Gly Asn
        35


<210> SEQ ID NO 95
<211> LENGTH: 23
<212> TYPE: PRT
<213> ORGANISM: Artificial Sequence
<220> FEATURE:
<223> OTHER INFORMATION: Protein domain

<400> SEQUENCE: 95

Ser Val Gly Ala Leu Gly Asn Leu Thr Leu Val Leu Ala Ile Ile Val
1               5                   10                  15

Phe Ile Phe Ala Val Val Gly
            20


<210> SEQ ID NO 96
<211> LENGTH: 60
<212> TYPE: PRT
<213> ORGANISM: Artificial Sequence
<220> FEATURE:
<223> OTHER INFORMATION: Protein domain

<400> SEQUENCE: 96

Met Gln Leu Phe Gly Lys Ser Tyr Lys Glu Cys Val Cys Lys Ile Asn
```

-continued

```
1               5                   10                  15

Asp Asp Cys Thr Leu Pro Arg Trp His Met Asn Asp Phe Phe His Ser
            20                  25                  30

Phe Leu Ile Val Phe Arg Val Leu Cys Gly Glu Trp Ile Glu Thr Met
        35                  40                  45

Trp Asp Cys Met Glu Val Ala Gly Gln Ala Met Cys
    50                  55                  60
```

<210> SEQ ID NO 97
<211> LENGTH: 23
<212> TYPE: PRT
<213> ORGANISM: Artificial Sequence
<220> FEATURE:
<223> OTHER INFORMATION: Protein domain

<400> SEQUENCE: 97

```
Leu Ile Val Tyr Met Met Val Met Val Ile Gly Asn Leu Val Val Leu
1               5                   10                  15

Asn Leu Phe Leu Ala Leu Leu
            20
```

<210> SEQ ID NO 98
<211> LENGTH: 224
<212> TYPE: PRT
<213> ORGANISM: Artificial Sequence
<220> FEATURE:
<223> OTHER INFORMATION: Protein domain

<400> SEQUENCE: 98

```
Leu Ser Ser Phe Ser Ser Asp Asn Leu Thr Ala Ile Glu Glu Asp Pro
1               5                   10                  15

Asp Ala Asn Asn Leu Gln Ile Ala Val Thr Arg Ile Lys Lys Gly Ile
            20                  25                  30

Asn Tyr Val Lys Gln Thr Leu Arg Glu Phe Ile Leu Lys Ala Phe Ser
        35                  40                  45

Lys Lys Pro Lys Ile Ser Arg Glu Ile Arg Gln Ala Glu Asp Leu Asn
    50                  55                  60

Thr Lys Lys Glu Asn Tyr Ile Ser Asn His Thr Leu Ala Glu Met Ser
65                  70                  75                  80

Lys Gly His Asn Phe Leu Lys Glu Lys Asp Lys Ile Ser Gly Phe Gly
                85                  90                  95

Ser Ser Val Asp Lys His Leu Met Glu Asp Ser Asp Gly Gln Ser Phe
            100                 105                 110

Ile His Asn Pro Ser Leu Thr Val Thr Val Pro Ile Ala Pro Gly Glu
        115                 120                 125

Ser Asp Leu Glu Asn Met Asn Ala Glu Glu Leu Ser Ser Asp Ser Asp
    130                 135                 140

Ser Glu Tyr Ser Lys Val Arg Leu Asn Arg Ser Ser Ser Ser Glu Cys
145                 150                 155                 160

Ser Thr Val Asp Asn Pro Leu Pro Gly Glu Gly Glu Glu Ala Glu Ala
                165                 170                 175

Glu Pro Met Asn Ser Asp Glu Pro Glu Ala Cys Phe Thr Asp Gly Cys
            180                 185                 190

Val Arg Arg Phe Ser Cys Cys Gln Val Asn Ile Glu Ser Gly Lys Gly
        195                 200                 205

Lys Ile Trp Trp Asn Ile Arg Lys Thr Cys Tyr Lys Ile Val Glu His
    210                 215                 220
```

-continued

<210> SEQ ID NO 99
<211> LENGTH: 20
<212> TYPE: PRT
<213> ORGANISM: Artificial Sequence
<220> FEATURE:
<223> OTHER INFORMATION: Protein domain

<400> SEQUENCE: 99

Ser Trp Phe Glu Ser Phe Ile Val Leu Met Ile Leu Leu Ser Ser Gly
1 5 10 15

Ala Leu Ala Phe
20

<210> SEQ ID NO 100
<211> LENGTH: 20
<212> TYPE: PRT
<213> ORGANISM: Artificial Sequence
<220> FEATURE:
<223> OTHER INFORMATION: Protein domain

<400> SEQUENCE: 100

Glu Asp Ile Tyr Ile Glu Arg Lys Lys Thr Ile Lys Ile Ile Leu Glu
1 5 10 15

Tyr Ala Asp Lys
20

<210> SEQ ID NO 101
<211> LENGTH: 23
<212> TYPE: PRT
<213> ORGANISM: Artificial Sequence
<220> FEATURE:
<223> OTHER INFORMATION: Protein domain

<400> SEQUENCE: 101

Ile Phe Thr Tyr Ile Phe Ile Leu Glu Met Leu Leu Lys Trp Ile Ala
1 5 10 15

Tyr Gly Tyr Lys Thr Tyr Phe
20

<210> SEQ ID NO 102
<211> LENGTH: 66
<212> TYPE: PRT
<213> ORGANISM: Artificial Sequence
<220> FEATURE:
<223> OTHER INFORMATION: Protein domain

<400> SEQUENCE: 102

Thr Asn Ala Trp Cys Trp Leu Asp Phe Leu Ile Val Asp Val Ser Leu
1 5 10 15

Val Thr Leu Val Ala Asn Thr Leu Gly Tyr Ser Asp Leu Gly Pro Ile
20 25 30

Lys Ser Leu Arg Thr Leu Arg Ala Leu Arg Pro Leu Arg Ala Leu Ser
35 40 45

Arg Phe Glu Gly Met Arg Val Val Val Asn Ala Leu Ile Gly Ala Ile
50 55 60

Pro Ser
65

<210> SEQ ID NO 103
<211> LENGTH: 23
<212> TYPE: PRT
<213> ORGANISM: Artificial Sequence -continued
<220> FEATURE:
<223> OTHER INFORMATION: Protein domain

<400> SEQUENCE: 103

Ile Met Asn Val Leu Leu Val Cys Leu Ile Phe Trp Leu Ile Phe Ser
1 5 10 15

Ile Met Gly Val Asn Leu Phe
20

<210> SEQ ID NO 104
<211> LENGTH: 48
<212> TYPE: PRT
<213> ORGANISM: Artificial Sequence
<220> FEATURE:
<223> OTHER INFORMATION: Protein domain

<400> SEQUENCE: 104

Ala Gly Lys Phe Tyr Glu Cys Ile Asn Thr Thr Asp Gly Ser Arg Phe
1 5 10 15

Pro Ala Ser Gln Val Pro Asn Arg Ser Glu Cys Phe Ala Leu Met Asn
20 25 30

Val Ser Gln Asn Val Arg Trp Lys Asn Leu Lys Val Asn Phe Asp Asn
35 40 45

<210> SEQ ID NO 105
<211> LENGTH: 23
<212> TYPE: PRT
<213> ORGANISM: Artificial Sequence
<220> FEATURE:
<223> OTHER INFORMATION: Protein domain

<400> SEQUENCE: 105

Val Gly Leu Gly Tyr Leu Ser Leu Leu Gln Val Ala Thr Phe Lys Gly
1 5 10 15

Trp Thr Ile Ile Met Tyr Ala
20

<210> SEQ ID NO 106
<211> LENGTH: 19
<212> TYPE: PRT
<213> ORGANISM: Artificial Sequence
<220> FEATURE:
<223> OTHER INFORMATION: Protein domain

<400> SEQUENCE: 106

Ala Val Asp Ser Val Asn Val Asp Lys Gln Pro Lys Tyr Glu Tyr Ser
1 5 10 15

Leu Tyr Met

<210> SEQ ID NO 107
<211> LENGTH: 23
<212> TYPE: PRT
<213> ORGANISM: Artificial Sequence
<220> FEATURE:
<223> OTHER INFORMATION: Protein domain

<400> SEQUENCE: 107

Tyr Ile Tyr Phe Val Val Phe Ile Ile Phe Gly Ser Phe Phe Thr Leu
1 5 10 15

Asn Leu Phe Ile Gly Val Ile
20

<210> SEQ ID NO 108

-continued

<211> LENGTH: 54
<212> TYPE: PRT
<213> ORGANISM: Artificial Sequence
<220> FEATURE:
<223> OTHER INFORMATION: Protein domain

<400> SEQUENCE: 108

Ile Asp Asn Phe Asn Gln Gln Lys Lys Lys Leu Gly Gly Gln Asp Ile
1 5 10 15

Phe Met Thr Glu Glu Gln Lys Lys Tyr Tyr Asn Ala Met Lys Lys Leu
20 25 30

Gly Ser Lys Lys Pro Gln Lys Pro Ile Pro Arg Pro Gly Asn Lys Ile
35 40 45

Gln Gly Cys Ile Phe Asp
50

<210> SEQ ID NO 109
<211> LENGTH: 23
<212> TYPE: PRT
<213> ORGANISM: Artificial Sequence
<220> FEATURE:
<223> OTHER INFORMATION: Protein domain

<400> SEQUENCE: 109

Leu Val Thr Asn Gln Ala Phe Asp Ile Ser Ile Met Val Leu Ile Cys
1 5 10 15

Leu Asn Met Val Thr Met Met
20

<210> SEQ ID NO 110
<211> LENGTH: 14
<212> TYPE: PRT
<213> ORGANISM: Artificial Sequence
<220> FEATURE:
<223> OTHER INFORMATION: Protein domain

<400> SEQUENCE: 110

Val Glu Lys Glu Gly Gln Ser Gln His Met Thr Glu Val Leu
1 5 10

<210> SEQ ID NO 111
<211> LENGTH: 20
<212> TYPE: PRT
<213> ORGANISM: Artificial Sequence
<220> FEATURE:
<223> OTHER INFORMATION: Protein domain

<400> SEQUENCE: 111

Tyr Trp Ile Asn Val Val Phe Ile Ile Leu Phe Thr Gly Glu Cys Val
1 5 10 15

Leu Lys Leu Ile
20

<210> SEQ ID NO 112
<211> LENGTH: 6
<212> TYPE: PRT
<213> ORGANISM: Artificial Sequence
<220> FEATURE:
<223> OTHER INFORMATION: Protein domain

<400> SEQUENCE: 112

Ser Leu Arg His Tyr Tyr
1 5

-continued

<210> SEQ ID NO 113
<211> LENGTH: 23
<212> TYPE: PRT
<213> ORGANISM: Artificial Sequence
<220> FEATURE:
<223> OTHER INFORMATION: Protein domain

<400> SEQUENCE: 113

```
Phe Thr Val Gly Trp Asn Ile Phe Asp Phe Val Val Val Ile Ile Ser
1               5                   10                  15

Ile Val Gly Met Phe Leu Ala
            20
```

<210> SEQ ID NO 114
<211> LENGTH: 50
<212> TYPE: PRT
<213> ORGANISM: Artificial Sequence
<220> FEATURE:
<223> OTHER INFORMATION: Protein domain

<400> SEQUENCE: 114

```
Asp Leu Ile Glu Thr Tyr Phe Val Ser Pro Thr Leu Phe Arg Val Ile
1               5                   10                  15

Arg Leu Ala Arg Ile Gly Arg Ile Leu Arg Leu Val Lys Gly Ala Lys
            20                  25                  30

Gly Ile Arg Thr Leu Leu Phe Ala Leu Met Met Ser Leu Pro Ala Leu
        35                  40                  45

Phe Asn
    50
```

<210> SEQ ID NO 115
<211> LENGTH: 23
<212> TYPE: PRT
<213> ORGANISM: Artificial Sequence
<220> FEATURE:
<223> OTHER INFORMATION: Protein domain

<400> SEQUENCE: 115

```
Ile Gly Leu Leu Leu Phe Leu Val Met Phe Ile Tyr Ala Ile Phe Gly
1               5                   10                  15

Met Ser Asn Phe Ala Tyr Val
            20
```

<210> SEQ ID NO 116
<211> LENGTH: 67
<212> TYPE: PRT
<213> ORGANISM: Artificial Sequence
<220> FEATURE:
<223> OTHER INFORMATION: Protein domain

<400> SEQUENCE: 116

```
Lys Lys Glu Asp Gly Ile Asn Asp Met Phe Asn Phe Glu Thr Phe Gly
1               5                   10                  15

Asn Ser Met Ile Cys Leu Phe Gln Ile Thr Thr Ser Ala Gly Trp Asp
            20                  25                  30

Gly Leu Leu Ala Pro Ile Leu Asn Ser Lys Pro Pro Asp Cys Asp Pro
        35                  40                  45

Lys Lys Val His Pro Gly Ser Ser Val Glu Gly Asp Cys Gly Asn Pro
    50                  55                  60

Ser Val Gly
65
```

-continued

<210> SEQ ID NO 117
<211> LENGTH: 23
<212> TYPE: PRT
<213> ORGANISM: Artificial Sequence
<220> FEATURE:
<223> OTHER INFORMATION: Protein domain

<400> SEQUENCE: 117

Ile Phe Tyr Phe Val Ser Tyr Ile Ile Ile Ser Phe Leu Val Val Val
1               5                   10                  15

Asn Met Tyr Ile Ala Val Ile
            20

<210> SEQ ID NO 118
<211> LENGTH: 229
<212> TYPE: PRT
<213> ORGANISM: Artificial Sequence
<220> FEATURE:
<223> OTHER INFORMATION: Protein domain

<400> SEQUENCE: 118

Leu Glu Asn Phe Ser Val Ala Thr Glu Glu Ser Thr Glu Pro Leu Ser
1               5                   10                  15

Glu Asp Asp Phe Glu Met Phe Tyr Glu Val Trp Glu Lys Phe Asp Pro
            20                  25                  30

Asp Ala Thr Gln Phe Ile Glu Phe Ser Lys Leu Ser Asp Phe Ala Ala
        35                  40                  45

Ala Leu Asp Pro Pro Leu Leu Ile Ala Lys Pro Asn Lys Val Gln Leu
    50                  55                  60

Ile Ala Met Asp Leu Pro Met Val Ser Gly Asp Arg Ile His Cys Leu
65                  70                  75                  80

Asp Ile Leu Phe Ala Phe Thr Lys Arg Val Leu Gly Glu Ser Gly Glu
                85                  90                  95

Met Asp Ser Leu Arg Ser Gln Met Glu Glu Arg Phe Met Ser Ala Asn
            100                 105                 110

Pro Ser Lys Val Ser Tyr Glu Pro Ile Thr Thr Thr Leu Lys Arg Lys
        115                 120                 125

Gln Glu Asp Val Ser Ala Thr Val Ile Gln Arg Ala Tyr Arg Arg Tyr
    130                 135                 140

Arg Leu Arg Gln Asn Val Lys Asn Ile Ser Ser Ile Tyr Ile Lys Asp
145                 150                 155                 160

Gly Asp Arg Asp Asp Asp Leu Leu Asn Lys Lys Asp Met Ala Phe Asp
                165                 170                 175

Asn Val Asn Glu Asn Ser Ser Pro Glu Lys Thr Asp Ala Thr Ser Ser
            180                 185                 190

Thr Thr Ser Pro Pro Ser Tyr Asp Ser Val Thr Lys Pro Asp Lys Glu
        195                 200                 205

Lys Tyr Glu Gln Asp Arg Thr Glu Lys Glu Asp Lys Gly Lys Asp Ser
    210                 215                 220

Lys Glu Ser Lys Lys
225

<210> SEQ ID NO 119
<211> LENGTH: 251
<212> TYPE: PRT
<213> ORGANISM: Artificial Sequence
<220> FEATURE:
<223> OTHER INFORMATION: Protein domain

<400> SEQUENCE: 119

-continued

```
Met Ala Ala Arg Gly Ser Gly Pro Arg Ala Leu Arg Leu Leu Leu Leu
1               5                   10                  15

Val Gln Leu Val Ala Gly Arg Cys Gly Leu Ala Gly Ala Ala Gly Gly
            20                  25                  30

Ala Gln Arg Gly Leu Ser Glu Pro Ser Ser Ile Ala Lys His Glu Asp
        35                  40                  45

Ser Leu Leu Lys Asp Leu Phe Gln Asp Tyr Glu Arg Trp Val Arg Pro
    50                  55                  60

Val Glu His Leu Asn Asp Lys Ile Lys Ile Lys Phe Gly Leu Ala Ile
65                  70                  75                  80

Ser Gln Leu Val Asp Val Asp Glu Lys Asn Gln Leu Met Thr Thr Asn
                85                  90                  95

Val Trp Leu Lys Gln Glu Trp Ile Asp Val Lys Leu Arg Trp Asn Pro
            100                 105                 110

Asp Asp Tyr Gly Gly Ile Lys Val Ile Arg Val Pro Ser Asp Ser Val
        115                 120                 125

Trp Thr Pro Asp Ile Val Leu Phe Asp Asn Ala Asp Gly Arg Phe Glu
    130                 135                 140

Gly Thr Ser Thr Lys Thr Val Ile Arg Tyr Asn Gly Thr Val Thr Trp
145                 150                 155                 160

Thr Pro Pro Ala Asn Tyr Lys Ser Ser Cys Thr Ile Asp Val Thr Phe
                165                 170                 175

Phe Pro Phe Asp Leu Gln Asn Cys Ser Met Lys Phe Gly Ser Trp Thr
            180                 185                 190

Tyr Asp Gly Ser Gln Val Asp Ile Ile Leu Glu Asp Gln Asp Val Asp
        195                 200                 205

Lys Arg Asp Phe Phe Asp Asn Gly Glu Trp Glu Ile Val Ser Ala Thr
    210                 215                 220

Gly Ser Lys Gly Asn Arg Thr Asp Ser Cys Cys Trp Tyr Pro Tyr Val
225                 230                 235                 240

Thr Tyr Ser Phe Val Ile Lys Arg Leu Pro Leu
                245                 250


<210> SEQ ID NO 120
<211> LENGTH: 23
<212> TYPE: PRT
<213> ORGANISM: Artificial Sequence
<220> FEATURE:
<223> OTHER INFORMATION: Protein domain

<400> SEQUENCE: 120

Phe Tyr Thr Leu Phe Leu Ile Ile Pro Cys Ile Gly Leu Ser Phe Leu
1               5                   10                  15

Thr Val Leu Val Phe Tyr Leu
            20


<210> SEQ ID NO 121
<211> LENGTH: 6
<212> TYPE: PRT
<213> ORGANISM: Artificial Sequence
<220> FEATURE:
<223> OTHER INFORMATION: Protein domain

<400> SEQUENCE: 121

Pro Ser Asn Glu Gly Glu
1               5
```

<210> SEQ ID NO 122
<211> LENGTH: 23
<212> TYPE: PRT
<213> ORGANISM: Artificial Sequence
<220> FEATURE:
<223> OTHER INFORMATION: Protein domain

<400> SEQUENCE: 122

```
Lys Ile Cys Leu Cys Thr Ser Val Leu Val Ser Leu Thr Val Phe Leu
1               5                   10                  15

Leu Val Ile Glu Glu Ile Ile
            20
```

<210> SEQ ID NO 123
<211> LENGTH: 9
<212> TYPE: PRT
<213> ORGANISM: Artificial Sequence
<220> FEATURE:
<223> OTHER INFORMATION: Protein domain

<400> SEQUENCE: 123

```
Pro Ser Ser Ser Lys Val Ile Pro Leu
1               5
```

<210> SEQ ID NO 124
<211> LENGTH: 23
<212> TYPE: PRT
<213> ORGANISM: Artificial Sequence
<220> FEATURE:
<223> OTHER INFORMATION: Protein domain

<400> SEQUENCE: 124

```
Ile Gly Glu Tyr Leu Val Phe Thr Met Ile Phe Val Thr Leu Ser Ile
1               5                   10                  15

Met Val Thr Val Phe Ala Ile
            20
```

<210> SEQ ID NO 125
<211> LENGTH: 94
<212> TYPE: PRT
<213> ORGANISM: Artificial Sequence
<220> FEATURE:
<223> OTHER INFORMATION: Protein domain

<400> SEQUENCE: 125

```
Asn Ile His His Arg Ser Ser Ser Thr His Asn Ala Met Ala Pro Leu
1               5                   10                  15

Val Arg Lys Ile Phe Leu His Thr Leu Pro Lys Leu Leu Cys Met Arg
            20                  25                  30

Ser His Val Asp Arg Tyr Phe Thr Gln Lys Glu Glu Thr Glu Ser Gly
        35                  40                  45

Ser Gly Pro Lys Ser Ser Arg Asn Thr Leu Glu Ala Ala Leu Asp Ser
    50                  55                  60

Ile Arg Tyr Ile Thr Arg His Ile Met Lys Glu Asn Asp Val Arg Glu
65                  70                  75                  80

Val Val Glu Asp Trp Lys Phe Ile Ala Gln Val Leu Asp Arg
                85                  90
```

<210> SEQ ID NO 126
<211> LENGTH: 23
<212> TYPE: PRT
<213> ORGANISM: Artificial Sequence
<220> FEATURE:
<223> OTHER INFORMATION: Protein domain -continued

<400> SEQUENCE: 126

Met Phe Leu Trp Thr Phe Leu Phe Val Ser Ile Val Gly Ser Leu Gly
1 5 10 15

Leu Phe Val Pro Val Ile Tyr
20

<210> SEQ ID NO 127
<211> LENGTH: 16
<212> TYPE: PRT
<213> ORGANISM: Artificial Sequence
<220> FEATURE:
<223> OTHER INFORMATION: Protein domain

<400> SEQUENCE: 127

Lys Trp Ala Asn Ile Leu Ile Pro Val His Ile Gly Asn Ala Asn Lys
1 5 10 15

<210> SEQ ID NO 128
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 128
cattgtggac gtgctggcc 19

<210> SEQ ID NO 129
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 129
tgttctttgg ctctgcagc 19

<210> SEQ ID NO 130
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 130
tgctgtgtgg tctaccgac 19

<210> SEQ ID NO 131
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 131
ctgcatgctg aatgagaac 19

<210> SEQ ID NO 132
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 132

-continued gatctcccgc ttcccgctc 19

<210> SEQ ID NO 133
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 133
gcccattgag acactgatc 19

<210> SEQ ID NO 134
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 134
gctcctcaga gtgcagcac 19

<210> SEQ ID NO 135
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 135
gcacatgcag catgagaac 19

<210> SEQ ID NO 136
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 136
gaagcctgaa gacacaaac 19

<210> SEQ ID NO 137
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 137
gtgttccttc agactcttc 19

<210> SEQ ID NO 138
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 138
tagcgctcct ttccgtaac 19

<210> SEQ ID NO 139
<211> LENGTH: 19
<212> TYPE: DNA

-continued

<213> ORGANISM: Artificial Sequence
<220> FEATURE:
<223> OTHER INFORMATION: Knock-down target sequence

<400> SEQUENCE: 139
tggcacttcg ggcaataac 19

<210> SEQ ID NO 140
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 140
cctgaatgtg actgtggac 19

<210> SEQ ID NO 141
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 141
gactgtgagc tgaagatcc 19

<210> SEQ ID NO 142
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 142
acagcttcct cctctattc 19

<210> SEQ ID NO 143
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 143
acaagacatc ctctttctc 19

<210> SEQ ID NO 144
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 144
cttggctctc ttccttgtc 19

<210> SEQ ID NO 145
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 145
ggtggaggtt atcctgaac 19

-continued

<210> SEQ ID NO 146
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 146
tgaagacgat gaagattgc 19

<210> SEQ ID NO 147
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 147
gaacagcgag atttatgac 19

<210> SEQ ID NO 148
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 148
tcacctccct gcagctttc 19

<210> SEQ ID NO 149
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 149
gcagccgttt gatgattcc 19

<210> SEQ ID NO 150
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 150
agaagctgaa cgacaaagc 19

<210> SEQ ID NO 151
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 151
gtgaatgagg actgtgaac 19

<210> SEQ ID NO 152
<211> LENGTH: 19
<212> TYPE: DNA
<213> ORGANISM: Artificial Sequence
<220> FEATURE:

-continued

<223> OTHER INFORMATION: Knock-down target sequence

<400> SEQUENCE: 152
ctggtctgtg ggctgtatc 19

<210> SEQ ID NO 153
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 153
tgaggagaag atccagtac 19

<210> SEQ ID NO 154
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 154
caacttctat gacttctac 19

<210> SEQ ID NO 155
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 155
ctacaaggag attgtgaac 19

<210> SEQ ID NO 156
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 156
tgtctacgac tctctagac 19

<210> SEQ ID NO 157
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 157
caagtctaac aacatcttc 19

<210> SEQ ID NO 158
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 158
ctacctccat gccaagaac 19

-continued

<210> SEQ ID NO 159
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 159
gtctgactgc ctcaagttc 19

<210> SEQ ID NO 160
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 160
cgaggtcctt gaagatgtc 19

<210> SEQ ID NO 161
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 161
acagtgtcca ggatttgtc 19

<210> SEQ ID NO 162
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 162
gacgcgacat gtcaacatc 19

<210> SEQ ID NO 163
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 163
tcccagctgt tcttcatgc 19

<210> SEQ ID NO 164
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 164
ctgccgtctc aagaagtgc 19

<210> SEQ ID NO 165
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 165
ccgtctcaag aagtgcttc 19

<210> SEQ ID NO 166
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 166
agcattacgg tgtcttcac 19

<210> SEQ ID NO 167
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 167
tgagacactg atcagagac 19

<210> SEQ ID NO 168
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 168
ttacggtgtc ttcacctgc 19

<210> SEQ ID NO 169
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 169
ccaaggatgt atatttgac 19

<210> SEQ ID NO 170
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 170
tgagggtcgt tgtgaatgc 19

<210> SEQ ID NO 171
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 171
acacctgctt tatatatgc 19

<210> SEQ ID NO 172
<211> LENGTH: 19

-continued

<212> TYPE: DNA
<213> ORGANISM: Artificial Sequence
<220> FEATURE:
<223> OTHER INFORMATION: Knock-down target sequence

<400> SEQUENCE: 172
gtcttgacat cttatttgc 19

<210> SEQ ID NO 173
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 173
tgattcggat agtgaatac 19

<210> SEQ ID NO 174
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 174
gaagaagctt tctgatgtc 19

<210> SEQ ID NO 175
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 175
caaactgcat atttatgac 19

<210> SEQ ID NO 176
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 176
acccaacaag ctgcacttc 19

<210> SEQ ID NO 177
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 177
catcgaggtg tactatttc 19

<210> SEQ ID NO 178
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 178

-continued ggagctgatg gaactcaac 19

<210> SEQ ID NO 179
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 179
tgggtatctt cgtcttctc 19

<210> SEQ ID NO 180
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 180
catcatcaac aactttgtc 19

<210> SEQ ID NO 181
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 181
gaagtgcgtc tggaagttc 19

<210> SEQ ID NO 182
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 182
gaaggtggac ctcaagttc 19

<210> SEQ ID NO 183
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 183
acaagccctt gactacttc 19

<210> SEQ ID NO 184
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 184
gtctggatat tcattacac 19

<210> SEQ ID NO 185
<211> LENGTH: 19
<212> TYPE: DNA
<213> ORGANISM: Artificial Sequence -continued
<220> FEATURE:
<223> OTHER INFORMATION: Knock-down target sequence

<400> SEQUENCE: 185
agaaatgttt cgtccaaac 19

<210> SEQ ID NO 186
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 186
ctacctcctg aatttcttc 19

<210> SEQ ID NO 187
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 187
tcacaagttt gaaatttcc 19

<210> SEQ ID NO 188
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 188
gatgcagtct ccattgttc 19

<210> SEQ ID NO 189
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 189
gaacaagaag gacgtcaac 19

<210> SEQ ID NO 190
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 190
tgtttgaccg agtctacac 19

<210> SEQ ID NO 191
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 191
acgttaccgt gctcaagac 19

-continued

<210> SEQ ID NO 192
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 192
acacgacctg tacatgatc 19

<210> SEQ ID NO 193
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 193
caaggagcta gaggttctc 19

<210> SEQ ID NO 194
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 194
cttgtttgac cgagtctac 19

<210> SEQ ID NO 195
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 195
gcacaacctc gactactac 19

<210> SEQ ID NO 196
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 196
actactacaa gaagacaac 19

<210> SEQ ID NO 197
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 197
atccgtatgt cacttactc 19

<210> SEQ ID NO 198
<211> LENGTH: 19
<212> TYPE: DNA
<213> ORGANISM: Artificial Sequence
<220> FEATURE:
<223> OTHER INFORMATION: Knock-down target sequence -continued

<400> SEQUENCE: 198
atagcccagg ttcttgatc 19

<210> SEQ ID NO 199
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 199
aagagatcat accatcatc 19

<210> SEQ ID NO 200
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 200
agagtatctg gtatttacc 19

<210> SEQ ID NO 201
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 201
catgagaagt catgtagac 19

<210> SEQ ID NO 202
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 202
acaaacgtct ggttgaaac 19

<210> SEQ ID NO 203
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 203
gtacttgtct tctatcttc 19

<210> SEQ ID NO 204
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 204
tcccaacgtc catatggtc 19

<210> SEQ ID NO 205

-continued

<211> LENGTH: 19
<212> TYPE: DNA
<213> ORGANISM: Artificial Sequence
<220> FEATURE:
<223> OTHER INFORMATION: Knock-down target sequence

<400> SEQUENCE: 205
tcacctccct gcagctttc 19

<210> SEQ ID NO 206
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 206
gagcgatgtg tggtccttc 19

<210> SEQ ID NO 207
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 207
taccctgtat tgggctctc 19

<210> SEQ ID NO 208
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 208
gctgcgctcg attctattc 19

<210> SEQ ID NO 209
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 209
ttccatggta atggtgtgc 19

<210> SEQ ID NO 210
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 210
ccgaagcaag gaataatcc 19

<210> SEQ ID NO 211
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 211

-continued cgtcaccttt gaggacgcc 19

<210> SEQ ID NO 212
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 212
tgtctgggtc aaggatggc 19

<210> SEQ ID NO 213
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 213
aagtttggca gcatccggc 19

<210> SEQ ID NO 214
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 214
tgacaaggac ctgtcggac 19

<210> SEQ ID NO 215
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 215
ggagctagag gttctctcc 19

<210> SEQ ID NO 216
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 216
tttcgtcgtg gaccagagc 19

<210> SEQ ID NO 217
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 217
cacggagaac gacctcaac 19

<210> SEQ ID NO 218
<211> LENGTH: 19
<212> TYPE: DNA

-continued

<213> ORGANISM: Artificial Sequence
<220> FEATURE:
<223> OTHER INFORMATION: Knock-down target sequence

<400> SEQUENCE: 218
gatgcaggac aagtaggac 19

<210> SEQ ID NO 219
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 219
gcgcgagttc tactttgac 19

<210> SEQ ID NO 220
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 220
gagctggagc tgatggaac 19

<210> SEQ ID NO 221
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 221
gaggtgctca gcttcaagc 19

<210> SEQ ID NO 222
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 222
gaagctgtat cggcccttc 19

<210> SEQ ID NO 223
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 223
agcggccaaa tcctacatc 19

<210> SEQ ID NO 224
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 224
catctggaag gaagagccc 19

-continued

<210> SEQ ID NO 225
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 225
tcctaggaca gccttgttc 19

<210> SEQ ID NO 226
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 226
cctcatctcc cagctgttc 19

<210> SEQ ID NO 227
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 227
gatgatgatg aagaagccc 19

<210> SEQ ID NO 228
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 228
cctcacctta gtgttggcc 19

<210> SEQ ID NO 229
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 229
tctcaccaac aagtggtac 19

<210> SEQ ID NO 230
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 230
accgaagatg atgttcatc 19

<210> SEQ ID NO 231
<211> LENGTH: 21
<212> TYPE: DNA
<213> ORGANISM: Artificial Sequence
<220> FEATURE:

-continued

<223> OTHER INFORMATION: Knock-down target sequence

<400> SEQUENCE: 231
aacattgtgg acgtgctggc c 21

<210> SEQ ID NO 232
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 232
aatgttcttt ggctctgcag c 21

<210> SEQ ID NO 233
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 233
actgctgtgt ggtctaccga c 21

<210> SEQ ID NO 234
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 234
aactgcatgc tgaatgagaa c 21

<210> SEQ ID NO 235
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 235
aagatctccc gcttcccgct c 21

<210> SEQ ID NO 236
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 236
acgcccattg agacactgat c 21

<210> SEQ ID NO 237
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 237
aagctcctca gagtgcagca c 21

-continued

<210> SEQ ID NO 238
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 238
aagcacatgc agcatgagaa c 21

<210> SEQ ID NO 239
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 239
aagaagcctg aagacacaaa c 21

<210> SEQ ID NO 240
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 240
acgtgttcct tcagactctt c 21

<210> SEQ ID NO 241
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 241
actagcgctc ctttccgtaa c 21

<210> SEQ ID NO 242
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 242
actggcactt cgggcaataa c 21

<210> SEQ ID NO 243
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 243
aacctgaatg tgactgtgga c 21

<210> SEQ ID NO 244
<211> LENGTH: 21
<212> TYPE: DNA
<213> ORGANISM: Artificial Sequence
<220> FEATURE:
<223> OTHER INFORMATION: Knock-down target sequence -continued

<400> SEQUENCE: 244
aagactgtga gctgaagatc c 21

<210> SEQ ID NO 245
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 245
gctgaccctg aagttcatc 19

<210> SEQ ID NO 246
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 246
gctgaccctg aagttcatc 19

<210> SEQ ID NO 247
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 247
atgaagagca aggcattcc 19

<210> SEQ ID NO 248
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 248
tgcctgggac cagagcttc 19

<210> SEQ ID NO 249
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 249
ggaagtaatt ggatcatgc 19

<210> SEQ ID NO 250
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 250
gctgaccctg aagttcatc 19

<210> SEQ ID NO 251
<211> LENGTH: 19

-continued

<212> TYPE: DNA
<213> ORGANISM: Artificial Sequence
<220> FEATURE:
<223> OTHER INFORMATION: Knock-down target sequence

<400> SEQUENCE: 251
gctgaccctg aagttcatc 19

<210> SEQ ID NO 252
<211> LENGTH: 18
<212> TYPE: DNA
<213> ORGANISM: Artificial Sequence
<220> FEATURE:
<223> OTHER INFORMATION: Knock-down target sequence

<400> SEQUENCE: 252
gtcatgttgg cagaactc 18

<210> SEQ ID NO 253
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 253
tgccgtgaat ggagaacac 19

<210> SEQ ID NO 254
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 254
aatgccgtga atggagaaca c 21

<210> SEQ ID NO 255
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 255
tccttagttc ctcagaggc 19

<210> SEQ ID NO 256
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 256
aatccttagt tcctcagagg c 21

<210> SEQ ID NO 257
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 257

-continued gattaccttg cctgttgac 19

<210> SEQ ID NO 258
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 258
aagattacct tgcctgttga c 21

<210> SEQ ID NO 259
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 259
ctgactttgg attctgtgc 19

<210> SEQ ID NO 260
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 260
aactgacttt ggattctgtg c 21

<210> SEQ ID NO 261
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 261
gacatgccgc tatttgagc 19

<210> SEQ ID NO 262
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 262
aagacatgcc gctatttgag c 21

<210> SEQ ID NO 263
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 263
agtgagacac tgacagaac 19

<210> SEQ ID NO 264
<211> LENGTH: 21
<212> TYPE: DNA
<213> ORGANISM: Artificial Sequence -continued
<220> FEATURE:
<223> OTHER INFORMATION: Knock-down target sequence

<400> SEQUENCE: 264
aaagtgagac actgacagaa c 21

<210> SEQ ID NO 265
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 265
ggccttgaaa ggacagtac 19

<210> SEQ ID NO 266
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 266
aaggccttga aaggacagta c 21

<210> SEQ ID NO 267
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 267
gactgagtca agtgtctgc 19

<210> SEQ ID NO 268
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 268
aagactgagt caagtgtctg c 21

<210> SEQ ID NO 269
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 269
tggtggctac aaccaactc 19

<210> SEQ ID NO 270
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 270
aatggtggct acaaccaact c 21

-continued

<210> SEQ ID NO 271
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 271
tgtgactgtg ggagtggac 19

<210> SEQ ID NO 272
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 272
aatgtgactg tgggagtgga c 21

<210> SEQ ID NO 273
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 273
actgctgctg tatgtggac 19

<210> SEQ ID NO 274
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 274
acactgctgc tgtatgtgga c 21

<210> SEQ ID NO 275
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 275
ctgtgttgat ttctctgcc 19

<210> SEQ ID NO 276
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 276
aactgtgttg atttctctgc c 21

<210> SEQ ID NO 277
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 277
tcccttgtat ccggacttc 19

<210> SEQ ID NO 278
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 278
aatcccttgt atccggactt c 21

<210> SEQ ID NO 279
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 279
caagagctgg taccgcgtc 19

<210> SEQ ID NO 280
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 280
aacaagagct ggtaccgcgt c 21

<210> SEQ ID NO 281
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 281
tgtggtggcc tacattggc 19

<210> SEQ ID NO 282
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 282
aatgtggtgg cctacattgg c 21

<210> SEQ ID NO 283
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 283
gaacctcact tccagtcac 19

<210> SEQ ID NO 284

-continued

<211> LENGTH: 21
<212> TYPE: DNA
<213> ORGANISM: Artificial Sequence
<220> FEATURE:
<223> OTHER INFORMATION: Knock-down target sequence

<400> SEQUENCE: 284
aagaacctca cttccagtca c 21

<210> SEQ ID NO 285
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 285
atcagtgggc tgtggattc 19

<210> SEQ ID NO 286
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 286
aaatcagtgg gctgtggatt c 21

<210> SEQ ID NO 287
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 287
cattgtggac tttgctggc 19

<210> SEQ ID NO 288
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 288
aacattgtgg actttgctgg c 21

<210> SEQ ID NO 289
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 289
atgactgagc cacacaaac 19

<210> SEQ ID NO 290
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 290
acatgactga gccacacaaa c 21

<210> SEQ ID NO 291
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 291
ctttgcacct atctctgac 19

<210> SEQ ID NO 292
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 292
acctttgcac ctatctctga c 21

<210> SEQ ID NO 293
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 293
tgcgctttgc caagatgcc 19

<210> SEQ ID NO 294
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 294
aatgcgcttt gccaagatgc c 21

<210> SEQ ID NO 295
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 295
acatgtgttc cagaaggac 19

<210> SEQ ID NO 296
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 296
gcacatgtgt tccagaagga c 21

<210> SEQ ID NO 297
<211> LENGTH: 19
<212> TYPE: DNA

-continued

<213> ORGANISM: Artificial Sequence
<220> FEATURE:
<223> OTHER INFORMATION: Knock-down target sequence

<400> SEQUENCE: 297
acctggcttc aacatcagc 19

<210> SEQ ID NO 298
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 298
aaacctggct tcaacatcag c 21

<210> SEQ ID NO 299
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 299
tggatgacca caagctgtc 19

<210> SEQ ID NO 300
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 300
aatggatgac cacaagctgt c 21

<210> SEQ ID NO 301
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 301
acatgcactg cagaaggcc 19

<210> SEQ ID NO 302
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 302
aaacatgcac tgcagaaggc c 21

<210> SEQ ID NO 303
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 303
atgtgccatc cagttgtgc 19

-continued

<210> SEQ ID NO 304
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 304
aaatgtgcca tccagttgtg c 21

<210> SEQ ID NO 305
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 305
ctatgtggac tggatcaac 19

<210> SEQ ID NO 306
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 306
aactatgtgg actggatcaa c 21

<210> SEQ ID NO 307
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 307
tgaaggcctc acgtgtgtc 19

<210> SEQ ID NO 308
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 308
actgaaggcc tcacgtgtgt c 21

<210> SEQ ID NO 309
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 309
catgaaggcc cgaaactac 19

<210> SEQ ID NO 310
<211> LENGTH: 21
<212> TYPE: DNA
<213> ORGANISM: Artificial Sequence
<220> FEATURE:

-continued

<223> OTHER INFORMATION: Knock-down target sequence

<400> SEQUENCE: 310
aacatgaagg cccgaaacta c 21

<210> SEQ ID NO 311
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 311
agatggccac aaacctgcc 19

<210> SEQ ID NO 312
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 312
aaagatggcc acaaacctgc c 21

<210> SEQ ID NO 313
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 313
atgaagagca aggcattcc 19

<210> SEQ ID NO 314
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 314
aaatgaagag caaggcattc c 21

<210> SEQ ID NO 315
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 315
catcccacac aagttcagc 19

<210> SEQ ID NO 316
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 316
aacatcccac acaagttcag c 21

-continued

<210> SEQ ID NO 317
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 317
ctcatgttta ccatggtcc 19

<210> SEQ ID NO 318
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 318
acctcatgtt taccatggtc c 21

<210> SEQ ID NO 319
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 319
attgttctcc cagatggcc 19

<210> SEQ ID NO 320
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 320
acattgttct cccagatggc c 21

<210> SEQ ID NO 321
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 321
ttcatgagaa gactggtgc 19

<210> SEQ ID NO 322
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 322
acttcatgag aagactggtg c 21

<210> SEQ ID NO 323
<211> LENGTH: 19
<212> TYPE: DNA
<213> ORGANISM: Artificial Sequence
<220> FEATURE:
<223> OTHER INFORMATION: Knock-down target sequence -continued

<400> SEQUENCE: 323
tgactgcacc tatgagagc 19

<210> SEQ ID NO 324
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 324
cctgactgca cctatgagag c 21

<210> SEQ ID NO 325
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 325
ttcagtgcat tcaaggacc 19

<210> SEQ ID NO 326
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 326
acttcagtgc attcaaggac c 21

<210> SEQ ID NO 327
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 327
acgtgccagt ttcttctcc 19

<210> SEQ ID NO 328
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 328
aaacgtgcca gtttcttctc c 21

<210> SEQ ID NO 329
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 329
gtgtatctta tgcctacac 19

<210> SEQ ID NO 330
<211> LENGTH: 21

-continued

<212> TYPE: DNA
<213> ORGANISM: Artificial Sequence
<220> FEATURE:
<223> OTHER INFORMATION: Knock-down target sequence

<400> SEQUENCE: 330
acgtgtatct tatgcctaca c 21

<210> SEQ ID NO 331
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 331
agctgctgga gatgttatc 19

<210> SEQ ID NO 332
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 332
acagctgctg gagatgttat c 21

<210> SEQ ID NO 333
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 333
caagtgactg tgattgccc 19

<210> SEQ ID NO 334
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 334
accaagtgac tgtgattgcc c 21

<210> SEQ ID NO 335
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 335
ttcagtgcct aacagtggc 19

<210> SEQ ID NO 336
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 336

-continued acttcagtgc ctaacagtgg c 21

<210> SEQ ID NO 337
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 337
cttgatcatg atggccttc 19

<210> SEQ ID NO 338
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 338
accttgatca tgatggcctt c 21

<210> SEQ ID NO 339
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 339
acccggcacc gtgtacttc 19

<210> SEQ ID NO 340
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 340
aaacccggca ccgtgtactt c 21

<210> SEQ ID NO 341
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 341
ctactgatgt ccctgatac 19

<210> SEQ ID NO 342
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 342
acctactgat gtccctgata c 21

<210> SEQ ID NO 343
<211> LENGTH: 19
<212> TYPE: DNA
<213> ORGANISM: Artificial Sequence -continued
<220> FEATURE:
<223> OTHER INFORMATION: Knock-down target sequence

<400> SEQUENCE: 343
tttctgtgag ctgtgaaac 19

<210> SEQ ID NO 344
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 344
actttctgtg agctgtgaaa c 21

<210> SEQ ID NO 345
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 345
tatactggag cctgtaacc 19

<210> SEQ ID NO 346
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 346
aatatactgg agcctgtaac c 21

<210> SEQ ID NO 347
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 347
tttgtggact cctacgatc 19

<210> SEQ ID NO 348
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 348
aatttgtgga ctcctacgat c 21

<210> SEQ ID NO 349
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 349
ggagacaagt tcgcatgtc 19

-continued

<210> SEQ ID NO 350
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 350
aaggagacaa gttcgcatgt c 21

<210> SEQ ID NO 351
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 351
cggctggttc accatgatc 19

<210> SEQ ID NO 352
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 352
accggctggt tcaccatgat c 21

<210> SEQ ID NO 353
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 353
gtattctgta caccctggc 19

<210> SEQ ID NO 354
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 354
acgtattctg tacaccctgg c 21

<210> SEQ ID NO 355
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 355
gactgctaga caagacgac 19

<210> SEQ ID NO 356
<211> LENGTH: 21
<212> TYPE: DNA
<213> ORGANISM: Artificial Sequence
<220> FEATURE:
<223> OTHER INFORMATION: Knock-down target sequence -continued

<400> SEQUENCE: 356
acgactgcta gacaagacga c 21

<210> SEQ ID NO 357
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 357
cctgtgttca gctctggac 19

<210> SEQ ID NO 358
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 358
aacctgtgtt cagctctgga c 21

<210> SEQ ID NO 359
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 359
acattctcct ggccaggtc 19

<210> SEQ ID NO 360
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 360
aaacattctc ctggccaggt c 21

<210> SEQ ID NO 361
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 361
gactgagaac cttgatgtc 19

<210> SEQ ID NO 362
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 362
aagactgaga accttgatgt c 21

<210> SEQ ID NO 363

-continued

<211> LENGTH: 19
<212> TYPE: DNA
<213> ORGANISM: Artificial Sequence
<220> FEATURE:
<223> OTHER INFORMATION: Knock-down target sequence

<400> SEQUENCE: 363
tattgccctg ttagtgttc 19

<210> SEQ ID NO 364
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 364
cctattgccc tgttagtgtt c 21

<210> SEQ ID NO 365
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 365
tgtggagtct ttgtgctcc 19

<210> SEQ ID NO 366
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 366
actgtggagt ctttgtgctc c 21

<210> SEQ ID NO 367
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 367
ttcctgtgga atgactgtc 19

<210> SEQ ID NO 368
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 368
aattcctgtg gaatgactgt c 21

<210> SEQ ID NO 369
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 369

-continued acgtggttgg aagctaacc 19

<210> SEQ ID NO 370
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 370
acacgtggtt ggaagctaac c 21

<210> SEQ ID NO 371
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 371
caagtctaca cgggctcac 19

<210> SEQ ID NO 372
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 372
aacaagtcta cacgggctca c 21

<210> SEQ ID NO 373
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 373
tcctggaggc tatccgcac 19

<210> SEQ ID NO 374
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 374
aatcctggag gctatccgca c 21

<210> SEQ ID NO 375
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 375
tcggcacaac aatctagac 19

<210> SEQ ID NO 376
<211> LENGTH: 21
<212> TYPE: DNA

-continued

<213> ORGANISM: Artificial Sequence
<220> FEATURE:
<223> OTHER INFORMATION: Knock-down target sequence

<400> SEQUENCE: 376
actcggcaca acaatctaga c 21

<210> SEQ ID NO 377
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 377
acgcgcctta atttagtcc 19

<210> SEQ ID NO 378
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 378
aaacgcgcct taatttagtc c 21

<210> SEQ ID NO 379
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 379
agcatgatga tagttcctc 19

<210> SEQ ID NO 380
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 380
ccagcatgat gatagttcct c 21

<210> SEQ ID NO 381
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 381
tgggcacaca tctccagtc 19

<210> SEQ ID NO 382
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 382
actgggcaca catctccagt c 21

<210> SEQ ID NO 383
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 383
accgtggaag gcctatcgc 19

<210> SEQ ID NO 384
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 384
aaaccgtgga aggcctatcg c 21

<210> SEQ ID NO 385
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 385
tgaatccaca gctctactc 19

<210> SEQ ID NO 386
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 386
aatgaatcca cagctctact c 21

<210> SEQ ID NO 387
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 387
caagtacaac aaggactcc 19

<210> SEQ ID NO 388
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 388
accaagtaca acaaggactc c 21

<210> SEQ ID NO 389
<211> LENGTH: 19
<212> TYPE: DNA
<213> ORGANISM: Artificial Sequence
<220> FEATURE:

-continued

<223> OTHER INFORMATION: Knock-down target sequence

<400> SEQUENCE: 389
cattcagtgc tgccttcac 19

<210> SEQ ID NO 390
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 390
tccattcagt gctgccttca c 21

<210> SEQ ID NO 391
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 391
gatggccatc ctgcagatc 19

<210> SEQ ID NO 392
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 392
aagatggcca tcctgcagat c 21

<210> SEQ ID NO 393
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 393
tcattgtgcc atcccaaac 19

<210> SEQ ID NO 394
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 394
aatcattgtg ccatcccaaa c 21

<210> SEQ ID NO 395
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 395
aacctggccc taatgctgc 19

-continued

<210> SEQ ID NO 396
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 396
tcaacctggc cctaatgctg c 21

<210> SEQ ID NO 397
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 397
ctgactcacc tggtactgc 19

<210> SEQ ID NO 398
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 398
aactgactca cctggtactg c 21

<210> SEQ ID NO 399
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 399
tgctgtgtgc tggagtacc 19

<210> SEQ ID NO 400
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 400
aatgctgtgt gctggagtac c 21

<210> SEQ ID NO 401
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 401
gcattgctat tgctcgggc 19

<210> SEQ ID NO 402
<211> LENGTH: 21
<212> TYPE: DNA
<213> ORGANISM: Artificial Sequence
<220> FEATURE:
<223> OTHER INFORMATION: Knock-down target sequence -continued

<400> SEQUENCE: 402
acgcattgct attgctcggg c 21

<210> SEQ ID NO 403
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 403
tgtggagtgt gagaagctc 19

<210> SEQ ID NO 404
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 404
aatgtggagt gtgagaagct c 21

<210> SEQ ID NO 405
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 405
tctgtgggcc tcctattcc 19

<210> SEQ ID NO 406
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 406
actctgtggg cctcctattc c 21

<210> SEQ ID NO 407
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 407
tgccggcatc tcaacgttc 19

<210> SEQ ID NO 408
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 408
aatgccggca tctcaacgtt c 21

<210> SEQ ID NO 409
<211> LENGTH: 19

-continued

<212> TYPE: DNA
<213> ORGANISM: Artificial Sequence
<220> FEATURE:
<223> OTHER INFORMATION: Knock-down target sequence

<400> SEQUENCE: 409
tgtgactgtc ctagttgcc 19

<210> SEQ ID NO 410
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 410
aatgtgactg tcctagttgc c 21

<210> SEQ ID NO 411
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 411
agctgtgttc atcaacatc 19

<210> SEQ ID NO 412
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 412
acagctgtgt tcatcaacat c 21

<210> SEQ ID NO 413
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 413
tgggcagaat gtcctggac 19

<210> SEQ ID NO 414
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 414
aatgggcaga atgtcctgga c 21

<210> SEQ ID NO 415
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 415

-continued cacatgctca acatggtgc 19

<210> SEQ ID NO 416
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 416
accacatgct caacatggtg c 21

<210> SEQ ID NO 417
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 417
cagtgactaa ccagaactc 19

<210> SEQ ID NO 418
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 418
accagtgact aaccagaact c 21

<210> SEQ ID NO 419
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 419
tacatgtgtc ggaggtttc 19

<210> SEQ ID NO 420
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 420
actacatgtg tcggaggttt c 21

<210> SEQ ID NO 421
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 421
gatgtagata ccacaaggc 19

<210> SEQ ID NO 422
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 422
acgatgtaga taccacaagg c 21

<210> SEQ ID NO 423
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 423
tggtggcaag tccatctac 19

<210> SEQ ID NO 424
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 424
actggtggca agtccatcta c 21

<210> SEQ ID NO 425
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 425
acatggtccg agtagaagc 19

<210> SEQ ID NO 426
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 426
aaacatggtc cgagtagaag c 21

<210> SEQ ID NO 427
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 427
atgtgttgtg gagtccgcc 19

<210> SEQ ID NO 428
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 428
aaatgtgttg tggagtccgc c 21

-continued

<210> SEQ ID NO 429
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 429
acttgggctg cagtgcatc 19

<210> SEQ ID NO 430
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 430
aaacttgggc tgcagtgcat c 21

<210> SEQ ID NO 431
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 431
gtggcctaac ccggagaac 19

<210> SEQ ID NO 432
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 432
aagtggccta acccggagaa c 21

<210> SEQ ID NO 433
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 433
agttcctggt gaacattcc 19

<210> SEQ ID NO 434
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 434
gcagttcctg gtgaacattc c 21

<210> SEQ ID NO 435
<211> LENGTH: 19
<212> TYPE: DNA
<213> ORGANISM: Artificial Sequence
<220> FEATURE:
<223> OTHER INFORMATION: Knock-down target sequence -continued

<400> SEQUENCE: 435
gttgtgttcc cgagactac 19

<210> SEQ ID NO 436
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 436
aagttgtgtt cccgagacta c 21

<210> SEQ ID NO 437
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 437
agagctgtgt ctgaacatc 19

<210> SEQ ID NO 438
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 438
aaagagctgt gtctgaacat c 21

<210> SEQ ID NO 439
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 439
tgcaaggtga tcggcttcc 19

<210> SEQ ID NO 440
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 440
aatgcaaggt gatcggcttc c 21

<210> SEQ ID NO 441
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 441
cgacaccaga aattcactc 19

<210> SEQ ID NO 442

-continued

<211> LENGTH: 21
<212> TYPE: DNA
<213> ORGANISM: Artificial Sequence
<220> FEATURE:
<223> OTHER INFORMATION: Knock-down target sequence

<400> SEQUENCE: 442
aacgacacca gaaattcact c 21

<210> SEQ ID NO 443
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 443
tgttctccat cttcttccc 19

<210> SEQ ID NO 444
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 444
aatgttctcc atcttcttcc c 21

<210> SEQ ID NO 445
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 445
atctgtgtgg caggttacc 19

<210> SEQ ID NO 446
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 446
acatctgtgt ggcaggttac c 21

<210> SEQ ID NO 447
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 447
tagtccagtg gatctcacc 19

<210> SEQ ID NO 448
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 448

-continued actagtccag tggatctcac c 21

<210> SEQ ID NO 449
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 449
ttccagggat tactccaac 19

<210> SEQ ID NO 450
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 450
aattccaggg attactccaa c 21

<210> SEQ ID NO 451
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 451
actgactcca gtttctgcc 19

<210> SEQ ID NO 452
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 452
aaactgactc cagtttctgc c 21

<210> SEQ ID NO 453
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 453
tggatgactt cagctctac 19

<210> SEQ ID NO 454
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 454
aatggatgac ttcagctcta c 21

<210> SEQ ID NO 455
<211> LENGTH: 19
<212> TYPE: DNA

-continued

<213> ORGANISM: Artificial Sequence
<220> FEATURE:
<223> OTHER INFORMATION: Knock-down target sequence

<400> SEQUENCE: 455
gcagtcgact ccagaagac 19

<210> SEQ ID NO 456
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 456
aagcagtcga ctccagaaga c 21

<210> SEQ ID NO 457
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 457
tgactctgct aggacggtc 19

<210> SEQ ID NO 458
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 458
aatgactctg ctaggacggt c 21

<210> SEQ ID NO 459
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 459
agaatctgca gaaagccac 19

<210> SEQ ID NO 460
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 460
ccagaatctg cagaaagcca c 21

<210> SEQ ID NO 461
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 461
ttccacaacg tgtgcctgc 19

-continued

<210> SEQ ID NO 462
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 462
aattccacaa cgtgtgcctg c 21

<210> SEQ ID NO 463
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 463
tgggcgggta gatggaatc 19

<210> SEQ ID NO 464
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 464
actgggcggg tagatggaat c 21

<210> SEQ ID NO 465
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 465
gtgactcatg atctagccc 19

<210> SEQ ID NO 466
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 466
acgtgactca tgatctagcc c 21

<210> SEQ ID NO 467
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 467
ggctgaagca gacacagac 19

<210> SEQ ID NO 468
<211> LENGTH: 21
<212> TYPE: DNA
<213> ORGANISM: Artificial Sequence
<220> FEATURE:

-continued

<223> OTHER INFORMATION: Knock-down target sequence

<400> SEQUENCE: 468
aaggctgaag cagacacaga c 21

<210> SEQ ID NO 469
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 469
ggacattcag atagcgctc 19

<210> SEQ ID NO 470
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 470
acggacattc agatagcgct c 21

<210> SEQ ID NO 471
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 471
gatgttctgt gtgggcttc 19

<210> SEQ ID NO 472
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 472
aagatgttct gtgtgggctt c 21

<210> SEQ ID NO 473
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 473
tttgtggacc tgagcttcc 19

<210> SEQ ID NO 474
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 474
actttgtgga cctgagcttc c 21

-continued

<210> SEQ ID NO 475
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 475
tactggcttc gctttcatc 19

<210> SEQ ID NO 476
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 476
actactggct tcgctttcat c 21

<210> SEQ ID NO 477
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 477
tggctcttac gtgattcac 19

<210> SEQ ID NO 478
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 478
aatggctctt acgtgattca c 21

<210> SEQ ID NO 479
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 479
ctatgttcag cccaagcgc 19

<210> SEQ ID NO 480
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 480
aactatgttc agcccaagcg c 21

<210> SEQ ID NO 481
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 481
gggaagacag agctgtttc 19

<210> SEQ ID NO 482
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 482
aagggaagac agagctgttt c 21

<210> SEQ ID NO 483
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 483
cctgagttcc cagcatgtc 19

<210> SEQ ID NO 484
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 484
accctgagtt cccagcatgt c 21

<210> SEQ ID NO 485
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 485
tggccttgga atctcttcc 19

<210> SEQ ID NO 486
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 486
actggccttg gaatctcttc c 21

<210> SEQ ID NO 487
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 487
tgctgtatcc ttcctggac 19

<210> SEQ ID NO 488
<211> LENGTH: 21

-continued

<212> TYPE: DNA
<213> ORGANISM: Artificial Sequence
<220> FEATURE:
<223> OTHER INFORMATION: Knock-down target sequence

<400> SEQUENCE: 488
aatgctgtat ccttcctgga c 21

<210> SEQ ID NO 489
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 489
taaccctgcc tactacgtc 19

<210> SEQ ID NO 490
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 490
aataaccctg cctactacgt c 21

<210> SEQ ID NO 491
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 491
tcgggcggat ctgcttatc 19

<210> SEQ ID NO 492
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 492
aatcgggcgg atctgcttat c 21

<210> SEQ ID NO 493
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 493
tgctgctgtc aaccctttc 19

<210> SEQ ID NO 494
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 494

-continued aatgctgctg tcaacccttt c 21

<210> SEQ ID NO 495
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 495
tcgtggaagg actcatggc 19

<210> SEQ ID NO 496
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 496
aatcgtggaa ggactcatgg c 21

<210> SEQ ID NO 497
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 497
acctggtaac caagcctgc 19

<210> SEQ ID NO 498
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 498
acacctggta accaagcctg c 21

<210> SEQ ID NO 499
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 499
tgctccatct ccctgagtc 19

<210> SEQ ID NO 500
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 500
tctgctccat ctccctgagt c 21

<210> SEQ ID NO 501
<211> LENGTH: 19
<212> TYPE: DNA
<213> ORGANISM: Artificial Sequence -continued
<220> FEATURE:
<223> OTHER INFORMATION: Knock-down target sequence

<400> SEQUENCE: 501
gtggaacaca cttcagtcc 19

<210> SEQ ID NO 502
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 502
acgtggaaca cacttcagtc c 21

<210> SEQ ID NO 503
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 503
tggaagagtc tgttgatcc 19

<210> SEQ ID NO 504
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 504
actggaagag tctgttgatc c 21

<210> SEQ ID NO 505
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 505
ttcttgacca gtgatgggc 19

<210> SEQ ID NO 506
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 506
acttcttgac cagtgatggg c 21

<210> SEQ ID NO 507
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 507
tgggcaagaa actaagccc 19

-continued

<210> SEQ ID NO 508
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 508
actgggcaag aaactaagcc c 21

<210> SEQ ID NO 509
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 509
cagatgtatc tgccaggac 19

<210> SEQ ID NO 510
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 510
tccagatgta tctgccagga c 21

<210> SEQ ID NO 511
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 511
ggcctgccaa tttaagcgc 19

<210> SEQ ID NO 512
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 512
aaggcctgcc aatttaagcg c 21

<210> SEQ ID NO 513
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 513
gcgtgtcctg acttctgtc 19

<210> SEQ ID NO 514
<211> LENGTH: 21
<212> TYPE: DNA
<213> ORGANISM: Artificial Sequence
<220> FEATURE:
<223> OTHER INFORMATION: Knock-down target sequence -continued

<400> SEQUENCE: 514
aagcgtgtcc tgacttctgt c 21

<210> SEQ ID NO 515
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 515
cacatacccg ggacactac 19

<210> SEQ ID NO 516
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 516
aacacatacc cgggacacta c 21

<210> SEQ ID NO 517
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 517
tgtagttgca aacccaggc 19

<210> SEQ ID NO 518
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 518
actgtagttg caaacccagg c 21

<210> SEQ ID NO 519
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 519
atgggcacca tgtttgaac 19

<210> SEQ ID NO 520
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 520
acatgggcac catgtttgaa c 21

<210> SEQ ID NO 521

-continued

<211> LENGTH: 19
<212> TYPE: DNA
<213> ORGANISM: Artificial Sequence
<220> FEATURE:
<223> OTHER INFORMATION: Knock-down target sequence

<400> SEQUENCE: 521
tctgctggtc atagcagcc 19

<210> SEQ ID NO 522
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 522
aatctgctgg tcatagcagc c 21

<210> SEQ ID NO 523
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 523
catgactgct agtgctcac 19

<210> SEQ ID NO 524
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 524
aacatgactg ctagtgctca c 21

<210> SEQ ID NO 525
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 525
ttgtgccatc gtgggcaac 19

<210> SEQ ID NO 526
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 526
acttgtgcca tcgtgggcaa c 21

<210> SEQ ID NO 527
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 527

-continued atccacagga aatgaagac 19

<210> SEQ ID NO 528
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 528
acatccacag gaaatgaaga c 21

<210> SEQ ID NO 529
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 529
cgtcatgatc gcgctcacc 19

<210> SEQ ID NO 530
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 530
aacgtcatga tcgcgctcac c 21

<210> SEQ ID NO 531
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 531
ccagaaatca ctccactgc 19

<210> SEQ ID NO 532
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 532
aaccagaaat cactccactg c 21

<210> SEQ ID NO 533
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 533
gctgctcacc aggaactac 19

<210> SEQ ID NO 534
<211> LENGTH: 21
<212> TYPE: DNA

-continued

<213> ORGANISM: Artificial Sequence
<220> FEATURE:
<223> OTHER INFORMATION: Knock-down target sequence

<400> SEQUENCE: 534
acgctgctca ccaggaacta c 21

<210> SEQ ID NO 535
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 535
catcccactc aagatgcac 19

<210> SEQ ID NO 536
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 536
aacatcccac tcaagatgca c 21

<210> SEQ ID NO 537
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 537
cacactagat gccatgatc 19

<210> SEQ ID NO 538
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 538
accacactag atgccatgat c 21

<210> SEQ ID NO 539
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 539
gccgaagacc tgttctatc 19

<210> SEQ ID NO 540
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 540
aagccgaaga cctgttctat c 21

-continued

<210> SEQ ID NO 541
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 541
gcaagacgga tatgcatgc 19

<210> SEQ ID NO 542
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 542
aagcaagacg gatatgcatg c 21

<210> SEQ ID NO 543
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 543
gagcagatgt ggaccatgc 19

<210> SEQ ID NO 544
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 544
aagagcagat gtggaccatg c 21

<210> SEQ ID NO 545
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 545
tgggcttgaa gctgcttac 19

<210> SEQ ID NO 546
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 546
aatgggcttg aagctgctta c 21

<210> SEQ ID NO 547
<211> LENGTH: 19
<212> TYPE: DNA
<213> ORGANISM: Artificial Sequence
<220> FEATURE:

-continued

<223> OTHER INFORMATION: Knock-down target sequence

<400> SEQUENCE: 547
ggtattggag gagatgctc 19

<210> SEQ ID NO 548
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 548
aaggtattgg aggagatgct c 21

<210> SEQ ID NO 549
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 549
cgtgaatgcc gagttgggc 19

<210> SEQ ID NO 550
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 550
aacgtgaatg ccgagttggg c 21

<210> SEQ ID NO 551
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 551
tcactgtgga gacatttgc 19

<210> SEQ ID NO 552
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 552
aatcactgtg gagacatttg c 21

<210> SEQ ID NO 553
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 553
gtgggcttca tcaactacc 19

-continued

<210> SEQ ID NO 554
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 554
acgtgggctt catcaactac c 21

<210> SEQ ID NO 555
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 555
cctgaccctg gagcacatc 19

<210> SEQ ID NO 556
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 556
aacctgaccc tggagcacat c 21

<210> SEQ ID NO 557
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 557
ggacaacata acgatgcac 19

<210> SEQ ID NO 558
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 558
acggacaaca taacgatgca c 21

<210> SEQ ID NO 559
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 559
atcagtgagg catttgacc 19

<210> SEQ ID NO 560
<211> LENGTH: 21
<212> TYPE: DNA
<213> ORGANISM: Artificial Sequence
<220> FEATURE:
<223> OTHER INFORMATION: Knock-down target sequence -continued

<400> SEQUENCE: 560
aaatcagtga ggcatttgac c 21

<210> SEQ ID NO 561
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 561
tggctggagg acaagttcc 19

<210> SEQ ID NO 562
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 562
aatggctgga ggacaagttc c 21

<210> SEQ ID NO 563
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 563
atggccattg ccatggctc 19

<210> SEQ ID NO 564
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 564
acatggccat tgccatggct c 21

<210> SEQ ID NO 565
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 565
ctggatgctg cgcaaacac 19

<210> SEQ ID NO 566
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 566
aactggatgc tgcgcaaaca c 21

<210> SEQ ID NO 567
<211> LENGTH: 19

-continued

<212> TYPE: DNA
<213> ORGANISM: Artificial Sequence
<220> FEATURE:
<223> OTHER INFORMATION: Knock-down target sequence

<400> SEQUENCE: 567
tgctgcttat caacaacgc 19

<210> SEQ ID NO 568
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 568
actgctgctt atcaacaacg c 21

<210> SEQ ID NO 569
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 569
acatgccaca ggaaactac 19

<210> SEQ ID NO 570
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 570
aaacatgcca caggaaacta c 21

<210> SEQ ID NO 571
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 571
cgagtcctag gctacatcc 19

<210> SEQ ID NO 572
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 572
aacgagtcct aggctacatc c 21

<210> SEQ ID NO 573
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 573

-continued tgtgcccaac gccaccatc 19

<210> SEQ ID NO 574
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 574
aatgtgccca acgccaccat c 21

<210> SEQ ID NO 575
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 575
gcctcggact ttcatcatc 19

<210> SEQ ID NO 576
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 576
aagcctcgga ctttcatcat c 21

<210> SEQ ID NO 577
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 577
ttgaacccat caggcactc 19

<210> SEQ ID NO 578
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 578
aattgaaccc atcaggcact c 21

<210> SEQ ID NO 579
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 579
tgaaccctgt tatctacac 19

<210> SEQ ID NO 580
<211> LENGTH: 21
<212> TYPE: DNA
<213> ORGANISM: Artificial Sequence -continued
<220> FEATURE:
<223> OTHER INFORMATION: Knock-down target sequence

<400> SEQUENCE: 580
actgaaccct gttatctaca c 21

<210> SEQ ID NO 581
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 581
cttcctgaag accaggttc 19

<210> SEQ ID NO 582
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 582
aacttcctga agaccaggtt c 21

<210> SEQ ID NO 583
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 583
atggacattg acgtgatcc 19

<210> SEQ ID NO 584
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 584
acatggacat tgacgtgatc c 21

<210> SEQ ID NO 585
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 585
tttcccttca aggccctgc 19

<210> SEQ ID NO 586
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 586
actttccctt caaggccctg c 21

-continued

<210> SEQ ID NO 587
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 587
aagtctcaag agtcacagc 19

<210> SEQ ID NO 588
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 588
acaagtctca agagtcacag c 21

<210> SEQ ID NO 589
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 589
aatagcaaga atgtgtgcc 19

<210> SEQ ID NO 590
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 590
tcaatagcaa gaatgtgtgc c 21

<210> SEQ ID NO 591
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 591
agaagaaggt ggtgtggac 19

<210> SEQ ID NO 592
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 592
gcagaagaag gtggtgtgga c 21

<210> SEQ ID NO 593
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 593
tgccgtggtg cactatagc 19

<210> SEQ ID NO 594
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 594
aatgccgtgg tgcactatag c 21

<210> SEQ ID NO 595
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 595
agtgtccact caggaactc 19

<210> SEQ ID NO 596
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 596
acagtgtcca ctcaggaact c 21

<210> SEQ ID NO 597
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 597
tgcatgatgt cggtcaccc 19

<210> SEQ ID NO 598
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 598
actgcatgat gtcggtcacc c 21

<210> SEQ ID NO 599
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 599
ctgtgcctgc cattacaac 19

<210> SEQ ID NO 600

-continued

<211> LENGTH: 21
<212> TYPE: DNA
<213> ORGANISM: Artificial Sequence
<220> FEATURE:
<223> OTHER INFORMATION: Knock-down target sequence

<400> SEQUENCE: 600
acctgtgcct gccattacaa c 21

<210> SEQ ID NO 601
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 601
gactacagtg attgtcggc 19

<210> SEQ ID NO 602
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 602
aagactacag tgattgtcgg c 21

<210> SEQ ID NO 603
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 603
ctctgtgttc cacttcggc 19

<210> SEQ ID NO 604
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 604
aactctgtgt tccacttcgg c 21

<210> SEQ ID NO 605
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 605
ggagatcgtg ctggagaac 19

<210> SEQ ID NO 606
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 606

-continued acggagatcg tgctggagaa c 21

<210> SEQ ID NO 607
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 607
cgtggcctac atcatcatc 19

<210> SEQ ID NO 608
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 608
aacgtggcct acatcatcat c 21

<210> SEQ ID NO 609
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 609
tgcagccagt ggaatgtcc 19

<210> SEQ ID NO 610
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 610
actgcagcca gtggaatgtc c 21

<210> SEQ ID NO 611
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 611
gtatggcatg cagctgtac 19

<210> SEQ ID NO 612
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 612
aagtatggca tgcagctgta c 21

<210> SEQ ID NO 613
<211> LENGTH: 19
<212> TYPE: DNA

-continued

<213> ORGANISM: Artificial Sequence
<220> FEATURE:
<223> OTHER INFORMATION: Knock-down target sequence

<400> SEQUENCE: 613
gaatggcttt gctgtggtc 19

<210> SEQ ID NO 614
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 614
aagaatggct ttgctgtggt c 21

<210> SEQ ID NO 615
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 615
atgttccagg agatcgtcc 19

<210> SEQ ID NO 616
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 616
aaatgttcca ggagatcgtc c 21

<210> SEQ ID NO 617
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 617
acattcagct gtgaactcc 19

<210> SEQ ID NO 618
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 618
acacattcag ctgtgaactc c 21

<210> SEQ ID NO 619
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 619
caagcccttc cgtgtactc 19

-continued

<210> SEQ ID NO 620
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 620
aacaagccct tccgtgtact c 21

<210> SEQ ID NO 621
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 621
ccagcatcct ttgcattac 19

<210> SEQ ID NO 622
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 622
acccagcatc ctttgcatta c 21

<210> SEQ ID NO 623
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 623
tgcagtcagt tgtccatac 19

<210> SEQ ID NO 624
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 624
aatgcagtca gttgtccata c 21

<210> SEQ ID NO 625
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 625
aggccaatcc tggtagcac 19

<210> SEQ ID NO 626
<211> LENGTH: 21
<212> TYPE: DNA
<213> ORGANISM: Artificial Sequence
<220> FEATURE:

<223> OTHER INFORMATION: Knock-down target sequence

<400> SEQUENCE: 626
acaggccaat cctggtagca c 21

<210> SEQ ID NO 627
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 627
atcctgggct attggactc 19

<210> SEQ ID NO 628
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 628
acatcctggg ctattggact c 21

<210> SEQ ID NO 629
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 629
catggcctgt gcaattatc 19

<210> SEQ ID NO 630
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 630
accatggcct gtgcaattat c 21

<210> SEQ ID NO 631
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 631
ggctggtata caggaacac 19

<210> SEQ ID NO 632
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 632
aaggctggta tacaggaaca c 21

-continued

<210> SEQ ID NO 633
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 633
acatgccatt accagcatc 19

<210> SEQ ID NO 634
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 634
aaacatgcca ttaccagcat c 21

<210> SEQ ID NO 635
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 635
ttgctgctat gtcagatcc 19

<210> SEQ ID NO 636
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 636
aattgctgct atgtcagatc c 21

<210> SEQ ID NO 637
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 637
acgtggacca agtcatgcc 19

<210> SEQ ID NO 638
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 638
acacgtggac caagtcatgc c 21

<210> SEQ ID NO 639
<211> LENGTH: 19
<212> TYPE: DNA
<213> ORGANISM: Artificial Sequence
<220> FEATURE:
<223> OTHER INFORMATION: Knock-down target sequence -continued

<400> SEQUENCE: 639
ttggatccta atgagctgc 19

<210> SEQ ID NO 640
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 640
acttggatcc taatgagctg c 21

<210> SEQ ID NO 641
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 641
gtcttgtgtc agaatttcc 19

<210> SEQ ID NO 642
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 642
acgtcttgtg tcagaatttc c 21

<210> SEQ ID NO 643
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 643
agtaggcaac gacagcagc 19

<210> SEQ ID NO 644
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 644
aaagtaggca acgacagcag c 21

<210> SEQ ID NO 645
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 645
ctaaggaggc tcggaaatc 19

<210> SEQ ID NO 646
<211> LENGTH: 21

-continued

<212> TYPE: DNA
<213> ORGANISM: Artificial Sequence
<220> FEATURE:
<223> OTHER INFORMATION: Knock-down target sequence

<400> SEQUENCE: 646
gcctaaggag gctcggaaat c 21

<210> SEQ ID NO 647
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 647
ggctctgtca aggccattc 19

<210> SEQ ID NO 648
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 648
tcggctctgt caaggccatt c 21

<210> SEQ ID NO 649
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 649
taatgacttt ggcgctgtc 19

<210> SEQ ID NO 650
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 650
cctaatgact ttggcgctgt c 21

<210> SEQ ID NO 651
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 651
ctacatggac cgcttcacc 19

<210> SEQ ID NO 652
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 652

-continued aactacatgg accgcttcac c 21

<210> SEQ ID NO 653
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 653
tagccaagag ttcagcccc 19

<210> SEQ ID NO 654
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 654
aatagccaag agttcagccc c 21

<210> SEQ ID NO 655
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 655
ctccacaaac tgatcagcc 19

<210> SEQ ID NO 656
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 656
aactccacaa actgatcagc c 21

<210> SEQ ID NO 657
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 657
acctgaagaa agggagagc 19

<210> SEQ ID NO 658
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 658
acacctgaag aaagggagag c 21

<210> SEQ ID NO 659
<211> LENGTH: 19
<212> TYPE: DNA
<213> ORGANISM: Artificial Sequence -continued
<220> FEATURE:
<223> OTHER INFORMATION: Knock-down target sequence

<400> SEQUENCE: 659
aaccctatgc tgcctatgc 19

<210> SEQ ID NO 660
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 660
acaaccctat gctgcctatg c 21

<210> SEQ ID NO 661
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 661
gaagttcatc agcgccatc 19

<210> SEQ ID NO 662
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 662
aagaagttca tcagcgccat c 21

<210> SEQ ID NO 663
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 663
agctgcctgg aagcattac 19

<210> SEQ ID NO 664
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 664
aaagctgcct ggaagcatta c 21

<210> SEQ ID NO 665
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 665
cagtgttaca cggctttcc 19

-continued

<210> SEQ ID NO 666
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 666
aacagtgtta cacggctttc c 21

<210> SEQ ID NO 667
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 667
gactgaatca ggccttccc 19

<210> SEQ ID NO 668
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 668
aagactgaat caggccttcc c 21

<210> SEQ ID NO 669
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 669
tgcctgggac cagagcttc 19

<210> SEQ ID NO 670
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 670
aatgcctggg accagagctt c 21

<210> SEQ ID NO 671
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 671
gtccaagatg gagctacac 19

<210> SEQ ID NO 672
<211> LENGTH: 21
<212> TYPE: DNA
<213> ORGANISM: Artificial Sequence
<220> FEATURE:
<223> OTHER INFORMATION: Knock-down target sequence -continued

<400> SEQUENCE: 672
gcgtccaaga tggagctaca c 21

<210> SEQ ID NO 673
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 673
atatcatgtg aacctcctc 19

<210> SEQ ID NO 674
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 674
ccatatcatg tgaacctcct c 21

<210> SEQ ID NO 675
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 675
cgtcgtccaa agcagaagc 19

<210> SEQ ID NO 676
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 676
aacgtcgtcc aaagcagaag c 21

<210> SEQ ID NO 677
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 677
tgtagtgcag gcattgggc 19

<210> SEQ ID NO 678
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 678
actgtagtgc aggcattggg c 21

<210> SEQ ID NO 679

-continued

<211> LENGTH: 19
<212> TYPE: DNA
<213> ORGANISM: Artificial Sequence
<220> FEATURE:
<223> OTHER INFORMATION: Knock-down target sequence

<400> SEQUENCE: 679
tgtgggagaa ctgaagtcc 19

<210> SEQ ID NO 680
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 680
actgtgggag aactgaagtc c 21

<210> SEQ ID NO 681
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 681
gaagaacagc agcctggac 19

<210> SEQ ID NO 682
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 682
aagaagaaca gcagcctgga c 21

<210> SEQ ID NO 683
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 683
gatggactca ggtggactc 19

<210> SEQ ID NO 684
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 684
aagatggact caggtggact c 21

<210> SEQ ID NO 685
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 685
tgctgcatcc gacagatcc 19

<210> SEQ ID NO 686
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 686
aatgctgcat ccgacagatc c 21

<210> SEQ ID NO 687
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 687
tttccaggtc atctgctcc 19

<210> SEQ ID NO 688
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 688
actttccagg tcatctgctc c 21

<210> SEQ ID NO 689
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 689
ttccaggtcc tgaagcgac 19

<210> SEQ ID NO 690
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 690
acttccaggt cctgaagcga c 21

<210> SEQ ID NO 691
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 691
ttgtggagag ctcgaattc 19

<210> SEQ ID NO 692
<211> LENGTH: 21
<212> TYPE: DNA

-continued

<213> ORGANISM: Artificial Sequence
<220> FEATURE:
<223> OTHER INFORMATION: Knock-down target sequence

<400> SEQUENCE: 692
acttgtggag agctcgaatt c 21

<210> SEQ ID NO 693
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 693
atggccagca acctgatgc 19

<210> SEQ ID NO 694
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 694
acatggccag caacctgatg c 21

<210> SEQ ID NO 695
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 695
ttctcaggca ccctctacc 19

<210> SEQ ID NO 696
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 696
aattctcagg caccctctac c 21

<210> SEQ ID NO 697
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 697
gtgctggatt ctgccatgc 19

<210> SEQ ID NO 698
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 698
aagtgctgga ttctgccatg c 21

-continued

<210> SEQ ID NO 699
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 699
gtgtgttagc acgactttc 19

<210> SEQ ID NO 700
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 700
aagtgtgtta gcacgacttt c 21

<210> SEQ ID NO 701
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 701
catcctgctg tccaacccc 19

<210> SEQ ID NO 702
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 702
aacatcctgc tgtccaaccc c 21

<210> SEQ ID NO 703
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 703
tggtggcaga catcccttc 19

<210> SEQ ID NO 704
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 704
actggtggca gacatccctt c 21

<210> SEQ ID NO 705
<211> LENGTH: 19
<212> TYPE: DNA
<213> ORGANISM: Artificial Sequence
<220> FEATURE:

-continued

<223> OTHER INFORMATION: Knock-down target sequence

<400> SEQUENCE: 705
gcacagcact tccacaagc 19

<210> SEQ ID NO 706
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 706
acgcacagca cttccacaag c 21

<210> SEQ ID NO 707
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 707
aggagtttgg gaaccagac 19

<210> SEQ ID NO 708
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 708
acaggagttt gggaaccaga c 21

<210> SEQ ID NO 709
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 709
cactggcatc atctgtacc 19

<210> SEQ ID NO 710
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 710
aacactggca tcatctgtac c 21

<210> SEQ ID NO 711
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 711
gtgactacac aaggactcc 19

-continued

<210> SEQ ID NO 712
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 712
aagtgactac acaaggactc c 21

<210> SEQ ID NO 713
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 713
cttctccttt ggtggctgc 19

<210> SEQ ID NO 714
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 714
aacttctcct ttggtggctg c 21

<210> SEQ ID NO 715
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 715
agtgggtaaa gccaatggc 19

<210> SEQ ID NO 716
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 716
acagtgggta aagccaatgg c 21

<210> SEQ ID NO 717
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 717
gctgctcaga aacgttctc 19

<210> SEQ ID NO 718
<211> LENGTH: 21
<212> TYPE: DNA
<213> ORGANISM: Artificial Sequence
<220> FEATURE:
<223> OTHER INFORMATION: Knock-down target sequence -continued

<400> SEQUENCE: 718
aagctgctca gaaacgttct c 21

<210> SEQ ID NO 719
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 719
accacactca cgcagtatc 19

<210> SEQ ID NO 720
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 720
acaccacact cacgcagtat c 21

<210> SEQ ID NO 721
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 721
gtctgtctgt aagaacacc 19

<210> SEQ ID NO 722
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 722
aagtctgtct gtaagaacac c 21

<210> SEQ ID NO 723
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 723
gatgtagagc tggcctacc 19

<210> SEQ ID NO 724
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 724
aagatgtaga gctggcctac c 21

<210> SEQ ID NO 725
<211> LENGTH: 19

<212> TYPE: DNA
<213> ORGANISM: Artificial Sequence
<220> FEATURE:
<223> OTHER INFORMATION: Knock-down target sequence

<400> SEQUENCE: 725
ggtgagcgtg gacatcttc 19

<210> SEQ ID NO 726
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 726
aaggtgagcg tggacatctt c 21

<210> SEQ ID NO 727
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 727
gtggaacaag aggtacaac 19

<210> SEQ ID NO 728
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 728
aagtggaaca agaggtacaa c 21

<210> SEQ ID NO 729
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 729
cgatggcttc cacgtctac 19

<210> SEQ ID NO 730
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 730
aacgatggct tccacgtcta c 21

<210> SEQ ID NO 731
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 731

-continued gtgggcaatg aatatggcc 19

<210> SEQ ID NO 732
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 732
aagtgggcaa tgaatatggc c 21

<210> SEQ ID NO 733
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 733
ttctgtggtg gttctggtc 19

<210> SEQ ID NO 734
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 734
aattctgtgg tggttctggt c 21

<210> SEQ ID NO 735
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 735
cttcattatc cacagggac 19

<210> SEQ ID NO 736
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 736
aacttcatta tccacaggga c 21

<210> SEQ ID NO 737
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 737
ggtggagcac taccgcatc 19

<210> SEQ ID NO 738
<211> LENGTH: 21
<212> TYPE: DNA
<213> ORGANISM: Artificial Sequence -continued
<220> FEATURE:
<223> OTHER INFORMATION: Knock-down target sequence

<400> SEQUENCE: 738
aaggtggagc actaccgcat c 21

<210> SEQ ID NO 739
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 739
aagttcccga acgatcacc 19

<210> SEQ ID NO 740
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 740
acaagttccc gaacgatcac c 21

<210> SEQ ID NO 741
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 741
ctctgtgtgc ctgtcgttc 19

<210> SEQ ID NO 742
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 742
acctctgtgt gcctgtcgtt c 21

<210> SEQ ID NO 743
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 743
tggcacctta actggagtc 19

<210> SEQ ID NO 744
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 744
aatggcacct taactggagt c 21

-continued

<210> SEQ ID NO 745
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 745
tcttctccca gaggaaggc 19

<210> SEQ ID NO 746
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 746
aatcttctcc cagaggaagg c 21

<210> SEQ ID NO 747
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 747
ctgctccagc atcactatc 19

<210> SEQ ID NO 748
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 748
acctgctcca gcatcactat c 21

<210> SEQ ID NO 749
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 749
attctgtggg ctcatcacc 19

<210> SEQ ID NO 750
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 750
aaattctgtg ggctcatcac c 21

<210> SEQ ID NO 751
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 751
gcaggacttc agaacacac 19

<210> SEQ ID NO 752
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 752
aagcaggact tcagaacaca c 21

<210> SEQ ID NO 753
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 753
agcctggttc attctaaac 19

<210> SEQ ID NO 754
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 754
acagcctggt tcattctaaa c 21

<210> SEQ ID NO 755
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 755
actgtgggat tgaccaggc 19

<210> SEQ ID NO 756
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 756
acactgtggg attgaccagg c 21

<210> SEQ ID NO 757
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 757
ttcagaattc aggcagctc 19

<210> SEQ ID NO 758

-continued

<211> LENGTH: 21
<212> TYPE: DNA
<213> ORGANISM: Artificial Sequence
<220> FEATURE:
<223> OTHER INFORMATION: Knock-down target sequence

<400> SEQUENCE: 758
acttcagaat tcaggcagct c 21

<210> SEQ ID NO 759
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 759
actgggcatt tcctactgc 19

<210> SEQ ID NO 760
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 760
acactgggca tttcctactg c 21

<210> SEQ ID NO 761
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 761
gctgtgggag aactatccc 19

<210> SEQ ID NO 762
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 762
aagctgtggg agaactatcc c 21

<210> SEQ ID NO 763
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 763
atggacctga cctgcattc 19

<210> SEQ ID NO 764
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 764

-continued tcatggacct gacctgcatt c 21

<210> SEQ ID NO 765
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 765
tcttctcaca tggaaatgc 19

<210> SEQ ID NO 766
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 766
actcttctca catggaaatg c 21

<210> SEQ ID NO 767
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 767
ccattccatg gtgtttacc 19

<210> SEQ ID NO 768
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 768
acccattcca tggtgtttac c 21

<210> SEQ ID NO 769
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 769
acatgggcta tctcaagcc 19

<210> SEQ ID NO 770
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 770
aaacatgggc tatctcaagc c 21

<210> SEQ ID NO 771
<211> LENGTH: 19
<212> TYPE: DNA

-continued

<213> ORGANISM: Artificial Sequence
<220> FEATURE:
<223> OTHER INFORMATION: Knock-down target sequence

<400> SEQUENCE: 771
cttcctgtct cccttctac 19

<210> SEQ ID NO 772
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 772
aacttcctgt ctcccttcta c 21

<210> SEQ ID NO 773
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 773
cgtctcacag tatgcattc 19

<210> SEQ ID NO 774
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 774
aacgtctcac agtatgcatt c 21

<210> SEQ ID NO 775
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 775
agctgctatc caactcacc 19

<210> SEQ ID NO 776
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 776
acagctgcta tccaactcac c 21

<210> SEQ ID NO 777
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 777
caacgtggag gaggagttc 19

<210> SEQ ID NO 778
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 778
accaacgtgg aggaggagtt c 21

<210> SEQ ID NO 779
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 779
caggcctgtg gaaacatac 19

<210> SEQ ID NO 780
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 780
aacaggcctg tggaaacata c 21

<210> SEQ ID NO 781
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 781
tgatggcctt tccctgtgc 19

<210> SEQ ID NO 782
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 782
actgatggcc tttccctgtg c 21

<210> SEQ ID NO 783
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 783
gactctgggc tgctctatc 19

<210> SEQ ID NO 784
<211> LENGTH: 21
<212> TYPE: DNA
<213> ORGANISM: Artificial Sequence
<220> FEATURE:

-continued

<223> OTHER INFORMATION: Knock-down target sequence

<400> SEQUENCE: 784
aagactctgg gctgctctat c 21

<210> SEQ ID NO 785
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 785
ttccgtggcc tgttcaatc 19

<210> SEQ ID NO 786
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 786
acttccgtgg cctgttcaat c 21

<210> SEQ ID NO 787
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 787
gggcaacaat gactgtgac 19

<210> SEQ ID NO 788
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 788
acgggcaaca atgactgtga c 21

<210> SEQ ID NO 789
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 789
acctggcttc ccttccttc 19

<210> SEQ ID NO 790
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 790
acacctggct tcccttcctt c 21

-continued

<210> SEQ ID NO 791
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 791
catgctcaag gccatgttc 19

<210> SEQ ID NO 792
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 792
accatgctca aggccatgtt c 21

<210> SEQ ID NO 793
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 793
tcagttccca gctctgcac 19

<210> SEQ ID NO 794
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 794
aatcagttcc cagctctgca c 21

<210> SEQ ID NO 795
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 795
catcacaatt ggccatcac 19

<210> SEQ ID NO 796
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 796
tccatcacaa ttggccatca c 21

<210> SEQ ID NO 797
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 797
tggaagatta tcctgtgtc 19

<210> SEQ ID NO 798
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 798
actggaagat tatcctgtgt c 21

<210> SEQ ID NO 799
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 799
tacattcacc ctgtgtgtc 19

<210> SEQ ID NO 800
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 800
actacattca ccctgtgtgt c 21

<210> SEQ ID NO 801
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 801
gatgtgcctg tcctgtgtc 19

<210> SEQ ID NO 802
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 802
aagatgtgcc tgtcctgtgt c 21

<210> SEQ ID NO 803
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 803
atttgtgggc aactcagcc 19

<210> SEQ ID NO 804
<211> LENGTH: 21

-continued

<212> TYPE: DNA
<213> ORGANISM: Artificial Sequence
<220> FEATURE:
<223> OTHER INFORMATION: Knock-down target sequence

<400> SEQUENCE: 804
aaatttgtgg gcaactcagc c 21

<210> SEQ ID NO 805
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 805
atcagaagaa agccatgac 19

<210> SEQ ID NO 806
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 806
acatcagaag aaagccatga c 21

<210> SEQ ID NO 807
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 807
catgtgtggg aagttgttc 19

<210> SEQ ID NO 808
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 808
accatgtgtg ggaagttgtt c 21

<210> SEQ ID NO 809
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 809
ttgctgagat gtgttaggc 19

<210> SEQ ID NO 810
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 810

-continued ccttgctgag atgtgttagg c 21

<210> SEQ ID NO 811
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 811
ccaccatgca gacaagtcc 19

<210> SEQ ID NO 812
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 812
aaccaccatg cagacaagtc c 21

<210> SEQ ID NO 813
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 813
actgacctca gagtaccac 19

<210> SEQ ID NO 814
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 814
aaactgacct cagagtacca c 21

<210> SEQ ID NO 815
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 815
cgacacagtg gtgctctac 19

<210> SEQ ID NO 816
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 816
accgacacag tggtgctcta c 21

<210> SEQ ID NO 817
<211> LENGTH: 19
<212> TYPE: DNA
<213> ORGANISM: Artificial Sequence -continued
<220> FEATURE:
<223> OTHER INFORMATION: Knock-down target sequence

<400> SEQUENCE: 817
cgtctactcg ctggccttc 19

<210> SEQ ID NO 818
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 818
aacgtctact cgctggcctt c 21

<210> SEQ ID NO 819
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 819
tgctggtgcc attgttgtc 19

<210> SEQ ID NO 820
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 820
aatgctggtg ccattgttgt c 21

<210> SEQ ID NO 821
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 821
acaactcaga gggaccttc 19

<210> SEQ ID NO 822
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 822
acacaactca gagggacctt c 21

<210> SEQ ID NO 823
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 823
aggtaatgtg gaacacagc 19

-continued

<210> SEQ ID NO 824
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 824
aaaggtaatg tggaacacag c 21

<210> SEQ ID NO 825
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 825
caactccaca ctggacttc 19

<210> SEQ ID NO 826
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 826
accaactcca cactggactt c 21

<210> SEQ ID NO 827
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 827
tgcagatggt tgtgctccc 19

<210> SEQ ID NO 828
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 828
aatgcagatg gttgtgctcc c 21

<210> SEQ ID NO 829
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 829
aacatgatat gtgctggac 19

<210> SEQ ID NO 830
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 830
acaacatgat atgtgctgga c 21

<210> SEQ ID NO 831
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 831
aacacggtgg agctgctgc 19

<210> SEQ ID NO 832
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 832
acaacacggt ggagctgctg c 21

<210> SEQ ID NO 833
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 833
ttccacagca tgaactggc 19

<210> SEQ ID NO 834
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 834
aattccacag catgaactgg c 21

<210> SEQ ID NO 835
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 835
agatgcatct tccctccac 19

<210> SEQ ID NO 836
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 836
aaagatgcat cttccctcca c 21

<210> SEQ ID NO 837

-continued

<211> LENGTH: 19
<212> TYPE: DNA
<213> ORGANISM: Artificial Sequence
<220> FEATURE:
<223> OTHER INFORMATION: Knock-down target sequence

<400> SEQUENCE: 837
ataagcggtt atcactgcc 19

<210> SEQ ID NO 838
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 838
aaataagcgg ttatcactgc c 21

<210> SEQ ID NO 839
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 839
agtcacaatg tcaagtgac 19

<210> SEQ ID NO 840
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 840
acagtcacaa tgtcaagtga c 21

<210> SEQ ID NO 841
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 841
ctcaacccag aacctgagc 19

<210> SEQ ID NO 842
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 842
acctcaaccc agaacctgag c 21

<210> SEQ ID NO 843
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 843

-continued agtatcagga gccaatacc 19

<210> SEQ ID NO 844
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 844
acagtatcag gagccaatac c 21

<210> SEQ ID NO 845
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 845
aatcctgtat tcaaggcgc 19

<210> SEQ ID NO 846
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 846
acaatcctgt attcaaggcg c 21

<210> SEQ ID NO 847
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 847
gagcgcatct actgtgcac 19

<210> SEQ ID NO 848
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 848
acgagcgcat ctactgtgca c 21

<210> SEQ ID NO 849
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 849
acatggacga gtgtctcac 19

<210> SEQ ID NO 850
<211> LENGTH: 21
<212> TYPE: DNA

-continued

<213> ORGANISM: Artificial Sequence
<220> FEATURE:
<223> OTHER INFORMATION: Knock-down target sequence

<400> SEQUENCE: 850
acacatggac gagtgtctca c 21

<210> SEQ ID NO 851
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 851
tccgagcgat ttaaggaac 19

<210> SEQ ID NO 852
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 852
actccgagcg atttaaggaa c 21

<210> SEQ ID NO 853
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 853
tggagtcctt caaggctac 19

<210> SEQ ID NO 854
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 854
aatggagtcc ttcaaggcta c 21

<210> SEQ ID NO 855
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 855
catcatggat gagtgtggc 19

<210> SEQ ID NO 856
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 856
accatcatgg atgagtgtgg c 21

<210> SEQ ID NO 857
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 857
attcagcaga agcccagac 19

<210> SEQ ID NO 858
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 858
acattcagca gaagcccaga c 21

<210> SEQ ID NO 859
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 859
tgagccacgg gaatgtgcc 19

<210> SEQ ID NO 860
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 860
aatgagccac gggaatgtgc c 21

<210> SEQ ID NO 861
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 861
ttccacctac cagtccacc 19

<210> SEQ ID NO 862
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 862
tcttccacct accagtccac c 21

<210> SEQ ID NO 863
<211> LENGTH: 19
<212> TYPE: DNA
<213> ORGANISM: Artificial Sequence
<220> FEATURE:

-continued

<223> OTHER INFORMATION: Knock-down target sequence

<400> SEQUENCE: 863
cagcacattc agctgcagc 19

<210> SEQ ID NO 864
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 864
accagcacat tcagctgcag c 21

<210> SEQ ID NO 865
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 865
atcatggctg tgaccacac 19

<210> SEQ ID NO 866
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 866
acatcatggc tgtgaccaca c 21

<210> SEQ ID NO 867
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 867
agtggccttc ctcaggaac 19

<210> SEQ ID NO 868
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 868
acagtggcct tcctcaggaa c 21

<210> SEQ ID NO 869
<211> LENGTH: 19
<212> TYPE: DNA
<213> ORGANISM: Artificial Sequence
<220> FEATURE:
<223> OTHER INFORMATION: Knock-down target sequence

<400> SEQUENCE: 869
agttctacga ctccaacac 19

-continued

<210> SEQ ID NO 870
<211> LENGTH: 21
<212> TYPE: DNA
<213> ORGANISM: Artificial Sequence
<220> FEATURE:
<223> OTHER INFORMATION: Knock-down target sequence

<400> SEQUENCE: 870
aaagttctac gactccaaca c 21

<210> SEQ ID NO 871
<211> LENGTH: 8
<212> TYPE: RNA
<213> ORGANISM: Artificial Sequence
<220> FEATURE:
<223> OTHER INFORMATION: Loop sequence

<400> SEQUENCE: 871 uugcuaua 8

<210> SEQ ID NO 872
<211> LENGTH: 12
<212> TYPE: RNA
<213> ORGANISM: Artificial Sequence
<220> FEATURE:
<223> OTHER INFORMATION: Loop sequence

<400> SEQUENCE: 872
guuugcuaua ac 12

<210> SEQ ID NO 873
<211> LENGTH: 25
<212> TYPE: DNA
<213> ORGANISM: Artificial Sequence
<220> FEATURE:
<223> OTHER INFORMATION: PCR primer

<400> SEQUENCE: 873
gttctggggt gtggtgtctc acagc 25

<210> SEQ ID NO 874
<211> LENGTH: 25
<212> TYPE: DNA
<213> ORGANISM: Artificial Sequence
<220> FEATURE:
<223> OTHER INFORMATION: PCR primer

<400> SEQUENCE: 874
caaactgagc cacatcaggc actcc 25

<210> SEQ ID NO 875
<211> LENGTH: 20
<212> TYPE: DNA
<213> ORGANISM: Artificial Sequence
<220> FEATURE:
<223> OTHER INFORMATION: PCR primer

<400> SEQUENCE: 875
ggtgggaggt ctatataagc 20

<210> SEQ ID NO 876
<211> LENGTH: 22
<212> TYPE: DNA
<213> ORGANISM: Artificial Sequence
<220> FEATURE:
<223> OTHER INFORMATION: PCR primer -continued

<400> SEQUENCE: 876
ggacaaacca caactagaat gc 22

<210> SEQ ID NO 877
<211> LENGTH: 25
<212> TYPE: DNA
<213> ORGANISM: Artificial Sequence
<220> FEATURE:
<223> OTHER INFORMATION: PCR primer

<400> SEQUENCE: 877
ccggtttttc aaagggaata agtac 25

<210> SEQ ID NO 878
<211> LENGTH: 24
<212> TYPE: DNA
<213> ORGANISM: Artificial Sequence
<220> FEATURE:
<223> OTHER INFORMATION: PCR primer

<400> SEQUENCE: 878
ttcacagttc tagggaagcc aaag 24

<210> SEQ ID NO 879
<211> LENGTH: 21
<212> TYPE: DNA
<213> ORGANISM: Artificial Sequence
<220> FEATURE:
<223> OTHER INFORMATION: PCR primer

<400> SEQUENCE: 879
ccgtttacgt ggagactcgc c 21

<210> SEQ ID NO 880
<211> LENGTH: 25
<212> TYPE: DNA
<213> ORGANISM: Artificial Sequence
<220> FEATURE:
<223> OTHER INFORMATION: PCR primer

<400> SEQUENCE: 880
cccccacctt atatatattc tttcc 25

MOLECULAR TARGETS AND COMPOUNDS, AND METHODS TO IDENTIFY THE SAME, USEFUL IN THE TREATMENT OF JOINT DEGENERATIVE AND INFLAMMATORY DISEASES

CROSS-REFERENCE TO RELATED APPLICATIONS

This application claims priority to U.S. Provisional Application No. 60/619,384, filed Oct. 15, 2004, the disclosure of which is incorporated herein by reference.

FIELD OF INVENTION

The present invention relates to methods for identifying compounds, and expression-inhibition agents, capable of inhibiting the expression of proteins involved in the pathway resulting in the degradation of extra-cellular matrix (ECM), which inhibition is useful in the prevention and treatment of joint degeneration and diseases involving such degradation and/or inflammation.

Diseases involving the degradation of extra-cellular matrix include, but are not limited to, psoriatic arthritis, juvenile arthritis, early arthritis, reactive arthritis, osteoarthritis, ankylosing spondylitis. osteoporosis, muscular skeletal diseases like tendonitis and periodontal disease, cancer metastasis, airway diseases (COPD, asthma), renal and liver fibrosis, cardio-vascular diseases like atherosclerosis and heart failure, and neurological diseases like neuroinflammation and multiple sclerosis. Diseases involving primarily joint degeneration include, but are not limited to, psoriatic arthritis, juvenile arthritis, early arthritis, reactive arthritis, osteoarthritis, ankylosing spondylitis.

Rheumatoid arthritis (RA) is a chronic joint degenerative disease, characterized by inflammation and destruction of the joint structures. When the disease is unchecked, it leads to substantial disability and pain due to loss of joint functionality and even premature death. The aim of an RA therapy, therefore, is not to slow down the disease but to attain remission in order to stop the joint destruction. Besides the severity of the disease outcome, the high prevalence of RA (~0.8% of the adults are affected worldwide) means a high socio- economic impact. (For reviews on RA, we refer to Smolen and Steiner (2003); Lee and Weinblatt (2001); Choy and Panayi (2001); O'Dell (2004) and Firestein (2003)).

Although it is widely accepted that RA is an auto-immune disease, there is no consensus concerning the precise mechanisms driving the 'initiation stage' of the disease. What is known is that the initial trigger(s) does mediate, in a predisposed host, a cascade of events that leads to the activation of various cell types (B-cells, T-cells, macrophages, fibroblasts, endothelial cells, dendritic cells and others). Concomitantly, an increased production of various cytokines is observed in the joints and tissues surrounding the joint (for example, TNF-α, IL-6, IL-1, IL-15, IL-18 and others). As the disease progresses, the cellular activation and cytokine production cascade becomes self-perpetuating. At this early stage, the destruction of joint structures is already very clear. Thirty percent of the patients have radiographic evidence of bony erosions at the time of diagnosis and this proportion increases to 60 percent after two years.

Histologic analysis of the joints of RA patients clearly evidences the mechanisms involved in the RA-associated degradative processes. The synovium is a cell layer, composed of a sublining and a lining region that separates the joint capsule from the synovial cavity. The inflamed synovium is central to the pathophysiology of RA. The synovial joint is shown as composed of two adjacent bony ends each covered with a layer of cartilage, separated by a joint space and surrounded by the synovial membrane and joint capsule. The synovial membrane is composed of the synovial lining (facing the cartilage and bone), which consists of a thin (1-3 cells) layer of synoviocytes and the sublining connective tissue layer that is highly vascularised. The synovial membrane covers almost all intra-articular structures except for cartilage. Histological differences in the synovium between normal and RA patients are indicated in FIG. 1.

Like many other forms of arthritis, rheumatoid arthritis (RA) is initially characterized by an inflammatory response of the synovial membrane ('synovitis') that is characterised by an important influx of various types of mononuclear cells as well as by the activation of the local or infiltrated mononuclear cells. The lining layer becomes hyperplastic (it can have a thickness of >20 cells) and the synovial membrane expands. However, in addition, the hallmark of RA is joint destruction: the joint spaces narrow or disappear as a sign of cartilage degradation and destructions of the adjacent bone, also termed 'erosions', have occurred. The destructive portion of the synovial membrane is termed 'pannus'. Enzymes secreted by synoviocytes lead to cartilage degradation.

This analysis shows that the main effector responsible for RA-associated joint degradation is the pannus, where the synovial fibroblast, by producing diverse proteolytic enzymes, is the prime driver of cartilage and bone erosion. In the advanced RA patient, the pannus mediates the degradation of the adjacent cartilage, leading to the narrowing of the joint space, and has the potential to invade adjacent bone and cartilage. As collagen type I or II are main components of bone and cartilage tissues, respectively, the pannus destructive and invasive properties are mediated by the secretion of collagenolytic proteases, principally the matrix metallo proteinases (MMPs). The erosion of the bone under and adjacent to the cartilage is also part of the RA process, and results principally from the presence of osteoclasts at the interface of bone and pannus. Osteoclasts adhere to the bone tissue and form a closed compartment, within which the osteoclasts secrete proteases (Cathepsin K, MMP9) that degrade the bone tissue. The osteoclast population in the joint is abnormally increased by osteoblast formation from precursor cells induced by the secretion of the receptor activator of NFkB ligand (RANKL) by activated SFs and T-cells.

Various collagen types have a key role in defining the stability of the extra-cellular matrix (ECM). Collagen type I and collagen type II, for example, are main components of bone and cartilage, respectively. Collagen proteins typically organize into multimeric structures referred to as collagen fibrils. Native collagen fibrils are very resistant to proteolytic cleavage. Only a few types of ECM-degrading proteins have been reported to have the capacity to degrade native collagen: matrix-metallo proteases (MMPs) and Cathepsins. Among the Cathepsins, cathepsin K, which is active mainly in osteoclasts, is the best characterised.

Matrix Metallo Proteases (MMPs) possess various physiological roles, for example, they are involved in the maturation of other proteases, growth factors, and the degradation of extra-cellular matrix components. Among the MMPs, MMP1, MMP2, MMP8 MMP13 and MMP14 are known to have collagenolytic properties. MMP1 is a member of the MMP family and is able to degrade native collagen, an important component of bone and cartilage. The correlation between an increased expression of MMP1 by synovial fibroblasts (SFs) and the progression of the arthritic disease is well-established and is predictive for joint erosive processes (Cunnane et al., 2001). In the context of RA, therefore, MMP1 represents a highly relevant collagen degrading protein. In vitro, the treatment of cultured SFs with cytokines relevant in the RA pathology (for example, TNF-α and IL1β) will increase the expression of MMP1 by these cells (Andreakos et al., 2003).

The activity of the ECM-degrading proteins can also be causative or correlate with the progression of various diseases other than RA, which diseases involve also the degradation of the joints. These diseases include, but are not limited to, psoriatic arthritis, juvenile arthritis, early arthritis, reactive arthritis, osteoarthritis, and ankylosing spondylitis. Other diseases that may be treatable with compounds identified according to the present invention and using the targets involved in the expression of MMPs as described herein are osteoporosis, muscular skeletal diseases like tendonitis and periodontal disease (Gapski et al., 2004), cancer metastasis (Coussens et al., 2002), airway diseases (COPD, asthma) (Suzuki et al., 2004), lung, renal fibrosis (Schanstra et al., 2002), liver fibrosis associated with chronic hepatitis C (Reiff et al., 2005), cardio-vascular diseases like atherosclerosis and heart failure (Creemers et al., 2001), and neurological diseases like neuro-inflammation and multiple sclerosis (Rosenberg, 2002). Patients suffering from such diseases may benefit from a therapy that protects the ECM from enzymatic degradation.

Reported Developments

NSAIDS (Non-steroidal anti-inflammatory drugs) are used to reduce the pain associated with RA and improve life quality of the patients. These drugs will not, however, put a brake on the RA-associated joint destruction.

Corticosteroids are found to decrease the progression of RA as detected radiographically and are used at low doses to treat part of the RA patients (30 to 60%). Serious side effects, however, are associated with long corticosteroid use (Skin thinning, osteoporosis, cataracts, hypertension, hyperlipidemia).

Synthetic DMARDs (Disease-Modifying Anti-Rheumatic Drugs) (for example, methotrexate, leflunomide, sulfasalazine) mainly tackle the immuno-inflammatory component of RA. As a main disadvantage, these drugs only have a limited efficacy (joint destruction is only slowed down but not blocked by DMARDs such that disease progression in the long term continues). The lack of efficacy is indicated by the fact that, on average, only 30% of the patients achieve an ACR50 score after 24 months treatment with methotrexate. This means that, according to the American College of Rheumatology, only 30% of the patients do achieve a 50% improvement of their symptoms (O'Dell et al., 1996). In addition, the precise mechanism of action of DMARDs is often unclear.

Biological DMARDs (Infliximab, Etanercept, Adalimumab, Rituximab, CTLA4-Ig) are therapeutic proteins that inactivate cytokines (for example, TNF-α) or cells (for example, T-cells or B-cells) that have an important role in the RA pathophysiology (Kremer et al., 2003; Edwards et al., 2004). Although the TNF-α-blockers (Infliximab, Etanercept, Adalimumab) and methotrexate combination therapy is the most effective RA treatment currently available, it is striking that even this therapy only achieves a 50% improvement (ACR50) in disease symptoms in 50-60% of patients after 12 months therapy (St Clair et al., 2004). Some adverse events warnings for anti-TNF-α drugs exist, shedding a light on the side effects associated to this type of drugs. Increased risk for infections (tuberculosis) hematologic events and demyelinating disorders have been described for the TNF-α blockers. (see also Gomez-Reino et al., 2003). Besides the serious side effects, the TNF-α blockers do also share the general disadvantages of the biological class of therapeutics, which are the unpleasant way of administration (frequent injections accompanied by infusion site reactions) and the high production cost. Newer agents in late development phase target T-cell co-stimulatory molecules and B-cells. The efficacy of these agents is expected to be similar to that of the TNF-α blockers. The fact that a variety of targeted therapies have similar but limited efficacies, suggests that there is a multiplicity of pathogenic factors for RA. This is also indicative for the deficiencies in our understanding of pathogenic events relevant to RA.

The current therapies for RA are not satisfactory due to a limited efficacy (no adequate therapy exists for 30% of the patients). This calls for additional strategies to achieve remission. Remission is required since residual disease bears the risk of progressive joint damage and thus progressive disability. Inhibiting the immuno-inflammatory component of the RA disease, which represents the main target of drugs currently used for RA treatment, does not result in a blockade of joint degradation, the major hallmark of the disease.

The histological analysis of RA patient joints clearly identifies the pannus, as an aggressive, invasive tissue that represents the main culprit in joint degradation. Within the pannus, the synovial fibroblasts represent a link between the initiation of the abnormally triggered immune system that lies at the basis of RA pathogenesis, and the ultimate joint erosion. As no current RA therapy efficiently abolishes the erosive activity of the pannus in the long term, the discovery of novel drugs and/or drug targets that inhibit the generation, and/or the activity, of the pannus would represent an important milestone for the development of novel RA treatments.

The present invention is based on the discovery of that certain proteins function in the pathway that results in the expression of extra-cellular matrix (ECM) degradation proteases, such as MMP1, and that inhibitors of the activity of these proteins, are useful for the treatment of diseases involving the abnormally high expression of such proteases.

SUMMARY OF THE INVENTION

The present invention relates to a method for identifying compounds that inhibit extra-cellular matrix (ECM) degradation, comprising contacting a compound with a polypeptide comprising an amino acid sequence selected from the group consisting of SEQ ID NO: 17-32 (hereinafter "TARGETS") and fragments thereof, under conditions that allow said polypeptide to bind to said compound, and measuring a compound-polypeptide property related to extra-cellular matrix (ECM) degradation.

Aspects of the present method include the in vitro assay of compounds using polypeptide of a TARGET, or fragments thereof, such fragments including the amino acid sequences described by SEQ ID NO: 33-127, and cellular assays wherein TARGET inhibition is followed by observing indicators of efficacy including, for example, TARGET expression levels, TARGET enzymatic activity and/or Matrix Metallo Proteinase-1 levels.

The present invention also relates to (1) expression inhibitory agents comprising a polynucleotide selected from the group of an antisense polynucleotide, a ribozyme, and a small interfering RNA (siRNA), wherein said polynucleotide comprises a nucleic acid sequence complementary to, or engineered from, a naturally occurring polynucleotide sequence encoding a polypeptide comprising an amino acid sequence selected from the group consisting of SEQ ID NO: 17-127, and (2) pharmaceutical compositions comprising said agent, useful in the treatment, or prevention, of chronic joint degenerative diseases such as rheumatoid arthritis.

Another aspect of the invention is a method of treatment, or prevention, of a condition involving extra-cellular matrix (ECM) degradation, in a subject suffering or susceptible thereto, by administering a pharmaceutical composition comprising an effective TARGET-expression inhibiting amount of a expression-inhibitory agent or an effective TARGET activity inhibiting amount of a activity-inhibitory agent.

A further aspect of the present invention is a method for diagnosis relating to disease conditions characterized by extra-cellular matrix (ECM) degradation comprising measurement of indicators of levels of TARGET expression in a subject.

Another aspect of this invention relates to the use of the present compound in a therapeutic method, a pharmaceutical composition, and the manufacture of such composition, useful for the treatment of a disease involving inflammation, and in particular, a disease characteristic of abnormal matrix metallo protease activity.

BRIEF DESCRIPTION OF THE DRAWINGS

FIG. 7. Layout and performance of the control plate produced for the reverse MMP1 ELISA assay.

FIG. 8. Representative example of the performance of the reverse MMP1 ELISA assay run on a subset of 384 Ad-siRNAs of the SilenceSelect collection that are tested in duplicate in a primary screen (A) and a repeat screen (B).

FIG. 10. Layout of the plates produced for the 3 MOI repeat screen of the reverse MMP1 assay (10A) and the cytotoxicity and secretion repeat screen of the reverse MMP1 assay (10B).

FIG. 12. Reduction of the expression of the TARGETS in primary SFs by Ad-siRNAs inhibits cytokine-induced native collagen degradation. The SF supernatant from "TNFα-based trigger"-treated SFs infected with the indicated Ad-siRNAs is subjected to the collagen degradation assay.

DETAILED DESCRIPTION

Figure 1:
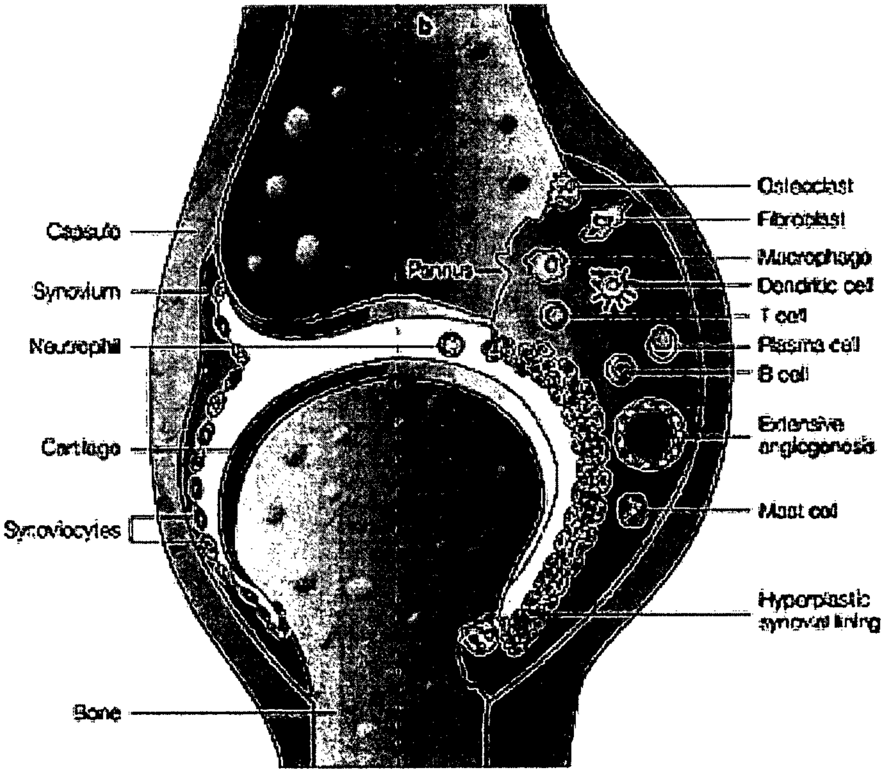
FIG. 1. Schematic view of a normal joint and its changes in rheumatoid arthritis (From Smolen and Steiner, 2003).

The following terms are intended to have the meanings presented therewith below and are useful in understanding the description and intended scope of the present invention.

The term "agent" means any molecule, including polypeptides, polynucleotides and small molecules.

The term "agonist" refers to a ligand that stimulates the receptor the ligand binds to in the broadest sense.

The term "assay" means any process used to measure a specific property of a compound. A "screening assay" means a process used to characterize or select compounds based upon their activity from a collection of compounds.

The term "binding affinity" is a property that describes how strongly two or more compounds associate with each other in a non-covalent relationship. Binding affinities can be characterized qualitatively, (such as "strong", "weak", "high", or "low") or quantitatively (such as measuring the $K_D$).

The term "carrier" means a non-toxic material used in the formulation of pharmaceutical compositions to provide a medium, bulk and/or useable form to a pharmaceutical composition. A carrier may comprise one or more of such materials such as an excipient, stabilizer, or an aqueous pH buffered solution. Examples of physiologically acceptable carriers include aqueous or solid buffer ingredients including phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The term "complex" means the entity created when two or more compounds bind to each other.

The term "compound" is used herein in the context of a "test compound" or a "drug candidate compound" described in connection with the assays of the present invention. As such, these compounds comprise organic or inorganic compounds, derived synthetically or from natural sources. The compounds include inorganic or organic compounds such as polynucleotides, lipids or hormone analogs that are characterized by relatively low molecular weights. Other biopolymeric organic test compounds include peptides comprising from about 2 to about 40 amino acids and larger polypeptides comprising from about 40 to about 500 amino acids, such as antibodies or antibody conjugates.

The term "condition" or "disease" means the overt presentation of symptoms (i.e., illness) or the manifestation of abnormal clinical indicators (for example, biochemical indicators). Alternatively, the term "disease" refers to a genetic or environmental risk of or propensity for developing such symptoms or abnormal clinical indicators.

The term "contact" or "contacting" means bringing at least two moieties together, whether in an in vitro system or an in vivo system.

The term "derivatives of a polypeptide" relates to those peptides, oligopeptides, polypeptides, proteins and enzymes that comprise a stretch of contiguous amino acid residues of the polypeptide and that retain the biological activity of the protein, for example, polypeptides that have amino acid mutations compared to the amino acid sequence of a naturally-occurring form of the polypeptide. A derivative may further comprise additional naturally occurring, altered, glycosylated, acylated or non-naturally occurring amino acid residues compared to the amino acid sequence of a naturally occurring form of the polypeptide. It may also contain one or more non-amino acid substituents compared to the amino acid sequence of a naturally occurring form of the polypeptide, for example a reporter molecule or other ligand, covalently or non-covalently bound to the amino acid sequence.

The term "derivatives of a polynucleotide" relates to DNA-molecules, RNA-molecules, and oligonucleotides that comprise a stretch or nucleic acid residues of the polynucleotide, for example, polynucleotides that may have nucleic acid mutations as compared to the nucleic acid sequence of a naturally occurring form of the polynucleotide. A derivative may further comprise nucleic acids with modified backbones such as PNA, polysiloxane, and 2'-O-(2-methoxy) ethylphosphorothioate, non-naturally occurring nucleic acid residues, or one or more nuclei acid substituents, such as methyl-, thio-, sulphate, benzoyl-, phenyl-, amino-, propyl-, chloro-, and methanocarbanucleosides, or a reporter molecule to facilitate its detection.

The terms "ECM-degrading protein" and "ECM-degrading activity" refer to a protein and activity, respectively, which are capable of degrading extra-cellular matrixes found in bone and cartilage.

The term "effective amount" or "therapeutically effective amount" means that amount of a compound or agent that will elicit the biological or medical response of a subject that is being sought by a medical doctor or other clinician.

The term "endogenous" shall mean a material that a mammal naturally produces. Endogenous in reference to the term "protease", "kinase", or G-Protein Coupled Receptor ("GPCR") shall mean that which is naturally produced by a mammal (for example, and not limitation, a human). In contrast, the term non-endogenous in this context shall mean that which is not naturally produced by a mammal (for example, and not limitation, a human). Both terms can be utilized to describe both "in vivo" and "in vitro" systems. For example, and not a limitation, in a screening approach, the endogenous or non-endogenous TARGET may be in reference to an in vitro screening system. As a further example and not limitation, where the genome of a mammal has been manipulated to include a non-endogenous TARGET, screening of a candidate compound by means of an in vivo system is viable.

The term "expressible nucleic acid" means a nucleic acid coding for a proteinaceous molecule, an RNA molecule, or a DNA molecule.

The term "expression" comprises both endogenous expression and overexpression by transduction.

The term "expression inhibitory agent" means a polynucleotide designed to interfere selectively with the transcription, translation and/or expression of a specific polypeptide or protein normally expressed within a cell. More particularly, "expression inhibitory agent" comprises a DNA or RNA molecule that contains a nucleotide sequence identical to or complementary to at least about 17 sequential nucleotides within the polyribonucleotide sequence coding for a specific polypeptide or protein. Exemplary expression inhibitory molecules include ribozymes, double stranded siRNA molecules, self-complementary single-stranded siRNA molecules, genetic antisense constructs, and synthetic RNA antisense molecules with modified stabilized backbones.

The term "expressible nucleic acid" means a nucleic acid coding for a proteinaceous molecule, an RNA molecule, or a DNA molecule.

The term "fragment of a polynucleotide" relates to oligonucleotides that comprise a stretch of contiguous nucleic acid residues that exhibit substantially a similar, but not necessarily identical, activity as the complete sequence.

The term "fragment of a polypeptide" relates to peptides, oligopeptides, polypeptides, proteins and enzymes that comprise a stretch of contiguous amino acid residues, and exhibit substantially a similar, but not necessarily identical, functional activity as the complete sequence.

The term "hybridization" means any process by which a strand of nucleic acid binds with a complementary strand through base pairing. The term "hybridization complex" refers to a complex formed between two nucleic acid sequences by virtue of the formation of hydrogen bonds between complementary bases. A hybridization complex may be formed in solution (for example, $C_{0t}$ or $R_{0t}$ analysis) or formed between one nucleic acid sequence present in solution and another nucleic acid sequence immobilized on a solid support (for example, paper, membranes, filters, chips, pins or glass slides, or any other appropriate substrate to which cells or their nucleic acids have been fixed). The term "stringent conditions" refers to conditions that permit hybridization between polynucleotides and the claimed polynucleotides. Stringent conditions can be defined by salt concentration, the concentration of organic solvent, for example, formamide, temperature, and other conditions well known in the art. In particular, reducing the concentration of salt, increasing the concentration of formamide, or raising the hybridization temperature can increase stringency.

The term “inhibit” or “inhibiting”, in relationship to the term “response” means that a response is decreased or prevented in the presence of a compound as opposed to in the absence of the compound.

The term “inhibition” refers to the reduction, down regulation of a process or the elimination of a stimulus for a process that results in the absence or minimization of the expression of a protein or polypeptide.

The term “induction” refers to the inducing, up-regulation, or stimulation of a process that results in the expression of a protein or polypeptide.

The term “ligand” means an endogenous, naturally occurring molecule specific for an endogenous, naturally occurring receptor.

The term “pharmaceutically acceptable salts” refers to the non-toxic, inorganic and organic acid addition salts, and base addition salts, of compounds of the present invention. These salts can be prepared in situ during the final isolation and purification of compounds useful in the present invention.

The term “polypeptide” relates to proteins, proteinaceous molecules, fractions of proteins, peptides, oligopeptides, enzymes (such as kinases, proteases, GCPR’s etc.).

The term “polynucleotide” means a polynucleic acid, in single or double stranded form, and in the sense or antisense orientation, complementary polynucleic acids that hybridize to a particular polynucleic acid under stringent conditions, and polynucleotides that are homologous in at least about 60 percent of its base pairs, and more preferably 70 percent of its base pairs are in common, most preferably 90 percent, and in a special embodiment 100 percent of its base pairs. The polynucleotides include polyribonucleic acids, polydeoxyribonucleic acids, and synthetic analogues thereof. It also includes nucleic acids with modified backbones such as peptide nucleic acid (PNA), polysiloxane, and 2'-O-(2-methoxy) ethylphosphorothioate. The polynucleotides are described by sequences that vary in length, that range from about 10 to about 5000 bases, preferably about 100 to about 4000 bases, more preferably about 250 to about 2500 bases. One polynucleotide embodiment comprises from about 10 to about 30 bases in length. A special embodiment of polynucleotide is the polyribonucleotide of from about 17 to about 22 nucleotides, more commonly described as small interfering RNAs (siRNAs). Another special embodiment are nucleic acids with modified backbones such as peptide nucleic acid (PNA), polysiloxane, and 2'-O-(2-methoxy)ethylphosphorothioate, or including non-naturally occurring nucleic acid residues, or one or more nucleic acid substituents, such as methyl-, thio-, sulphate, benzoyl-, phenyl-, amino-, propyl-, chloro-, and methanocarbanucleosides, or a reporter molecule to facilitate its detection.

The term “polypeptide” relates to proteins (such as TARGETS), proteinaceous molecules, fractions of proteins peptides and oligopeptides.

The term “solvate” means a physical association of a compound useful in this invention with one or more solvent molecules. This physical association includes hydrogen bonding. In certain instances the solvate will be capable of isolation, for example when one or more solvent molecules are incorporated in the crystal lattice of the crystalline solid. “Solvate” encompasses both solution-phase and isolable solvates. Representative solvates include hydrates, ethanolates and methanolates.

The term “subject” includes humans and other mammals.

The term “TARGET” or “TARGETS” means the protein(s) identified in accordance with the assays described herein and determined to be involved in the modulation of MMP1 expression levels.

“Therapeutically effective amount” means that amount of a drug or pharmaceutical agent that will elicit the biological or medical response of a subject that is being sought by a medical doctor or other clinician. In particular, with regard to treating an disease condition characterized by the degradation of extracellular matrix, the term “effective matrix metallo-protease inhibiting amount” is intended to mean that effective amount of an compound of the present invention that will bring about a biologically meaningful decrease in the production of MMP-1 in the subject’s disease affected tissues such that extracellular matrix degradation is meaningfully reduced. A compound having matrix metallo-protease inhibiting properties or a “matrix metallo-protease inhibiting compound” means a compound that provided to a cell in effective amounts is able to cause a biologically meaningful decrease in the production of MMP-1 in such cells.

The term “treating” means an intervention performed with the intention of preventing the development or altering the pathology of, and thereby alleviating a disorder, disease or condition, including one or more symptoms of such disorder or condition. Accordingly, “treating” refers to both therapeutic treatment and prophylactic or preventative measures. Those in need of treating include those already with the disorder as well as those in which the disorder is to be prevented. The related term “treatment,” as used herein, refers to the act of treating a disorder, symptom, disease or condition, as the term “treating” is defined above.

Applicants’ Invention Based on TARGET Relationship to Extra-cellular Matrix Degradation MMP1 expression by SFs is relevant to ECM degradation as it correlates to the activation of SFs towards an erosive phenotype that, in vivo, is responsible for cartilage degradation. This has been demonstrated by the administration to TNFα transgenic mice, which spontaneously develop an arthritic phenotype, of adenovirus that overexpress TIMP1, an inhibitor of MMPs,, which administration results in the reduction of joint degradation (Shett et al., Arthritis Rheum. (2001) 44:2888-98). Therefore, inhibition of the MMP1 expression by SFs represents a valuable therapeutic approach towards the treatment of RA. Accordingly, if the reduction in expression of a candidate protein in activated SFs leads to a corresponding reduction of MMP1 expression, then such protein is involved in the regulation of MMP1 expression and is a relevant target for the development of therapeutic strategies for the treatment of RA. The present inventors have identified such target proteins by screening recombinant adenoviruses mediating the expression of a library of shRNAs, referred to herein as “Ad-siRNAs.” The collection used herein is further referred to as “adenoviral siRNA library” or “SilenceSelect” collection. These libraries contain recombinant adenoviruses, further referred to as knock-down (KD) viruses or Ad-siRNAs, that mediate the expression in cells of shRNAs which reduce the expression levels of targeted genes by a RNA interference (RNAi)-based mechanism (WO03/020931). The screening work is described below in Example 1.

As noted above, the present invention is based on the present inventors’ discovery that the TARGET polypeptides, identified as a result of a variety of screens described below in the Examples, are factors not only in the up-regulation and/or induction of MMP1, but even in the up-regulation and/or induction of extra-cellular matrix degradation. The activity of the ECM-degrading proteins is believed to be causative and to correlate with the progression of various diseases associated with an increased degradation of the extra-cellular matrix, including diseases that involve the degradation of the joint.

In one aspect, the present invention relates to a method for assaying for drug candidate compounds that inhibit extra-cellular matrix degradation, comprising contacting the compound with a polypeptide comprising an amino acid sequence of SEQ ID NO: 17-127, or fragment thereof, under conditions that allow said polypeptide to bind to the compound, and detecting the formation of a complex between the polypeptide and the compound. One preferred means of measuring the complex formation is to determine the binding affinity of said compound to said polypeptide.

More particularly, the invention relates to a method for identifying an agent that inhibits extra-cellular matrix degradation, the method comprising further:

(a) contacting a population of mammalian cells with one or more compound that exhibits binding affinity for a TARGET polypeptide, or fragment thereof, and (b) measuring a compound-polypeptide property related to extra-cellular matrix degradation.

The compound-polypeptide property referred to above is related to the expression and/or activity of the TARGET, and is a measurable phenomenon chosen by the person of ordinary skill in the art. The measurable property may be, for example, the binding affinity for a peptide domain of the polypeptide TARGET such as for SEQ ID NO: 33-127, or the level of any one of a number of biochemical marker levels of extra-cellular matrix degradation. Extra-cellular matrix degradation can be measured, for example, by measuring the level of enzymes that are induced during the process, such as expression of a MMP and/or a Cathepsin polypeptide.

In a preferred embodiment of the invention, the TARGET polypeptide comprises an amino acid sequence selected from the group consisting of SEQ ID No: 17-32 as listed in Table 1.

TABLE 1

| Hit No. | Gene Name | Description | Ref/SEQ Accession (DNA) | SEQ ID NO DNA | REF/SEQ Accession (Protein) | SEQ ID No Protein | Protein Class | SEQ ID KD Target 19-Mer | SEQ ID KD Target 21-Mer |
|---|---|---|---|---|---|---|---|---|---|
| H46-030 | KCNF1 | *Homo sapiens* potassium voltage-gated channel, subfamily F, member 1 | NM_002236 | 1 | NP_002227 | 17 | Ion Channel | 128<br>176-182<br>219-220 | 231 |
| H46-137 | SLC9A8 | *Homo sapiens* solute carrier family 9 (sodium/hydrogen exchanger), isoform 8 | NM_015266 | 2 | NP_056081 | 18 | Ion Channel | 129<br>183-189<br>229-230 | 232 |
| H46-160 | ARAF1 | *Homo sapiens* v-raf murine sarcoma 3611 viral oncogene homolog | NM_001654 | 3 | NP_001645 | 19 | Kinase | 130<br>156-162<br>204 | 233 |
| H46-010 | AXL | *Homo sapiens* AXL receptor tyrosine kinase (AXL), transcript variant 2 | NM_001699 | 4 | NP_001690 | 20 | Kinase | 131<br>142-148<br>205-206 | 234 |
| H46-010 | AXL | *Homo sapiens* AXL receptor tyrosine kinase (AXL), transcript variant 1 | NM_021913 | 5 | NP_068713 | 21 | Kinase | 131<br>205-206 | 234 |
| H46-393 | FGFR3 | *Homo sapiens* fibroblast growth factor receptor 3, transcript variant 1 | NM_000142 | 6 | NP_000133 | 22 | Kinase | 132<br>190-196<br>211-215 | 235 |
| H46-189 | NR2F6 | *Homo sapiens* nuclear receptor subfamily 2, group F, member 6 | NM_005234 | 7 | NP_005225 | 23 | NHR | 133<br>163-168<br>225-226 | 236 |
| H46-020 | SCN9A | *Homo sapiens* sodium channel, voltage-gated, type IX, alpha | NM_002977 | 8 | NP_002968 | 24 | Ion Channel | 134<br>169-175<br>227-228 | 237 |
| H46-359 | MAPK13 | *Homo sapiens* mitogen-activated protein kinase 13 | NM_002754 | 9 | NP_002745 | 25 | Kinase | 135<br>149-155<br>223 | 238 |
| H46-343 | ILK | *Homo sapiens* integrin-linked kinase (ILK), transcript variant 1 | NM_004517 | 10 | NP_004508 | 26 | Kinase | 136<br>216-218 | 239 |
| H46-226 | CHRNA5 | *Homo sapiens* cholinergic receptor, nicotinic, alpha polypeptide 5 | M83712 | 11 | AAA58357 | 27 | Ion Channel/ Receptor | 137<br>197-203<br>207-208 | 240 |
| H46-129 | NQO2 | *Homo sapiens* NAD(P)H dehydrogenase, quinone 2 | NM_000904 | 12 | NP_000895 | 28 | Dehydrogenase | 138-139<br>224 | 241-242 |
| H46-021 | DGKB | *Homo sapiens* diacylglycerol kinase, beta 90 kDa (DGKB), transcript variant 2 | NM_145695 | 13 | NP_663733 | 29 | Kinase | 140<br>209 | 243 |

TABLE 1-continued

| Hit No. | Gene Name | Description | Ref/SEQ Accession (DNA) | SEQ ID NO DNA | REF/SEQ Accession (Protein) | SEQ ID No Protein | Protein Class | SEQ ID KD Target 19-Mer | SEQ ID KD Target 21-Mer |
|---|---|---|---|---|---|---|---|---|---|
| H46-021 | DGKB | *Homo sapiens* diacylglycerol kinase, beta 90 kDa (DGKB), transcript variant 1 | NM_004080 | 14 | NP_004071 | 30 | Kinase | 140 209-210 | 243 |
| H46-021 | INCENP | *Homo sapiens* inner centromere protein antigens 135/155 kDa (INCENP) | NM_020238 | 15 | NP_064623 | 31 | Not Classified | 140 | 243 |
| H46-265 | MAPK12 | *Homo sapiens* mitogen-activated protein kinase 12 | NM_002969 | 16 | NP_002960 | 32 | Kinase | 141 221-222 | 244 |

Another special embodiment of the invention comprises the kinase TARGETS identified as SEQ ID NOS. 19-22, 25, 26, 29, 30, and 32. Another special embodiment of the invention comprises the ion channel TARGETS identified as SEQ ID NOS. 17, 18, 24, and 27. A further preferred embodiment is the Nuclear Hormone Receptors (NHRs) TARGET identified as SEQ. ID NO. 23.

Depending on the choice of the skilled artisan, the present assay method may be designed to function as a series of measurements, each of which is designed to determine whether the drug candidate compound is indeed acting on the polypeptide to thereby inhibit extra-cellular matrix degradation. For example, an assay designed to determine the binding affinity of a compound to the polypeptide, or fragment thereof, may be necessary, but not sufficient, to ascertain whether the test compound would be useful for inhibiting extra-cellular matrix degradation when administered to a subject.

Such binding information would be useful in identifying a set of test compounds for use in an assay that would measure a different property, further down the biochemical pathway, such as for example MMP-1 expression. Such second assay may be designed to confirm that the test compound, having binding affinity for the polypeptide, actually inhibits extra-cellular matrix degradation. Suitable controls should always be in place to insure against false positive readings.

The order of taking these measurements is not believed to be critical to the practice of the present invention, which may be practiced in any order. For example, one may first perform a screening assay of a set of compounds for which no information is known respecting the compounds' binding affinity for the polypeptide. Alternatively, one may screen a set of compounds identified as having binding affinity for a polypeptide domain, or a class of compounds identified as being an inhibitor of the polypeptide. However, for the present assay to be meaningful to the ultimate use of the drug candidate compounds, a measurement of extra-cellular matrix degradation activity is necessary. Validation studies including controls and measurements of binding affinity to the polypeptides of the invention are nonetheless useful in identifying a compound useful in any therapeutic or diagnostic application.

The present assay method may be practiced in vitro, using one or more of the TARGET proteins, or fragments thereof. The amino acid sequences of exemplary protein domain fragments of selected TARGETS are SEQ ID NO: 33-127, listed in Table 1A below.

TABLE 1A

| Accession | Name | Protein Segment | SEQ ID NO Protein segment |
|---|---|---|---|
| NM_002236 | KCNF1 | Intracellular domain | 33 |
| NM_002236 | KCNF1 | Transmembrane domain | 34 |
| NM_002236 | KCNF1 | Extracellular domain | 35 |
| NM_002236 | KCNF1 | Transmembrane domain | 36 |
| NM_002236 | KCNF1 | Intracellular domain | 37 |
| NM_002236 | KCNF1 | Transmembrane domain | 38 |
| NM_002236 | KCNF1 | Extracellular domain | 39 |
| NM_002236 | KCNF1 | Transmembrane domain | 40 |
| NM_002236 | KCNF1 | Intracellular domain | 41 |
| NM_015266 | SLC9A8 | Intracellular domain | 42 |
| NM_015266 | SLC9A8 | Transmembrane domain | 43 |
| NM_015266 | SLC9A8 | Extracellular domain | 44 |
| NM_015266 | SLC9A8 | Transmembrane domain | 45 |
| NM_015266 | SLC9A8 | Intracellular domain | 46 |
| NM_015266 | SLC9A8 | Transmembrane domain | 47 |
| NM_015266 | SLC9A8 | Extracellular domain | 48 |
| NM_015266 | SLC9A8 | Transmembrane domain | 49 |
| NM_015266 | SLC9A8 | Intracellular domain | 50 |
| NM_015266 | SLC9A8 | Transmembrane domain | 51 |
| NM_015266 | SLC9A8 | Extracellular domain | 52 |
| NM_015266 | SLC9A8 | Transmembrane domain | 53 |
| NM_015266 | SLC9A8 | Intracellular domain | 54 |
| NM_015266 | SLC9A8 | Transmembrane domain | 55 |
| NM_015266 | SLC9A8 | Extracellular domain | 56 |
| NM_015266 | SLC9A8 | Transmembrane domain | 57 |
| NM_015266 | SLC9A8 | Intracellular domain | 58 |
| NM_015266 | SLC9A8 | Transmembrane domain | 59 |
| NM_015266 | SLC9A8 | Extracellular domain | 60 |
| NM_015266 | SLC9A8 | Transmembrane domain | 61 |
| NM_015266 | SLC9A8 | Intracellular domain | 62 |
| NM_015266 | SLC9A8 | Transmembrane domain | 63 |
| NM_015266 | SLC9A8 | Extracellular domain | 64 |
| NM_001699 | AXL | Extracellular domain | 65 |
| NM_001699 | AXL | Transmembrane domain | 66 |
| NM_001699 | AXL | Intracellular domain | 67 |
| NM_021913 | AXL | Extracellular domain | 68 |
| NM_021913 | AXL | Transmembrane domain | 69 |
| NM_021913 | AXL | Intracellular domain | 70 |
| NM_000142 | FGFR3 | Extracellular domain | 71 |
| NM_000142 | FGFR3 | Transmembrane domain | 72 |
| NM_000142 | FGFR3 | Intracellular domain | 73 |
| NM_000142 | FGFR3 | Transmembrane domain | 74 |
| NM_000142 | FGFR3 | Extracellular domain | 75 |
| NM_002977 | SCN9A | Intracellular domain | 76 |
| NM_002977 | SCN9A | Transmembrane domain | 77 |
| NM_002977 | SCN9A | Extracellular domain | 78 |
| NM_002977 | SCN9A | Transmembrane domain | 79 |
| NM_002977 | SCN9A | Intracellular domain | 80 |
| NM_002977 | SCN9A | Transmembrane domain | 81 |
| NM_002977 | SCN9A | Extracellular domain | 82 |
| NM_002977 | SCN9A | Transmembrane domain | 83 |

TABLE 1A-continued

| Accession | Name | Protein Segment | SEQ ID NO Protein segment |
|---|---|---|---|
| NM_002977 | SCN9A | Intracellular domain | 84 |
| NM_002977 | SCN9A | Transmembrane domain | 85 |
| NM_002977 | SCN9A | Extracellular domain | 86 |
| NM_002977 | SCN9A | Transmembrane domain | 87 |
| NM_002977 | SCN9A | Intracellular domain | 88 |
| NM_002977 | SCN9A | Transmembrane domain | 89 |
| NM_002977 | SCN9A | Extracellular domain | 90 |
| NM_002977 | SCN9A | Transmembrane domain | 91 |
| NM_002977 | SCN9A | Intracellular domain | 92 |
| NM_002977 | SCN9A | Transmembrane domain | 93 |
| NM_002977 | SCN9A | Extracellular domain | 94 |
| NM_002977 | SCN9A | Transmembrane domain | 95 |
| NM_002977 | SCN9A | Intracellular domain | 96 |
| NM_002977 | SCN9A | Transmembrane domain | 97 |
| NM_002977 | SCN9A | Extracellular domain | 98 |
| NM_002977 | SCN9A | Transmembrane domain | 99 |
| NM_002977 | SCN9A | Intracellular domain | 100 |
| NM_002977 | SCN9A | Transmembrane domain | 101 |
| NM_002977 | SCN9A | Extracellular domain | 102 |
| NM_002977 | SCN9A | Transmembrane domain | 103 |
| NM_002977 | SCN9A | Intracellular domain | 104 |
| NM_002977 | SCN9A | Transmembrane domain | 105 |
| NM_002977 | SCN9A | Extracellular domain | 106 |
| NM_002977 | SCN9A | Transmembrane domain | 107 |
| NM_002977 | SCN9A | Intracellular domain | 108 |
| NM_002977 | SCN9A | Transmembrane domain | 109 |
| NM_002977 | SCN9A | Extracellular domain | 110 |
| NM_002977 | SCN9A | Transmembrane domain | 111 |
| NM_002977 | SCN9A | Intracellular domain | 112 |
| NM_002977 | SCN9A | Transmembrane domain | 113 |
| NM_002977 | SCN9A | Extracellular domain | 114 |
| NM_002977 | SCN9A | Transmembrane domain | 115 |
| NM_002977 | SCN9A | Intracellular domain | 116 |
| NM_002977 | SCN9A | Transmembrane domain | 117 |
| NM_002977 | SCN9A | Extracellular domain | 118 |
| M83712 | CHRNA5 | Extracellular domain | 119 |
| M83712 | CHRNA5 | Transmembrane domain | 120 |
| M83712 | CHRNA5 | Intracellular domain | 121 |
| M83712 | CHRNA5 | Transmembrane domain | 122 |
| M83712 | CHRNA5 | Extracellular domain | 123 |
| M83712 | CHRNA5 | Transmembrane domain | 124 |
| M83712 | CHRNA5 | Intracellular domain | 125 |
| M83712 | CHRNA5 | Transmembrane domain | 126 |
| M83712 | CHRNA5 | Extracellular domain | 127 |

The binding affinity of a compound with the polypeptide TARGET can be measured by methods known in the art, such as using surface plasmon resonance biosensors (Biacore), by saturation binding analysis with a labeled compound (for example, Scatchard and Lindmo analysis), by differential UV spectrophotometer, fluorescence polarization assay, Fluorometric Imaging Plate Reader (FLIPR®) system, Fluorescence resonance energy transfer, and Bioluminescence resonance energy transfer. The binding affinity of compounds can also be expressed in dissociation constant (Kd) or as IC50 or EC50. The IC50 represents the concentration of a compound that is required for 50% inhibition of binding of another ligand to the polypeptide. The EC50 represents the concentration required for obtaining 50% of the maximum effect in any assay that measures TARGET function. The dissociation constant, Kd, is a measure of how well a ligand binds to the polypeptide, it is equivalent to the ligand concentration required to saturate exactly half of the binding-sites on the polypeptide. Compounds with a high affinity binding have low Kd, IC50 and EC50 values, for example, in the range of 100 nM to 1 pM; a moderate- to low-affinity binding relates to high Kd, IC50 and EC50 values, for example in the micromolar range.

The present assay method may also be practiced in a cellular assay, A host cell expressing the TARGET can be a cell with endogenous expression or a cell over-expressing the TARGET, for example, by transduction. When the endogenous expression of the polypeptide is not sufficient to determine a baseline that can easily be measured, one may use using host cells that over-express TARGET. Over-expression has the advantage that the level of the TARGET substrate end-products is higher than the activity level by endogenous expression. Accordingly, measuring such levels using presently available techniques is easier.

One embodiment of the present method for identifying a compound that decreases extra-cellular matrix (ECM) degradation comprises culturing a population of mammalian cells expressing a TARGET polypeptide, or a functional fragment or derivative thereof; determining a first level of ECM degradation in said population of cells; eventually activating the population of cells; exposing said population of cells to a compound, or a mixture of compounds; determining a second level of ECM degradation in said population of cells during or after exposure of said population of cells to said compound, or the mixture of said compounds; and identifying the compound(s) that decreases ECM degradation. As noted above, ECM degradation may be determined by measuring the expression and/or activity of the TARGET polypeptide and/or a known ECM-degrading protein. In a preferred embodiment, said ECM-degrading protein is able to degrade collagen, and more preferably, is able to degrade collagen type I and/or collagen type II. In another preferred embodiment of the present invention, said ECM-degrading protein is a Matrix Metallo Proteinase (MMP), and more preferably is selected from the group consisting of MMP1, MMP2, MMP3, MMP8, MMP9, MMP13 and MMP14. In this context, the most preferred ECM-degrading protein is Matrix Metalloprotease 1 (MMP1). In yet another preferred embodiment, said ECM-degrading protein is Cathepsin K.

The expression of an ECM-degrading protein can be determined by methods known in the art such as Western blotting using specific antibodies, or an ELISA using antibodies specifically recognizing a particular ECM-degrading protein.

The activity of an ECM-degrading protein can be determined by using fluorogenic small peptide substrates. The specificity of these substrates, however, is often limited. In general, the use of these substrates is limited to the testing of purified proteases in biochemical assays, to avoid interference of other proteases.

The present inventors have developed a protocol allowing the detection, in a high throughput mode, of the activity of collagen degrading enzymes in complex media such as the supernatant of cultured cells. This protocol makes use of native collagen, being labelled with a fluorescent label, as a substrate.

The present inventors identified TARGET genes involved in ECM-degradation by using a 'knock-down' library. This type of library is a screen in which siRNA molecules are transduced into cells by recombinant adenoviruses, which siRNA molecules inhibit or repress the expression of a specific gene as well as expression and activity of the corresponding gene product in a cell. Each siRNA in a viral vector corresponds to a specific natural gene. By identifying a siRNA that represses ECM-degradation, a direct correlation can be drawn between the specific gene expression and ECM degradation. The TARGET genes identified using the knock-down library (the protein expression products thereof herein referred to as "TARGET" polypeptides) are then used in the present inventive method for identifying compounds that can be used to prevent ECM-degradation. Indeed, shRNA compounds comprising the sequences listed in Table 2 (SEQ ID NO: 128-141 and 231-244) inhibit the expression and/or activity of these TARGET genes and decrease the ECM-degrading activity of cells, confirming the role of the TARGETS in ECM-degradation.

TABLE 2

List of target sequences selected within the coding sequences of the genes identified as modulators of the collagenolytic activity of SFs for use in RNAi-based down-regulation of the expression of these genes.

| GENE NAME | ACCESSION | PLASMID NAME | siRNA NAME | SEQ ID NO 19-mer | SEQ ID NO 21-mer |
|---|---|---|---|---|---|
| KCNF1 | NM_002236 | A150100-KCNF1_v2 | NM_002236_idx1263 | 128 | 231 |
| SLC9A8 | NM_015266 | A150100-KIAA0939_v4 | XM_030524_idx840 | 129 | 232 |
| ARAF1 | NM_001654 | A150100-ARAF1_v1 | NM_001654_idx372 | 130 | 233 |
| AXL | NM_001699 | A150100-AXL_v1 | NM_021913_idx2487 | 131 | 234 |
| AXL | NM_021913 | A150100-AXL_v1 | NM_021913_idx2487 | 131 | 234 |
| FGFR3 | NM_000142 | A150100-FGFR3_v2 | oKD173 | 132 | 235 |
| NR2F6 | NM_005234 | A150100-NR2F6_v1 | NM_005234_idx1269 | 133 | 236 |
| SCN9A | NM_002977 | A150100-SCN9A_v1 | NM_002977_idx3381 | 134 | 237 |
| MAPK13 | NM_002754 | A150100-MAPK13_v6 | oKD090 | 135 | 238 |
| ILK | NM_004517 | A150100-ILK_v2 | NM_004517_idx1243 | 136 | 239 |
| CHRNA5 | M83712 | A150100-CHRNA5_v3 | NM_000745_idx511 | 137 | 240 |
| NQO2 | NM_000904 | A150100-NQO2_v1 | NM_000904_idx598 | 138-139 | 241-242 |
| DGKB | NM_145695 | A150100-DGKB_v2 | NM_004080_idx1064 | 140 | 243 |
| DGKB | NM_004080 | A150100-DGKB_v2 | NM_004080_idx1064 | 140 | 243 |
| INCENP | NM_020238 | A150100-DGKB_v2 | NM_004080_idx1064 | 140 | 243 |
| MAPK12 | NM_002969 | A150100-MAPK12_v6 | NM_002969_idx797 | 141 | 244 |

Specific methods to determine the activity of a kinase by measuring the phosphorylation of a substrate by the kinase, which measurements are performed in the presence or absence of a compound, are well known in the art.

Ion channels are membrane protein complexes and their function is to facilitate the diffusion of ions across biological membranes. Membranes, or phospholipid bilayers, build a hydrophobic, low dielectric barrier to hydrophilic and charged molecules. Ion channels provide a high conducting, hydrophilic pathway across the hydrophobic interior of the membrane. The activity of an ion channel can be measured using classical patch clamping. High-throughput fluorescence-based or tracer-based assays are also widely available to measure ion channel activity. These fluorescent-based assays screen compounds on the basis of their ability to either open or close an ion channel thereby changing the concentration of specific fluorescent dyes across a membrane. In the case of the tracer-based assay, the changes in concentration of the tracer within and outside the cell are measured by radioactivity measurement or gas absorption spectrometry.

Nuclear receptor activation is believed to involve a conformational change of the receptor that is induced by ligand binding. The results of protease protection assays have confirmed that nuclear hormone agonists and antagonists cause receptor proteins to adopt different conformations (Keidel et al. Mol Cell. Biol. 14:287 (1994); Allan et al. J. Biol. Chem. 267:19513 (1992)). Accordingly, a protease protection assay can be used to measure the activity of a NHR. Recruitment of co-activators or repressors is another basis on which assays for assessment of NHR activity are developed.

Specific methods to determine the activity of a dehydrogenase by measuring the oxidation of a substrate by the dehydrogenase, which measurements are performed in the presence or absence of a compound, are well known in the art.

Specific methods to determine the inhibition by the compound by measuring the cleavage of the substrate by the polypeptide, which is a protease, are well known in the art. Classically, substrates are used in which a fluorescent group is linked to a quencher through a peptide sequence that is a substrate that can be cleaved by the target protease. Cleavage of the linker separates the fluorescent group and quencher, giving rise to an increase in fluorescence.

Table 4 lists a large number of other polypeptide types identified using applicant's knock-down library against the MMP1 assay described below. One such polypeptide class are the G-protein coupled receptors (GPCR), which are capable of activating an effector protein, resulting in changes in second messenger levels in the cell. The activity of a GPCR can be measured by measuring the activity level of such second messengers. Two important and useful second messengers in the cell are cyclic AMP (cAMP) and $Ca^{2+}$. The activity levels can be measured by methods known to persons skilled in the art, either directly by ELISA or radioactive technologies or by using substrates that generate a fluorescent or luminescent signal when contacted with $Ca^{2+}$ or indirectly by reporter gene analysis. The activity level of the one or more secondary messengers may typically be determined with a reporter gene controlled by a promoter, wherein the promoter is responsive to the second messenger. Promoters known and used in the art for such purposes are the cyclic-AMP responsive promoter that is responsive for the cyclic-AMP levels in the cell, and the NF-AT responsive promoter that is sensitive to cytoplasmic $Ca^{2+}$-levels in the cell. The reporter gene typically has a gene product that is easily detectable. The reporter gene can either be stably infected or transiently transfected in the host cell. Useful reporter genes are alkaline phosphatase, enhanced green fluorescent protein, destabilized green fluorescent protein, luciferase and β-galactosidase.

It should be understood that the cells expressing the polypeptides, may be cells naturally expressing the polypeptides, or the cells may be may be transfected to express the polypeptides, as described above.

In one embodiment it is preferred that the methods of the present invention further comprise the step of contacting the population of cells with an agonist of the polypeptide. This is useful in methods wherein the expression of the polypeptide in a certain chosen population of cells is too low for a proper detection of its activity. By using an agonist the polypeptide may be triggered, enabling a proper read-out if the compound inhibits the polypeptide. Similar considerations apply to the measurement of ECM degradation. In a preferred embodiment, the cells used in the present method are mammalian synovial fibroblasts and the triggers that may be used to induce the ECM-degrading activity are cytokines relevant in the field of arthritis: for instance TNFalpha, IL1beta, IL6, OSM, IL17, IL15, IL18 and MIF1alpha. In another preferred embodiment, the trigger is a mixture of factors generated by contacting cytokine-producing cells relevant in the field of arthritis, such as monocytes, macrophages, T-cells, and B-cells. The cytokine-producing cells will respond to the contact by producing a complex and unbiased mixture of factors. If the cytokine-producing cell used is also found in the pannus, and the cytokine applied to this trigger is found in the synovial fluid of rheumatoid arthritis patients, the mixture of factors ultimately produced will contain factors that are present in the joints of arthritis patients.

The present invention further relates to a method for identifying a compound that inhibits extra-cellular matrix degradation, comprising:

(a) contacting a compound with a polypeptide comprising an amino acid sequence selected from the group consisting of SEQ ID NO: 17-127;
(b) determining the binding affinity of the compound to the polypeptide;
(c) contacting a population of mammalian cells expressing said polypeptide with the compound that exhibits a binding affinity of at least 10 micromolar; and
(d) identifying the compound that inhibits extra-cellular matrix degradation.

The population of cells may be exposed to the compound or the mixture of compounds through different means, for instance by direct incubation in the medium, or by nucleic acid transfer into the cells. Such transfer may be achieved by a wide variety of means, for instance by direct transfection of naked isolated DNA, or RNA, or by means of delivery systems, such as recombinant vectors. Other delivery means such as liposomes, or other lipid-based vectors may also be used. Preferably, the nucleic acid compound is delivered by means of a (recombinant) vector such as a recombinant virus.

For high-throughput purposes, libraries of compounds may be used such as antibody fragment libraries, peptide phage display libraries, peptide libraries (for example, LOPAP™, Sigma Aldrich), lipid libraries (BioMol), synthetic compound libraries (for example, LOPAC™, Sigma Aldrich) or natural compound libraries (Specs, TimTec).

Preferred drug candidate compounds are low molecular weight compounds. Low molecular weight compounds, for example, with a molecular weight of 500 Dalton or less, are likely to have good absorption and permeation in biological systems and are consequently more likely to be successful drug candidates than compounds with a molecular weight above 500 Dalton (Lipinski et al. (1997)). Peptides comprise another preferred class of drug candidate compounds. Peptides may be excellent drug candidates and there are multiple examples of commercially valuable peptides such as fertility hormones and platelet aggregation inhibitors. Natural compounds are another preferred class of drug candidate compound. Such compounds are found in and extracted from natural sources, and which may thereafter be synthesized. The lipids are another preferred class of drug candidate compound.

Another preferred class of drug candidate compounds is an antibody. The present invention also provides antibodies directed against a TARGET. These antibodies may be endogenously produced to bind to the TARGET within the cell, or added to the tissue to bind to TARGET polypeptide present outside the cell. These antibodies may be monoclonal antibodies or polyclonal antibodies. The present invention includes chimeric, single chain, and humanized antibodies, as well as FAb fragments and the products of a FAb expression library, and Fv fragments and the products of an Fv expression library. In another embodiment, the compound may be a nanobody, the smallest functional fragment of naturally occurring single-domain antibodies (Cortez-Retamozo et al. 2004).

In certain embodiments, polyclonal antibodies may be used in the practice of the invention. The skilled artisan knows methods of preparing polyclonal antibodies. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. Antibodies may also be generated against the intact TARGET protein or polypeptide, or against a fragment, derivatives including conjugates, or other epitope of the TARGET protein or polypeptide, such as the TARGET embedded in a cellular membrane, or a library of antibody variable regions, such as a phage display library.

It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants that may be employed include Freund's complete adjuvant and MPL-TDM adjuvant (monophosphoryl Lipid A, synthetic trehalose dicorynomycolate). One skilled in the art without undue experimentation may select the immunization protocol.

In some embodiments, the antibodies may be monoclonal antibodies. Monoclonal antibodies may be prepared using methods known in the art. The monoclonal antibodies of the present invention may be "humanized" to prevent the host from mounting an immune response to the antibodies. A "humanized antibody" is one in which the complementarity determining regions (CDRS) and/or other portions of the light and/or heavy variable domain framework are derived from a non-human immunoglobulin, but the remaining portions of the molecule are derived from one or more human immunoglobulins. Humanized antibodies also include antibodies characterized by a humanized heavy chain associated with a donor or acceptor unmodified light chain or a chimeric light chain, or vice versa. The humanization of antibodies may be accomplished by methods known in the art (see, for example, Mark and Padlan, (1994) "Chapter 4. Humanization of Monoclonal Antibodies", The Handbook of Experimental Pharmacology Vol. 113, Springer-Verlag, New York). Transgenic animals may be used to express humanized antibodies.

Human antibodies can also be produced using various techniques known in the art, including phage display libraries (Hoogenboom and Winter, (1991) J. Mol. Biol. 227:381-8; Marks et al. (1991). J. Mol. Biol. 222:581-97). The techniques of Cole, et al. and Boemer, et al. are also available for the preparation of human monoclonal antibodies (Cole, et al. (1985) Monoclonal Antibodies and Cancer Therapy, Alan R. Liss, p. 77; Boerner, et al (1991). J. Immunol., 147(1):86-95).

Techniques known in the art for the production of single chain antibodies can be adapted to produce single chain antibodies to the TARGET polypeptides and proteins of the present invention. The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain cross-linking. Alternatively, the relevant cysteine residues are substituted with another amino acid residue or are deleted so as to prevent cross-linking.

Bispecific antibodies are monoclonal, preferably human or humanized, antibodies that have binding specificities for at least two different antigens and preferably for a cell-surface protein or receptor or receptor subunit. In the present case, one of the binding specificities is for one domain of the TARGET, while the other one is for another domain of the same or different TARGET.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, (1983) Nature 305:537-9). Because of the random assortment of immunoglobulin heavy and light chains, these hybridomas (quadromas) produce a potential mixture of ten different antibody molecules, of which only one has the correct bispecific structure. Affinity chromatography steps usually accomplish the purification of the correct molecule. Similar procedures are disclosed in Trauneeker, et al. (1991) EMBO J. 10:3655-9.

According to another preferred embodiment, the assay method uses a drug candidate compound identified as having a binding affinity for a TARGET, and/or has already been identified as having down-regulating activity such as antagonist activity vis-à-vis one or more TARGET.

The present invention further relates to a method for inhibiting extra-cellular matrix degradation comprising contacting mammalian cells with an expression inhibitory agent comprising a polyribonucleotide sequence that complements at least about 17 to about 30 contiguous nucleotides of the nucleotide sequence selected from the group consisting of SEQ ID NO: 1-16.

Another aspect of the present invention relates to a method for inhibiting extra-cellular matrix degradation, comprising by contacting mammalian cells with an expression-inhibiting agent that inhibits the translation in the cell of a polyribonucleotide encoding a TARGET polypeptide. A particular embodiment relates to a composition comprising a polynucleotide including at least one antisense strand that functions to pair the agent with the TARGET mRNA, and thereby down-regulate or block the expression of TARGET polypeptide. The inhibitory agent preferably comprises antisense polynucleotide, a ribozyme, and a small interfering RNA (siRNA), wherein said agent comprises a nucleic acid sequence complementary to, or engineered from, a naturally-occurring polynucleotide sequence selected from the group consisting of SEQ ID NO: 1-16.

A special embodiment of the present invention relates to a method wherein the expression-inhibiting agent is selected from the group consisting of antisense RNA, antisense oligodeoxynucleotide (ODN), a ribozyme that cleaves the polyribonucleotide coding for SEQ ID NO: 1-16, a small interfering RNA (siRNA, preferably shRNA,) that is sufficiently homologous to a portion of the polyribonucleotide corresponding to SEQ ID NO: 1-16, such that the siRNA, preferably shRNA, interferes with the translation of the TARGET polyribonucleotide to the TARGET polypeptide.

Another embodiment of the present invention relates to a method wherein the expression-inhibiting agent is a nucleic acid expressing the antisense RNA, antisense oligodeoxynucleotide (ODN), a ribozyme that cleaves the polyribonucleotide encoded by SEQ ID NO: 1-16, a small interfering RNA (siRNA, preferably shRNA,) that is sufficiently complementary to a portion of the polyribonucleotide corresponding to SEQ ID NO: 1-16, such that the siRNA, preferably shRNA, interferes with the translation of the TARGET polyribonucleotide to the TARGET polypeptide. Preferably the expression-inhibiting agent is an antisense RNA, ribozyme, antisense oligodeoxynucleotide, or siRNA, preferably shRNA, comprising a polyribonucleotide sequence that complements at least about 17 to about 30 contiguous nucleotides of a nucleotide sequence selected from the group consisting of SEQ ID NO: 1-16. More preferably, the expression-inhibiting agent is an antisense RNA, ribozyme, antisense oligodeoxynucleotide, or siRNA, preferably shRNA, comprising a polyribonucleotide sequence that complements at least about 17 to about 25 contiguous nucleotides of a nucleotide sequence selected from the group consisting of SEQ ID NO: 1-16. A special embodiment comprises a polyribonucleotide sequence that complements a polynucleotide sequence selected from the group consisting of SEQ ID NO: 128-141 and 231-244.

The down regulation of gene expression using antisense nucleic acids can be achieved at the translational or transcriptional level. Antisense nucleic acids of the invention are preferably nucleic acid fragments capable of specifically hybridizing with all or part of a nucleic acid encoding a TARGET polypeptide or the corresponding messenger RNA. In addition, antisense nucleic acids may be designed which decrease expression of the nucleic acid sequence capable of encoding a TARGET polypeptide by inhibiting splicing of its primary transcript. Any length of antisense sequence is suitable for practice of the invention so long as it is capable of down-regulating or blocking expression of a nucleic acid coding for a TARGET. Preferably, the antisense sequence is at least about 17 nucleotides in length. The preparation and use of antisense nucleic acids, DNA encoding antisense RNAs and the use of oligo and genetic antisense is known in the art.

One embodiment of expression-inhibitory agent is a nucleic acid that is antisense to a nucleic acid comprising SEQ ID NO: 1-16, for example, an antisense nucleic acid (for example, DNA) may be introduced into cells in vitro, or administered to a subject in vivo, as gene therapy to inhibit cellular expression of nucleic acids comprising SEQ ID NO: 1-16. Antisense oligonucleotides comprise preferably a sequence containing from about 17 to about 100 nucleotides and more preferably the antisense oligonucleotides comprise from about 18 to about 30 nucleotides. Antisense nucleic acids may be prepared from about 17 to about 30 contiguous nucleotides selected from the sequences of SEQ ID NO: 1-16, expressed in the opposite orientation.

The antisense nucleic acids are preferably oligonucleotides and may consist entirely of deoxyribo-nucleotides, modified deoxyribonucleotides, or some combination of both. The antisense nucleic acids can be synthetic oligonucleotides. The oligonucleotides may be chemically modified, if desired, to improve stability and/or selectivity. Since oligonucleotides are susceptible to degradation by intracellular nucleases, the modifications can include, for example, the use of a sulfur group to replace the free oxygen of the phosphodiester bond. This modification is called a phosphorothioate linkage. Phosphorothioate antisense oligonucleotides are water soluble, polyanionic, and resistant to endogenous nucleases. In addition, when a phosphorothioate antisense oligonucleotide hybridizes to its TARGET site, the RNA-DNA duplex activates the endogenous enzyme ribonuclease (RNase) H, which cleaves the mRNA component of the hybrid molecule.

In addition, antisense oligonucleotides with phosphoramidite and polyamide (peptide) linkages can be synthesized. These molecules should be very resistant to nuclease degradation. Furthermore, chemical groups can be added to the 2' carbon of the sugar moiety and the 5 carbon (C-5) of pyrimidines to enhance stability and facilitate the binding of the antisense oligonucleotide to its TARGET site. Modifications may include 2'-deoxy, O-pentoxy, O-propoxy, O-methoxy, fluoro, methoxyethoxy phosphorothioates, modified bases, as well as other modifications known to those of skill in the art.

Another type of expression-inhibitory agent that reduces the levels of TARGETS is the ribozyme. Ribozymes are catalytic RNA molecules (RNA enzymes) that have separate catalytic and substrate binding domains. The substrate binding sequence combines by nucleotide complementarity and, possibly, non-hydrogen bond interactions with its TARGET sequence. The catalytic portion cleaves the TARGET RNA at a specific site. The substrate domain of a ribozyme can be engineered to direct it to a specified mRNA sequence. The ribozyme recognizes and then binds a TARGET mRNA through complementary base pairing. Once it is bound to the correct TARGET site, the ribozyme acts enzymatically to cut the TARGET mRNA. Cleavage of the mRNA by a ribozyme destroys its ability to direct synthesis of the corresponding polypeptide. Once the ribozyme has cleaved its TARGET sequence, it is released and can repeatedly bind and cleave at other mRNAs.

Ribozyme forms include a hammerhead motif, a hairpin motif, a hepatitis delta virus, group I intron or RNaseP RNA (in association with an RNA guide sequence) motif or Neurospora VS RNA motif. Ribozymes possessing a hammerhead or hairpin structure are readily prepared since these catalytic RNA molecules can be expressed within cells from eukaryotic promoters (Chen, et al. (1992) Nucleic Acids Res. 20:4581-9). A ribozyme of the present invention can be expressed in eukaryotic cells from the appropriate DNA vector. If desired, the activity of the ribozyme may be augmented by its release from the primary transcript by a second ribozyme (Ventura, et al. (1993) Nucleic Acids Res. 21:3249-55).

Ribozymes may be chemically synthesized by combining an oligodeoxyribonucleotide with a ribozyme catalytic domain (20 nucleotides) flanked by sequences that hybridize to the TARGET mRNA after transcription. The oligodeoxyribonucleotide is amplified by using the substrate binding sequences as primers. The amplification product is cloned into a eukaryotic expression vector.

Ribozymes are expressed from transcription units inserted into DNA, RNA, or viral vectors. Transcription of the ribozyme sequences are driven from a promoter for eukaryotic RNA polymerase I (pol (I), RNA polymerase II (pol II), or RNA polymerase III (pol III). Transcripts from pol II or pol III promoters will be expressed at high levels in all cells; the levels of a given pol II promoter in a given cell type will depend on nearby gene regulatory sequences. Prokaryotic RNA polymerase promoters are also used, providing that the prokaryotic RNA polymerase enzyme is expressed in the appropriate cells (Gao and Huang, (1993) Nucleic Acids Res. 21:2867-72). It has been demonstrated that ribozymes expressed from these promoters can function in mammalian cells (Kashani-Sabet, et al. (1992) Antisense Res. Dev. 2:3-15).

A particularly preferred inhibitory agent is a small interfering RNA (siRNA, preferably small hairpin RNA, "shRNA"). siRNA, preferably shRNA, mediate the post-transcriptional process of gene silencing by double stranded RNA (dsRNA) that is homologous in sequence to the silenced RNA. siRNA according to the present invention comprises a sense strand of 17-25 nucleotides complementary or homologous to a contiguous 17-25 nucleotide sequence selected from the group of sequences described in SEQ ID NO: 1-16, preferably from the group of sequences described in SEQ ID No: 128-141 and 231-244, and an antisense strand of 17-25 nucleotides complementary to the sense strand. The most preferred siRNA comprises sense and anti-sense strands that are 100 percent complementary to each other and the TARGET polynucleotide sequence. Preferably the siRNA further comprises a loop region linking the sense and the antisense strand.

A self-complementing single stranded shRNA molecule polynucleotide according to the present invention comprises a sense portion and an antisense portion connected by a loop region linker. Preferably, the loop region sequence is 4-30 nucleotides long, more preferably 5-15 nucleotides long and most preferably 8 nucleotides long. In a most preferred embodiment the linker sequence is UUGCUAUA (SEQ ID NO: 871) or GUUUGCUAUAAC (SEQ ID NO: 872). Self-complementary single stranded siRNAs form hairpin loops and are more stable than ordinary dsRNA. In addition, they are more easily produced from vectors.

Analogous to antisense RNA, the siRNA can be modified to confirm resistance to nucleolytic degradation, or to enhance activity, or to enhance cellular distribution, or to enhance cellular uptake, such modifications may consist of modified internucleoside linkages, modified nucleic acid bases, modified sugars and/or chemical linkage the siRNA to one or more moieties or conjugates. The nucleotide sequences are selected according to siRNA designing rules that give an improved reduction of the TARGET sequences compared to nucleotide sequences that do not comply with these siRNA designing rules (For a discussion of these rules and examples of the preparation of siRNA, WO2004094636, published Nov. 4, 2004, and UA20030198627, are hereby incorporated by reference).

The present invention also relates to compositions, and methods using said compositions, comprising a DNA expression vector capable of expressing a polynucleotide capable of inhibiting extra-cellular matrix degradation and described hereinabove as an expression inhibition agent.

A special aspect of these compositions and methods relates to the down-regulation or blocking of the expression of a TARGET polypeptide by the induced expression of a polynucleotide encoding an intracellular binding protein that is capable of selectively interacting with the TARGET polypeptide. An intracellular binding protein includes any protein capable of selectively interacting, or binding, with the polypeptide in the cell in which it is expressed and neutralizing the function of the polypeptide. Preferably, the intracellular binding protein is a neutralizing antibody or a fragment of a neutralizing antibody having binding affinity to an epitope of the TARGET polypeptide of SEQ ID NO: 17-32, preferably to a domain of SEQ ID NO: 33-127. More preferably, the intracellular binding protein is a single chain antibody.

A special embodiment of this composition comprises the expression-inhibiting agent selected from the group consisting of antisense RNA, antisense oligodeoxynucleotide (ODN), a ribozyme that cleaves the polyribonucleotide coding for SEQ ID NO: 17-32, and a small interfering RNA (siRNA) that is sufficiently homologous to a portion of the polyribonucleotide corresponding to SEQ ID NO: 1-16, such that the siRNA interferes with the translation of the TARGET polyribonucleotide to the TARGET polypeptide.

The polynucleotide expressing the expression-inhibiting agent is preferably included within a vector. The polynucleic acid is operably linked to signals enabling expression of the nucleic acid sequence and is introduced into a cell utilizing, preferably, recombinant vector constructs, which will express the antisense nucleic acid once the vector is introduced into the cell. A variety of viral-based systems are available, including adenoviral, retroviral, adeno-associated viral, lentiviral, herpes simplex viral or a sendaviral vector systems, and all may be used to introduce and express polynucleotide sequence for the expression-inhibiting agents in TARGET cells.

Preferably, the viral vectors used in the methods of the present invention are replication defective. Such replication defective vectors will usually pack at least one region that is necessary for the replication of the virus in the infected cell. These regions can either be eliminated (in whole or in part), or be rendered non-functional by any technique known to a person skilled in the art. These techniques include the total removal, substitution, partial deletion or addition of one or more bases to an essential (for replication) region. Such techniques may be performed in vitro (on the isolated DNA) or in situ, using the techniques of genetic manipulation or by treatment with mutagenic agents. Preferably, the replication defective virus retains the sequences of its genome, which are necessary for encapsidating, the viral particles.

In a preferred embodiment, the viral element is derived from an adenovirus. Preferably, the vehicle includes an adenoviral vector packaged into an adenoviral capsid, or a functional part, derivative, and/or analogue thereof. Adenovirus biology is also comparatively well known on the molecular level. Many tools for adenoviral vectors have been and continue to be developed, thus making an adenoviral capsid a preferred vehicle for incorporating in a library of the invention. An adenovirus is capable of infecting a wide variety of cells. However, different adenoviral serotypes have different preferences for cells. To combine and widen the TARGET cell population that an adenoviral capsid of the invention can enter in a preferred embodiment, the vehicle includes adenoviral fiber proteins from at least two adenoviruses. Preferred adenoviral fiber protein sequences are serotype 17, 45 and 51. Techniques or construction and expression of these chimeric vectors are disclosed in US Published Patent Applications 20030180258 and 20040071660, hereby incorporated by reference.

In a preferred embodiment, the nucleic acid derived from an adenovirus includes the nucleic acid encoding an adenoviral late protein or a functional part, derivative, and/or analogue thereof. An adenoviral late protein, for instance an adenoviral fiber protein, may be favorably used to TARGET the vehicle to a certain cell or to induce enhanced delivery of the vehicle to the cell. Preferably, the nucleic acid derived from an adenovirus encodes for essentially all adenoviral late proteins, enabling the formation of entire adenoviral capsids or functional parts, analogues, and/or derivatives thereof. Preferably, the nucleic acid derived from an adenovirus includes the nucleic acid encoding adenovirus E2A or a functional part, derivative, and/or analogue thereof. Preferably, the nucleic acid derived from an adenovirus includes the nucleic acid encoding at least one E4-region protein or a functional part, derivative, and/or analogue thereof, which facilitates, at least in part, replication of an adenoviral derived nucleic acid in a cell. The adenoviral vectors used in the examples of this application are exemplary of the vectors useful in the present method of treatment invention.

Certain embodiments of the present invention use retroviral vector systems. Retroviruses are integrating viruses that infect dividing cells, and their construction is known in the art. Retroviral vectors can be constructed from different types of retrovirus, such as, MoMuLV ("murine Moloney leukemia virus" MSV ("murine Moloney sarcoma virus"), HaSV ("Harvey sarcoma virus"); SNV ("spleen necrosis virus"); RSV ("Rous sarcoma virus") and Friend virus. Lentiviral vector systems may also be used in the practice of the present invention. Retroviral systems and herpes virus system may be preferred vehicles for transfection of neuronal cells.

In other embodiments of the present invention, adeno-associated viruses ("AAV") are utilized. The AAV viruses are DNA viruses of relatively small size that integrate, in a stable and site-specific manner, into the genome of the infected cells. They are able to infect a wide spectrum of cells without inducing any effects on cellular growth, morphology or differentiation, and they do not appear to be involved in human pathologies.

In the vector construction, the polynucleotide agents of the present invention may be linked to one or more regulatory regions. Selection of the appropriate regulatory region or regions is a routine matter, within the level of ordinary skill in the art. Regulatory regions include promoters, and may include enhancers, suppressors, etc.

Promoters that may be used in the expression vectors of the present invention include both constitutive promoters and regulated (inducible) promoters. The promoters may be prokaryotic or eukaryotic depending on the host. Among the prokaryotic (including bacteriophage) promoters useful for practice of this invention are lac, lacZ, T3, T7, lambda P.sub.r, P.sub.1, and trp promoters. Among the eukaryotic (including viral) promoters useful for practice of this invention are ubiquitous promoters (for example, HPRT, vimentin, actin, tubulin), intermediate filament promoters (for example, desmin, neurofilaments, keratin, GFAP), therapeutic gene promoters (for example, MDR type, CFTR, factor VIII), tissue-specific promoters (for example, actin promoter in smooth muscle cells, or Flt and Flk promoters active in endothelial cells), including animal transcriptional control regions, which exhibit tissue specificity and have been utilized in transgenic animals: elastase I gene control region which is active in pancreatic acinar cells (Swift, et al. (1984) Cell 38:639-46; Ornitz, et al. (1986) Cold Spring Harbor Symp. Quant. Biol. 50:399-409; MacDonald, (1987) Hepatology 7:425-515); insulin gene control region which is active in pancreatic beta cells (Hanahan, (1985) Nature 315:115-22), immunoglobulin gene control region which is active in lymphoid cells (Grosschedl, et al. (1984) Cell 38:647-58; Adames, et al. (1985) Nature 318:533-8; Alexander, et al. (1987) Mol. Cell. Biol. 7:1436-44), mouse mammary tumor virus control region which is active in testicular, breast, lymphoid and mast cells (Leder, et al. (1986) Cell 45:485-95), albumin gene control region which is active in liver (Pinkert, et al. (1987) Genes and Devel. 1:268-76), alpha-fetoprotein gene control region which is active in liver (Krumlauf, et al. (1985) Mol. Cell. Biol., 5:1639-48; Hammer, et al. (1987) Science 235:53-8), alpha 1-antitrypsin gene control region which is active in the liver (Kelsey, et al. (1987) Genes and Devel., 1: 161-71), beta-globin gene control region which is active in myeloid cells (Mogram, et al. (1985) Nature 315:338-40; Kollias, et al. (1986) Cell 46:89-94), myelin basic protein gene control region which is active in oligodendrocyte cells in the brain (Readhead, et al. (1987) Cell 48:703-12), myosin light chain-2 gene control region which is active in skeletal muscle (Sani, (1985) Nature 314.283-6), and gonadotropic releasing hormone gene control region which is active in the hypothalamus (Mason, et al. (1986) Science 234:1372-8).

Other promoters which may be used in the practice of the invention include promoters which are preferentially activated in dividing cells, promoters which respond to a stimulus (for example, steroid hormone receptor, retinoic acid receptor), tetracycline-regulated transcriptional modulators, cytomegalovirus immediate-early, retroviral LTR, metallothionein, SV-40, E1a, and MLP promoters.

Additional vector systems include the non-viral systems that facilitate introduction of polynucleotide agents into a patient, for example, a DNA vector encoding a desired sequence can be introduced in vivo by lipofection. Synthetic cationic lipids designed to limit the difficulties encountered with liposome-mediated transfection can be used to prepare liposomes for in vivo transfection of a gene encoding a marker (Feigner, et. al. (1987) Proc. Natl. Acad Sci. USA 84:7413-7); see Mackey, et al. (1988) Proc. Natl. Acad. Sci. USA 85:8027-31; Ulmer, et al. (1993) Science 259:1745-8). The use of cationic lipids may promote encapsulation of negatively charged nucleic acids, and also promote fusion with negatively charged cell membranes (Feigner and Ringold, (1989) Nature 337:387-8). Particularly useful lipid compounds and compositions for transfer of nucleic acids are described in International Patent Publications WO 95/18863 and WO 96/17823, and in U.S. Pat. No. 5,459,127. The use of lipofection to introduce exogenous genes into the specific organs in vivo has certain practical advantages and directing transfection to particular cell types would be particularly advantageous in a tissue with cellular heterogeneity, for example, pancreas, liver, kidney, and the brain. Lipids may be chemically coupled to other molecules for the purpose of targeting. Targeted peptides, for example, hormones or neurotransmitters, and proteins, for example, antibodies, or non-peptide molecules could be coupled to liposomes chemically. Other molecules are also useful for facilitating transfection of a nucleic acid in vivo, for example, a cationic oligopeptide (for example, International Patent Publication WO 95/21931), peptides derived from DNA binding proteins (for example, International Patent Publication WO 96/25508), or a cationic polymer (for example, International Patent Publication WO 95/21931).

It is also possible to introduce a DNA vector in vivo as a naked DNA plasmid (see U.S. Pat. Nos. 5,693,622; 5,589,466; and 5,580,859). Naked DNA vectors for therapeutic purposes can be introduced into the desired host cells by methods known in the art, for example, transfection, electroporation, microinjection, transduction, cell fusion, DEAE dextran, calcium phosphate precipitation, use of a gene gun, or use of a DNA vector transporter (see, for example, Wilson, et al. (1992) J. Biol. Chem. 267:963-7; Wu and Wu, (1988) J. Biol. Chem. 263:14621-4; Hartmut, et al. Canadian Patent Application No. 2,012,311, filed Mar. 15, 1990; Williams, et al (1991). Proc. Natl. Acad. Sci. USA 88:2726-30). Receptor-mediated DNA delivery approaches can also be used (Curiel, et al. (1992) Hum. Gene Ther. 3:147-54; Wu and Wu, (1987) J. Biol. Chem. 262:4429-32).

The present invention also provides biologically compatible, extra-cellular matrix degradation inhibiting compositions comprising an effective amount of one or more compounds identified as TARGET inhibitors, and/or the expression-inhibiting agents as described hereinabove.

A biologically compatible composition is a composition, that may be solid, liquid, gel, or other form, in which the compound, polynucleotide, vector, and antibody of the invention is maintained in an active form, for example, in a form able to effect a biological activity. For example, a compound of the invention would have inverse agonist or antagonist activity on the TARGET; a nucleic acid would be able to replicate, translate a message, or hybridize to a complementary mRNA of a TARGET; a vector would be able to transfect a TARGET cell and expression the antisense, antibody, ribozyme or siRNA as described hereinabove; an antibody would bind a TARGET polypeptide domain.

A preferred biologically compatible composition is an aqueous solution that is buffered using, for example, Tris, phosphate, or HEPES buffer, containing salt ions. Usually the concentration of salt ions will be similar to physiological levels. Biologically compatible solutions may include stabilizing agents and preservatives. In a more preferred embodiment, the biocompatible composition is a pharmaceutically acceptable composition. Such compositions can be formulated for administration by topical, oral, parenteral, intranasal, subcutaneous, and intraocular, routes. Parenteral administration is meant to include intravenous injection, intramuscular injection, intraarterial injection or infusion techniques. The composition may be administered parenterally in dosage unit formulations containing standard, well-known non-toxic physiologically acceptable carriers, adjuvants and vehicles as desired.

A particularly preferred embodiment of the present composition invention is a extra-cellular matrix degradation inhibiting pharmaceutical composition comprising a therapeutically effective amount of an expression-inhibiting agent as described hereinabove, in admixture with a pharmaceutically acceptable carrier. Another preferred embodiment is a pharmaceutical composition for the treatment or prevention of a condition involving ECM degradation, or a susceptibility to the condition, comprising an effective extra-cellular matrix degradation inhibiting amount of a TARGET antagonist or inverse agonist, its pharmaceutically acceptable salts, hydrates, solvates, or prodrugs thereof in admixture with a pharmaceutically acceptable carrier.

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient. Pharmaceutical compositions for oral use can be prepared by combining active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethyl-cellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate. Dragee cores may be used in conjunction with suitable coatings, such as concentrated sugar solutions, which may also contain gum arabic, talc, polyvinyl-pyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations that can be used orally include push-fit capsules made of gelatin, as well as soft, sealed capsules made of gelatin and a coating, such as glycerol or sorbitol. Push-fit capsules can contain active ingredients mixed with filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Preferred sterile injectable preparations can be a solution or suspension in a non-toxic parenterally acceptable solvent or diluent. Examples of pharmaceutically acceptable carriers are saline, buffered saline, isotonic saline (for example, monosodium or disodium phosphate, sodium, potassium; calcium or magnesium chloride, or mixtures of such salts), Ringer's solution, dextrose, water, sterile water, glycerol, ethanol, and combinations thereof 1,3-butanediol and sterile fixed oils are conveniently employed as solvents or suspending media. Any bland fixed oil can be employed including synthetic mono- or di-glycerides. Fatty acids such as oleic acid also find use in the preparation of injectables.

The composition medium can also be a hydrogel, which is prepared from any biocompatible or non-cytotoxic homo- or hetero-polymer, such as a hydrophilic polyacrylic acid polymer that can act as a drug absorbing sponge. Certain of them, such as, in particular, those obtained from ethylene and/or propylene oxide are commercially available. A hydrogel can be deposited directly onto the surface of the tissue to be treated, for example during surgical intervention.

Embodiments of pharmaceutical compositions of the present invention comprise a replication defective recombinant viral vector encoding the polynucleotide inhibitory agent of the present invention and a transfection enhancer, such as poloxamer. An example of a poloxamer is Poloxamer 407, which is commercially available (BASF, Parsippany, N.J.) and is a non-toxic, biocompatible polyol. A poloxamer impregnated with recombinant viruses may be deposited directly on the surface of the tissue to be treated, for example during a surgical intervention. Poloxamer possesses essentially the same advantages as hydrogel while having a lower viscosity.

The active expression-inhibiting agents may also be entrapped in microcapsules prepared, for example, by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (1980) 16th edition, Osol, A. Ed.

Sustained-release preparations may be prepared. Suitable examples of sustained-release preparations include semi-permeable matrices of solid hydrophobic polymers containing the antibody, which matrices are in the form of shaped articles, for example, films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™. (injectable microspheres composed of lactic acid-glycolic acid copolymer and leuprolide acetate), and poly-D-(—)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S-S bond formation through thio-disulfide interchange, stabilization may be achieved by modifying sulfhydryl residues, lyophilizing from acidic solutions, controlling moisture content, using appropriate additives, and developing specific polymer matrix compositions.

As defined above, therapeutically effective dose means that amount of protein, polynucleotide, peptide, or its antibodies, agonists or antagonists, which ameliorate the symptoms or condition. Therapeutic efficacy and toxicity of such compounds can be determined by standard pharmaceutical procedures in cell cultures or experimental animals, for example, ED50 (the dose therapeutically effective in 50% of the population) and LD50 (the dose lethal to 50% of the population). The dose ratio of toxic to therapeutic effects is the therapeutic index, and it can be expressed as the ratio, LD50/ED50. Pharmaceutical compositions that exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

For any compound, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans. The exact dosage is chosen by the individual physician in view of the patient to be treated. Dosage and administration are adjusted to provide sufficient levels of the active moiety or to maintain the desired effect. Additional factors which may be taken into account include the severity of the disease state, age, weight and gender of the patient; diet, desired duration of treatment, method of administration, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

The pharmaceutical compositions according to this invention may be administered to a subject by a variety of methods. They may be added directly to targeted tissues, complexed with cationic lipids, packaged within liposomes, or delivered to targeted cells by other methods known in the art. Localized administration to the desired tissues may be done by direct injection, transdermal absorption, catheter, infusion pump or stent. The DNA, DNA/vehicle complexes, or the recombinant virus particles are locally administered to the site of treatment. Alternative routes of delivery include, but are not limited to, intravenous injection, intramuscular injection, subcutaneous injection, aerosol inhalation, oral (tablet or pill form), topical, systemic, ocular, intraperitoneal and/or intrathecal delivery. Examples of ribozyme delivery and administration are provided in Sullivan et al. WO 94/02595.

Antibodies according to the invention may be delivered as a bolus only, infused over time or both administered as a bolus and infused over time. Those skilled in the art may employ different formulations for polynucleotides than for proteins. Similarly, delivery of polynucleotides or polypeptides will be specific to particular cells, conditions, locations, etc.

As discussed hereinabove, recombinant viruses may be used to introduce DNA encoding polynucleotide agents useful in the present invention. Recombinant viruses according to the invention are generally formulated and administered in the form of doses of between about $10^4$ and about $10^{14}$ pfu. In the case of AAVs and adenoviruses, doses of from about $10^6$ to about $10^{11}$ pfu are preferably used. The term pfu ("plaqueforming unit") corresponds to the infective power of a suspension of virions and is determined by infecting an appropriate cell culture and measuring the number of plaques formed. The techniques for determining the pfu titre of a viral solution are well documented in the prior art.

The present invention also provides methods of inhibiting extra-cellular matrix degradation, comprising administering, to a subject suffering from a disease condition involving extra-cellular matrix degradation, an extra-cellular matrix degradation inhibiting pharmaceutical composition as described herein, preferably a therapeutically effective amount of an expression-inhibiting agent of the present invention. The diseases involving extra-cellular matrix degradation, include psoriatic arthritis, juvenile arthritis, early arthritis, reactive arthritis, osteoarthritis, ankylosing spondylitis, osteoporosis, muscular skeletal diseases such as tendinitis and periodontal disease, cancer metastasis, airway diseases (COPD, asthma), renal and liver fibrosis, cardiovascular diseases such as atherosclerosis and heart failure, and neurological diseases such as neuroinflammation and multiple sclerosis. More preferred diseases for treatment in accordance with the present invention are the degenerative joint diseases such as psoriatic arthritis, juvenile arthritis, early arthritis, reactive arthritis, osteoarthritis, ankylosing spondylitis. The most preferred degenerative joint disease for treatment in accordance with the present method is rheumatoid arthritis. The present invention also provides methods for treatment of inflammatory diseases.

Administering of the expression-inhibiting agent of the present invention to the subject patient includes both self-administration and administration by another person. The patient may be in need of treatment for an existing disease or medical condition, or may desire prophylactic treatment to prevent or reduce the risk for diseases and medical conditions affected by a disturbance in bone metabolism. The expression-inhibiting agent of the present invention may be delivered to the subject patient orally, transdermally, via inhalation, injection, nasally, rectally or via a sustained release formulation.

A preferred regimen of the present method comprises the administration to a subject in suffering from a disease condition characterized by inflammatory, with an effective inhibiting amount of an expression-inhibiting agent of the present invention for a period of time sufficient to reduce the abnormal levels of extracellular matrix degradation in the patient, and preferably terminate, the self-perpetuating processes responsible for said degradation. A special embodiment of the method comprises administering of an effective matrix metallo-protease inhibiting amount of a expression-inhibiting agent of the present invention to a subject patient suffering from or susceptible to the development of rheumatoid arthritis, for a period of time sufficient to reduce or prevent, respectively, collagen and bone degradation in the joints of said patient, and preferably terminate, the self-perpetuating processes responsible for said degradation.

The invention also relates to the use of an agent as described above for the preparation of a medicament for treating or preventing a disease involving extra-cellular matrix degradation. Preferably the pathological condition is arthritis. More preferably, the pathological condition is rheumatoid arthritis.

The polypeptides and polynucleotides useful in the practice of the present invention described herein may be free in solution, affixed to a solid support, borne on a cell surface, or located intracellularly. To perform the methods it is feasible to immobilize either the TARGET polypeptide or the compound to facilitate separation of complexes from uncomplexed forms of the polypeptide, as well as to accommodate automation of the assay. Interaction (for example, binding of) of the TARGET polypeptide with a compound can be accomplished in any vessel suitable for containing the reactants. Examples of such vessels include microtitre plates, test tubes, and microcentrifuge tubes. In one embodiment, a fusion protein can be provided which adds a domain that allows the polypeptide to be bound to a matrix. For example, the TARGET polypeptide can be "His" tagged, and subsequently adsorbed onto Ni-NTA microtitre plates, or ProtA fusions with the TARGET polypeptides can be adsorbed to IgG, which are then combined with the cell lysates (for example, $(35)^S$-labelled) and the candidate compound, and the mixture incubated under conditions favorable for complex formation (for example, at physiological conditions for salt and pH). Following incubation, the plates are washed to remove any unbound label, and the matrix is immobilized. The amount of radioactivity can be determined directly, or in the supernatant after dissociation of the complexes. Alternatively, the complexes can be dissociated from the matrix, separated by SDS-PAGE, and the level of the protein binding to the TARGET protein quantified from the gel using standard electrophoretic techniques.

Other techniques for immobilizing protein on matrices can also be used in the method of identifying compounds. For example, either the TARGET or the compound can be immobilized utilizing conjugation of biotin and streptavidin. Biotinylated TARGET protein molecules can be prepared from biotin-NHS(N-hydroxy-succinimide) using techniques well known in the art (for example, biotinylation kit, Pierce Chemicals, Rockford, Ill.), and immobilized in the wells of streptavidin-coated 96 well plates (Pierce Chemical). Alternatively, antibodies reactive with the TARGETS but which do not interfere with binding of the TARGET to the compound can be derivatized to the wells of the plate, and the TARGET can be trapped in the wells by antibody conjugation. As described above, preparations of a labeled candidate compound are incubated in the wells of the plate presenting the TARGETS, and the amount of complex trapped in the well can be quantitated.

The polynucleotides encoding the TARGET polypeptides are identified as SEQ ID NO: 1-16. The present inventors show herein that transfection of mammalian cells with Ad-siRNAs targeting these genes decreases the release of factors that promote extra-cellular matrix degradation.

The present invention also relates to a method for diagnosis of a pathological condition involving ECM degradation, comprising determining the nucleic acid sequence of at least one of the genes of SEQ ID NO: 1-16 within the genomic DNA of a subject; comparing the sequence with the nucleic acid sequence obtained from a database and/or a healthy subject; and identifying any difference(s) related to the onset of the pathological condition.

Still another aspect of the invention relates to a method for diagnosing a pathological condition involving extra-cellular matrix degradation or a susceptibility to the condition in a subject, comprising determining the amount of polypeptide comprising an amino acid sequence selected from the group consisting of SEQ ID NO: 17-32 in a biological sample, and comparing the amount with the amount of the polypeptide in a healthy subject, wherein an increase of the amount of polypeptide compared to the healthy subject is indicative of the presence of the pathological condition.

The invention is further illustrated in the following figures and examples.

EXAMPLES

The following assays, when used in combination with arrayed adenoviral shRNA (small hairpin RNA) expression libraries (the production and use of which are described in WO99/64582), are useful for the discovery of factors that modulate the capacity of synovial fibroblasts (SFs) to produce MMP1 and degrade collagen, an important component of cartilage. Candidate factors are filtered first through a primary followed by a secondary assay.

Example 1 describes the development and setup of the primary assay screen of an adenoviral siRNA library using an ELISA for detection of protein levels of Matrix Metalloprotease 1 (MMP1), and is referred to herein as the "reverse MMP1 assay". Example 2 describes the screening and its results. Example 3 describes a further screen that eliminates any targets that inhibit MMP1 expression in a nonspecific way. Example 4 describes the testing of a subset of the targets for the endogenous SF expression. Example 5 describes a dose response experiment that tests a subset of the Ad-siRNAs for the inhibition of cytokine-induced MMP1 expression. Example 6 describes the secondary assay referred to herein as the "collagen degradation assay", which is more functionally oriented, and which detects collagen degradation in the supernatant of SFs. Example 7 describes the testing of a subset of the Ad-siRNAs for the inhibition of cytokine-induced IL-8 expression.

Control Viruses Used:

The control viruses used in these studies are listed below. dE1/dE2A adenoviruses are generated by co-transfection of adapter plasmids described below with the helper plasmid pWEAd5AflII-rITR.dE2A in PER.E2A packaging cells, as described in WO99/64582.

(A) Negative Control Viruses:

Ad5-LacZ: Described as pIPspAdApt6-lacZ in WO02/070744.

Ad5-ALPP: The 1.9 kb insert is isolated from pGT65-PLAP (Invitrogen) by digestion with NsiI; blunted; followed by digestion with EcoRI and cloned into EcoRI and HpaI-digested pIPspAdApt6.

Ad5-eGFP: Described as pIPspAdApt6-EGFP in WO02/070744.

Ad5-eGFP_KD: Target sequence: GCTGACCCTGAAGTTCATC (SEQ ID NO: 245). Cloned using Sap1-sites into vector and virus generated as described in WO03/020931.

Ad5-Luciferase_v13_KD: Target sequence: GCTGACCCTGAAGTTCATC (SEQ ID NO: 246). Cloned using Sap1-sites into vector and virus generated as described in WO03/020931.

Ad5-DCK_v1_KD: Target sequence ATGAAGAGCAAGGCATTCC (SEQ ID NO: 247). Cloned using Sap1-sites into vector and virus generated as described in WO03/020931.

Ad5-PRKCL1_v1_KD: Target sequence TGCCTGGGACCAGAGCTTC (SEQ ID NO: 248). Cloned using Sap1-sites into vector and virus generated as described in WO03/020931.

Ad5-TNFSF15_v1_KD: Target sequence GGAAGTAATTGGATCATGC (SEQ ID NO: 249). Cloned using Sap1-sites into vector and virus generated as described in WO03/020931.

Ad5-M6PR_v1_KD: Target sequence: GCTGACCCTGAAGTTCATC (SEQ ID NO: 250). Cloned using Sap1-sites into vector and virus generated as described in WO03/020931.

(B) Positive Control Viruses:

Ad5-MMP1: The cDNA encoding MMP1, cloned into the pIPspAdapt6 plasmid, is isolated from a human placenta cDNA library (see WO02/070744) by classical filter colony hybridization strategy. A human placental cDNA library is transformed into bacteria and plated out on agar plates. Thousands of individual colonies are picked (using a Q-pix device (Genetix)) and re-arrayed on agar plates. After growing bacteria up, these plates are overlaid on hybridization filters. These filters are subjected to a classical hybridization procedure with a MMP1 specific probe. This probe is obtained by PCR on a placenta cDNA library using the following primers:

upstream: GTTCTGGGGTGTGGTGTCTCACAGC (SEQ ID NO: 873); and downstream: CAAACTGAGCCACATCAGGCACTCC (SEQ ID NO: 874).

A bacterial colony, at a position corresponding to that of a positive signal spot on the filter after hybridization, is picked and used for plasmid preparation. 5' sequence verification confirms that the 5' sequence of the insert corresponds to NM_002421.

Ad5-MMP13: The cDNA of MMP13 is isolated from a cDNA preparation from human synovial fibroblasts by PCR. The 1498 bp PCR product is cloned into pIPspAdapt6 using a HindIII/EcoRI cloning strategy. Sequence verification confirms that the insert corresponds to bp 18 to 1497 of NM_002427.

Ad5-MYD88: This cDNA is isolated from a human placenta cDNA library constructed in pIPspAdapt6. The virus mediating the expression of MYD88 is identified as a hit in one of the genomic screen run at Galapagos Genomics. Sequence verification of the insert confirms that the insert corresponds to bp 40 to 930 of NM_002468.

Ad5-MMP1_v10_KD: Target sequence: GCTGACCCTGAAGTTCATC (SEQ ID NO: 251). Cloned using Sap1-sites into vector and virus generated as described in WO03/020931.

Ad5-PRKCE_v11_KD: Target sequence GTCATGTTGGCAGAACTC (SEQ ID NO: 252). Cloned using Sap1-sites into vector and virus generated as described in WO03/020931.

Example 1

Development of the Reverse MMP1 Assay

The MMP1 assay is developed by first testing the capacity of synovial fibroblasts (SFs) to produce MMP1.

To evaluate the capacity of SFs to produce MMP1, these cells were infected with a recombinant adenovirus mediating the expression of the MYD88 adaptor molecule involved in the pro-inflammatory IL1 signaling pathway. This virus is expected to increase MMP1 expression in these cells (see Vincenti and Brinckerhoff, 2002).

40,000 SFs are seeded per well of a 6-well plate in DMEM+10% FBS and each well is either infected with a recombinant adenovirus mediating the expression of eGFP, MYD88 or MMP1 (with a multiplicity of infection (MOI) of 7500 viral particles per cell (vp/cell)) or left uninfected (blank). The SF expression of MMP1 is first determined at the mRNA level, by means of real-time, quantitative PCR. RNA of the cells infected with the control viruses is prepared 48 hours post infection using the SV RNA isolation kit (Promega), according to the instructions of the manufacturer. cDNA is prepared from this RNA using Multiscribe reverse transcriptase (50 U/μl, Applied Biosystems) and random hexamers. cDNA synthesis is performed in 25 μl total volume consisting of 1× TaqMan buffer A (PE Applied Biosystems), 5 mM MgCl2, dNTPs (500 μM final per dNTP), 2.5 mM random hexamers, 0.4 U/μl RNase Inhibitor, and 1.25 U/μl MultiScribe Reverse Transcriptase. The mixture is incubated for 10 minutes at 25° C., 30 minutes at 48° C., and 5 minutes at 95° C. Specific DNA products are amplified from the resulting cDNA with AmpliTaq Gold DNA polymerase (Applied BioSystems) during 40 PCR cycles using suited primer pairs. Amplification of the specific DNA products is monitored on an ABI PRISM® 7000 Sequence Detection System. The subsequent real time PCR reaction contained 5 μl of the RT reaction product in a total volume of 25 μl consisting of 1× SYBR Green mix (Applied Biosystems), 300 nM forward primer, and 300 nM reverse primer. Each sample is analyzed in duplicate. The PCR reaction is performed using the following program: 10 minutes at 95° C. followed by 40 cycles of (15 sec. 95° C., 1 minutes 60° C.). After each PCR reaction the products are analyzed by measuring the dissociation curve by incubating for 15 sec. 95° C., and 15 sec. at 60° C., followed by increasing the temperature to 95° C. over a 20 minutes time period, ending with 15 sec. at 95° C. The sequences of the primer pairs used for the detection of MMP1 expression are listed in Table 3.

TABLE 3

List of primers and their sequences used herein.

| Primer name | Primer sequence | SEQ ID NO |
|---|---|---|
| pAdapt_FW | GGTGGGAGGTCTATATAAGC | 875 |
| pAdapt_REV | GGACAAACCACAACTAGAATGC | 876 |
| MMP1_For | CCGGTTTTTCAAAGGGAATAAGTAC | 877 |
| MMP1_Rev | TTCACAGTTCTAGGGAAGCCAAAG | 878 |

Figure 2:
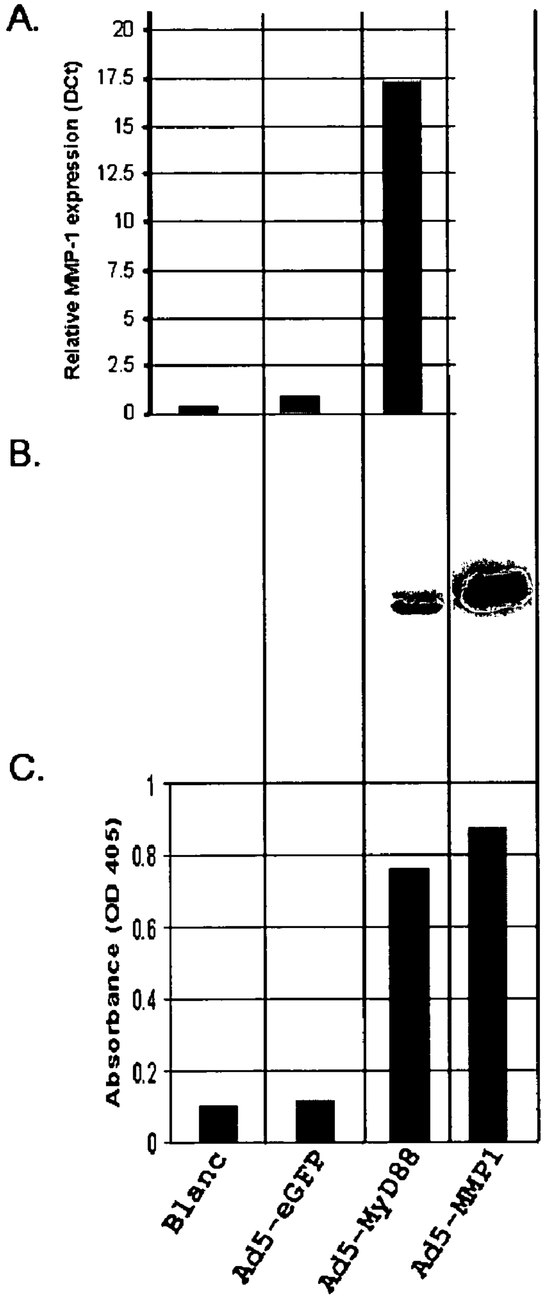
FIG. 2. Characterization of the expression of MMP1 by synovial fibroblasts. In panel A, the MMP1 mRNA levels present in the SF lysate are determined by real-time PCR. These MMP1 levels are normalized to the 18S levels that are also determined by real-time PCR for the same samples. Panel B shows the MMP1 signal detected from the supernatant that is subjected to Western blotting for detection of MMP1 protein levels using an MMP1-specific polyclonal antibody. Panel C shows the results of subjecting the supernatant to a commercially available MMP1 "activity ELISA" (Amersham Biosciences). The signal represented is proportional to the MMP1 activity present in the samples tested.

MMP1 is detected using the SYBR Green method, whereas the levels of 18S rRNA, used as internal calibrator for the PCR reaction, is measured using a commercially available set of primers and Taqman probe (TaqMan® Ribosomal RNA Control Reagents, Applied Biosystems). The amplification plot and the resulting threshold Ct value are indicators for the amount of specific mRNAs present in the samples. Delta-delta Ct values are presented, meaning the normalized (relative to the 18S calibrator) levels of MMP1 mRNA in the samples infected with the positive control viruses relative to the expression levels in a Ad5-eGFP infected control sample. Results indicate a strong up-regulation of the MMP1 mRNA levels upon expression of MYD88 in SFs as compared to the non-infected or Ad5-eGFP-infected SFs (FIG. 2, panel A).

The level of MMP1 expressed by SFs is also determined at the protein level by Western Blotting. Two days after infection, supernatant of cells, infected with various recombinant adenoviruses as indicated for the Real-time PCR experiment, is collected and concentrated 15 times by classical TCA precipitation. 15 μl of the supernatant are resolved by SDS-PAGE using a 10% polyacrylamide gel. For these experiments, the medium used is M199 medium+1% FBS. For the MMP1 control sample, non-concentrated supernatant of cells infected with Ad5-MMP1 is loaded onto the gel. The resolved proteins are transferred onto a nitrocellulose membrane. The quality of the transfer and equal loading of the samples are verified by Ponceau-S staining of the membrane. Immunodetection is performed using a goat anti-MMP1 polyclonal antibody as primary antibody (R&D Systems, 1/500 dilution) and an HRP-linked rabbit anti-goat antibody (DAKO, 1/10000 dilution) as secondary antibody and ECL plus HRP substrate (Amersham Biosciences). The Western Blotting revealed a strongly increased level of MMP1 protein in the supernatant of the SFs infected with the adenoviruses mediating expression of Ad5-MYD88 as compared to the Ad5-eGFP infected cells. A very strong signal is detected for the supernatant of cells infected with Ad5-MMP1 (FIG. 2, panel B).

The high levels of MMP1 protein present in the supernatant of the Ad5-MYD88 infected SFs are confirmed using a commercially available MMP1 activity ELISA (RPN2629, Amersham Biosciences). In this ELISA, MMP1 is captured by an antibody immobilized in a well and the amount is subsequently quantified based on the conversion of a MMP1 substrate. 50 μl of non-concentrated supernatant of SFs (prepared as indicated for the western blotting experiment) are processed in this ELISA as recommended by the manufacturer (FIG. 2, panel C).

These experiments confirm the capacity of SFs, in general, and of the cell batch used for screening and validation experiments, in particular, to produce MMP1 protein upon triggering of inflammatory pathways.

A 384-well format ELISA for measurement of MMP1 is developed. Various primary antibodies are tested, as well as various ELISA protocols. The following protocol is developed and validated to measure MMP1 levels in SF supernatant in 384 well plates: white Lumitrac 600 384 well plates (Greiner) are coated with 2 μg/ml anti-MMP1 antibody MAB1346 (Chemicon). The antibody is diluted in buffer 40 (1.21 g Tris base (Sigma), 0.58 g NaCl (Calbiochem) and 5 ml 10% NaN3 (Sigma) in 1 L milliQ water and adjusted to pH 8.5). After overnight incubation at 4° C., plates are washed with PBS (80 g NaCl, 2 g KCl (Sigma), 11.5 g Na2HPO4.7H2O and 2 g KH2PO4 in 10 L milliQ; pH 7.4) and blocked with 100 μl/well Casein buffer (2% Casein (VWR International) in PBS). Next day, casein buffer is removed from ELISA plates and replaced by 50 μl/well EC buffer (4 g casein, 2.13 g Na2HPO4 (Sigma), 2 g bovine albumin (Sigma), 0.69 g NaH2PO4.H2O (Sigma), 0.5 g CHAPS (Roche), 23.3 g NaCl, 4 ml 0.5 M EDTA pH 8 (Invitrogen), 5 ml 10% NaN3 in 1 L milliQ and adjusted to pH 7.0). 0.25 mM DTT (Sigma) are added to the thawed samples plates. After removal of the EC buffer, 20 μl of sample are transferred to the ELISA plates. After overnight incubation at 4° C., the plates are washed twice with PBS, once with PBST (PBS with 0.05% Tween-20 (Sigma)), and incubated with 35 μl/well biotinylated anti-MMP1 antibody solution (R&D). This secondary antibody is diluted in buffer C (0.82 g NaH2PO4.H2O, 4.82 g Na2HPO4, 46.6 g NaCl, 20 g bovine albumin and 4 ml 0.5M EDTA pH 8 in 2 L milliQ and adjusted to pH 7.0) at a concentration of 5 μg/ml. After 2 hours of incubation at RT, the plates are washed as described above and incubated with 50 μl/well streptavidin-HRP conjugate (Biosource). Streptavidin-HRP conjugate is diluted in buffer C at a concentration of 0.25 μg/ml. After 45 minutes, the plates are washed as described above and incubated for 5 minutes with 50 μl/well BM Chem ELISA Substrate (Roche). Readout is performed on the Luminoscan Ascent Luminometer (Labsystems) with an integration time of 200 msec or with an Envision reader (Perkin Elmer).

Figure 3:
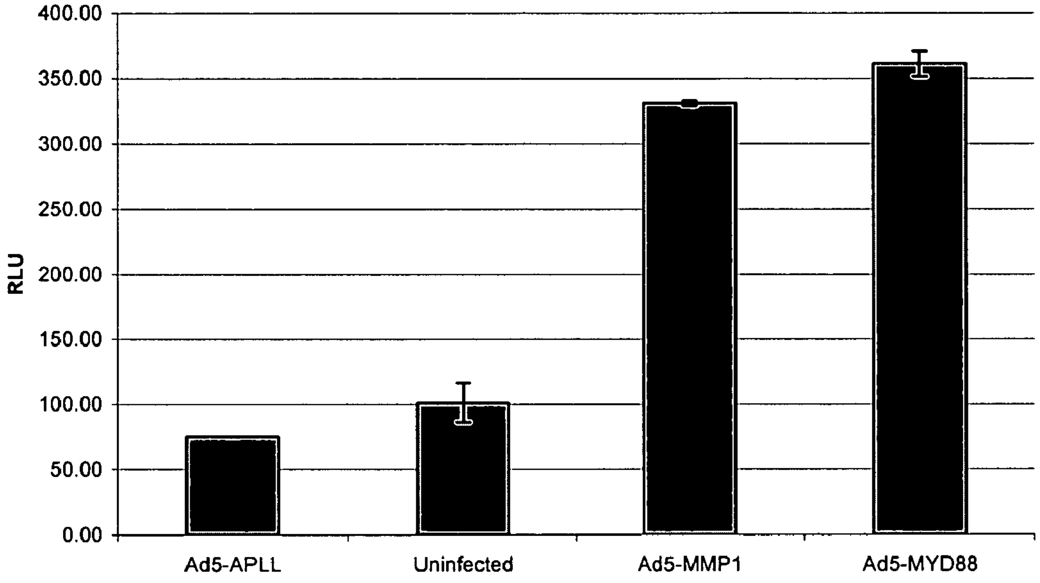
FIG. 3. Increased expression of MMP1 by SFs triggered with various model adenoviruses. The SF supernatant from uninfected SFs and SFs infected with the indicated model recombinant adenoviruses is subjected to the MMP1 ELISA and the MMP1 level measured by using a luminescence generating substrate is shown.

Typical results obtained with the MMP1 ELISA developed are shown in FIG. 3. For this experiment, 3000 SFs are seeded in a 96 well plate in DMEM+10% FBS. 24 hours later, SFs are either infected at an MOI of 10000 with adenoviruses mediating the expression of ALPP, MYD88, MMP1, or left uninfected. One day after the infection, the medium of the cells is replaced by M199 medium (Invitrogen) supplemented with 1% FBS. After an incubation time of 48 hours, the supernatant is harvested, transferred to a 384 well plate and subjected to the MMP1 ELISA procedure described above. A robust, more than 3.5-fold up-regulation of the signal is observed. This experiment demonstrated the robustness and specificity of the MMP1 ELISA.

Figure 4:
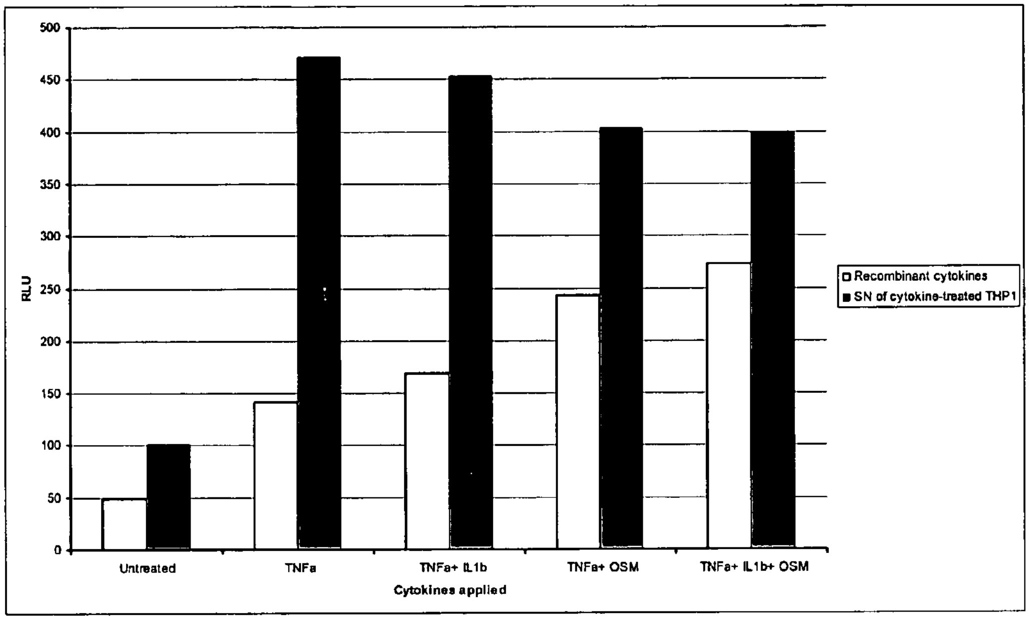
FIG. 4. Increased expression of MMP1 by SFs triggered with various cytokines relevant in rheumatoid arthritis pathology. The SF supernatant is subjected to the MMP1 ELISA and the MMP1 level measured by using a luminescence generating substrate is shown. The white bars show the MMP1 levels of the SF supernatant from untreated SFs and SFs treated with the indicated cytokine or combination of cytokines. The grey bars show the MMP1 levels of the SF supernatant treated with the supernatant of THP1 cells that were either untreated or treated with the indicated cytokine or combination of cytokines.

The increase of MMP1 expression by SFs upon treatment with cytokines relevant in the field of RA (TNFα, IL1β and OSM) or a combination thereof is monitored. Results are shown in FIG. 4 as white bars. For this experiment, SFs are seeded in 96 well plates at 3000 cells/well. 24 hours later, the medium is changed to M199 medium supplemented with 1% FBS. One day after the medium change, cytokines or combinations thereof are added to the cultures, each cytokine is added to a final concentration of 25 ng/ml. 72 hours after cytokine addition, the supernatant is collected and processed in the ELISA, as described for FIG. 3. As shown by the white bars in FIG. 4, TNFα alone induces an almost 3-fold increase in MMP1 expression over the untreated cells. Triggering of SFs with a combination of TNFα and OSM and/or IL1β leads to even higher MMP1 expression levels. This experiment demonstrates that the sensitivity of the MMP1 ELISA developed is sufficient to measure increases in MMP1 expression by SFs induced by cytokines relevant in RA pathogenesis.

In parallel with the above experiment, SFs are triggered, using the same protocol, with the supernatant of THP1 cells (2-fold diluted in M199+1% FBS) that are treated with the same cytokines or combinations of cytokines for 48 hours in M199 medium+1% FBS. MMP1 levels for these samples are shown in FIG. 4 as grey bars. The supernatant of TNFα-treated THP1 cells alone induces a more than 4.5-fold increase in MMP1 expression as compared to the level for untreated supernatant of THP1 cells. The 4.5-fold increase is more than the 3-fold induction with recombinant TNFα alone, and almost equals the 5-fold induction obtained by a mixture of 3 purified cytokines (TNFα, IL1b, OSM). Thus, the supernatant of TNFα-induced THP1 cells contains, besides TNFα, additional pro-inflammatory factors that activate MMP1 expression in SFs. This TNFα-based trigger mixture (prepared by contacting THP-1 cells with TNFα) will likely contain factors present in the joints of RA patients and therefore is relevant to RA. This TNFα-based complex trigger further referred to as the "TNFα-based trigger," will be used as a basis for the "reverse MMP1 assay".

Figure 5:
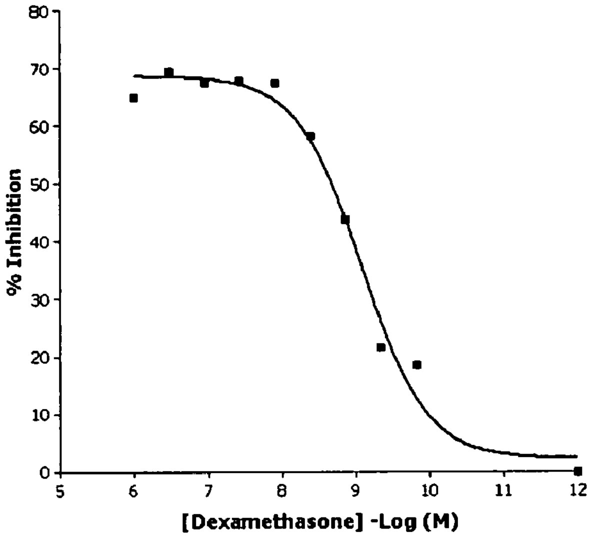
FIG. 5. Dose-dependent inhibition of the "TNFα-based trigger"-induced expression of MMP1 by SFs by a known anti-inflammatory compound. The SF supernatant from SFs treated with the "TNFα-based trigger" and the anti-inflammatory compound at various concentrations is subjected to the MMP1 ELISA and the percent inhibition of MMP1 expression versus the log concentration of the anti-inflammatory compound is shown.

The activation of SFs by the "TNFα-based trigger" can be inhibited in a dose-dependent manner by treating the SFs with dexamethasone, a potent anti-inflammatory agent that also strongly reduces collagen-induced arthritis in rodents (Yang et al., 2004) (FIG. 5). SFs are seeded at a density of 3000 cells/well in 96 well plates. Twenty-four hours after seeding, dexamethasone at various concentrations is added to the cells. Following overnight incubation, the media from each cell is refreshed with the supernatant of THP-1 cells treated with TNFα (50% diluted in M199+0.5% FBS), and dexamethasone at the same concentration as previously added. Forty-eight hours after treatment, the supernatant is collected and subjected to the MMP1 ELISA described above. MMP1 expression by SFs is reduced in a dose-dependent manner by the addition of dexamethasone, which exhibits an IC50 value of about 1 nM (see FIG. 5). This data shows that MMP1 expression by activated SFs can be reduced by the addition of a physiologically relevant inhibitor and validates the principal for the "reverse MMP1 assay".

Example 2

Screening of 11,744 "Ad-siRNAs" in a Reverse MMP1 Assay

Primary Screening

Figure 6:
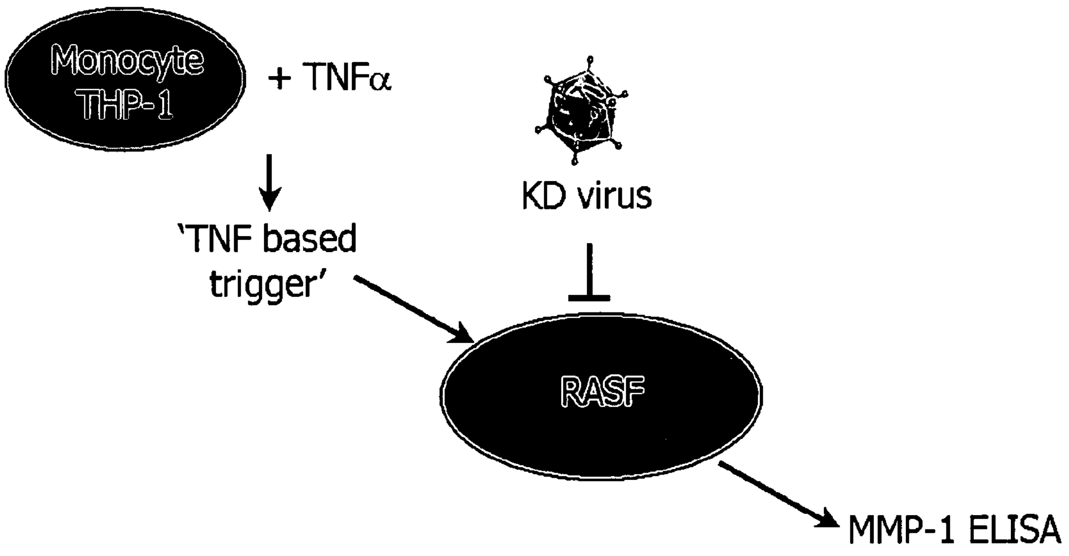
FIG. 6. Schematic representation of the screening of the SilenceSelect collection using the "reverse MMP1 assay."

An arrayed collection of 11,744 different recombinant adenoviruses mediating the expression of shRNAs in SFs are screened using the reverse MMP1 assay. These shRNAs cause a reduction in expression levels of genes that contain homologous sequences by a mechanism known as RNA interference (RNAi). The 11,744 Ad-siRNAs contained in the arrayed collection target 5046 different transcripts. On average, every transcript is targeted by two to three independent Ad-siRNAs. A schematic representation of the screening process is illustrated in FIG. 6. As discussed in more detail below, SFs are seeded in 384 well plates and infected the day thereafter with the arrayed shRNA library, whereby each well is infected with one individual Ad-siRNA. Five days after infection, the medium is refreshed and cells are triggered with the supernatant of TNFα treated THP-1 cells. Two days after addition of the trigger, supernatant is collected and subjected to the MMP1 ELISA.

A 384 well control plate is generated to assess the quality of the assay during different screening runs. The composition of this plate is shown in FIG. 7A. Wells are filled with control viruses that are produced under the same conditions as the SilenceSelect adenoviral collection. The viruses include three sets of 48 positive control viruses ($P_1$(Ad5-DCK_v1_KD), $P_2$ (Ad5-PRKCL1_v1_KD), $P_3$ (Ad5-TNFSF15_v1_KD)), arranged in diagonal, interspaced with three sets of 48 negative control viruses ($N_1$(Ad5-eGFP_v5_KD), $N_2$ (Ad5-Luc_v15_KD), $N_3$ (Ad5-eGFP_v1_KD), Bl: blanco, uninfected). Every well of a control plate contained 50 μl of virus crude lysate. Multiple aliquots of this control plate are produced and stored at −80° C.

Optimal screening protocol: RASFs at passage 1 (Cell Applications) are cultured in DMEM medium (Invitrogen), supplemented with 10% fetal calf serum (ICN), 100 units/ml penicillin (Invitrogen) and 100 μg/ml streptomycin (Invitrogen), and incubated at 37° C. and 10% $CO_2$. The cells are passed once a week by a ⅓ split. The maximal passage number for RASFs used in the screening is 11. For screening, the SFs are seeded in transparent 384 well plates (Greiner) coated with 0.1% gelatin (Merck) at a density of 1150 cells/well in 501 μl Synovial Cell growth medium (Cell Applications, Inc.). One day later, 2 μl Ad-siRNA virus from the SilenceSelect collection (WO 03/020931) are transferred to each individual well of the 384 well plates containing the SFs. The average titer of the adenoviral is $1\times10^9$ viral particles/ml, representing a MOI of about 1700. The SilenceSelect collection is stored in 384 well plates and transferred to the SFs by using a 96/384-channel dispenser. Five days after infection, the medium is removed and the wells are rinsed once by addition and subsequent removal of 80 μl of M199 medium supplemented with 1% FBS. The wells are then filled with 60 μl of "TNFalpha based trigger" diluted 2-fold in M199 medium containing 1% FBS. Two days after addition of the "TNFalpha based trigger", the supernatant is collected in 384 well plates (Greiner) and stored at −80° C. until further processing in the MMP1 ELISA. The infection, rinsing, and medium collection steps are performed with a TECAN Freedom pipette (Tecan Freedom 200 equipped with TeMO96, TeMO384 and RoMa, Tecan AG, Switzerland). 25 μl of the collected supernatant is subjected to the MMP1 ELISA. The ELISA step is performed as indicated in Example 1.

The "TNFalpha based trigger" is produced from THP-1 cells at passage 8 to 16 grown in suspension cultures in RPMI supplemented with 10% FBS (Invitrogen) and penicillin (100 units/ml) and Streptomycin (100 μg/ml) (Invitrogen). The cultures are diluted weekly to a cell density of $2 \times 10^5$ cells/ml, avoiding densities exceeding $1.5 \times 10^6$ cells/ml. The production of the "TNFalpha based trigger" is initiated by seeding the THP-1 cells in M199 medium supplemented with 1% serum at a density of $1 \times 10^6$ cells/ml. One day after seeding, recombinant human TNFalpha (Sigma) is added to the culture flasks to a final concentration of 25 ng/ml. 48 hours after addition of the cytokine, the supernatant is collected and stored at −80° C. in aliquots until further use. Every new batch of "TNFalpha based trigger" is characterized for its efficacy at inducing MMP1 expression by SFs.

A representative example of the performance of the control plate tested with the screening protocol described above is shown in FIG. 7B. The raw luminescence signal obtained for every well is shown. The positive control samples are selected as the 3 strongest hits picked up in a limited, preliminary screening of one 384 well SilenceSelect plate.

A stringent cutoff is applied, that is, the average of all 144 negative control viruses minus 1.82 times the standard deviation. Samples scoring below this cutoff are considered positive hits. These positive hits are indicated as white numbers on a gray background. As expected, the positive control viruses score very well in the assay with 88%, 81% and 94% of the samples falling below the cutoff for the P1, P2 and P3 positive controls samples, respectively. As non-infected wells display lower signals as compared to infected wells, the blanco samples often score positive. The reason for this is not known. To rule out that a sample would be positive because of the absence of virus, the virus content of all wells is monitored by checking the cytopathic effect (CPE) when propagating hit viruses as well as checking the amount of adenoviral particles per well in a quantitative real-time PCR (Ma et al., 2000). Of the 3 negative control viruses, the N1 virus gives rise to some false positives due to toxicity. During screening, about 5% false positives for the N1 negative control are allowed. In this Example, 2 samples in 48 (+/−4%) score positive for the N1 control.

The complete SilenceSelect collection, consisting of 11,744 Ad-siRNAs targeting 5046 transcripts contained on 30×384 well plates, is screened in the "reverse MMP1 assay" according to the protocol described above. Every Ad-siRNA plate is screened in duplicate in a primary screen and a repeat screen. As such, four data points are obtained for each Ad-siRNA. Ad-siRNA viruses are nominated as hits if at least 1 data point in both the primary screen and repeat screen scored below threshold. A representative example of screening results and of the analysis performed to identify hits is shown in FIG. 8.

To determine the cutoff value for hit calling, the average as well as standard deviation is calculated on all data points per plate. The cutoff value is then defined as the average minus 1.82 times the standard deviation. This cutoff is indicated as a horizontal line in the graphs shown in FIG. 8. The data represented in FIG. 8 are expressed relative to the plate average as follows: the relative signal for a sample=[(raw luminescence signal for the sample)−(average signal over the plate)]/(the standard deviation over the plate). The average of the 2 duplicate signals obtained for all the 384 Ad-siRNAs in the primary screen (FIG. 8A) and in the repeat screen (FIG. 8B) are shown. The data points identified as hits are indicated as circles. A total of 408 hits that scored below the cutoff are isolated for the 3 MOI repeat screen discussed below. Almost all the same Ad-siRNAs score positive in both the primary screen and repeat screen. These data are indicative of the quality of the screening and of the SilenceSelect collection.

Figure 9:
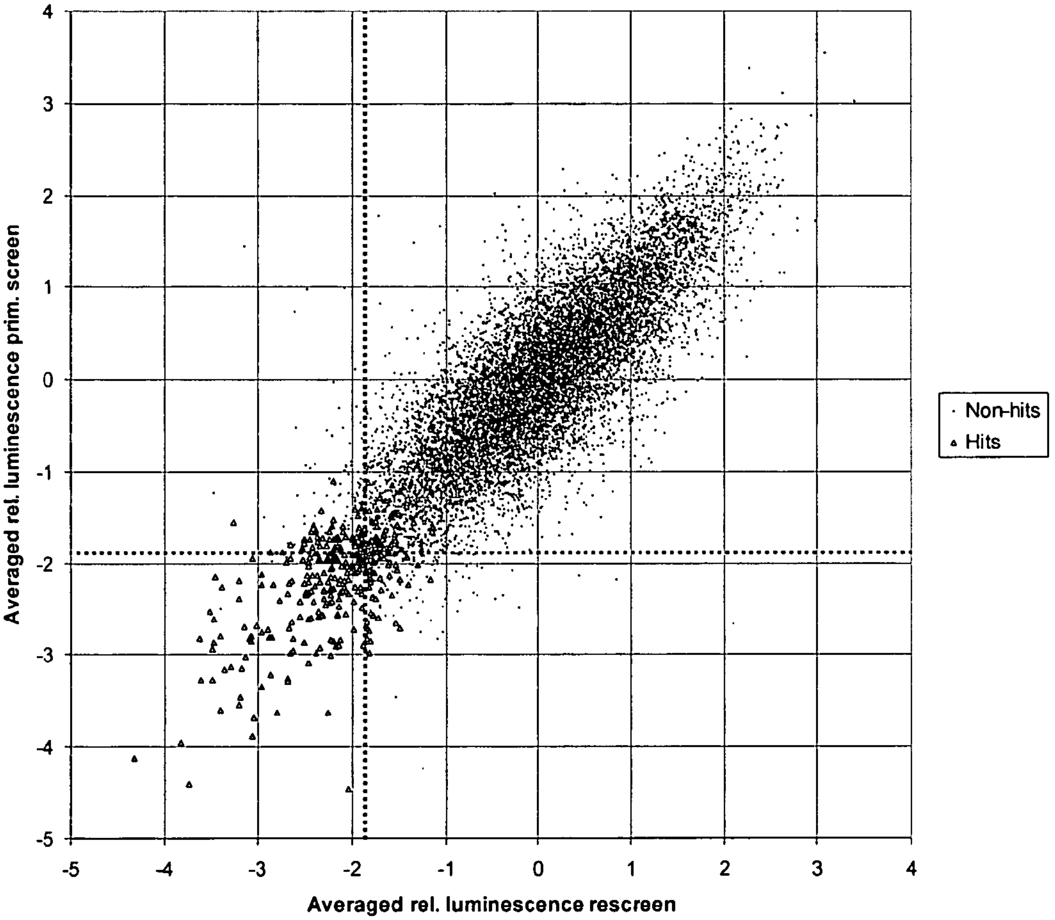
FIG. 9. All data points obtained in the screening of the SilenceSelect collection against the reverse MMP1 assay are shown. The averaged relative luminescence data obtained from the duplicate samples in the primary screen (Y-axis) is plotted against the averaged relative luminescence data for the corresponding Ad-siRNA obtained in the repeat screen (X-axis).

In FIG. 9, all data points obtained in the screening of the SilenceSelect collection against the reverse MMP1 assay are shown. The averaged relative luminescence data obtained from the duplicate samples in the primary screen (Y-axis) is plotted against the averaged relative luminescence data for the corresponding Ad-siRNA obtained in the repeat screen (X-axis). The cutoff (−1.82 times standard deviation) is indicated by dotted lines. The data points for Ad-siRNAs nominated as hits are indicated as triangles, the data points for the non-hit Ad-siRNAs are indicated as squares. The strong symmetry observed between the data of the primary screen and of the repeat screen (the data points are concentrated around a straight line) is indicative of the quality and reproducibility of the screening.

"3" MOI Repeat Screen

The 408 hits identified above are re-propagated. The crude lysates of the hit Ad-siRNAs samples from the SilenceSelect collection are picked and arranged together with negative controls in 9×96 well plates. As the containers of crude lystates are labeled with a barcode (Screenmates™, Matrix technologies), quality checks are performed on the plates. The general layout of such a "3" MOI repeat screen plate is shown in FIG. 10A. To propagate the viruses, $2.25 \times 10^4$ PerC6.E2A cells are seeded in 200 μl of DMEM containing 10% non-heat inactivated FCS in each well of a 96 well plate and incubated overnight at 39° C. in a humidified incubator at 10% $CO_2$. One μl of crude lysate from each hit Ad-siRNAs, arranged in the 96 well plates as indicated above, is then added to separate wells of PerC6E2A cells using a 96 well dispenser. After 7 to 10 days of incubation in a humidified incubator at 10% $CO_2$, the re-propagation plates are frozen at −20° C., provided that complete CPE could be observed.

For the "3" MOI repeat screen, SFs are seeded in 96 well plates (Greiner, tissue culture treated) at a density of 3000 cells/well in 100 μl Synovial Cell growth medium (Cell Applications, Inc.). One day later, the SFs are infected with 3, 6, or 12 μl of the crude lysate contained in the re-propagation plates described above using a 96 well dispenser (TECAN freedom 200). Five days after infection, medium is removed from the plates, using a VacuSafe device (Integra), and 100 μl of two-fold diluted TNFalpha based trigger is added. After an incubation of 2 days, medium is collected with a 96 well dispenser (TECAN Freedom 200) and stored at −80° C. in 384 well plates until further processed in the reverse MMP1 ELISA according to the protocol described in Example 1.

The data from the MMP1 ELISA is analyzed as follows: To determine the cutoff value for hit calling, the average of the negative controls is calculated for every plate. For every MOI, a percentage is selected such that less than 3% of the negative controls would score as a hit over the 9 plates. The percentages are 23%, 26% and 19% for the 3 μl, 6 μl, and 12 μl infections, respectively. Of the 408 hits tested, 339 scored in duplicate at one MOI and are identified as a hit. 84% of the hits of the primary screen are thus confirmed in this 3 MOI repeat screen using repropagated Ad-siRNA material.

Quality Control of Target Ad-siRNAs

Target Ad-siRNAs are propagated using derivatives of PER.C6© cells (Crucell, Leiden, The Netherlands) in 96-well plates, followed by sequencing the siRNAs encoded by the target Ad-siRNA viruses. PERC6.E2A cells are seeded in 96 well plates at a density of 40,000 cells/well in 180 μl PER.E2A medium. Cells are then incubated overnight at 39° C. in a 10% $CO_2$ humidified incubator. One day later, cells are infected with 1 μl of crude cell lysate from SilenceSelect stocks containing target Ad-siRNAs. Cells are incubated further at 34° C., 10% $CO_2$ until appearance of cytopathic effect (as revealed by the swelling and rounding up of the cells, typically 7 days post infection). The supernatant is collected, and the virus crude lysate is treated with proteinase K by adding to 4 μl Lysis buffer (1× Expand High Fidelity buffer with $MgCl_2$ (Roche Molecular Biochemicals, Cat. No 1332465) supplemented with 1 mg/ml proteinase K (Roche Molecular Biochemicals, Cat No 745 723) and 0.45% Tween-20 (Roche Molecular Biochemicals, Cat No 1335465) to 12 μl crude lysate in sterile PCR tubes. These tubes are incubated at 55° C. for 2 hours followed by a 15 minutes inactivation step at 95° C. For the PCR reaction, 1 μl lysate is added to a PCR master mix composed of 5 μl 10× Expand High Fidelity buffer with $MgCl_2$, 0.5 μl of dNTP mix (10 mM for each dNTP), 1 μl of "Forward primer" (10 mM stock, sequence: 5' CCG TTT ACG TGG AGA CTC GCC 3') (SEQ. ID NO. 879), 1 μl of "Reverse Primer" (10 mM stock, sequence: 5' CCC CCA CCT TAT ATA TAT TCT TTC C) (SEQ. ID NO. 880), 0.2 μl of Expand High Fidelity DNA polymerase (3.5 U/μl, Roche Molecular Biochemicals) and 41.3 μl of $H_2O$. PCR is performed in a PE Biosystems GeneAmp PCR system 9700 as follows: the PCR mixture (50 μl in total) is incubated at 95° C. for 5 minutes; each cycle runs at 95° C. for 15 sec., 55° C. for 30 sec., 68° C. for 4 minutes, and is repeated for 35 cycles. A final incubation at 68° C. is performed for 7 minutes 5 μl of the PCR mixture is mixed with 2 μl of 6× gel loading buffer, loaded on a 0.8% agarose gel containing 0.5 μg/μl ethidium bromide to resolve the amplification products. The size of the amplified fragments is estimated from a standard DNA ladder loaded on the same gel. The expected size is approximately 500 bp. For sequencing analysis, the siRNA constructs expressed by the target adenoviruses are amplified by PCR using primers complementary to vector sequences flanking the SapI site of the pIPspAdapt6-U6 plasmid. The sequence of the PCR fragments is determined and compared with the expected sequence. All sequences are found to be identical to the expected sequence.

Example 3A

Testing of 339 Hits of the "Reverse MMP1 Assay" to Exclude Hits that Influence MMP1 Expression Levels in a Nonspecific Way To eliminate general toxicity (reduced viability) of SFs by the Ad-siRNAs as the cause of reduced expression of MMP1 in the reverse MMP1 assay, the CellTiter-Glo Luminescent Cell Viability Assay (Promega) is used. This Assay determines the number of viable cells in culture based on the quantity of ATP present, which is proportional to the presence of metabolically active cells. In this assay, cells are grown in a white 96 well plate at a density of 3000 cells/well in 100 μl Synovial Cell growth medium (Cell Applications, Inc.). After overnight incubation, cells are infected with the confirmed hits from the reverse MMP1 assay. Five days after infection, the medium is removed and replaced by 50 μl M199 medium supplemented with 1% FBS. The plate and its content are equilibrated to room temperature for 30 minutes. 50 μl cell-titer-Glo reagent is added to the wells, followed by an incubation on an orbital shaker (5 minutes) in the dark. The measurement is performed on a luminoskan Ascent (Labsystems) luminometer, 100 ms integration time.

In a primary test, 12 μl of the viruses contained in the 3 MOI repeat screen plates (layout depicted in FIG. 10A) are used to infect the RASFs, and the readout is performed as described above. To determine which hit viruses cause general toxicity, a cutoff is calculated by averaging the signal for all data points contained in the plate (50 hits and 10 controls) and subtracting 1.5 times the standard deviation over all data points. The hits scoring under the cutoff value in the primary screen are retested as follows: The hits are picked, arranged in 96 well plates (according to the layout depicted in FIG. 10B) and used to infect SFs at 3 MOIs (3, 6, and 12 μl) according to the protocol described above. For the repeat screen, a cutoff is calculated by averaging the signal for all the controls and subtracting 2 times the standard deviation over the controls. Hits scoring under the cutoff in duplicate at one MOI are considered as inducing toxicity.

The secretion of TIMP-2 by SFs is determined to eliminate the factor of general suppression of SF secretory activity by the Ad-siRNAs as the cause of reduced expression of MMP1 in the reverse MMP1 assay. TIMP-2 is a protein that SFs express and secret constitutively. Secretion of TIMP-2 into the SF supernatant is blocked by the addition of BrefeldinA, a small molecule inhibitor of secretion. The level of SF TIMP-2 protein secretion is detected by ELISA. RASF cells are seeded in 96-well gelatin coated plates at 3000 cells/well in 100 μl synovial growth medium. After overnight incubation, cells are infected and incubated for 5 days at 37° C. in a 10% CO2 incubator. Virus is removed and 100 μl M199+1% FBS(HI) medium is applied on top of the cells. The supernatant is harvested after another 48 hours incubation and stored at −20° C. TIMP2 levels are determined by a standard ELISA assay, essentially as outlined for the MMP1 ELISA. In brief, 384-well white Greiner plates (Lumitrac 600) are coated overnight at 4° C. with 40 μl of anti-hTIMP2 capture antibody (Cat. No. MAB9711; R&D systems) at 1 μg/ml in PBS. Blocking is done for 4 hours at room temperature with 80 μl 0.1% caseine buffer and after a washing step (30 μl EC-buffer), 40 μl of the samples are added to the wells. Plates are incubated overnight at 4° C., and after washing twice with PBST (0.05% Tween-20) and PBS, 40 μl of the biotinylated anti-hTIMP2 detection antibody (100 ng/ml in Buffer C) (Cat.no. BAF971; R&D systems) is added to the wells. After 2 hours of incubation at room temperature, plates are washed again and incubated at room temperature for another 45 minutes after an addition of 40 μl of Streptavidin-HRP conjugate (Cat. No. SNN2004; BioSource) diluted 1/3000 in Buffer C. Finally, plates are washed and 501 μl of BM Chemiluminescence ELISA substrate (POD)(Cat. No. 1582950; Roche Diagnostic) is added to the wells. After 5 minutes incubation at room temperature in the dark, luminescence is quantified on a luminometer (Luminoscan Ascent).

The procedure described above (plate layout, MOI, method for determination of the cutoff) applied for these experiments is identical to the one described for the toxicity measurements (i.e., a primary test with 12 μl infection volume and a retest with 3, 6, 12 μl infection volumes) differing only in that the cutoff applied in the primary test is determined as the average over all samples minus 2 times standard deviation over all samples. In this assay, viruses mediating a reduction of the TIMP2 levels under the cutoff in duplicate for at least one MOI in the retest are considered as influencing the SF general secretion machinery.

From the 339 hits tested in the toxicity and TIMP secretion assay, 16 scored positive in these assays and considered mediating the reduction in cytokine induced MMP1 expression in an aspecific way. As such, 323 hits were identified as modulators of cytokine induced MMP1 expression, 16 of which are most preferred hits and listed in Table 1.

We conclude, from this experiment, that the genes associated with these hits and their expressed proteins represent valuable drug targets that are shown by these studies to modulate MMP1 expression in SFs.

TABLE 4

| Hit No. | SEQ KD Targets 19-mer and 21-mer | SEQ ID NO | Gene Name | Protein Class | Accession |
|---|---|---|---|---|---|
| H46-001 | TGCCGTGAATGGAGAACAC<br>AATGCCGTGAATGGAGAACAC | 253<br>254 | DGK1 | Kinase | NM_004717 |
| H46-002 | TCCTTAGTTCCTCAGAGGC<br>AATCCTTAGTTCCTCAGAGGC | 255<br>256 | LATS1 | Kinase | NM_004690 |
| H46-004 | GATTACCTTGCCTGTTGAC<br>AAGATTACCTTGCCTGTTGAC | 257<br>258 | PGK1 | Kinase | NM_000291 |
| H46-006 | CTGACTTTGGATTCTGTGC<br>AACTGACTTTGGATTCTGTGC | 259<br>260 | PAK1 | Kinase | NM_002576 |
| H46-008 | GACATGCCGCTATTTGAGC<br>AAGACATGCCGCTATTTGAGC | 261<br>262 | PTK7 | Kinase | NM_152881; NM_002821; NM_152880; NM_152883; NM_152882 |
| H46-009 | AGTGAGACACTGACAGAAC<br>AAAGTGAGACACTGACAGAAC | 263<br>264 | JAK2 | Kinase | NM_004972 |
| H46-010 | CTGCATGCTGAATGAGAAC<br>AACTGCATGCTGAATGAGAAC | 131<br>234 | AXL | Kinase | NM_021913; NM_001699; SK044 |
| H46-011 | GGCCTTGAAAGGACAGTAC<br>AAGGCCTTGAAAGGACAGTAC | 265<br>266 | UCK1 | Kinase | NM_031432 |
| H46-012 | GACTGAGTCAAGTGTCTGC<br>AAGACTGAGTCAAGTGTCTGC | 267<br>268 | STK31 | Kinase | NM_031414; NM_032944 |
| | | | SgK396 | Kinase | SK652 |
| H46-013 | TGGTGGCTACAACCAACTC<br>AATGGTGGCTACAACCAACTC | 269<br>270 | MAP4K5 | Kinase | NM_198794; NM_006575 |
| H46-014 | TGTGACTGTGGGAGTGGAC<br>AATGTGACTGTGGGAGTGGAC | 271<br>272 | HK1 | Kinase | NM_033498; NM_033500; NM_033496; NM_000188; NM_033497 |
| H46-015 | ACTGCTGCTGTATGTGGAC<br>ACACTGCTGCTGTATGTGGAC | 273<br>274 | AK1 | Kinase | NM_000476 |
| H46-016 | CTGTGTTGATTTCTCTGCC<br>AACTGTGTTGATTTCTCTGCC | 275<br>276 | DNAH8 | Protease | NM_001371 |
| H46-017 | TCCCTTGTATCCGGACTTC<br>AATCCCTTGTATCCGGACTTC | 277<br>278 | GALK2 | Kinase | NM_002044; NM_001001556 |
| H46-019 | CAAGAGCTGGTACCGCGTC<br>AACAAGAGCTGGTACCGCGTC | 279<br>280 | CTK | Kinase | SK418 |
| | | | MATK | Kinase | NM_002378; NM_139354; NM_139355 |
| H46-020 | GCTCCTCAGAGTGCAGCAC<br>AAGCTCCTCAGAGTGCAGCAC | 134<br>237 | SCN9A | Ion Channel | NM_002977 |
| H46-021 | CCTGAATGTGACTGTGGAC<br>AACCTGAATGTGACTGTGGAC | 140<br>243 | DGKB | Kinase | NM_145695; NM_004080 |
| | | | INCENP | Not drugable | NM_020238 |
| H46-022 | TGTGGTGGCCTACATTGGC<br>AATGTGGTGGCCTACATTGGC | 281<br>282 | GCK | Kinase | SK048 |
| | | | MAP4K2 | Kinase | NM_004579 |
| H46-024 | GAACCTCACTTCCAGTCAC<br>AAGAACCTCACTTCCAGTCAC | 283<br>284 | MPP6 | Kinase | NM_016447 |
| H46-025 | ATCAGTGGGCTGTGGATTC<br>AAATCAGTGGGCTGTGGATTC | 285<br>286 | MASTL | Kinase | NM_032844 |
| H46-026 | CATTGTGGACTTTGCTGGC<br>AACATTGTGGACTTTGCTGGC | 287<br>288 | IRAK1 | Kinase | NM_001569 |
| | | | AF346607 | Kinase | AF346607 |

TABLE 4-continued

| Hit No. | SEQ KD Targets 19-mer and 21-mer | SEQ ID NO | Gene Name | Protein Class | Accession |
|---|---|---|---|---|---|
| H46-028 | ATGACTGAGCCACACAAAC<br>ACATGACTGAGCCACACAAAC | 289<br>290 | LOC160848 | Kinase | XM_090535 |
| | | | MAPK6 | Kinase | NM_002748 |
| H46-030 | CATTGTGGACGTGCTGGCC<br>AACATTGTGGACGTGCTGGCC | 128<br>231 | KCNF1 | Ion Channel | NM_002236 |
| H46-033 | CTTTGCACCTATCTCTGAC<br>ACCTTTGCACCTATCTCTGAC | 291<br>292 | NEK8 | Kinase | SK476; NM_178170 |
| H46-034 | TGCGCTTTGCCAAGATGCC<br>AATGCGCTTTGCCAAGATGCC | 293<br>294 | BRD4 | Not drugable | NM_014299; SK763;<br>NM_058243 |
| H46-035 | ACATGTGTTCCAGAAGGAC<br>GCACATGTGTTCCAGAAGGAC | 295<br>296 | AMACO | Not drugable | NM_198496 |
| | | | LOC118680 | Kinase | XM_061091 |
| H46-036 | ACCTGGCTTCAACATCAGC<br>AAACCTGGCTTCAACATCAGC | 297<br>298 | LOC163720 | Cytochrome P450 | XM_089093 |
| | | | CYP4Z1 | Cytochrome P450 | NM_178134 |
| H46-038 | TGGATGACCACAAGCTGTC<br>AATGGATGACCACAAGCTGTC | 299<br>300 | ATP1A2 | Ion Channel | NM_000702 |
| H46-039 | ACATGCACTGCAGAAGGCC<br>AAACATGCACTGCAGAAGGCC | 301<br>302 | CACNA1E | Ion Channel | NM_000721 |
| H46-040 | ATGTGCCATCCAGTTGTGC<br>AAATGTGCCATCCAGTTGTGC | 303<br>304 | LOC136062 | Kinase | XM_069683 |
| H46-041 | CTATGTGGACTGGATCAAC<br>AACTATGTGGACTGGATCAAC | 305<br>306 | HGFAC | Protease | NM_001528 |
| H46-042 | TGAAGGCCTCACGTGTGTC<br>ACTGAAGGCCTCACGTGTGTC | 307<br>308 | CTRL | Protease | NM_001907 |
| H46-043 | CATGAAGGCCCGAAACTAC<br>AACATGAAGGCCCGAAACTAC | 309<br>310 | MAPK3 | Kinase | NM_002746; XM_055766 |
| H46-044 | AGATGGCCACAAACCTGCC<br>AAAGATGGCCACAAACCTGCC | 311<br>312 | ACVR2 | Kinase | NM_001616 |
| H46-045 | ATGAAGAGCAAGGCATTCC<br>AAATGAAGAGCAAGGCATTCC | 313<br>314 | DCK | Kinase | NM_000788 |
| H46-046 | CATCCCACACAAGTTCAGC<br>AACATCCCACACAAGTTCAGC | 315<br>316 | PRKCH | Kinase | NM_006255 |
| H46-047 | CTCATGTTTACCATGGTCC<br>ACCTCATGTTTACCATGGTCC | 317<br>318 | CHRNB1 | Ion Channel | NM_000747 |
| H46-049 | ATTGTTCTCCCAGATGGCC<br>ACATTGTTCTCCCAGATGGCC | 319<br>320 | CYP4F12 | Cytochrome P450 | NM_023944 |
| H46-050 | TTCATGAGAAGACTGGTGC<br>ACTTCATGAGAAGACTGGTGC | 321<br>322 | NRK | Kinase | NM_198465 |
| H46-051 | TGACTGCACCTATGAGAGC<br>CCTGACTGCACCTATGAGAGC | 323<br>324 | LOC126392 | Kinase | XM_065057 |
| H46-053 | TTCAGTGCATTCAAGGACC<br>ACTTCAGTGCATTCAAGGACC | 325<br>326 | FAD104 | Receptor | NM_022763 |
| | | | LOC205527 | Receptor | XM_116009 |
| H46-054 | ACGTGCCAGTTTCTTCTCC<br>AAACGTGCCAGTTTCTTCTCC | 327<br>328 | LOC200959 | Ion Channel | XM_116036 |
| H46-055 | GTGTATCTTATGCCTACAC<br>ACGTGTATCTTATGCCTACAC | 329<br>330 | DOK5L | Receptor | NM_152721 |
| H46- | AGCTGCTGGAGATGTTATC | 331 | UQCRC2 | Protease | NM_003366 |

TABLE 4-continued

| Hit No. | SEQ KD Targets 19-mer and 21-mer | SEQ ID NO | Gene Name | Protein Class | Accession |
|---|---|---|---|---|---|
| 056 | ACAGCTGCTGGAGATGTTATC | 332 | | | |
| H46-<br>058 | CAAGTGACTGTGTTGCCC<br>ACCAAGTGACTGTGATTGCCC | 333<br>334 | COL7A1 | Not drugable | NM_000094 |
| H46-<br>060 | TTCAGTGCCTAACAGTGGC<br>ACTTCAGTGCCTAACAGTGGC | 335<br>336 | CDC7 | Kinase | NM_003503 |
| H46-<br>061 | CTTGATCATGATGGCCTTC<br>ACCTTGATCATGATGGCCTTC | 337<br>338 | PPAP2B | Phosphatase | NM_177414; NM_003713 |
| H46-<br>062 | ACCCGGCACCGTGTACTTC<br>AAACCCGGCACCGTGTACTTC | 339<br>340 | CRLF1 | Receptor | NM_004750 |
| H46-<br>063 | CTACTGATGTCCCTGATAC<br>ACCTACTGATGTCCCTGATAC | 341<br>342 | PPP1CB | Phosphatase | NM_206877; NM_206876;<br>NM_002709 |
| H46-<br>064 | TTTCTGTGAGCTGTGAAAC<br>ACTTTCTGTGAGCTGTGAAAC | 343<br>344 | SCYL2 | Kinase | SK475 |
| | | | FLJ10074 | Kinase | NM_017988 |
| H46-<br>066 | TATACTGGAGCCTGTAACC<br>AATATACTGGAGCCTGTAACC | 345<br>346 | TNFRSF10D | Drugable/<br>Secreted | NM_003840 |
| H46-<br>067 | TTTGTGGACTCCTACGATC<br>AATTTGTGGACTCCTACGATC | 347<br>348 | RHEB | Enzyme | NM_005614 |
| H46-<br>068 | GGAGACAAGTTCGCATGTC<br>AAGGAGACAAGTTCGCATGTC | 349<br>350 | RASGRP1 | Drugable/<br>Secreted | NM_005739 |
| H46-<br>070 | CGGCTGGTTCACCATGATC<br>ACCGGCTGGTTCACCATGATC | 351<br>352 | SIAT7D | Enzyme | NM_175039; NM_014403;<br>NM_175040 |
| H46-<br>071 | GTATTCTGTACACCCTGGC<br>ACGTATTCTGTACACCCTGGC | 353<br>354 | RDH11 | Enzyme | NM_016026 |
| H46-<br>072 | GACTGCTAGACAAGACGAC<br>ACGACTGCTAGACAAGACGAC | 355<br>356 | NQO3A2 | Enzyme | NM_016243 |
| H46-<br>073 | CCTGTGTTCAGCTCTGGAC<br>AACCTGTGTTCAGCTCTGGAC | 357<br>358 | IKBKAP | Kinase | NM_003640 |
| H46-<br>075 | ACATTCTCCTGGCCAGGTC<br>AAACATTCTCCTGGCCAGGTC | 359<br>360 | ARHGAP21 | Drugable/<br>Secreted | NM_020824 |
| H46-<br>078 | GACTGAGAACCTTGATGTC<br>AAGACTGAGAACCTTGATGTC | 361<br>362 | ATP1B2 | Ion Channel | NM_001678 |
| H46-<br>079 | TATTGCCCTGTTAGTGTTC<br>CCTATTGCCCTGTTAGTGTTC | 363<br>364 | LOC201803 | Enzyme | XM_116196 |
| H46-<br>080 | TGTGGAGTCTTTGTGCTCC<br>ACTGTGGAGTCTTTGTGCTCC | 365<br>366 | LOC254017 | Protease | NM_172342 |
| | | | SENP5 | Protease | NM_152699 |
| H46-<br>081 | TTCCTGTGGAATGACTGTC<br>AATTCCTGTGGAATGACTGTC | 367<br>368 | LRRK1 | Kinase | NM_024652 |
| H46-<br>085 | ACGTGGTTGGAAGCTAACC<br>ACACGTGGTTGGAAGCTAACC | 369<br>370 | ABCB1 | Transporter | NM_000927 |
| H46-<br>086 | CAAGTCTACACGGGCTCAC<br>AACAAGTCTACACGGGCTCAC | 371<br>372 | HSD17B12 | Enzyme | NM_016142 |
| H46-<br>087 | TCCTGGAGGCTATCCGCAC<br>AATCCTGGAGGCTATCCGCAC | 373<br>374 | DNMT3B | Enzyme | NM_175850; NM_175848;<br>NM_006892; NM_175849 |
| H46-<br>088 | TCGGCACAACAATCTAGAC<br>ACTCGGCACAACAATCTAGAC | 375<br>376 | IDH3B | Enzyme | NM_006899; NM_174855;<br>NM_174856 |
| H46-<br>089 | ACGCGCCTTAATTTAGTCC<br>AAACGCGCCTTAATTTAGTCC | 377<br>378 | LDHL | Enzyme | NM_033195 |
| H46- | AGCATGATGATAGTTCCTC | 379 | TOP2B | Enzyme | NM_001068 |

TABLE 4-continued

| Hit No. | SEQ KD Targets 19-mer and 21-mer | SEQ ID NO | Gene Name | Protein Class | Accession |
|---|---|---|---|---|---|
| 090 | CCAGCATGATGATAGTTCCTC | 380 | | | |
| H46-091 | TGGGCACACATCTCCAGTC<br>ACTGGGCACACATCTCCAGTC | 381<br>382 | LOC219756 | Kinase | XM_166676 |
| H46-092 | ACCGTGGAAGGCCTATCGC<br>AAACCGTGGAAGGCCTATCGC | 383<br>384 | CYP24A1 | Cytochrome P450 | NM_000782 |
| H46-093 | TGAATCCACAGCTCTACTC<br>AATGAATCCACAGCTCTACTC | 385<br>386 | LOC400301 | Kinase | XM_375150 |
| | | | LOC256238 | Kinase | XM_171744 |
| H46-094 | CAAGTACAACAAGGACTCC<br>ACCAAGTACAACAAGGACTCC | 387<br>388 | CYP46A1 | Cytochrome P450 | NM_006668 |
| H46-095 | CATTCAGTGCTGCCTTCAC<br>TCCATTCAGTGCTGCCTTCAC | 389<br>390 | MGC16169 | Kinase | NM_033115 |
| | | | TBCK | Kinase | SK664 |
| H46-096 | GATGGCCATCCTGCAGATC<br>AAGATGGCCATCCTGCAGATC | 391<br>392 | TIF1b | Kinase | SK784 |
| | | | TRIM28 | Kinase | NM_005762 |
| H46-097 | TCATTGTGCCATCCCAAAC<br>AATCATTGTGCCATCCCAAAC | 393<br>394 | LOC169505 | Kinase | XM_095725 |
| H46-098 | AACCTGGCCCTAATGCTGC<br>TCAACCTGGCCCTAATGCTGC | 395<br>396 | LOC220075 | Receptor | XM_169246 |
| H46-099 | CTGACTCACCTGGTACTGC<br>AACTGACTCACCTGGTACTGC | 397<br>398 | KCTD3 | Ion Channel | NM_016121 |
| H46-100 | TGCTGTGTGCTGGAGTACC<br>AATGCTGTGTGCTGGAGTACC | 399<br>400 | HAT | Protease | NM_004262 |
| H46-101 | GCATTGCTATTGCTCGGGC<br>ACGCATTGCTATTGCTCGGGC | 401<br>402 | ABCB11 | Transporter | NM_003742 |
| H46-102 | TGTGGAGTGTGAGAAGCTC<br>AATGTGGAGTGTGAGAAGCTC | 403<br>404 | LOC131136 | Transporter | XM_067219 |
| H46-104 | TCTGTGGGCCTCCTATTCC<br>ACTCTGTGGGCCTCCTATTCC | 405<br>406 | APRT | Enzyme | NM_000485 |
| H46-105 | TGCCGGCATCTCAACGTTC<br>AATGCCGGCATCTCAACGTTC | 407<br>408 | BDH | Enzyme | NM_203315; NM_203314; NM_004051 |
| H46-106 | TGTGACTGTCCTAGTTGCC<br>AATGTGACTGTCCTAGTTGCC | 409<br>410 | UGT2A1 | Enzyme | NM_006798 |
| H46-107 | AGCTGTGTTCATCAACATC<br>ACAGCTGTGTTCATCAACATC | 411<br>412 | GRHPR | Enzyme | NM_012203 |
| H46-108 | TGGGCAGAATGTCCTGGAC<br>AATGGGCAGAATGTCCTGGAC | 413<br>414 | ITPR3 | Ion Channel | NM_002224 |
| H46-110 | CACATGCTCAACATGGTGC<br>ACCACATGCTCAACATGGTGC | 415<br>416 | RASGRP4 | Drugable/ Secreted | NM_170602; NM_170604; NM_052949; NM_170603 |
| H46-112 | CAGTGACTAACCAGAACTC<br>ACCAGTGACTAACCAGAACTC | 417<br>418 | LOC402692 | Enzyme | XM_380039 |
| H46-113 | TACATGTGTCGGAGGTTTC<br>ACTACATGTGTCGGAGGTTTC | 419<br>420 | GNPNAT1 | Enzyme | NM_198066 |
| H46-114 | GATGTAGATACCACAAGGC<br>ACGATGTAGATACCACAAGGC | 421<br>422 | LOC160469 | Enzyme | XM_090320 |
| H46-115 | TGGTGGCAAGTCCATCTAC<br>ACTGGTGGCAAGTCCATCTAC | 423<br>424 | LOC341457 | Enzyme | XM_292085 |
| | | | LOC159692 | Enzyme | XM_089755 |

TABLE 4-continued

| Hit No. | SEQ KD Targets 19-mer and 21-mer | SEQ ID NO | Gene Name | Protein Class | Accession |
|---|---|---|---|---|---|
| | | | LOC399780 | Enzyme | XM_374813 |
| | | | LOC401706 | Enzyme | XM_377240 |
| | | | LOC122552 | Enzyme | XM_063182 |
| | | | LOC402644 | Enzyme | XM_379998 |
| | | | LOC391807 | Enzyme | XM_373092 |
| | | | LOC139318 | Enzyme | XM_066617 |
| | | | LOC402252 | Enzyme | XM_377934 |
| | | | LOC133419 | Enzyme | XM_068341 |
| | | | LOC165317 | Enzyme | XM_092514 |
| | | | LOC222940 | Enzyme | XM_167261 |
| | | | LOC401859 | Enzyme | XM_377444 |
| H46-116 | ACATGGTCCGAGTAGAAGC<br>AAACATGGTCCGAGTAGAAGC | 425<br>426 | LOC167127 | Enzyme | NM_174914; XM_094300 |
| H46-117 | ATGTGTTGTGGAGTCCGCC<br>AAATGTGTTGTGGAGTCCGCC | 427<br>428 | LOC254142 | Enzyme | XM_171406 |
| H46-118 | ACTTGGGCTGCAGTGCATC<br>AAACTTGGGCTGCAGTGCATC | 429<br>430 | CYP19A1 | Cytochrome P450 | NM_000103; NM_031226 |
| H46-119 | GTGGCCTAACCCGGAGAAC<br>AAGTGGCCTAACCCGGAGAAC | 431<br>432 | CYP1B1 | Cytochrome P450 | NM_000104 |
| H46-120 | AGTTCCTGGTGAACATTCC<br>GCAGTTCCTGGTGAACATTCC | 433<br>434 | TJP3 | Kinase | NM_014428 |
| H46-121 | GTTGTGTTCCCGAGACTAC<br>AAGTTGTGTTCCCGAGACTAC | 435<br>436 | FLJ10986 | Kinase | NM_018291 |
| H46-122 | AGAGCTGTGTCTGAACATC<br>AAGAGCTGTGTCTGAACATC | 437<br>438 | PTHLH | Drugable/ Secreted | NM_002820; NM_198966; NM_198965; NM_198964 |
| H46-123 | TGCAAGGTGATCGGCTTCC<br>AATGCAAGGTGATCGGCTTCC | 439<br>440 | RASGRF1 | Drugable/ Secreted | NM_153815; NM_002891 |
| H46-125 | CGACACCAGAAATTCACTC<br>AACGACACCAGAAATTCACTC | 441<br>442 | FGF16 | Drugable/ Secreted | NM_003868 |
| H46-126 | TGTTCTCCATCTTCTTCCC<br>AATGTTCTCCATCTTCTTCCC | 443<br>444 | SLC12A3 | Transporter | NM_000339 |
| H46-127 | ATCTGTGTGGCAGGTTACC<br>ACATCTGTGTGGCAGGTTACC | 445<br>446 | MTHFR | Enzyme | NM_005957 |
| H46-129 | TAGCGCTCCTTTCCGTAAC<br>ACTAGCGCTCCTTTCCGTAAC | 138<br>241 | NQO2 | Enzyme | NM_000904 |
| H46-130 | TAGTCCAGTGGATCTCACC<br>ACTAGTCCAGTGGATCTCACC | 447<br>448 | LOC222593 | Enzyme | XM_167104 |
| H46-131 | TTCCAGGGATTACTCCAAC<br>AATTCCAGGGATTACTCCAAC | 449<br>450 | CYP20A1 | Cytochrome P450 | NM_020674; NM_177538 |
| H46-132 | ACTGACTCCAGTTTCTGCC<br>AAACTGACTCCAGTTTCTGCC | 451<br>452 | CYP20A1 | Cytochrome P450 | NM_020674; NM_177538 |
| H46-133 | TGGATGACTTCAGCTCTAC<br>AATGGATGACTTCAGCTCTAC | 453<br>454 | GGTLA4 | Enzyme | NM_080920; NM_178312; NM_178311 |
| H46-135 | GCAGTCGACTCCAGAAGAC<br>AAGCAGTCGACTCCAGAAGAC | 455<br>456 | USP47 | Protease | NM_017944 |
| H46-136 | TGACTCTGCTAGGACGGTC<br>AATGACTCTGCTAGGACGGTC | 457<br>458 | IL1R2 | Receptor | NM_004633; NM_173343 |

TABLE 4-continued

| Hit No. | SEQ KD Targets 19-mer and 21-mer | SEQ ID NO | Gene Name | Protein Class | Accession |
|---|---|---|---|---|---|
| H46-137 | TGTTCTTTGGCTCTGCAGC<br>AATGTTCTTTGGCTCTGCAGC | 129<br>232 | SLC9A8 | Ion Channel | NM_015266 |
| H46-139 | AGAATCTGCAGAAAGCCAC<br>CCAGAATCTGCAGAAAGCCAC | 459<br>460 | LOC159948 | GPCR | XM_089955 |
| H46-140 | TTCCACAACGTGTGCCTGC<br>AATTCCACAACGTGTGCCTGC | 461<br>462 | DUSP14 | Phosphatase | NM_007026 |
| H46-141 | TGGGCGGGTAGATGGAATC<br>ACTGGGCGGGTAGATGGAATC | 463<br>464 | NAP1 | Protease | NM_004851 |
| H46-142 | GTGACTCATGATCTAGCCC<br>ACGTGACTCATGATCTAGCCC | 465<br>466 | GGTL3 | Protease | NM_052830; NM_178026 |
| H46-144 | GGCTGAAGCAGACACAGAC<br>AAGGCTGAAGCAGACACAGAC | 467<br>468 | RNPEPL1 | Protease | NM_018226 |
| H46-146 | GGACATTCAGATAGCGCTC<br>ACGGACATTCAGATAGCGCTC | 469<br>470 | DUT | Enzyme | NM_001948 |
| H46-147 | GATGTTCTGTGTGGGCTTC<br>AAGATGTTCTGTGTGGGCTTC | 471<br>472 | TRY6 | Protease | NM_139000 |
| H46-148 | TTTGTGGACCTGAGCTTCC<br>ACTTTGTGGACCTGAGCTTCC | 473<br>474 | XPNPEP1 | Protease | NM_006523; NM_020383 |
| H46-149 | TACTGGCTTCGCTTTCATC<br>ACTACTGGCTTCGCTTTCATC | 475<br>476 | LOC119714 | Protease | XM_061638 |
| H46-150 | TGGCTCTTACGTGATTCAC<br>AATGGCTCTTACGTGATTCAC | 477<br>478 | LOC150426 | Protease | XM_086914 |
| H46-151 | CTATGTTCAGCCCAAGCGC<br>AACTATGTTCAGCCCAAGCGC | 479<br>480 | LOC147221 | Protease | XM_102809 |
| H46-152 | GGGAAGACAGAGCTGTTTC<br>AAGGGAAGACAGAGCTGTTTC | 481<br>482 | LOC124739 | Protease | XM_058840 |
| | | | USP43 | Protease | XM_371015 |
| H46-154 | CCTGAGTTCCCAGCATGTC<br>ACCCTGAGTTCCCAGCATGTC | 483<br>484 | BAA03370 | Protease | 3392317CA2 |
| | | | LOC205016 | Protease | XM_114823 |
| | | | LOC388743 | Protease | XM_371344 |
| H46-155 | TGGCCTTGGAATCTCTTCC<br>ACTGGCCTTGGAATCTCTTCC | 485<br>486 | LOC206841 | Protease | XM_116753 |
| H46-157 | TGCTGTATCCTTCCTGGAC<br>AATGCTGTATCCTTCCTGGAC | 487<br>488 | LOC256618 | Protease | XM_171760 |
| H46-159 | TAACCCTGCCTACTACGTC<br>AATAACCCTGCCTACTACGTC | 489<br>490 | INPPL1 | Phosphatase | NM_001567 |
| H46-160 | TGCTGTGTGGTCTACCGAC<br>ACTGCTGTGTGGTCTACCGAC | 130<br>233 | ARAF1 | Kinase | NM_001654 |
| H46-161 | TCGGGCGGATCTGCTTATC<br>AATCGGGCGGATCTGCTTATC | 491<br>492 | SLC26A6 | Transporter | NM_134263; NM_134426;<br>NM_022911 |
| H46-163 | TGCTGCTGTCAACCCTTTC<br>AATGCTGCTGTCAACCCTTTC | 493<br>494 | DHRS4 | Enzyme | NM_021004 |
| | | | DHRS4L2 | Enzyme | NM_198083 |
| H46-164 | TCGTGGAAGGACTCATGGC<br>AATCGTGGAAGGACTCATGGC | 495<br>496 | LOC125850 | Enzyme | XM_064826 |
| H46-166 | ACCTGGTAACCAAGCCTGC<br>ACACCTGGTAACCAAGCCTGC | 497<br>498 | LOC133486 | Enzyme | XM_068376 |
| H46-167 | TGCTCCATCTCCCTGAGTC<br>TCTGCTCCATCTCCCTGAGTC | 499<br>500 | DRD3 | GPCR | NM_033660 |

TABLE 4-continued

| Hit No. | SEQ KD Targets 19-mer and 21-mer | SEQ ID NO | Gene Name | Protein Class | Accession |
|---|---|---|---|---|---|
| H46-168 | GTGGAACACACTTCAGTCC<br>ACGTGGAACACACTTCAGTCC | 501<br>502 | BLP1 | GPCR | NM_031940; NM_078473 |
| H46-169 | TGGAAGAGTCTGTTGATCC<br>ACTGGAAGAGTCTGTTGATCC | 503<br>504 | GPR139 | GPCR | NM_001002911 |
| H46-170 | TTCTTGACCAGTGATGGGC<br>ACTTCTTGACCAGTGATGGGC | 505<br>506 | LOC163107 | GPCR | XM_092005 |
| H46-171 | TGGGCAAGAAACTAAGCCC<br>ACTGGGCAAGAAACTAAGCCC | 507<br>508 | LOC255993 | Enzyme | XM_171939 |
| H46-172 | CAGATGTATCTGCCAGGAC<br>TCCAGATGTATCTGCCAGGAC | 509<br>510 | LOC254796 | Kinase | XM_172160 |
| H46-174 | GGCCTGCCAATTTAAGCGC<br>AAGGCCTGCCAATTTAAGCGC | 511<br>512 | ATP1B4 | Ion Channel | NM_012069 |
| H46-175 | GCGTGTCCTGACTTCTGTC<br>AAGCGTGTCCTGACTTCTGTC | 513<br>514 | KSR | Kinase | XM_290793; XM_034172 |
| | | | KSR1 | Kinase | SK205 |
| H46-176 | CACATACCCGGGACACTAC<br>AACACATACCCGGGACACTAC | 515<br>516 | PDHX | Enzyme | NM_003477 |
| H46-177 | TGTAGTTGCAAACCCAGGC<br>ACTGTAGTTGCAAACCCAGGC | 517<br>518 | VN1R1 | GPCR | NM_020633 |
| H46-178 | ATGGGCACCATGTTTGAAC<br>ACATGGGCACCATGTTTGAAC | 519<br>520 | NR1I3 | NHR | NM_005122 |
| H46-179 | TCTGCTGGTCATAGCAGCC<br>AATCTGCTGGTCATAGCAGCC | 521<br>522 | EDG4 | GPCR | NM_004720 |
| H46-180 | CATGACTGCTAGTGCTCAC<br>AACATGACTGCTAGTGCTCAC | 523<br>524 | TGFBR2 | Kinase | NM_003242 |
| H46-182 | TTGTGCCATCGTGGGCAAC<br>ACTTGTGCCATCGTGGGCAAC | 525<br>526 | SIAT8B | Enzyme | NM_006011 |
| H46-183 | ATCCACAGGAAATGAAGAC<br>ACATCCACAGGAAATGAAGAC | 527<br>528 | FOLH1 | Protease | NM_004476 |
| | | | PSMAL/GCP III | Protease | NM_153696 |
| H46-185 | CGTCATGATCGCGCTCACC<br>AACGTCATGATCGCGCTCACC | 529<br>530 | HTR5A | GPCR | NM_024012 |
| H46-186 | CCAGAAATCACTCCACTGC<br>AACCAGAAATCACTCCACTGC | 531<br>532 | F2RL2 | GPCR | NM_004101 |
| H46-187 | GCTGCTCACCAGGAACTAC<br>ACGCTGCTCACCAGGAACTAC | 533<br>534 | GPR14 | GPCR | NM_018949 |
| H46-188 | CATCCCACTCAAGATGCAC<br>AACATCCCACTCAAGATGCAC | 535<br>536 | GPR80 | GPCR | NM_080818 |
| H46-189 | GCCCATTGAGACACTGATC<br>ACGCCCATTGAGACACTGATC | 133<br>236 | NR2F6 | NHR | XM_373407; NM_005234 |
| H46-190 | CACACTAGATGCCATGATC<br>ACCACACTAGATGCCATGATC | 537<br>538 | AGA | Protease | NM_000027 |
| H46-191 | GCCGAAGACCTGTTCTATC<br>AAGCCGAAGACCTGTTCTATC | 539<br>540 | ACE2 | Protease | 3699373CA2; NM_021804 |
| H46-192 | GCAAGACGGATATGCATGC<br>AAGCAAGACGGATATGCATGC | 541<br>542 | ADAM23 | Protease | NM_003812 |
| H46-193 | GAGCAGATGTGGACCATGC<br>AAGAGCAGATGTGGACCATGC | 543<br>544 | MMP1 | Protease | NM_002421 |
| H46- | TGGGCTTGAAGCTGCTTAC | 545 | MMP1 | Protease | NM_002421 |

TABLE 4-continued

| Hit No. | SEQ KD Targets 19-mer and 21-mer | SEQ ID NO | Gene Name | Protein Class | Accession |
|---|---|---|---|---|---|
| 194 | AATGGGCTTGAAGCTGCTTAC | 546 | | | |
| H46-<br>195 | GGTATTGGAGGAGATGCTC<br>AAGGTATTGGAGGAGATGCTC | 547<br>548 | MMP8 | Protease | NM_002424 |
| H46-<br>196 | CGTGAATGCCGAGTTGGGC<br>AACGTGAATGCCGAGTTGGGC | 549<br>550 | MGC13186 | Protease | NM_032324 |
| H46-<br>197 | TCACTGTGGAGACATTTGC<br>AATCACTGTGGAGACATTTGC | 551<br>552 | ADAM9 | Protease | NM_003816 |
| H46-<br>199 | GTGGGCTTCATCAACTACC<br>ACGTGGGCTTCATCAACTACC | 553<br>554 | SLC7A8 | Transporter | NM_012244; NM_182728 |
| H46-<br>200 | CCTGACCCTGGAGCACATC<br>AACCTGACCCTGGAGCACATC | 555<br>556 | LCAT | Enzyme | NM_000229 |
| H46-<br>201 | GGACAACATAACGATGCAC<br>ACGGACAACATAACGATGCAC | 557<br>558 | GPD2 | Enzyme | NM_000408 |
| H46-<br>202 | ATCAGTGAGGCATTTGACC<br>AAATCAGTGAGGCATTTGACC | 559<br>560 | ADH4 | Enzyme | NM_000670 |
| H46-<br>203 | TGGCTGGAGGACAAGTTCC<br>AATGGCTGGAGGACAAGTTCC | 561<br>562 | GSTT2 | Enzyme | NM_000854 |
| H46-<br>204 | ATGGCCATTGCCATGGCTC<br>ACATGGCCATTGCCATGGCTC | 563<br>564 | IMPDH1 | Enzyme | NM_183243 |
| | | | IMPDH1 | Enzyme | NM_000883 |
| H46-<br>205 | CTGGATGCTGCGCAAACAC<br>AACTGGATGCTGCGCAAACAC | 565<br>566 | GCNT1 | Enzymes for KD | NM_001490 |
| H46-<br>206 | TGCTGCTTATCAACAACGC<br>ACTGCTGCTTATCAACAACGC | 567<br>568 | SPR | Enzyme | NM_003124 |
| H46-<br>207 | ACATGCCACAGGAAACTAC<br>AAACATGCCACAGGAAACTAC | 569<br>570 | DPM1 | Enzyme | NM_003859 |
| H46-<br>208 | CGAGTCCTAGGCTACATCC<br>AACGAGTCCTAGGCTACATCC | 571<br>572 | ALDH1B1 | Enzyme | NM_000692 |
| H46-<br>209 | TGTGCCCAACGCCACCATC<br>AATGTGCCCAACGCCACCATC | 573<br>574 | ABCA3 | Transporter | NM_001089 |
| H46-<br>210 | GCCTCGGACTTTCATCATC<br>AAGCCTCGGACTTTCATCATC | 575<br>576 | ABCD2 | Transporter | NM_005164 |
| H46-<br>211 | TTGAACCCATCAGGCACTC<br>AATTGAACCCATCAGGCACTC | 577<br>578 | ADAM21 | Protease | NM_003813 |
| H46-<br>213 | TGAACCCTGTTATCTACAC<br>ACTGAACCCTGTTATCTACAC | 579<br>580 | ADRA2B | GPCR | NM_000682 |
| H46-<br>214 | CTTCCTGAAGACCAGGTTC<br>AACTTCCTGAAGACCAGGTTC | 581<br>582 | AF200815 | Kinase | AF200815 |
| | | | STK36 | Kinase | XM_050803; NM_015690 |
| H46-<br>217 | ATGGACATTGACGTGATCC<br>ACATGGACATTGACGTGATCC | 583<br>584 | ALPI | Phosphatase | NM_001631 |
| | | | ALPP | Phosphatase | NM_001632 |
| H46-<br>219 | TTTCCCTTCAAGGCCCTGC<br>ACTTTCCCTTCAAGGCCCTGC | 585<br>586 | CAD35089 | Drugable/ Secreted | 3663102CA2 |
| | | | ART5 | Enzyme | NM_053017 |
| H46-<br>220 | AAGTCTCAAGAGTCACAGC<br>ACAAGTCTCAAGAGTCACAGC | 587<br>588 | BAP1 | Protease | NM_004656 |
| H46-<br>222 | AATAGCAAGAATGTGTGCC<br>TCAATAGCAAGAATGTGTGCC | 589<br>590 | PANK2 | Kinase | NM_153641; NM_153638; NM_153637; NM_024960; NM_153639; NM_153640 |

TABLE 4-continued

| Hit No. | SEQ KD Targets 19-mer and 21-mer | SEQ ID NO | Gene Name | Protein Class | Accession |
|---|---|---|---|---|---|
| H46-223 | AGAAGAAGGTGGTGTGGAC<br>GCAGAAGAAGGTGGTGTGGAC | 591<br>592 | CARD14 | Kinase | NM_024110 |
| H46-224 | TGCCGTGGTGCACTATAGC<br>AATGCCGTGGTGCACTATAGC | 593<br>594 | CELSR2 | GPCR | NM_001408 |
| H46-225 | AGTGTCCACTCAGGAACTC<br>ACAGTGTCCACTCAGGAACTC | 595<br>596 | CHEK2 | Kinase | NM_145862; NM_007194 |
| H46-226 | GTGTTCCTTCAGACTCTTC<br>ACGTGTTCCTTCAGACTCTTC | 137<br>240 | CHRNA5 | Ion Channel | NM_000745 |
| H46-227 | TGCATGATGTCGGTCACCC<br>ACTGCATGATGTCGGTCACCC | 597<br>598 | COX10 | Enzyme | NM_001303 |
| H46-228 | CTGTGCCTGCCATTACAAC<br>ACCTGTGCCTGCCATTACAAC | 599<br>600 | CTGF | Drugable/ Secreted | NM_001901 |
| H46-229 | GACTACAGTGATTGTCGGC<br>AAGACTACAGTGATTGTCGGC | 601<br>602 | CYP17A1 | Cytochrome P450 | NM_000102 |
| H46-232 | CTCTGTGTTCCACTTCGGC<br>AACTCTGTGTTCCACTTCGGC | 603<br>604 | DPYD | Enzyme | NM_000110 |
| H46-233 | GGAGATCGTGCTGGAGAAC<br>ACGGAGATCGTGCTGGAGAAC | 605<br>606 | FGF17 | Drugable/ Secreted | NM_003867 |
| H46-235 | CGTGGCCTACATCATCATC<br>AACGTGGCCTACATCATCATC | 607<br>608 | GPR108 | GPCR | XM_290854 |
| H46-236 | TGCAGCCAGTGGAATGTCC<br>ACTGCAGCCAGTGGAATGTCC | 609<br>610 | GPRC5D | GPCR | NM_018654 |
| H46-237 | GTATGGCATGCAGCTGTAC<br>AAGTATGGCATGCAGCTGTAC | 611<br>612 | GRB14 | Drugable/ Secreted | NM_004490 |
| H46-238 | GAATGGCTTTGCTGTGGTC<br>AAGAATGGCTTTGCTGTGGTC | 613<br>614 | HDAC4 | Enzyme | NM_006037 |
| H46-239 | ATGTTCCAGGAGATCGTCC<br>AATGTTCCAGGAGATCGTCC | 615<br>616 | CNDP1 | Protease | NM_032649 |
| H46-240 | ACATTCAGCTGTGAACTCC<br>ACACATTCAGCTGTGAACTCC | 617<br>618 | HSD11B2 | Enzyme | NM_000196 |
| H46-241 | CAAGCCCTTCCGTGTACTC<br>AACAAGCCCTTCCGTGTACTC | 619<br>620 | INPP5A | Phosphatase | NM_005539 |
| H46-242 | CCAGCATCCTTTGCATTAC<br>ACCCAGCATCCTTTGCATTAC | 621<br>622 | ITGAE | Drugable/ Secreted | NM_002208 |
| H46-243 | TGCAGTCAGTTGTCCATAC<br>AATGCAGTCAGTTGTCCATAC | 623<br>624 | KCNA4 | Ion Channel | NM_002233 |
| H46-245 | AGGCCAATCCTGGTAGCAC<br>ACAGGCCAATCCTGGTAGCAC | 625<br>626 | KIAA0669 | Receptor | NM_014779 |
| H46-246 | ATCCTGGGCTATTGGACTC<br>ACATCCTGGGCTATTGGACTC | 627<br>628 | LDHA | Enzyme | NM_005566 |
| H46-247 | CATGGCCTGTGCAATTATC<br>ACCATGGCCTGTGCAATTATC | 629<br>630 | LOC343066 | Enzyme | XM_291392 |
| H46-248 | GGCTGGTATACAGGAACAC<br>AAGGCTGGTATACAGGAACAC | 631<br>632 | LOC128183 | Enzyme | XM_060863 |
| H46-249 | ACATGCCATTACCAGCATC<br>AAACATGCCATTACCAGCATC | 633<br>634 | FLJ16046 | Protease | NM_207407 |
| | | | LOC389208 | Protease | XM_371695 |
| | | | LOC133177 | Protease | XM_068225 |
| H46-250 | TTGCTGCTATGTCAGATCC<br>AATTGCTGCTATGTCAGATCC | 635<br>636 | LOC138967 | Cytochrome P450 | XM_071222 |

TABLE 4-continued

| Hit No. | SEQ KD Targets 19-mer and 21-mer | SEQ ID NO | Gene Name | Protein Class | Accession |
|---|---|---|---|---|---|
| H46-<br>251 | ACGTGGACCAAGTCATGCC<br>ACACGTGGACCAAGTCATGCC | 637<br>638 | DUSP18 | Phosphatase | NM_152511 |
| H46-<br>253 | TTGGATCCTAATGAGCTGC<br>ACTTGGATCCTAATGAGCTGC | 639<br>640 | IMP5 | Protease | NM_175882 |
| H46-<br>254 | GTCTTGTGTCAGAATTTCC<br>ACGTCTTGTGTCAGAATTTCC | 641<br>642 | LOC163107 | GPCR | XM_092005 |
| H46-<br>256 | AGTAGGCAACGACAGCAGC<br>AAAGTAGGCAACGACAGCAGC | 643<br>644 | LOC222656 | GPGR | XM_167080 |
| H46-<br>259 | CTAAGGAGGCTCGGAAATC<br>GCCTAAGGAGGCTCGGAAATC | 645<br>646 | LOC256669 | Kinase | XM_171416 |
| H46-<br>260 | GGCTCTGTCAAGGCCATTC<br>TCGGCTCTGTCAAGGCCATTC | 647<br>648 | LOC257260 | Protease | XM_174353 |
| H46-<br>261 | TAATGACTTTGGCGCTGTC<br>CCTAATGACTTTGGCGCTGTC | 649<br>650 | ADCK1 | Kinase | SK401; NM_020421 |
| H46-<br>262 | CTACATGGACCGCTTCACC<br>AACTACATGGACCGCTTCACC | 651<br>652 | SPINL | Transporter | NM_032038 |
| H46-<br>263 | TAGCCAAGAGTTCAGCCCC<br>AATAGCCAAGAGTTCAGCCCC | 653<br>654 | MAP3K14 | Kinase | NM_003954 |
| H46-<br>264 | CTCCACAAACTGATCAGCC<br>AACTCCACAAACTGATCAGCC | 655<br>656 | MAP3K14 | Kinase | NM_003954 |
| H46-<br>265 | GACTGTGAGCTGAAGATCC<br>AAGACTGTGAGCTGAAGATCC | 141<br>244 | MAPK12 | Kinase | NM_002969 |
| H46-<br>266 | ACCTGAAGAAAGGGAGAGC<br>ACACCTGAAGAAAGGGAGAGC | 657<br>658 | MIDORI | Kinase | NM_020778; XM_057651 |
| H46-<br>269 | AACCCTATGCTGCCTATGC<br>ACAACCCTATGCTGCCTATGC | 659<br>660 | NAALADL1 | Protease | NM_005468 |
| H46-<br>271 | TGGCACTTCGGGCAATAAC<br>ACTGGCACTTCGGGCAATAAC | 139<br>242 | NQO2 | Enzyme | NM_000904 |
| H46-<br>272 | GAAGTTCATCAGCGCCATC<br>AAGAAGTTCATCAGCGCCATC | 661<br>662 | NTSR1 | GPCR | NM_002531 |
| H46-<br>273 | AGCTGCCTGGAAGCATTAC<br>AAAGCTGCCTGGAAGCATTAC | 663<br>664 | PDK1 | Kinase | NM_002610 |
| H46-<br>275 | CAGTGTTACACGGCTTTCC<br>AACAGTGTTACACGGCTTTCC | 665<br>666 | PIK3C3 | Kinase | NM_002647 |
| H46-<br>278 | GACTGAATCAGGCCTTCCC<br>AAGACTGAATCAGGCCTTCCC | 667<br>668 | PPIH | Enzyme | NM_006347 |
| H46-<br>279 | TGCCTGGGACCAGAGCTTC<br>AATGCCTGGGACCAGAGCTTC | 669<br>670 | PKN1 | Kinase | SK317 |
| | | | PRKCL1 | Kinase | NM_213560; NM_002741 |
| H46-<br>280 | GTCCAAGATGGAGCTACAC<br>GCGTCCAAGATGGAGCTACAC | 671<br>672 | PSMB10 | Protease | NM_002801 |
| H46-<br>281 | ATATCATGTGAACCTCCTC<br>CCATATCATGTGAACCTCCTC | 673<br>674 | PSMB2 | Protease | NM_002794 |
| H46-<br>282 | CGTCGTCCAAAGCAGAAGC<br>AACGTCGTCCAAAGCAGAAGC | 675<br>676 | PTGIR | GPCR | NM_000960 |
| H46-<br>283 | TGTAGTGCAGGCATTGGGC<br>ACTGTAGTGCAGGCATTGGGC | 677<br>678 | PTPN2 | Phosphatase | NM_080423; NM_002828;<br>NM_080422 |
| H46-<br>284 | TGTGGGAGAACTGAAGTCC<br>ACTGTGGGAGAACTGAAGTCC | 679<br>680 | PTPN4 | Phosphatase | NM_002830 |
| H46- | GAAGAACAGCAGCCTGGAC | 681 | RASD1 | Enzyme | NM_016084 |

TABLE 4-continued

| Hit No. | SEQ KD Targets 19-mer and 21-mer | SEQ ID NO | Gene Name | Protein Class | Accession |
|---|---|---|---|---|---|
| 285 | AAGAAGAACAGCAGCCTGGAC | 682 | | | |
| H46-286 | GATGGACTCAGGTGGACTC<br>AAGATGGACTCAGGTGGACTC | 683<br>684 | SENP3 | Protease | NM_015670 |
| H46-287 | TGCTGCATCCGACAGATCC<br>AATGCTGCATCCGACAGATCC | 685<br>686 | DustyPK | Kinase | NM_015375; NM_199462 |
| H46-288 | TTTCCAGGTCATCTGCTCC<br>ACTTTCCAGGTCATCTGCTCC | 687<br>688 | SLC28A2 | Transporter | NM_004212 |
| H46-289 | TTCCAGGTCCTGAAGCGAC<br>ACTTCCAGGTCCTGAAGCGAC | 689<br>690 | SLC6A2 | Transporter | NM_001043 |
| H46-290 | TTGTGGAGAGCTCGAATTC<br>ACTTGTGGAGAGCTCGAATTC | 691<br>692 | SLC8A1 | Ion Channel | NM_021097 |
| H46-291 | ATGGCCAGCAACCTGATGC<br>ACATGGCCAGCAACCTGATGC | 693<br>694 | GPR124 | GPCR | NM_032777 |
| H46-292 | TTCTCAGGCACCCTCTACC<br>AATTCTCAGGCACCCTCTACC | 695<br>696 | TLK1 | Kinase | XM_002626; AB004885; SK373; NM_012290 |
| H46-293 | GTGCTGGATTCTGCCATGC<br>AAGTGCTGGATTCTGCCATGC | 697<br>698 | TPST1 | Enzyme | NM_003596 |
| H46-294 | GTGTGTTAGCACGACTTTC<br>AAGTGTGTTAGCACGACTTTC | 699<br>700 | TPTE | Ion Channel | NM_013315; NM_199259 |
| H46-296 | CATCCTGCTGTCCAACCCC<br>AACATCCTGCTGTCCAACCCC | 701<br>702 | ULK1 | Kinase | NM_003565 |
| H46-297 | TGGTGGCAGACATCCCTTC<br>ACTGGTGGCAGACATCCCTTC | 703<br>704 | XDH | Enzyme | NM_000379 |
| H46-299 | GCACAGCACTTCCACAAGC<br>ACGCACAGCACTTCCACAAGC | 705<br>706 | GDF10 | Drugable/ Secreted | NM_004962 |
| H46-300 | AGGAGTTTGGGAACCAGAC<br>ACAGGAGTTTGGGAACCAGAC | 707<br>708 | DO | Enzyme | NM_021071 |
| H46-301 | CACTGGCATCATCTGTACC<br>AACACTGGCATCATCTGTACC | 709<br>710 | LOC339395 | Kinase | XM_290872 |
| | | | PKM2 | Kinase | NM_182471; NM_002654; NM_182470 |
| H46-322 | GTGACTACACAAGGACTCC<br>AAGTGACTACACAAGGACTCC | 711<br>712 | CCR2 | GPCR | NM_000647 |
| H46-323 | CTTCTCCTTTGGTGGCTGC<br>AACTTCTCCTTTGGTGGCTGC | 713<br>714 | HTR4 | GPCR | NM_000870 |
| H46-324 | AGTGGGTAAAGCCAATGGC<br>ACAGTGGGTAAAGCCAATGGC | 715<br>716 | RPE | Enzyme | XM_030834; NM_199229; NM_006916 |
| | | | LOC90470 | Enzyme | XM_031975 |
| H46-325 | GCTGCTCAGAAACGTTCTC<br>AAGCTGCTCAGAAACGTTCTC | 717<br>718 | RPE | Enzyme | XM_030834; NM_199229; NM_006916 |
| | | | LOC90470 | Enzyme | XM_031975 |
| H46-326 | ACCACACTCACGCAGTATC<br>ACACCACACTCACGCAGTATC | 719<br>720 | RHOBTB1 | Enzyme | NM_198225; NM_014836 |
| H46-328 | GTCTGTCTGTAAGAACACC<br>AAGTCTGTCTGTAAGAACACC | 721<br>722 | USP31 | Protease | NM_020718 |
| | | | KIAA1203 | Protease | XM_049683 |
| H46-329 | GATGTAGAGCTGGCCTACC<br>AAGATGTAGAGCTGGCCTACC | 723<br>724 | LOC150537 | Kinase | XM_086946 |
| | | | LOC389069 | Not drugable | XM_371588 |

TABLE 4-continued

| Hit No. | SEQ KD Targets 19-mer and 21-mer | SEQ ID NO | Gene Name | Protein Class | Accession |
|---|---|---|---|---|---|
| | | | SEPHS1 | Kinase | MM_012247 |
| H46-330 | GGTGAGCGTGGACATCTTC<br>AAGGTGAGCGTGGACATCTTC | 725<br>726 | ABCA2 | Transporter | NM_001606; NM_212533 |
| H46-331 | GTGGAACAAGAGGTACAAC<br>AAGTGGAACAAGAGGTACAAC | 727<br>728 | ABCA6 | Transporter | NM_080284; NM_172346 |
| H46-332 | CGATGGCTTCCACGTCTAC<br>AACGATGGCTTCCACGTCTAC | 729<br>730 | ACVR1 | Kinase | NM_001105 |
| H46-333 | GTGGGCAATGAATATGGCC<br>AAGTGGGCAATGAATATGGCC | 731<br>732 | ADORA2B | GPCR | NM_000676 |
| H46-334 | TTCTGTGGTGGTTCTGGTC<br>AATTCTGTGGTGGTTCTGGTC | 733<br>734 | CCR4 | GPCR | NM_005508 |
| H46-335 | CTTCATTATCCACAGGGAC<br>AACTTCATTATCCACAGGGAC | 735<br>736 | CDK10 | Kinase | NM_003674; NM_052987;<br>NM_052988 |
| H46-336 | GGTGGAGCACTACCGCATC<br>AAGGTGGAGCACTACCGCATC | 737<br>738 | CSK | Kinase | NM_004383 |
| H46-338 | AAGTTCCCGAACGATCACC<br>ACAAGTTCCCGAACGATCACC | 739<br>740 | ENSG000001<br>17094 | Protease | ENSG00000117094 |
| H46-339 | CTCTGTGTGCCTGTCGTTC<br>ACCTCTGTGTGCCTGTCGTTC | 741<br>742 | KAZALD1 | Drugable/<br>Secreted | NM_030929 |
| H46-341 | TGGCACCTTAACTGGAGTC<br>AATGGCACCTTAACTGGAGTC | 743<br>744 | GPR64 | GPCR | NM_005756 |
| H46-343 | GAAGCCTGAAGACACAAAC<br>AAGAAGCCTGAAGACACAAAC | 136<br>239 | ILK | Kinase | NM_004517 |
| H46-345 | TCTTCTCCCAGAGGAAGGC<br>AATCTTCTCCCAGAGGAAGGC | 745<br>746 | DPP10 | Protease | NM_020868 |
| | | | KIAA1492 | Protease | XM_035312 |
| H46-346 | CTGCTCCAGCATCACTATC<br>ACCTGCTCCAGCATCACTATC | 747<br>748 | KLK10 | Protease | NM_002776; NM_145888 |
| H46-347 | ATTCTGTGGGCTCATCACC<br>AAATTCTGTGGGCTCATCACC | 749<br>750 | LIFR | Receptor | NM_002310 |
| H46-348 | GCAGGACTTCAGAACACAC<br>AAGCAGGACTTCAGAACACAC | 751<br>752 | LOC118461 | Transporter | XM_060969 |
| H46-349 | AGCCTGGTTCATTCTAAAC<br>ACAGCCTGGTTCATTCTAAAC | 753<br>754 | LOC150287 | Transporter | XM_086889 |
| H46-351 | ACTGTGGGATTGACCAGGC<br>ACACTGTGGGATTGACCAGGC | 755<br>756 | LOC151234 | Enzyme | XM_087136 |
| H46-352 | TTCAGAATTCAGGCAGCTC<br>ACTTCAGAATTCAGGCAGCTC | 757<br>758 | C9orf52 | Protease | NM_152574 |
| | | | LOC158219 | Protease | XM_088514 |
| H46-353 | ACTGGGCATTTCCTACTGC<br>ACACTGGGCATTTCCTACTGC | 759<br>760 | IMP5 | Protease | NM_175882 |
| H46-354 | GCTGTGGGAGAACTATCCC<br>AAGCTGTGGGAGAACTATCCC | 761<br>762 | LOC205678 | Protease | XM_120320 |
| H46-356 | ATGGACCTGACCTGCATTC<br>TCATGGACCTGACCTGCATTC | 763<br>764 | LOC255782 | Enzyme | XM_172181 |
| H46-357 | TCTTCTCACATGGAAATGC<br>ACTCTTCTCACATGGAAATGC | 765<br>766 | C9orf77 | Protease | NM_016014 |
| H46-358 | CCATTCCATGGTGTTTACC<br>ACCCATTCCATGGTGTTTACC | 767<br>768 | MALT1 | Protease | NM_006785; NM_173844 |
| H46- | GCACATGCAGCATGAGAAC | 135 | MAPK13 | Kinase | NM_002754 |

TABLE 4-continued

| Hit No. | SEQ KD Targets 19-mer and 21-mer | SEQ ID NO | Gene Name | Protein Class | Accession |
|---|---|---|---|---|---|
| 359 | AAGCACATGCAGCATGAGAAC | 238 | | | |
| H46-360 | ACATGGGCTATCTCAAGCC<br>AAACATGGGCTATCTCAAGCC | 769<br>770 | MC2R | GPCR | NM_000529 |
| H46-362 | CTTCCTGTCTCCCTTCTAC<br>AACTTCCTGTCTCCCTTCTAC | 771<br>772 | SLC22A13 | Transporter | NM_004256 |
| H46-363 | CGTCTCACAGTATGCATTC<br>AACGTCTCACAGTATGCATTC | 773<br>774 | 7050585CA2 | Drugable/ Secreted | 7050585CA2 |
| | | | PCTK2 | Kinase | NM_002595 |
| H46-364 | AGCTGCTATCCAACTCACC<br>ACAGCTGCTATCCAACTCACC | 775<br>776 | TP53I3 | Enzyme | NM_147184; NM_004881 |
| H46-365 | CAACGTGGAGGAGGAGTTC<br>ACCAACGTGGAGGAGGAGTTC | 777<br>778 | PP1665 | PDE | NM_030792 |
| H46-366 | CAGGCCTGTGGAAACATAC<br>AACAGGCCTGTGGAAACATAC | 779<br>780 | PPP2R2A | Phosphatase | NM_002717 |
| H46-368 | TGATGGCCTTTCCCTGTGC<br>ACTGATGGCCTTTCCCTGTGC | 781<br>782 | PLA1A | Enzyme | NM_015900 |
| H46-369 | GACTCTGGGCTGCTCTATC<br>AAGACTCTGGGCTGCTCTATC | 783<br>784 | PTPRN | Phosphatase | NM_002846 |
| H46-371 | TTCCGTGGCCTGTTCAATC<br>ACTTCCGTGGCCTGTTCAATC | 785<br>786 | SIAT7B | Enzyme | NM_006456 |
| H46-372 | GGGCAACAATGACTGTGAC<br>ACGGGCAACAATGACTGTGAC | 787<br>788 | TEX14 | Kinase | NM_031272; NM_198393 |
| H46-373 | ACCTGGCTTCCCTTCCTTC<br>ACACCTGGCTTCCCTTCCTTC | 789<br>790 | TFR2 | Protease | NM_003227 |
| H46-374 | CATGCTCAAGGCCATGTTC<br>ACCATGCTCAAGGCCATGTTC | 791<br>792 | TNFAIP1 | Ion Channel | NM_021137 |
| H46-375 | TCAGTTCCCAGCTCTGCAC<br>AATCAGTTCCCAGCTCTGCAC | 793<br>794 | TNFSF15 | Drugable/ Secreted | NM_005118 |
| H46-376 | CATCACAATTGGCCATCAC<br>TCCATCACAATTGGCCATCAC | 795<br>796 | TOP2B | Enzyme | NM_001068 |
| H46-377 | TGGAAGATTATCCTGTGTC<br>ACTGGAAGATTATCCTGTGTC | 797<br>798 | TRPM8 | Ion Channel | NM_024080 |
| H46-379 | TACATTCACCCTGTGTGTC<br>ACTACATTCACCCTGTGTGTC | 799<br>800 | F2 | Protease | NM_000506 |
| H46-380 | GATGTGCCTGTCCTGTGTC<br>AAGATGTGCCTGTCCTGTGTC | 801<br>802 | IL1RN | Receptor | NM_000577; NM_173843; NM_173842; NM_173841 |
| H46-381 | ATTTGTGGGCAACTCAGCC<br>AAATTTGTGGGCAACTCAGCC | 803<br>804 | LOC133179 | Protease | XM_068227 |
| H46-382 | ATCAGAAGAAAGCCATGAC<br>ACATCAGAAGAAAGCCATGAC | 805<br>806 | ATAD1 | Enzyme | NM_032810 |
| H46-385 | CATGTGTGGGAAGTTGTTC<br>ACCATGTGTGGGAAGTTGTTC | 807<br>808 | ADAM28 | Protease | NM_014265; NM_021778 |
| H46-387 | TTGCTGAGATGTGTTAGGC<br>CCTTGCTGAGATGTGTTAGGC | 809<br>810 | LOC145624 | Protease | XM_096824 |
| H46-389 | CCACCATGCAGACAAGTCC<br>AACCACCATGCAGACAAGTCC | 811<br>812 | ADAMTS6 | Protease | NM_014273 |
| H46-390 | ACTGACCTCAGAGTACCAC<br>AAACTGACCTCAGAGTACCAC | 813<br>814 | ADORA3 | GPCR | NM_000677 |
| H46-392 | CGACACAGTGGTGCTCTAC<br>ACCGACACAGTGGTGCTCTAC | 815<br>816 | DUSP6 | Phosphatase | NM_022652; NM_001946 |

TABLE 4-continued

| Hit No. | SEQ KD Targets 19-mer and 21-mer | SEQ ID NO | Gene Name | Protein Class | Accession |
|---|---|---|---|---|---|
| H46-393 | GATCTCCCGCTTCCCGCTC<br>AAGATCTCCCGCTTCCCGCTC | 132<br>235 | FGFR3 | Kinase | NM_000142 |
| H46-394 | CGTCTACTCGCTGGCCTTC<br>AACGTCTACTCGCTGGCCTTC | 817<br>818 | FZD9 | GPCR | NM_003508 |
| H46-395 | TGCTGGTGCCATTGTTGTC<br>AATGCTGGTGCCATTGTTGTC | 819<br>820 | GLS2 | Enzyme | NM_138566; NM_013267 |
| H46-396 | ACAACTCAGAGGGACCTTC<br>ACACAACTCAGAGGGACCTTC | 821<br>822 | GALNT6 | Enzyme | NM_007210 |
| H46-398 | AGGTAATGTGGAACACAGC<br>AAAGGTAATGTGGAACACAGC | 823<br>824 | GSR | Enzyme | NM_000637 |
| H46-399 | CAACTCCACACTGGACTTC<br>ACCAACTCCACACTGGACTTC | 825<br>826 | LOC138685 | Drugable/ Secreted | XM_071038 |
| | | | LOC158017 | Drugable/ Secreted | XM_095763 |
| | | | IFNW1 | Drugable/ Secreted | NM_002177 |
| H46-400 | TGCAGATGGTTGTGCTCCC<br>AATGCAGATGGTTGTGCTCCC | 827<br>828 | IL24 | Drugable/ Secreted | NM_006850 |
| H46-401 | AACATGATATGTGCTGGAC<br>ACAACATGATATGTGCTGGAC | 829<br>830 | KLK10 | Protease | NM_002776; NM_145888 |
| H46-404 | AACACGGTGGAGCTGCTGC<br>ACAACACGGTGGAGCTGCTGC | 831<br>832 | FLJ37478 | Enzyme | NM_178557 |
| H46-406 | TTCCACAGCATGAACTGGC<br>AATTCCACAGCATGAACTGGC | 833<br>834 | LOC221757 | Kinase | XM_167231 |
| H46-407 | AGATGCATCTTCCCTCCAC<br>AAAGATGCATCTTCCCTCCAC | 835<br>836 | LOC255449 | Protease | XM_171993 |
| | | | LOC442045 | Protease | XM_497874 |
| H46-409 | ATAAGCGGTTATCACTGCC<br>AAATAAGCGGTTATCACTGCC | 837<br>838 | PCTK2 | Kinase | NM_002595 |
| H46-410 | AGTCACAATGTCAAGTGAC<br>ACAGTCACAATGTCAAGTGAC | 839<br>840 | PDHX | Enzyme | NM_003477 |
| H46-411 | CTCAACCCAGAACCTGAGC<br>ACCTCAACCCAGAACCTGAGC | 841<br>842 | PPP1R12C | Phosphatase | NM_017607 |
| H46-412 | AGTATCAGGAGCCAATACC<br>ACAGTATCAGGAGCCAATACC | 843<br>844 | PSMA4 | Protease | NM_002789 |
| H46-413 | AATCCTGTATTCAAGGCGC<br>ACAATCCTGTATTCAAGGCGC | 845<br>846 | PSMB1 | Protease | NM_002793 |
| H46-414 | GAGCGCATCTACTGTGCAC<br>ACGAGCGCATCTACTGTGCAC | 847<br>848 | PSMB9 | Protease | NM_148954; NM_002800 |
| H46-415 | ACATGGACGAGTGTCTCAC<br>ACACATGGACGAGTGTCTCAC | 849<br>850 | RYR2 | Ion Channel | NM_001035 |
| H46-416 | TCCGAGCGATTTAAGGAAC<br>ACTCCGAGCGATTTAAGGAAC | 851<br>852 | SHH | Protease | NM_000193 |
| H46-417 | TGGAGTCCTTCAAGGCTAC<br>AATGGAGTCCTTCAAGGCTAC | 853<br>854 | SRD5A2 | Enzyme | NM_000348 |
| H46-418 | CATCATGGATGAGTGTGGC<br>ACCATCATGGATGAGTGTGGC | 855<br>856 | SV2B | Transporter | NM_014848 |
| H46-419 | ATTCAGCAGAAGCCCAGAC<br>ACATTCAGCAGAAGCCCAGAC | 857<br>858 | UGT1A6 | Enzyme | NM_001072 |
| H46-420 | TGAGCCACGGGAATGTGCC<br>AATGAGCCACGGGAATGTGCC | 859<br>860 | ULK2 | Kinase | NM_014683 |

TABLE 4-continued

| Hit No. | SEQ KD Targets 19-mer and 21-mer | SEQ ID NO | Gene Name | Protein Class | Accession |
|---|---|---|---|---|---|
| H46-423 | TTCCACCTACCAGTCCACC<br>TCTTCCACCTACCAGTCCACC | 861<br>862 | PGA5 | Protease | NM_014224 |
| H46-424 | CAGCACATTCAGCTGCAGC<br>ACCAGCACATTCAGCTGCAGC | 863<br>864 | FGF1 | Drugable/<br>Secreted | NM_000800 |
| H46-426 | ATCATGGCTGTGACCACAC<br>ACATCATGGCTGTGACCACAC | 865<br>866 | NDUFS2 | Enzyme | NM_004550 |
| H46-427 | AGTGGCCTTCCTCAGGAAC<br>ACAGTGGCCTTCCTCAGGAAC | 867<br>868 | NR0B2 | NHR | NM_021969 |
| H46-429 | AGTTCTACGACTCCAACAC<br>AAAGTTCTACGACTCCAACAC | 869<br>870 | PAK2 | Kinase | NM_002577 |

Example 3B

Application of Additional Assays and Exclusion Criteria

The 323 hits identified through the primary "reverse MMP1 assay" are further prioritized using the "reverse collagen degradation assay", which is based on the observation that the supernatant of RA SFs treated with "TNFα-based trigger" has collagenolytic potential. As degradation of native collagen is mediated by multiple proteases (collagenases), the reduction in the degradation of collagen is a more stringent readout compared to reading out only MMP1 expression. The effect of TARGET expression reduction in RA SFs (by means of KD-viruses) on the cytokine-induced collagen degradation by RA SFs is tested using an assay developed in house. In this assay, the degradation of FITC-labeled native collagen gives rise to an increase in fluorescence signal. (The protocol of this assay is detailed in the description of Example 6 (FIG. 12).).

The 323 hit KD viruses identified in the "reverse MMP1 assay" are arrayed in 96 well plates ("Hit plates") such that every plate contained 60 hit viruses along with 4 positive control viruses and 16 negative control viruses. RA SF, seeded in 96 well plates at a density of 3000 cells/well in complete synovial growth medium (Cell Applications) are infected, one day later, with 5 or 10 μl of the viruses contained in the "hit plates". The virus load is completed by addition 6 μl of the neutral virus Ad5-Luciferase-v13_KD. This correction guarantees that the effects observed do not result from differences in the virus load applied to the cells. 5 days after infection, the activation step is performed. This step involves the replacement, in every well, of the growth medium by 45 μl of M199 medium supplemented with 15 μl of "TNFα-based trigger". 4 days later, the supernatant is collected and subjected to the miniaturized collagen type I degradation assay according to the protocol described for the experiment depicted in FIG. 12. Two independent propagation materials for every target KD virus are tested twice at both MOIs, giving rise to 4 data points for each MOI. The results are analysed as follows:

For every plate, the samples with corresponding fluorescence value lower then the average over all negative controls minus 2.1 times (5 μl infection) or 1.6 times (10 μl infection) the standard deviation over all negative controls are considered as giving a positive response in the assay. Every Target KD virus giving rise to 3 out of 4 data points giving a positive readout in the assay is considered as significantly reducing "TNF-based trigger"-induced collagen degradation by RA SFs. Alternatively, every Target KD virus generating 2 positive responses in the assay (out of 4 data points) for each MOI tested are considered as significantly reducing collagen degradation. Of the 323 target KD viruses tested, 192 significantly reduced the "TNF-based trigger"-induced collagen degradation by RA SFs.

To select for the preferred hits, we used a second assay that tests for the effect of the target expression reduction in RA SFs (by means of KD-viruses) on the LPS or TNFα-induced IL8 expression by RA SFs. This assay (1) confirms that the target KD viruses selected are not inhibiting the LPS signaling in RA SFs too much, as LPS signaling is required for the response of patients to pathogens and its complete inhibition would compromise the patients' innate immunity.; and (2) confirms that the targets do not enhance the TNFα-induced expression of an inflammation marker. The chemokine IL8 is selected as a readout in this assay. This chemokine plays a role in the recruitment of cells of the immune system (e.g. monocytes, neutrophils) to the site of inflammation (the joint in the case of RA), further increasing the local inflammatory events. Increase of IL8 expression is not a desired feature for a RA therapy.

Figure 13:
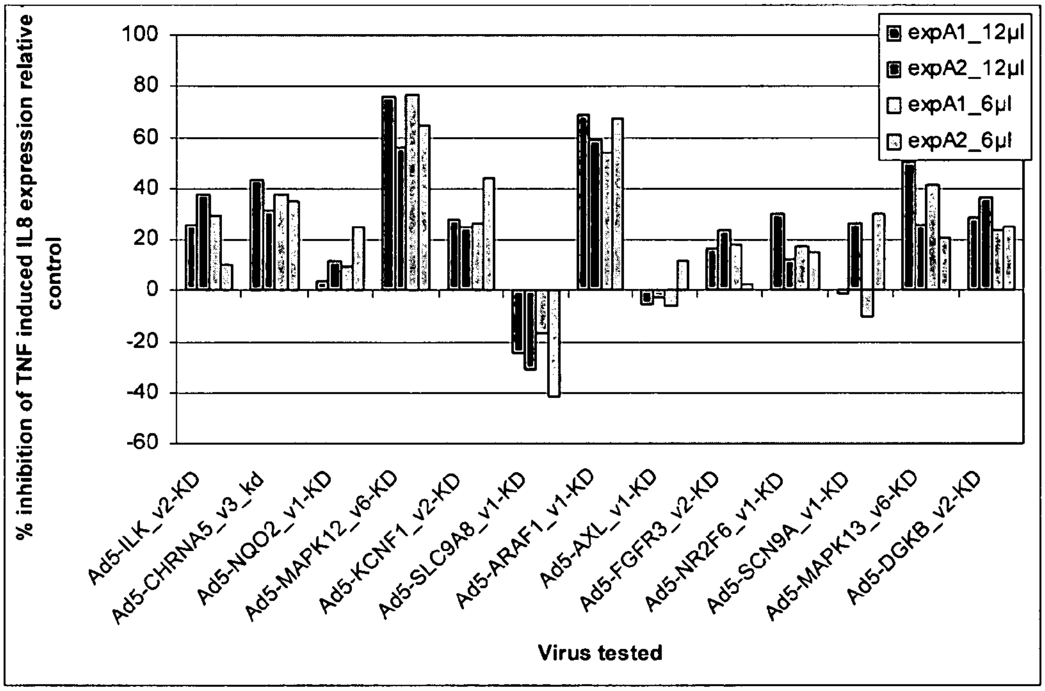
FIG. 13. Reduction of the expression of the TARGETS in primary SFs by Ad-siRNAs modulates TNFα-induced IL-8 expression. The supernatant from SFs infected with the indicated Ad-siRNAs is subjected to the IL-8 ELISA assay and the percent inhibition of IL-8 expression relative to negative controls is shown.

The target KD viruses identified in the "reverse MMP1 assay" and giving a positive readout in the "reverse collagen degradation assay" are tested in the LPS/TNFα-induced IL8 assay as follows: 192 target KD viruses are arrayed in 96 well plates ("Hit plates") such that every plate contained 60 target viruses along with 20 negative control viruses. Day 1, SFs (passage 9 to 12) are seeded in 96 well plates at a density of 3000 cells per well in complete synovial growth medium (Cell Applications). One day later, the cells are infected with two amounts (6 or 12 μl) of the target KD viruses arrayed in 96 well plates as indicated above. The cells are then incubated for 5 days before the activation step, which involves the replacement, in every well, of the growth medium by 150 μl of DMEM supplemented with 10% Fetal bovine serum (heat inactivated) and the trigger (2 ng/ml recombinant human TNFα or 1 μg/ml LPS). 48 hrs after the activation step, 80 μl of the supernatant is collected and a dilution from this is used for the IL-8 ELISA as described for the experiment depicted in FIG. 13. For the samples triggered with TNFα a 40-fold dilution is made in PBS+1% BSA, and for LPS samples, a 16 fold dilution is performed. 35 μl from these dilutions is subjected to the IL-8 ELISA. Two independent preparations of the target KD viruses are tested at 2 MOI in 2 independent experiments giving rise to 4 data points per MOI for every target KD virus tested.

Data are analysed as follows: the 96 well plates containing the KD viruses designed to reduce the expression of the targets also contained 20 negative controls. The percentage inhibition of IL8 expression is calculated as percentage relative to the negative controls as follows: First, the background signal of the ELISA (in the absence of IL8) is subtracted from all values for all samples. Then the following formula is applied for every plate: % inhibition=[100×(((Average value all negative controls)−value Target sample)/(Average value all negative controls))]. All the Target KD viruses are ranked depending on their performance in the TNFα and LPS induced IL8 assay. 10% of the target KD viruses giving the strongest inhibition of LPS-induced IL8 are considered less preferred as well as 5% of the target KD viruses giving rise to the strongest increase of the TNFα-induced IL8 expression by RA SFs. As such, 40 out of the 192 Target KD viruses tested in this assay are considered to be less preferred. Further exclusion criteria used to define the present invention with more particularity are described below.

The TARGETS identified in this invention represent the basis for the identification of small molecule inhibitors developed for the treatment of RA. As such, the testing of such new candidate RA therapies in experimental models of arthritis is required before running experiments in human. The collagen-induced arthritis model in rat or mice is generally used as experimental model of arthritis. Consequently, targets, for which no ortholog can be found in rat or mice, are less preferred. Analysis of the 152 targets (identified through the experimental cascade (the "reverse MMP1" primary assay, the "reverse collagen degradation" secondary assay and the "TNFα/LPS IL8 induction assay") revealed that 27 had no ortholog in rat or mice, leaving only 125 preferred targets. Further exclusion criteria involved the following in silico analyses:

"Drugability". Targets were excluded if it could be determined that the development of a small molecule inhibitor would be predicted to be the least successful within a short timeframe. This analysis involved the assessment of the general drugability of the gene class to which a certain Target belongs based on pharmacology precedents. In addition, the existence of assays allowing the discovery of small molecule inhibitors of the Targets is evaluated. We found assays available for 69 out of the 125 Targets subjected to this analysis.

"Risk profile". Target genes for which the corresponding "knock-out mice" phenotype is diseased or lethal are considered as having lower priority, as inhibition of the product of these genes by means of a small molecule is expected to cause part of this phenotype. The Targets that play an important role in basal metabolic functions of the cells or of the organism are also given lower priority. The risk profile is considered high for 18 out of the 69 targets analysed.

"Disease relevance." Targets that are already linked to inflammatory processes or autoimmune processes are considered as more preferred.

The forgoing set of experiments and analyses permitted the narrowing of the present set of 16 most preferred TARGETs from the list of 323 targets.

Example 4

Analysis of the Expression Levels for Certain Targets Identified in Human Primary Synovial Fibroblasts Derived from Synovium of RA Patients Expression levels for certain identified targets are determined in at least two different isolates of primary human synovial fibroblasts.

The RASFs isolates are obtained as cryo-preserved passage 2 cells from Cell Applications Inc. (Cat. No. 404-05). These cells are cultured and propagated in DMEM (Invitrogen) supplemented with 10% (v/v) heat-inactivated FBS (ICN) and 1× Pen/Strep (Invitrogen). For expression analysis, cells are cultured to passage 11.

For RNA preparation, the primary human synovial fibroblasts are seeded in 10-cm Petri dishes (500,000 cells/dish) in 6-well plates. After overnight incubation, medium is refreshed with 6 ml of M199 medium supplemented with 1% (v/v) heat-inactivated FBS containing 1× Pen/Strep. 24 hours later, total RNA is extracted using the "SV Total RNA Isolation kit" (Promega).

The concentration of RNA in each sample is fluorimetrically quantified using the "Ribogreen RNA quantitation kit" (Molecular Probes). A similar amount of RNA from each preparation is reverse transcribed into first strand cDNA with the "Taqman reverse transcription kit" from Applied Biosystems. Briefly, 40 ng RNA is included per 20 μl reaction mix containing 50 pmol of random hexamers, 10 U Rnase inhibitor, 25 U Multiscribe reverse transcriptase, 5 mM $MgCl_2$ and 0.5 mM of each dNTP. The reaction mixture is incubated at 25° C. for 10 minutes, followed by 30 minutes incubation at 48° C. and heat inactivation (5 minutes 95° C.) of the reverse transcriptase in a thermocycler (Dyad, M J Research). Reactions are immediately chilled to 4° C. at the end of the program. To avoid multiple freeze/thaw cycles of the obtained cDNA, the different samples are pooled in 96-well plates, aliquoted and stored at −20° C.

Real-time PCR reactions are performed and monitored using the "ABI PRISM 7000 Sequence Detection System Instrument" (Applied Biosystems). Pre-designed, gene-specific Taqman probe and primer sets for quantitative gene expression are purchased from Applied Biosystems as part of the "Assays on Demand" Gene expression products. These commercially available kits are quality checked by the supplier and allow quantitative determination of the amount of target cDNA in the sample. The "Assays on Demand" gene expression products are used according to the protocol delivered by the supplier. The PCR mixture consisted of 1× "Taqman Universal PCR Mastermix no AmpErase UNG" and 1× "Taqman Gene Expression Assay on Demand mix" and 5 ul of the retro-transcription reaction product (1-100 ng of RNA converted into cDNA) in a total volume of 25 ul. After an initial denaturation step at 95° C. for 10 minutes, the cDNA products are amplified with 40 cycles consisting of 95° C. for 15 sec, and 60° C. for 1 minutes To normalize for variability in the initial quantities of cDNA between different samples, amplification reactions with the same cDNA are performed for the housekeeping gene β-actin using the predeveloped β-actin "Assays on demand" primer set and Taqman probe mix and "Taqman Universal PCR Mastermix" (all Applied Biosystems) according to the manufacturer's instructions. To identify any contamination resulting from residual genomic DNA, real-time PCR reactions with product from a control (—RT) reverse transcription reaction that is performed under the same conditions but without the addition of the reverse transcriptase are included for each sample. Threshold cycle values (Ct), for example, the cycle number at which the amount of amplified gene of interest reached a fixed threshold are determined for each sample. For each sample, the ΔCt value is determined by substracting the Ct value of the endogenous control (β-actin) from the Ct value obtained for the target gene. A gene is considered as expressed in primary human SFs if the ΔCt value obtained for this hit is lower than 13.3 in at least one of the available 2 synovial isolates, activated or not. Genes with a ΔCt value below 9.9 are considered highly expressed in RASFs. The results of the expression profiling experiments are summarized in Table 5. The ΔCt value relative to β-actin obtained for various targets in 2 isolates of untriggered SFs are given in this Table 5.

TABLE 5

Determination of the Relative Expression Levels of the TARGETS in Primary Synovial Fibroblasts by Real-Time PCR

| Target gene | Applied Biosystems Assay on demand, | RA SF batch 2 | | RA SF batch 3 | |
|---|---|---|---|---|---|
| symbol | Catalog number | Ct | DCt | Ct | DCt |
| ARAF1 | Hs00176427_m1 | 27 | 2.8 | 25.3 | 2.2 |
| AXL | Hs00242357_m1 | 25.9 | 1.6 | 23.6 | 0.5 |
| KCNF1 | Hs00266908_s1 | 40 | 14.86 | 29.3 | 4.46 |
| MAPK12 | | NT | NT | NT | NT |
| MAPK13 | Hs00559623_m1 | 29.9 | 6.2 | 29 | 6 |
| NR2F6 | Hs00172870_m1 | 27.2 | 2.9 | 24.2 | 1.83 |
| SCN9A | Hs00161567_m1 | 37.02 | 11.88 | 34.54 | 9.7 |
| SLC9A8 | Hs00392302_m1 | 30.76 | 5.62 | 28.56 | 3.72 |
| CHRNA5 | Hs00181248_m1 | 34.8 | 11.1 | 32.2 | 9.1 |
| DGKB | | NT | NT | NT | NT |
| FGFR3 | Hs00179829_m1 | 36.41 | 13.08 | 34.48 | 11.74 |
| ILK | Hs00177914_m1 | 26.8 | 3.2 | 24.4 | 1.3 |
| NQO2 | Hs00168552_m1 | 28.05 | 4.72 | 25.36 | 2.62 |

Example 5

Ad-siRNA Reduction of RASF Expression of ILK, CHRNA5, NQO2, KCNF1, SLC9A8. ARAF1, AXL, FGFR3, NR2F6, SCN9A, MAPK13 and DGKB Inhibit Cytokine-Induced MMP1 Expression in a Dose Dependent Manner As described above, the screening of the SilenceSelect collection identifies a set of Ad5-siRNAs that exhibit the capacity to reduce the cytokine-induced RASF MMP1 expression. A subset of these viruses is tested in the "reverse MMP1 assay" at various concentrations in a dose response experiment.

Figure 11A:
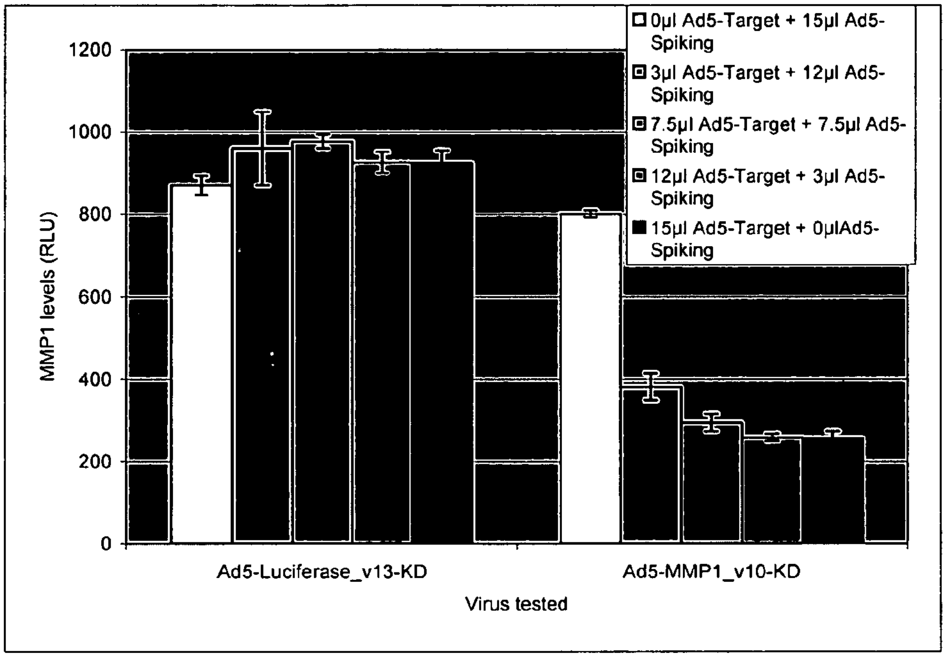
FIG. 11. Reduction of the expression of the TARGETS in primary SFs by Ad-siRNAs inhibits cytokine-induced MMP1 expression in a dose dependent manner. The supernatant from SFs infected with various doses of Ad-siRNAs targeting the expression of control genes (11A) and the genes listed in Table 1 (11B) is subjected to the MMP1 ELISA and the MMP1 level (11A) or MMP1 level relevant to the negative control (11B) is shown.

SFs (passage 9 to 10) are seeded in 96 well plates at a density of 3000 cells/well in complete synovial growth medium (Cell Applications). One day later, the cells are infected with increasing amounts (3, 7.5, 12, or 15 μl) of the Ad5-MMP1_v10_KD (positive control) or Ad5-Luciferase_v13_KD (negative control). The virus load is corrected by addition of the neutral virus Ad5-Luciferase_v13_KD to bring the final virus volume on the cells to 15 μl in every well. This correction guarantees that the effects observed do not result from differences in the virus load applied to the cells. The cells are then incubated for 5 days before the activation step. This step involves the replacement, in every well, of the growth medium by 75 μl of M199 medium supplemented with 25 μl of "complex trigger". 48 hours after the activation step, the supernatant is collected and subjected to the MMP1 ELISA as described previously. FIG. 11A shows the average of duplicate measurements.

This experiment clearly demonstrates that the application of increased amounts of Ad5-siRNA to RASFs will lead to an increased reduction of the expression of the target in the RASFs. In this case, applying increasing amounts of Ad5-MMP1_v10_KD to the cells leads to higher reduction in MMP1 protein expression by the cells. (FIG. 11A) Taken together, as increasing the amounts of Ad5-siRNA applied to RASFs will lead to greater reduction of the expression of the target in the RASFs, increasing the amounts of Ad5-siRNA targeting the genes listed in Table 1 is expected also to result in greater reduction of the cytokine induced MMP1 expression. The results of such dose response experiments are illustrated in FIG. 11B.

The Ad-siRNAs used in these dose response experiments are generated according to the procedure described in WO03/020931. The target sequences of these genes, on which the siRNAs are designed and used to generate the recombinant adenoviruses, are listed in Table 1. The Ad5-siRNA efficacy in the MMP1 ELISA is tested as described above with respect to the positive and negative controls with the only difference being that multiple Ad-siRNAs targeting the genes listed in Table 1 are used to infect the cells. The viruses used to infect the cells are shown on FIG. 1B with Ad5-eGFP-v5_KD, Ad5-Luciferase-v13_KD and Ad-M6PR-v1_KD used as negative controls, and Ad5-MMP1-v10_KD used as a positive control. The results of the experiment are shown in FIG. 11B.

Figure 11B:
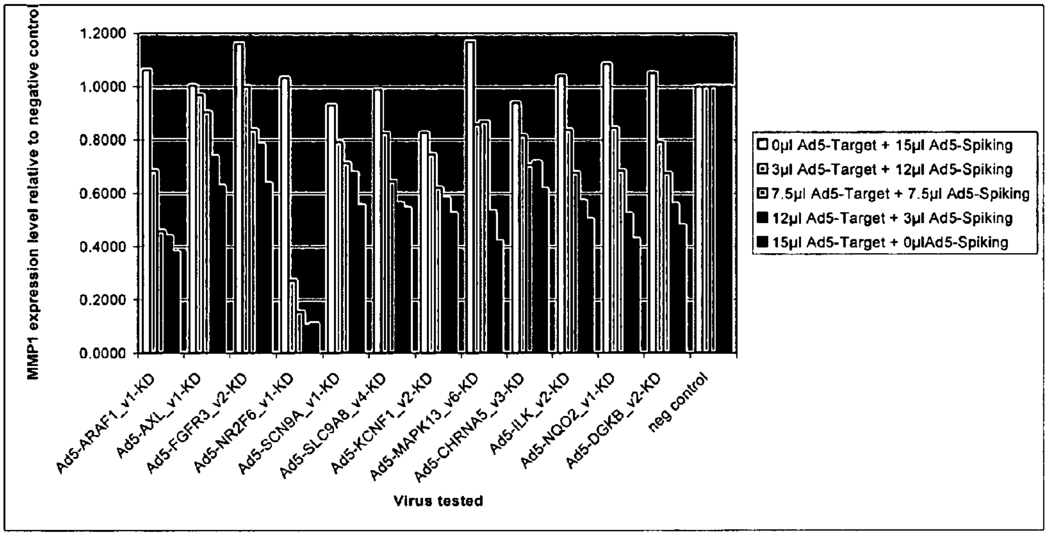

The data shown in FIG. 11B is calculated as follows: For each plate analyzed, the raw signal (RLU) for Ad5-MMP1_v10-KD (positive control) at 15 μl is considered as the lowest possible signal (i.e., the strongest reduction of MMP1 expression that can be obtained), and therefore, is set as the background of the assay. All other signals for this plate are adjusted to account for this background signal. For each MOI, the signal obtained for a particular Ad5-Target-KD virus is then normalized to (divided by) the signal of the negative control virus obtained on the same plate (Ad5-eGFP-v5_KD, Ad5-Luciferase-v13_KD or Ad-M6PR-v1_KD). FIG. 11B shows that the Ad-siRNA viruses mediating the reduction in expression of ILK, CHRNA5, NQO2, KCNF1, SLC9A8, ARAF1, AXL, FGFR3, NR2F6, SCN9A, MAPK13 and DGKB in RASFs cause a significant reduction of cytokine-induced MMP1 expression by these cells. Clearly, greater amounts of Ad5-siRNAs result in greater reduction in MMP1 expression levels. These results indicate that the amount of Ad5-siRNA applied to the cells determines the strength of the reduction in MMP1 expression observed.

We conclude, from this experiment, that these genes represent valuable drug targets that are shown to modulate MMP1 expression in SFs, and that the inhibition of the activity of the protein product of these genes by an inhibitory agent, such as a small molecule compound, is expected to reduce "complex cytokine" induced MMP1 expression in the "reverse MMP1 assay". We also believe that the inhibition of the activity of the protein products of these genes by such agents would also reduce the joint degradation observed in RA patients.

Table 1 lists multiple KD sequences produced for every TARGET gene identified in Table 1. Different Ad-siRNAs are generated from different target sequences within the TARGET mRNA. Although some of the Ad-siRNA viruses exhibit efficacy in the "reverse MMP1 assay," we observe that some of these Ad-siRNA viruses do not exhibit efficacy in the "reverse MMP1 assay". It should be understood, however, that not all shRNAs are as efficient in reducing target expression. There may be many cause of this difference in knockdown efficacy, including the physical availability of the target RNA to the siRNA degradation machinery (for example, in a three dimensional folding of any TARGET mRNA which is in close proximity with and/or binding to other cellular proteins, only a fraction of the mRNA may be "exposed" so as to provide a binding site for siRNA association), the potency of the target protein, degradation processes affecting the particular shRNA itself, and others. More particularly, the low efficacy of certain Ad-siRNAs in the "reverse MMP1 assay" may be explained by the level of reduction in target gene expression required to reduce cytokine-induced MMP1 expression by the cells. Some targets may require only 50% reduction to shut down the MMP1 pathway, while others may require 90% to achieve the same effect. Some targets may participate in metabolic pathways that compensate for target depletion, while others do not. As a consequence, testing these viruses at higher doses might lead to higher efficacy in the reverse MMP1 assay.

Example 6

Ad-siRNA-Induced Reduction of the RASF Expression of ILK, CHRNA5, NQO2, KCNF1, SLC9A8. ARAF1, AXL, FGFR3, NR2F6, SCN9A, MAPK12, MAPK13 and DGKB Inhibit Cytokine-Induced Collagen Degradation Certain MMP subtypes (for example, MMP1, MMP13) are collagenases and have the remarkable capacity of degrading native collagen. Native collagen is organized in stable fibrils that are quite resistant to proteolytic events. As such, the degradation of native collagen can be used to monitor not only MMP1 but also the complete complement of collagenases produced by RASFs. Described herein is an assay developed to detect the cytokine-induced degradation of native collagen in the supernatant of RASF cultures.

"Miniaturized Collagen Type I Degradation Assay" protocol: (Reagents are from Chondrex, Redmond, Wash. (Collagenase assay kit) unless specified differently). A 96 well plate (V-bottom, Greiner) is filled with 9 μl of solution B and 1 μl of trypsin solution per well. 10 μl of sample (RASF supernatant) is added per well, followed by incubation for 15 minutes at 34° C. After incubation, 1 μl SBTI is added. 20 μl of FITC-Collagen mix (10 μl FITC-labeled collagen type I+10 μl solution A) are added to the activated sample followed by incubation for 24 hours at 34° C. 1 μl of 1,10 Phenantroline (Sigma) is added to the reaction mixture. One μl of enhancer solution (elastase) is added, followed by incubation for 30 minutes at 34° C. When the reaction mixture is at room temperature, 40 μl extraction buffer are added and the plate is sealed (Nunc seals) and vortexed. After centrifugation for 25 minutes at 4000 rpm (Beckman centrifuge), 50 μl of the supernatant are transferred into a black F-bottom plate (Greiner) and fluorescence is measured on a Fluostar reader (BMG), 480 nm excitation wavelength, 520 nm emission wavelength).

Figure 12A:
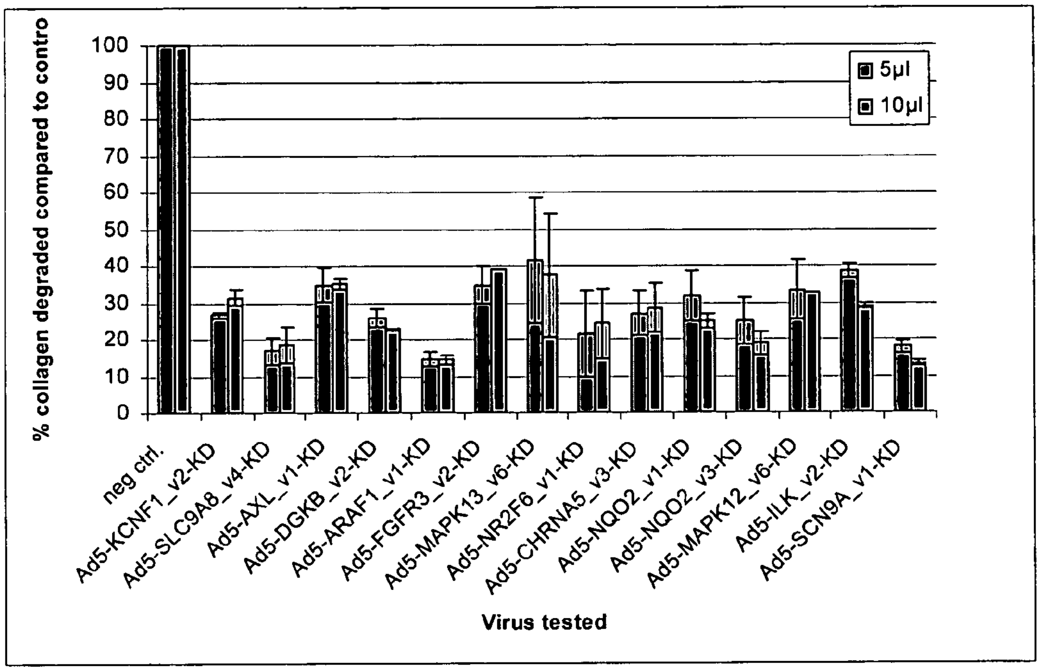
FIG. 12A shows the percent collagen degraded as compared to the control.

Ad5-siRNA efficacy in the "miniaturized collagen type I degradation assay" is tested as follows: SFs (passage 9 to 10) are seeded in 96 well plates at a density of 3000 cells/well in complete synovial growth medium (Cell Applications). One day later, the cells are infected with 5 or 10 μl of the Ad-siRNAs indicated on FIG. 12A. These KD viruses are arrayed on a 96 well plate along with 12 negative control viruses. The virus load is corrected by the addition of the neutral virus Ad5-Luciferase-v13_KD to bring the final virus volume on the cells to 15 μl in every well. This correction guarantees that the effects observed do not result from differences in the virus load applied to the cells. The cells are then incubated for 5 days before the activation step. This step involves the replacement, in every well, of the growth medium by 45 μl of M199 medium supplemented with 15 μl of "complex trigger". Four days later, the supernatant is collected and subjected to the miniaturized collagen type I degradation assay according to the protocol described above. The results are analyzed as follows: The fluorescence signal obtained for the 12 negative controls is averaged for every plate. For each plate and each MOI (5 μl or 10 μl), the fluorescence signal observed for the samples emanating from cells infected with the KD viruses targeting the genes listed in Table 1 is expressed as a percent of the negative control average (set at 100%). Data shown in FIG. 12A are the average of duplicate measurements. The Ad-siRNAs targeting the genes listed in Table 2 do mediate a clear reduction of the complex trigger-induced collagen degradation by primary human SFs. We conclude, from this experiment, that these genes represent valuable drug targets that are shown to modulate not only MMP1 expression by RASFs but also collagen degradation by RASFs. Similarly, the inhibition of the activity of the protein product of these genes by an inhibitory agent, such as a small molecule compound, is expected to reduce the "complex cytokine" induced collagen degradation by SFs. We also believe that the inhibition of the activity of the protein products of these genes by such agents would also reduce the joint degradation observed in RA patients.

Figure 12B:
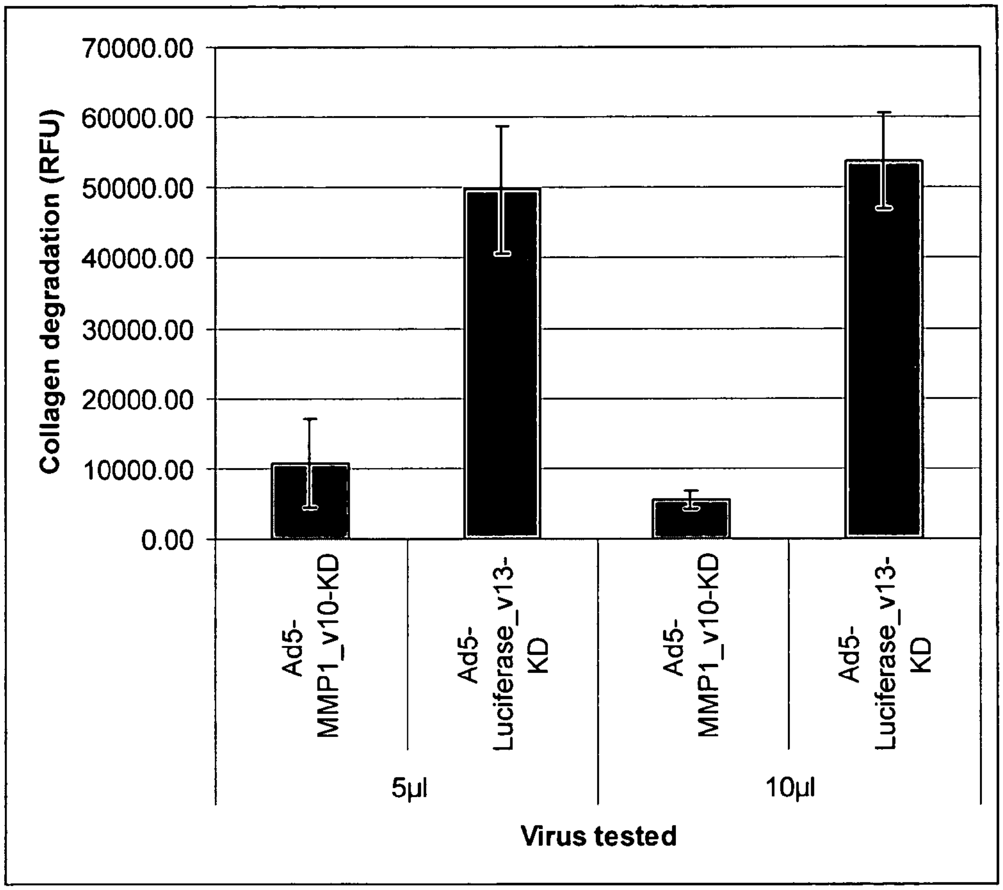
FIG. 12B shows the raw fluorescence signal.

In similar experiments (FIG. 12 B), the Ad5-MMP1 v10-KD virus is shown to strongly reduce the cytokine induced collagen degradation by SFs, which suggests that MMP1 is the main collagenase responsible for the cytokine induced collagen degradation by SFs. This experiment is run according to the protocol described for the experiment depicted in FIG. 12A. Data shown in FIG. 12B are the average and standard deviation over the raw fluorescence signal emanating from eight data points. As such, this experiment demonstrates that modulation of SF expression of MMP1 is sufficient to reduce cartilage degradation associated with RA. As such, the reduction of MMP1 expression by RASFs is predictive for a reduced degradation of native collagen, one of the main components of bone and cartilage.

Example 7

Reduction of the Expression in RASFs of ARAF1, CHRNA5, DGKB, FGFR3, ILK, KCNF1, MAPK12, MAPK13, NQO2, NR2F6, and SCN9A by Ad-siRNAs Inhibit Cytokine-Induced IL-8 Expression To better understand the profile of the TARGETS (identified according to the experiments described in previous examples), and to probe for the specificity of TARGET expression reduction effects, IL8, another inflammation marker different from MMP1, is used in the following example. This example measures the effect of TARGET expression reduction in RA SFs on TNFα-induced IL8 expression. IL8 expression is increased by TNFα, and plays a role in inflammatory events. Additionally, a small molecule inhibitor of the IL8 receptor has been shown to have efficacy in an animal model of arthritis (See Weidner-Wells MA et al., Bioorg Med Chem Lett. (2004)14:4307-11, "Synthesis and structure-activity relationships of 3,5-diarylisoxazoles and 3,5-diaryl-1,2,4-oxadiazoles, novel classes of small molecule interleukin-8 (IL-8) receptor antagonists". As such, achieving inhibition of IL8 expression is a desired feature for an RA therapeutic.

"IL-8 assay" protocol: SFs (passage 9 to 12) are seeded in 96 well plates at a density of 3000 cells/well in complete synovial growth medium (Cell Applications). One day later, the cells are infected with two amounts (6 or 12 μl) of the KD viruses. The cells are then incubated for 5 days before the activation step. The activation step involves the replacement, in every well, of the growth medium by 150 μl of DMEM supplemented with 10% Fetal Bovine serum (heat inactivated) and the trigger (2 ng/ml recombinant human TNFalpha). 48 hours after the activation step, 80 μl of the supernatant is collected and diluted for use in the IL-8 ELISA described below. For the samples triggered with TNFalpha, a 40 fold dilution is made in PBS+1% BSA. 35 μl from these dilutions are added to the IL-8 ELISA plates.

White Lumitrac 600 384 well plates (Greiner) are coated with 0.5 μg/ml anti-IL8 antibody MAB208(R&D). The antibody is diluted in 1× PBS (Gibco). After overnight incubation at 4° C., plates are washed once with 1× PBST (80 g NaCl, 2 g KCl (Sigma), 11.5 g $Na_2HPO_4 \cdot 7H_2O$ and 2 g $KH_2PO_4$ in 10 L milliQ; pH 7.4=10× PBS solution+0.05% tween-20 (sigma)), once with PBS 1×, and blocked with 80 μl blocking buffer (1% BSA+5% sucrose+0.05% NaN3). One day later, the blocking buffer is removed from the ELISA plates by inverting the plate and tapping it on an absorbent paper. The plate is washed with 90 μl PBST and 90 μl PBS 1×. Immediately thereafter, the plate is further processed and 35 μl of the diluted supernatant is added. After overnight incubation at 4° C., the plates are washed once with PBST and once with PBS (as described above) and incubated with 35 μl/well biotinylated anti-IL 8 antibody solution BAF208 (R&D) 50 ng/ml in PBS 1×+1% BSA. After 2 hours of incubation at room temperature, plates are washed as described above and incubated with 50 μl/well streptavidin-HRP conjugate (Biosource). Streptavidin-HRP conjugate is diluted 1/2000 times in PBS 1×+1% BSA. After 45 minutes, plates are washed as described above and incubated for 5 minutes with 50 μl/well BM Chem ELISA Substrate (Roche). Readout is performed on the Luminoscan Ascent Luminometer (Labsystems) with an integration time of 100 msec.

Twenty negative controls are included in the 96 well plates. The percentage inhibition of IL8 expression is calculated as follows. First, the background signal of the ELISA (in the absence of IL8) is substracted from all values for all samples. Then the following formula is applied: % inhibition=[100×(((Average value all negative controls)−value TARGET sample)/(Average value all negative controls))]. From the results depicted in FIG. 13, we conclude that expression for most TARGETS mediated a reduced TNFα-driven IL8 expression, with strongest effects seen for MAPK12, MAPK13 and ARAF1 and weakest effects observed for SLC9A8 and AXL.

TABLE 6

Summary of the Features of the TARGET Genes

| | | Knock down data | | |
|---|---|---|---|---|
| Gene symbol | Expression* | MMP1 Inhibition** | Inhibition of collagen degradation*** | IL-8 Inhibition**** |
| ARAF1 | SP | SP | SP | SP |
| AXL | SP | P | SP | N |
| CHRNA5 | P | P | SP | P |
| DGKB | NT | SP | SP | P |
| FGFR3 | P | P | SP | P |
| ILK | SP | SP | SP | P |
| KCNF1 | SP | P | SP | P |
| MAPK12 | NT | N | SP | SP |
| MAPK13 | SP | SP | SP | SP |
| NQO2 | SP | SP | SP | P |
| NR2F6 | SP | SP | SP | P |
| SCN9A | P | P | SP | P |
| SLC9A8 | SP | P | SP | N |

P: positive response in the assay

SP: Strong positive response in the assay

NT: not tested

N: negative response in the assay

*Expression in primary RASFs: Genes with DCt <13 are considered expressed (P), genes with DCt >9.9 are considered strongly expressed (SP)

**Inhibition of cytokine mixture induced MMP1 expression by RASFs >50% reduction in MMP1 expression is considered a strong positive response in the assay

***Inhibition of cytokine induced collagen degradation by RASFs >50% reduction in cytokine induced collagen degradation is considered a strong positive response in the assay

****Inhibition of TNFα induced IL-8 expression by RASFs >20% inhibition of TNFα induced IL-8 expression is considered a significant response in the assay (P), >50 inhibition is considered a strong positive response in the assay

We claim:

1. A method for identifying a compound that inhibits extra-cellular matrix degradation comprising contacting a compound with a polypeptide comprising the amino acid sequence of SEQ ID NO:18, 42, 44, 46, 48, 50, 52, 54, 56, 58, 60, 62 or 64 in an in vitro cell-free preparation;

and measuring the binding affinity of said compound in said in vitro preparation;

selecting a candidate compound for confirmation as an inhibitor of extra-cellular matrix degradation, which candidate compound is selected based on its binding affinity for one or more of the polypeptide of the afore-said SEQ ID Nos.

2. The method according to claim 1, wherein said compound is a peptide in a phage display library or an antibody fragment library.

3. A method for identifying a compound that inhibits extra-cellular matrix degradation in a mammalian cell that expresses an extra-cellular matrix degrading protein, and that expresses a polypeptide comprising the amino acid sequence of SEQ ID NO: 18, said method comprising (a) contacting a compound with a polypeptide comprising the amino acid sequence of SEQ ID NO:18, 42, 44, 46, 48, 50, 52, 54, 56, 58, 60, 62 or 64, in an in vitro cell-free preparation;

(b) determining the binding affinity of said compound in said in vitro preparation;

(c) contacting said compound having binding affinity to, and capable of forming a complex with, said polypeptide of SEQ ID NO:18 with a mammalian cell, in which said polypeptide comprising the amino acid sequence of SEQ ID NO:18 is expressed, and which expresses an extra-cellular matrix degrading protein; and (d) measuring levels of one or more extra-cellular matrix degrading proteins expressed by said mammalian cell; and (e) determining if said levels of said one or more extra-cellular matrix degrading proteins are decreased compared to levels of said extra-cellular matrix degrading proteins expressed in said mammalian cell that is not contacted with said compound.

4. The method according to claim 3, wherein the extra-cellular matrix degrading protein is selected from the group consisting of matrix metallo protease and Cathepsin.

5. The method according to claim 3 wherein said compound having binding affinity to, and capable of forming a complex with, said polypeptide of SEQ ID NO:18 exhibits a binding affinity of at least 10 micromolar.

6. The method according to claim 5, wherein said mammalian cell is a synovial fibroblast.

7. The method according to claim 6, wherein each of said mammalian synovial fibroblast that is contacted with said compound and that is not contacted with said compound is contacted with a cytokine agonist or with cytokine-producing cells.

8. A method for identifying a compound that inhibits extra-cellular matrix degradation in a mammalian cell that expresses an extra-cellular matrix degrading protein, and that expresses a polypeptide comprising the amino acid sequence of SEQ ID NO: 18, said method comprising (a) contacting a compound with a polypeptide comprising the amino acid sequence of SEQ ID NO:18, 42, 44, 46, 48, 50, 52, 54, 56, 58, 60, 62 or 64, in an in vitro cell-free preparation;

(b) determining the binding affinity of said compound in said in vitro preparation;

(c) contacting said compound having binding affinity to, and capable of forming a complex with, said polypeptide of SEQ ID NO:18 with a mammalian cell, in which said polypeptide comprising the amino acid sequence of SEQ ID NO:18 is expressed, and which expresses an extra-cellular matrix degrading protein; and (d) measuring levels of ion channel activity in said mammalian cell; and (e) determining if said levels of ion channel activity in said mammalian cell contacted with said compound are decreased as compared to levels of said ion channel activity in said mammalian cell that is not contacted with said compound;

selecting a candidate compound, based on its level of ion channel activity, for confirmation as an inhibitor of extra-cellular matrix degradation.

9. The method according to claim 8 further comprising the steps of (f) measuring levels of one or more extra-cellular matrix degrading protein expressed by said mammalian cell; and (g) determining if said levels of said one or more extra-cellular matrix degrading protein expressed by said mammalian cell are decreased as compared to levels of said extra-cellular matrix degrading protein expressed in said mammalian cell that is not contacted with said compound.

10. The method according to claim 9, wherein the extra-cellular matrix degrading protein is selected from the group consisting of matrix metallo protease and Cathepsin.

11. The method according to claim 9, wherein said compound having binding affinity to, and capable of forming a complex with, said polypeptide of SEQ ID NO:18 exhibits a binding affinity of at least 10 micromolar.

12. The method according to claim 9, wherein said mammalian cell is a synovial fibroblast.

13. The method according to claim 12, wherein each of said mammalian synovial fibroblast that is contacted with said compound and that is not contacted with said compound is contacted with a cytokine agonist or with cytokine-producing cells.

14. The method according to claim 3, wherein said polypeptide comprises the amino acid sequence of SEQ ID NO:18.

15. The method according to claim 3, wherein said polypeptide comprises the amino acid sequence of SEQ ID NO: 42, 44, 46, 48, 50, 52, 54, 56, 58, 60, 62 or 64.

16. The method according to claim 8, wherein said polypeptide comprises the amino acid sequence of SEQ ID NO:18.

17. The method according to claim 8, wherein said polypeptide comprises the amino acid sequence of SEQ ID NO: 42, 44, 46, 48, 50, 52, 54, 56, 58, 60, 62 or 64.

* * * * *